(12) United States Patent
Sydorenko et al.

(10) Patent No.: US 11,858,941 B2
(45) Date of Patent: Jan. 2, 2024

(54) HETEROCYCLIC AND HETEROARYL COMPOUNDS FOR TREATING HUNTINGTON'S DISEASE

(71) Applicant: PTC THERAPEUTICS, INC., South Plainfield, NJ (US)

(72) Inventors: Nadiya Sydorenko, Princeton, NJ (US); Md Rauful Alam, Piscataway, NJ (US); Michael A. Arnold, Flemington, NJ (US); Suresh Babu, Pennington, NJ (US); Anuradha Bhattacharyya, Edison, NJ (US); Guangming Chen, Bridgewater, NJ (US); Aleksey I. Gerasyuto, Flemington, NJ (US); Gary Mitchell Karp, Princeton Junction, NJ (US); Andrew J. Kassick, Wexford, PA (US); Anthony R. Mazzotti, Rahway, NJ (US); Young-Choon Moon, Belle Mead, NJ (US); Jana Narasimhan, Scotch Plains, NJ (US); Jigar Patel, Edison, NJ (US); Anthony Turpoff, Hillsborough, NJ (US); Matthew G. Woll, Dunellen, NJ (US); Wuming Yan, Wayne, NJ (US); Nanjing Zhang, Princeton, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 188 days.

(21) Appl. No.: 17/254,660

(22) PCT Filed: Jun. 25, 2019

(86) PCT No.: PCT/US2019/038889
§ 371 (c)(1),
(2) Date: Dec. 21, 2020

(87) PCT Pub. No.: WO2020/005873
PCT Pub. Date: Jan. 2, 2020

(65) Prior Publication Data
US 2021/0238186 A1 Aug. 5, 2021

Related U.S. Application Data

(60) Provisional application No. 62/690,653, filed on Jun. 27, 2018.

(51) Int. Cl.
| | | |
|---|---|---|
| *C07D 487/04* | (2006.01) | |
| *A61P 25/28* | (2006.01) | |
| *C07D 519/00* | (2006.01) | |
| *A61P 25/14* | (2006.01) | |
| *C07D 491/048* | (2006.01) | |
| *C07D 495/04* | (2006.01) | |

(52) U.S. Cl.
CPC ............ *C07D 487/04* (2013.01); *A61P 25/14* (2018.01); *A61P 25/28* (2018.01); *C07D 491/048* (2013.01); *C07D 495/04* (2013.01); *C07D 519/00* (2013.01)

(58) Field of Classification Search
CPC .......................... C07D 487/04; C07D 519/00
See application file for complete search history.

(56) References Cited

U.S. PATENT DOCUMENTS

| | | |
|---|---|---|
| 3,558,618 A | 1/1971 | Trepanier |
| 4,122,274 A | 10/1978 | Juby |
| 4,342,870 A | 8/1982 | Kennis et al. |
| 4,613,603 A | 9/1986 | Biziere et al. |
| 5,089,633 A | 2/1992 | Powers et al. |
| 5,599,816 A | 2/1997 | Chu et al. |
| 5,627,274 A | 5/1997 | Kole et al. |

(Continued)

FOREIGN PATENT DOCUMENTS

| | | |
|---|---|---|
| CN | 101360738 A | 2/2009 |
| CN | 104768960 B | 3/2017 |

(Continued)

OTHER PUBLICATIONS

Chloé Copin et al, "SnAr versus Buchwald-Hartwig Amination/Amidation in the Imidazo[2, 1-b][1,3,4]thiadiazole Series", European Journal of Organic Chemistry, vol. 2015(31), Sep. 29, 2015, p. 6932-6942.

(Continued)

*Primary Examiner* — Susanna Moore
(74) *Attorney, Agent, or Firm* — Hoffmann and Baron, LLP

(57) ABSTRACT

The present description relates to compounds, forms, and pharmaceutical compositions thereof and methods of using such compounds, forms, or compositions thereof for treating or ameliorating Huntington's disease.

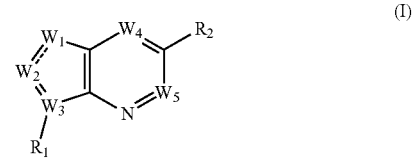

In particular, the present description relates to substituted bicyclic heterocyclic and heteroaryl compounds of Formula (I), forms and pharmaceutical compositions thereof and methods of using such compounds, forms, or compositions thereof for treating or ameliorating Huntington's disease.

16 Claims, No Drawings

(56) References Cited

U.S. PATENT DOCUMENTS

| | | |
|---|---|---|
| 5,665,593 A | 9/1997 | Kole et al. |
| 5,916,808 A | 6/1999 | Kole et al. |
| 5,916,916 A | 6/1999 | Hauser et al. |
| 5,976,879 A | 11/1999 | Kole et al. |
| 6,172,216 B1 | 1/2001 | Bennett et al. |
| 6,210,892 B1 | 4/2001 | Bennett et al. |
| 6,214,986 B1 | 4/2001 | Bennett et al. |
| 6,468,607 B1 | 10/2002 | Takehara et al. |
| 6,630,488 B1 | 10/2003 | Lamothe et al. |
| 6,977,255 B2 | 12/2005 | Robertson et al. |
| 7,326,711 B2 | 2/2008 | Wang et al. |
| 7,399,767 B2 | 7/2008 | Zhang et al. |
| 7,473,784 B2 | 1/2009 | Liu et al. |
| 7,569,337 B2 | 8/2009 | Auberson |
| 7,655,657 B2 | 2/2010 | Stoner et al. |
| 7,897,792 B2 | 3/2011 | Iikura et al. |
| 7,910,578 B2 | 3/2011 | Peters et al. |
| 8,143,274 B2 | 3/2012 | Hattori et al. |
| 8,314,119 B2 | 11/2012 | Schrimpf et al. |
| 8,337,941 B2 | 12/2012 | Gubernator et al. |
| 8,563,550 B2 | 10/2013 | Pevarello et al. |
| 8,633,019 B2 | 1/2014 | Paushkin et al. |
| 8,846,661 B2 | 9/2014 | Schrimpf et al. |
| 8,921,361 B2 | 12/2014 | Cmiljanovic et al. |
| 9,371,336 B2 | 6/2016 | Lee et al. |
| 9,399,649 B2 | 7/2016 | Chen et al. |
| 9,617,268 B2 | 4/2017 | Woll et al. |
| 9,969,754 B2 | 5/2018 | Ratni et al. |
| 2002/0099208 A1 | 7/2002 | Yu et al. |
| 2003/0004164 A1 | 1/2003 | Bebbington et al. |
| 2003/0199526 A1 | 10/2003 | Choquette et al. |
| 2005/0054836 A1 | 3/2005 | Krainer et al. |
| 2005/0074801 A1 | 4/2005 | Monia et al. |
| 2005/0159597 A1 | 7/2005 | Ji et al. |
| 2006/0172962 A1 | 8/2006 | Vickers et al. |
| 2006/0205741 A1 | 9/2006 | Zhang et al. |
| 2007/0078144 A1 | 4/2007 | Stockwell et al. |
| 2007/0105807 A1 | 5/2007 | Sazani et al. |
| 2007/0191374 A1 | 8/2007 | Hodgetts |
| 2008/0171792 A1 | 7/2008 | Jobdevairakkam et al. |
| 2008/0255162 A1 | 10/2008 | Bruendl et al. |
| 2009/0163464 A1 | 6/2009 | Black et al. |
| 2009/0163515 A1 | 6/2009 | Birault et al. |
| 2009/0170793 A1 | 7/2009 | Gaur |
| 2009/0264433 A1 | 10/2009 | Russell et al. |
| 2010/0004233 A1 | 1/2010 | Iikura et al. |
| 2010/0035279 A1 | 2/2010 | Gubernator et al. |
| 2010/0267721 A1 | 10/2010 | Hohlweg et al. |
| 2011/0086833 A1 | 4/2011 | Paushkin et al. |
| 2011/0118289 A1 | 5/2011 | Giordani et al. |
| 2012/0083495 A1 | 4/2012 | Heemskerk et al. |
| 2013/0046093 A1 | 2/2013 | Lee et al. |
| 2014/0051672 A1 | 2/2014 | Cheung et al. |
| 2014/0121197 A1* | 5/2014 | Burli ............... C07D 519/00 544/236 |
| 2014/0206661 A1 | 7/2014 | Axford et al. |
| 2014/0329825 A1 | 11/2014 | Heback et al. |
| 2015/0005289 A1 | 1/2015 | Qi et al. |
| 2015/0018301 A1 | 1/2015 | Lee et al. |
| 2015/0057218 A1 | 2/2015 | Zhong et al. |
| 2015/0080383 A1 | 3/2015 | Yang et al. |
| 2015/0119380 A1 | 4/2015 | Woll et al. |
| 2016/0244762 A1 | 8/2016 | Vorechovsky et al. |
| 2017/0000794 A1 | 1/2017 | Naryshkin |
| 2017/0001995 A1 | 1/2017 | Metzger et al. |
| 2017/0002016 A1 | 1/2017 | Shishido et al. |
| 2017/0096411 A1 | 4/2017 | Vechorkin et al. |
| 2017/0121197 A1 | 5/2017 | Tale |
| 2017/0151225 A1 | 6/2017 | Dahl |
| 2017/0355989 A1 | 12/2017 | Konstantinova et al. |
| 2018/0118748 A1 | 5/2018 | Slaugenhaupt et al. |
| 2018/0161456 A1 | 6/2018 | Naryshkin et al. |
| 2018/0282347 A1 | 10/2018 | Arlt et al. |
| 2019/0264267 A1 | 8/2019 | Yang et al. |
| 2020/0056173 A1 | 2/2020 | Vargeese et al. |
| 2020/0080083 A1 | 3/2020 | Vargeese et al. |

FOREIGN PATENT DOCUMENTS

| | | |
|---|---|---|
| DE | 2345064 A1 | 4/1974 |
| EP | 1227084 A1 | 7/2002 |
| EP | 2560008 A2 | 2/2013 |
| EP | 2841428 B1 | 8/2018 |
| FR | 2914188 A1 | 10/2008 |
| GB | 1047935 | 11/1966 |
| GB | 1383409 | 2/1975 |
| JP | 1981-150091 A | 3/1983 |
| JP | S61-36282 | 2/1986 |
| JP | 2006219453 A | 8/2006 |
| JP | 2009-545540 | 12/2009 |
| JP | 2013-40945 | 2/2013 |
| JP | 2017-512834 | 5/2017 |
| WO | 1993/023398 A1 | 11/1993 |
| WO | 1994/026887 A1 | 11/1994 |
| WO | 1996/039407 A1 | 12/1996 |
| WO | 1998/025930 A1 | 6/1998 |
| WO | 2001/053266 A1 | 7/2001 |
| WO | 2002/062290 A2 | 8/2002 |
| WO | 2002/087589 A1 | 11/2002 |
| WO | 2004/009558 A1 | 1/2004 |
| WO | 2004/019002 A2 | 3/2004 |
| WO | 2004/029053 A1 | 4/2004 |
| WO | 2004/113335 A2 | 12/2004 |
| WO | 2005/012288 A1 | 2/2005 |
| WO | 2005/019215 A1 | 3/2005 |
| WO | 2005/061513 A1 | 7/2005 |
| WO | 2005/066166 A2 | 7/2005 |
| WO | 2005/072720 A1 | 8/2005 |
| WO | 2005/105801 A1 | 11/2005 |
| WO | 2006/131835 A2 | 12/2006 |
| WO | 2006/138418 A2 | 12/2006 |
| WO | 2007/003604 A2 | 1/2007 |
| WO | 2007/016392 A2 | 2/2007 |
| WO | 2007/018738 A1 | 2/2007 |
| WO | 2007/047913 A2 | 4/2007 |
| WO | 2007/065892 A1 | 6/2007 |
| WO | 2007/071055 A1 | 6/2007 |
| WO | 2007/089584 A2 | 8/2007 |
| WO | 2007/089611 A2 | 8/2007 |
| WO | 2007/090073 A2 | 8/2007 |
| WO | 2007/109211 A2 | 9/2007 |
| WO | 2007/110364 A1 | 10/2007 |
| WO | 2007/130383 A2 | 11/2007 |
| WO | 2007/133561 A2 | 11/2007 |
| WO | 2007/133756 A2 | 11/2007 |
| WO | 2007/135121 A1 | 11/2007 |
| WO | 2008/011109 A2 | 1/2008 |
| WO | 2008/014822 A1 | 2/2008 |
| WO | 2008/049864 A1 | 5/2008 |
| WO | 2008/077188 A1 | 7/2008 |
| WO | 2009/042907 A1 | 4/2009 |
| WO | 2009/085945 A1 | 7/2009 |
| WO | 2009/114874 A2 | 9/2009 |
| WO | 2009/126635 A1 | 10/2009 |
| WO | 2009/151546 A2 | 12/2009 |
| WO | 2009/156861 A2 | 12/2009 |
| WO | 2010/000032 A1 | 1/2010 |
| WO | 2010/019236 A1 | 2/2010 |
| WO | 2010/024903 A1 | 3/2010 |
| WO | 2010/045303 A2 | 4/2010 |
| WO | 2010/071819 A1 | 6/2010 |
| WO | 2010/093425 A1 | 8/2010 |
| WO | 2010/130934 A2 | 11/2010 |
| WO | 2010/145208 A1 | 12/2010 |
| WO | 2011/032045 A1 | 3/2011 |
| WO | 2011/050245 A1 | 4/2011 |
| WO | 2011/057204 A2 | 5/2011 |
| WO | 2011/062853 A2 | 5/2011 |
| WO | 2011/085990 A1 | 7/2011 |
| WO | 2011/097641 A1 | 8/2011 |
| WO | 2011/097643 A1 | 8/2011 |
| WO | 2011/097644 A2 | 8/2011 |

(56) References Cited

FOREIGN PATENT DOCUMENTS

| | | |
|---|---|---|
| WO | 2012/012467 A2 | 1/2012 |
| WO | 2012/019106 A2 | 2/2012 |
| WO | 2012/075393 A2 | 6/2012 |
| WO | 2012/103806 A1 | 8/2012 |
| WO | 2012/104823 A2 | 8/2012 |
| WO | 2012/109395 A1 | 8/2012 |
| WO | 2012/116965 A1 | 9/2012 |
| WO | 2013/019938 A1 | 2/2013 |
| WO | 2013/020993 A1 | 2/2013 |
| WO | 2013/022990 A1 | 2/2013 |
| WO | 2013/033223 A1 | 3/2013 |
| WO | 2013/059606 A1 | 4/2013 |
| WO | 2013/068769 A1 | 5/2013 |
| WO | 2013/101974 A1 | 7/2013 |
| WO | 2013/112788 A1 | 8/2013 |
| WO | 2013/119916 A1 | 8/2013 |
| WO | 2013/130689 A1 | 9/2013 |
| WO | 2013/142236 A1 | 9/2013 |
| WO | 2013/163190 A1 | 10/2013 |
| WO | 2014/012050 A2 | 1/2014 |
| WO | 2014/028459 A1 | 2/2014 |
| WO | 2014/059341 A1 | 4/2014 |
| WO | 2014/059356 A2 | 4/2014 |
| WO | 2014/066836 A1 | 5/2014 |
| WO | 2014/069675 A1 | 5/2014 |
| WO | 2014/116845 A1 | 7/2014 |
| WO | 2014/121287 A2 | 8/2014 |
| WO | 2014/135244 A1 | 9/2014 |
| WO | 2014/184163 A1 | 11/2014 |
| WO | 2014/209841 A2 | 12/2014 |
| WO | 2015/024876 A2 | 12/2014 |
| WO | 2015/017589 A1 | 2/2015 |
| WO | 2015/095446 A1 | 6/2015 |
| WO | 2015/095449 A1 | 6/2015 |
| WO | 2015/105657 A1 | 7/2015 |
| WO | 2015/107425 A2 | 7/2015 |
| WO | 2015/107494 A1 | 7/2015 |
| WO | 2015/110446 A1 | 7/2015 |
| WO | 2017/080967 A1 | 7/2015 |
| WO | 2015/143185 A1 | 9/2015 |
| WO | 2015/173181 A1 | 11/2015 |
| WO | 2015/197503 A1 | 12/2015 |
| WO | 2016/087417 A1 | 6/2016 |
| WO | 2016/128343 A1 | 8/2016 |
| WO | 2016/131776 A1 | 8/2016 |
| WO | 2016/144351 A1 | 9/2016 |
| WO | 2016/170163 A1 | 10/2016 |
| WO | 2016/184832 A1 | 11/2016 |
| WO | 2017/023987 A1 | 2/2017 |
| WO | 2017/081111 A1 | 5/2017 |
| WO | 2017/097728 A1 | 6/2017 |
| WO | 2017/100726 A1 | 6/2017 |
| WO | 2017/175068 A1 | 10/2017 |
| WO | 2017/189829 A1 | 11/2017 |
| WO | 2017/210134 A1 | 12/2017 |
| WO | 2018/081091 A1 | 5/2018 |
| WO | 2018/187209 A1 | 10/2018 |
| WO | 2018/218133 A1 | 11/2018 |
| WO | 2018/226622 A1 | 12/2018 |
| WO | 2019/005980 A1 | 1/2019 |
| WO | 2019/005993 A1 | 1/2019 |
| WO | 2019/028440 A1 | 2/2019 |
| WO | 2019/165073 A1 | 8/2019 |
| WO | 2019/183364 A1 | 9/2019 |
| WO | 2019/183367 A1 | 9/2019 |
| WO | 2019/191092 A1 | 10/2019 |
| WO | 2019/191229 A1 | 10/2019 |
| WO | 2020/005873 A1 | 1/2020 |
| WO | 2020/005877 A1 | 1/2020 |
| WO | 2020/005882 A1 | 1/2020 |
| WO | 2020/190793 A1 | 9/2020 |
| WO | 2020/231977 A1 | 11/2020 |
| WO | 2021/007378 A1 | 1/2021 |
| WO | 2021/084495 A1 | 5/2021 |
| WO | 2021/207453 A1 | 10/2021 |
| WO | 2022/103980 A1 | 5/2022 |
| WO | 2023/009816 A1 | 2/2023 |

OTHER PUBLICATIONS

Database Registry, Chemical Abstracts Service, Feb. 22, 2018, Database Accession No. 2178867-25-7.

Database Registry, Chemical Abstracts Service, Sep. 18, 2017, Database Accession No. 2128311-64-6.

Database Registry, Chemical Abstracts Service, Sep. 24, 2017, Database Accession No. 2130300-22-8.

Database Registry, Chemical Abstracts Service, Sep. 25, 2017, Database Accession No. 2130694-60-7.

Fascio Mirta L et al, "Synthesis and antiviral activity of some imidazo[1,2-b][1,3,4]thiadiazole carbohydrate derivatives", Carbohydrate Research, vol. 480, May 21, 2019 , p. 61-66.

Ingo Knepper et al., "3-Acylindoles as versatile starting materials for pyridine ring annulation: synthesis of 1-deazapurine isosteres", Tetrahedron,vol. 67(29):5293-5303, May 14, 2011.

K.K. Abdul Khader et al., "Regioselective synthesis of C-2 substituted imidazo[4,5-b]pyridines utilizing palladium catalysed C-N bond forming reactions with enolizable heterocy", Tetrahedron Letters, vol. 55(10):1778-1783, Feb. 1, 2014.

Mariusz Mojzych et al., "Synthesis of pyrazolo[4,3-e][1,2,4]triazine sulfonamides, novel Sildenafil analogs with tyrosinase inhibitory activity", Bioorganic & Medicinal Chemistry, vol. 22, pp. 6616-6624, Oct. 18, 2014.

Mazzone G et al, "Sintesi e valutazione biologica preliminare di imidazo[2,1-b]-1,3,4-tiadiazoli-2,6-diarilsostituti", Farmaco, Edizione Scientifica, Societa Chimica Italiana, Pavia, IT,vol. 39(7), Jan. 1, 1984, p. 585-598. English Abstract Only.

Patel Harun M et al, "2,5,6-Trisubstituted imidazo[2,1-b][1,3,4]thiadiazoles: Search for antihyperlipidemnic agents", European Journal of Medicinal Chemistry, Editions Scientifique Elsevier, Paris, FR, vol. 65, Apr. 18, 2013, p. 119-133.

ISR in PCT/US2019/038889, mailed Aug. 8, 2019.
WO in PCT/US2019/038889, mailed Aug. 8, 2019.
ISR in PCT/US2019/038895, mailed Aug. 14, 2019.
WO in PCT/US2019/038895, mailed Aug. 14, 2019.
ISR in PCT/US19/38900, mailed Aug. 20, 2019.
WO in PCT/US19/38900, mailed Aug. 20, 2019.

J. S. Nair et al: "Synthesis and Fluorescence Properties of 3-Benzoxa- and Thiazol-2-ylquinoline-5 or 7-maleimides.", Cheminform, vol. 36, No. 2, Sep. 1, 2004 (Sep. 1, 2004), pp. 1944-1949.

Naik et al: "Studies in the Vilsmeier-Haack reaction: Part XVI., Synthesis of 7-amino-3-hetrarylquinoline fluorophore and derivatives", Indian Journal of Chemistry, Council of Scientific and Industrial Research (CS I R), DE, vol. 15B, No. 6, Jan. 1, 1977 (Jan. 1, 1977), pp. 506-508.

USPTO, Office Action dated Feb. 4, 2021 in U.S. Appl. No. 16/617,450. See whole document in general and compounds on pp. 10-14 and 15-18 in particular.

MacDonald et al., "Quantification Assays for Total and Polyglutamine-Expanded Huntingtin Proteins", PLOS One, 2014, vol. 9(5), dated May 2014, e96854, pp. 1-17.

Palacino et al., "SMN2 splice modulators enhance U1-pre-mRNA association and rescue SM0A mice", Nature: Chemical Biology, pp. 511-517 and 5 Supplemental Pages + S1-S20, vol. 11, Jun. 1, 2015.

Pryor et al., "Huntingtin promotes mTORC1 signaling in the pathogenesis of Huntington's disease", Sci. Signal, dated Oct. 28, 2014, vol. 7, Issue 349, ra103, pp. 1-12.

Cheung et al., "Discovery of Small Molecule Splicing Modulators of Survival Motor Neuron-2 (SMN2) for the Treatment of Spinal Muscular Atrophy (SMA)", J. Med. Chem. XXXX, XXX, XXX-XXX, Nov. 8, 2018 (published), pp. A-P.

Brunhilde Wirth et al., "Moving towards treatments for spinal muscular atrophy: hopes and limits", Expert Opinion on Emerging drugs, 20(3):353-356, Apr. 28, 2015.

Chiara Zanetta et al., "Molecular Therapeutic Strategies for Spinal Muscular Atrophies: Current and Future Clinical Trials", Clinical Therapeutics, 36(1):128-140, Dec. 17, 2013.

(56) References Cited

OTHER PUBLICATIONS

Coady et al., 2010, "Trans-splicing-mediated improvement in a severe mouse model of spinal muscular atrophy", J. Neurosci., vol. 30(1), pp. 126-130, 2010.
Combring et al., "Respiratory syncytial virus fusion inhibitors. Part 6: An examination of the effect of structural variation for the benzimidazol-2-one heterocycle moiety", Bioorganic & Medicinal Chemistry Letters, 17(17):4784-4790, Aug. 4, 2007.
European Patent Office, Communication pursuant to Article 94(3) EPC, European Application No. 14877918.4, dated Mar. 23, 2018.
Greene, Protective Groups in Organic Syntehsis, 1991, Wiley, New York, pp. v-xxi and 1-17.
Higuchi and W. Stella, "Pro-drugs as novel delivery systems", vol. 14 of the A.C.S., Symposium Series and in Bioreversible Carriers in Drug Design, ed., Edward B. Roche, American Pharmaceutical Association and Pergamon Press (1975).
Hua et al., "Peripheral SMN restoration is essential or long-term rescue of a severe SMA mouse model", Nature, vol. 4178(7367), pp. 123-126, 2012.
Jarecki et al., "Diverse small-molecule modulators of SMN expression found by high-throughput compound screening: early leads towards a therapeutic for spinal muscular atrophy", Human molecular genetics, 14(14):2003-2018, 2005.
Knight et al., "Isoform-specific phosphoinositide 3-kinase inhibitors from an arylmorpholine scaffold", Bioorganic & Medicinal Chemistry, vol. 12(17):4749-4759, 2004.
Kocar, Transformations of 3-aminopyridazines. Synthesis of 4-oxo 4H-pyrimido [1,2-b]pyridazine and 1-(substituted pyridazin-3-yl)-1H-1,2,3-triazole derivatives, Arkivoc, vol. 8, 2002, 143-156.
Le et al., "SMND7, the major product of the centromeric survival motor neuron (SMN2) gene, extends survival in mice with spinal muscular atrophy and associates with full-length SMN", Human Molecular Genetics, vol. 14(5), pp. 845-857, 2005.
Liu et al., "A novel nuclear structure containing the survival of motor neurons protein", EMBO J. vol. 15(14), pp. 3555-3565 (1996).
Makhortova et al., "A screen for regulators of survival of motor neuron proteins levels", Nature chemical biology, vol. 7 (8):544-552, 2011.
Markus Riessland et al., "The benzamide M344, a novel histone deacetylase inhibitor, significantly increases SMN2 RNA/protein levels in spinal muscular atrophy cells", Hum Genet 120:101-110, May 26, 2006.
Naryshkin et al., "SMN2 splicing modifiers improve motor function and longevity in mice with spinal muscular atrophy", Science, vol. 345(6197):688-693, 2014 (including supplementary materials).
Passini et al., "Antisense Oligonucleotides delivered to the mouse CNS ameliorate symptoms of severe spinal muscular atrophy", Sci Transl. Med., vol. 3(72), 2001.
Peng, Lijie et al., "Identification of pyrido[1,2-alpha]pyrimidine 4-ones as new molecules improving the transcriptional functions of estrogen-related receptor alpha", Journal of medicinal chemistry, vol. 54(21):7729-7733, 2011.
PubChem/NCBI Database accession No. CID 377422 [online], 2005, retrieved on Jul. 4, 2016, URL http://pubchem.nci.hlm.nih.gov/compound/377422.
Seisuke Mimori et al., "Protective Effects of 4-phenylbutyrate derivatives on the neuronal cell death and endoplasmic reticulum stress," Biological & Pharmaceutical Bulletin of Japan, 35(1):84-90, Jan. 1, 2012.
Shao, Ning et al., "Synthesis and structure-activity relationship (SAR) study of 4-azabenzoxazole analogues as H3 antagonists", Bioorganic & Medicinal chemistry letters, vol. 22(5):2075-2078, 2012.
Sin et al., "Respiratory syncytial virus fusion inhibitors. Part 7: Structure-activity relationships associated with a series of isatin oximes that demonstrate antiviral activity in vivo", Bioorganic & Medicinal Chemistry Letters, 19 (16):4857-4862, Aug. 15, 2009.

Yuo et al., 2008, "5-(N-ethyl-N-isopropyl)-amiloride enhances SMN2 exon 7 inclusion and protein expression in spinal muscular atrophy cells", Annals of neurology, vol. 63(1):26-34, 2008.
Lazarev et al., "Factors Affecting Aggregate Formation in Cell Models of Huntington's Disease and Amyotrophic Lateral Sclerosis", Acta Naturae, vol. 5(2):81-89, Apr. 2013.
International Search Report for PCT/US2018/035954, dated Oct. 1, 2018.
Written Opinion of the International Searching Authority for PCT/US2018/035954, dated Oct. 1, 2018.
International Search Report for PCT/US2018/039775, dated Oct. 29, 2018.
Written Opinion of the International Searching Authority for PCT/US2018/039775, dated Oct. 29, 2018.
International Search Report in PCT/US2016/066042, dated Mar. 16, 2017.
Written Opinion of the International Searching Authority for PCT/US2016/066042, dated Mar. 16, 2017.
International Search Report for PCT/US2019/024068, dated Jul. 10, 2019.
Written Opinion of the International Searching Authority for PCT/US2019/024068, dated Jul. 10, 2019.
International Search Report for PCT/US2019/024278, dated May 28, 2019.
Written Opinion of the International Searching Authority for PCT/US2019/024278, dated May 28, 2019.
International Search Report for PCT/EP2012/065499, dated Sep. 28, 2012.
Written Opinion of the International Searching Authority for PCT/EP2012/065499, dated Sep. 28, 2012.
International Search Report for PCT/EP2014/059699, dated Aug. 25, 2014.
Written Opinion of the International Searching Authority for PCT/EP2014/059699, dated Aug. 25, 2014.
International Search Report for PCT/EP2015/051066, dated Feb. 19, 2015.
Written Opinion of the International Searching Authority for PCT/EP2015/051066, dated Feb. 19, 2015.
International Search Report for PCT/EP2015/060343, dated Jul. 13, 2015.
Written Opinion of the International Searching Authority for PCT/EP2015/060343, dated Jul. 13, 2015.
International Search Report for PCT/EP2016/060952, dated Jun. 29, 2016.
Written Opinion of the International Searching Authority for PCT/EP2016/060952, dated Jun. 29, 2016.
International Search Report for PCT/EP2016/063894, dated Jan. 19, 2017.
Written Opinion of the International Searching Authority for PCT/EP2016/063894, dated Jan. 19, 2017.
International Search Report for PCT/EP2016/076905, dated Feb. 9, 2017.
Written Opinion of the International Searching Authority for PCT/EP2016/076905, dated Feb. 9, 2017.
International Search Report for PCT/EP2016/077190, dated Mar. 1, 2017.
Written Opinion of the International Searching Authority for PCT/EP2016/077190, dated Mar. 1, 2017.
International Search Report for PCT/EP2016/079816, dated Jan. 19, 2016.
Written Opinion of the International Searching Authority for PCT/EP2016/079816, dated Jan. 19, 2016.
International Search Report for PCT/US2013/025292, dated Aug. 30, 2013.
Written Opinion of the International Searching Authority for PCT/US2013/025292, dated Aug. 30, 2013.
International Search Report in PCT/US2018/039794, dated Oct. 25, 2018.
Written Opinion of the International Searching Authority in PCT/US2018/039794, dated Oct. 25, 2018.
International Search Report from PCT/US2020/041300, dated Oct. 16, 2020.
Written Opinion from PCT/US2020/041300, dated Oct. 16, 2020.

(56) References Cited

OTHER PUBLICATIONS

Pubchem, Substance Record for SID 249779947, Mar. 31, 2015, "4H-Quinolizin-4-one1; Hydrobromide".
Potkin et al., "New directions in therapeutics for Huntington disease", Future Neurology, vol. 13(2):101-121, May 2018.
Wermuth, "The Practice of Medicinal Chemistry", 2nd ed., 2003, Chapters 9-10.
H. Kubinyi, "3D QSAR in Drug Design—Theory Methods and Applications", pp. vii-ix and pp. 243-244, 1998.
Andreassi, C. et al. 2001. Human Molecular Genetics 10, 2841-2849. "Aclarubicin treatment restores SMN levels to cells derived from type I spinal muscular atrophy patients."
Artursson P., et al. 1991. Biochem Biophys Res Comm 175, 880-5. "Correlation between oral drug absorption in humans and apparent drug permeability coefficients in human intestinal epithelial (Caco-2) cells."
Baldo, B. et al. 2012. J. Biol. Chem. 287, 1406-1414. "A screen for enhancers of clearance identifies huntingtin as a heat shock protein 90 (Hsp90) client protein."
Barbaro, B.A. et al. 2015. Human Molecular Genetics 24, 913-925 (published online Oct. 9, 2014). "Comparative study of naturally occurring huntingtin fragments in *Drosophila* points to exon 1 as the most pathogenic species in Huntington's disease."
Bates, G.P. et al. 2015. Nature Reviews, Disease Primers 1, 15005 (published online Apr. 23, 2015). "Huntington disease."
Bengart, P. et al. 2004. Nucleic Acids Res. 32, W154-W159. "Riboswitch finder—a tool for indentification of riboswitch RNAs."
Bhattacharyya, A. et al. 2007 Drug Discovery Today 12, 553-560. "Mining the GEMS—a novel platform technology targeting post-transcriptional control mechanisms.".
Bibillo, A. and Eickbush, T.H. 2002. J. Biol. Chem. 277, 34836-34845. "High Processivity of the Reverse Transcriptase from a Non-long Terminal Repeat Retrotransposon."
Carroll, J.B. et al. 2015. Lancet Neurol 14, 1135-1142 (No. 11—Nov. 2015). "Treating the whole body in Huntington's disease."
Cartegni, L. et al. 2003. Nucleic Acids Res. 31, 3568-3571. "ESEfinder: a web resource to identify exonic splicing enhancers."
Crooks, G. E., et al. 2004. Genome Research 14, 1188-1190. "WebLogo: a sequence logo generator."
Daguenet et al. 2015. EMBO reports 16, 1640-1655 (published online Nov. 13, 2015). "The pathogenicity of splicing defects: mechanistic insights into pre-mRNA processing inform novel therapeutic approaches."
DiFiglia, et al 1997. Science 277, 1990-1993. "Aggregation of Huntingtin in Neuronal Intranuclear Inclusions and Dystrophic Neurites in Brain".
Dobin, A. et al. 2013. Bioinformatics 29, 15-21. "STAR: ultrafast universal RNA-seq aligner."
Evers, M.M. et al. 2015. Molecular Neurodegeneration 10, Article No. 21 (published online Apr. 28, 2015). "Making (anti-) sense out of huntingtin levels in Huntington disease."
Fardaei, M. et al. 2002. Human Molecular Genetics 11, 805-814. "Three proteins, MBNL, MBLL and MBXL, co-localize in vivo with nuclear foci of expanded-repeat transcripts in DM1 and DM2 cells."
Fernandez-Nogales, M. et al. 2014. Nature Medicine 20, 881-885. "Huntington's disease is a four-repeat tauopathy with tau nuclear rods."
Gipson, T. A. et al. 2013. RNA Biology 10, 1647-1652. "Aberrantly spliced HTT, a new player in Huntington's disease pathogenesis."
Gray, M. et al. 2008. J. Neurosci. 28, 6182-6195. "Full-length human mutant huntingtin with a stable polyglutamine repeat can elicit progressive and selective neuropathogenesis in BACHD mice."
Griffiths-Jones, S. et al. 2005. Nucleic Acids Res. 33, D121-D124. "Rfam: annotating non-coding RNAs in complete genomes."
Griffiths-Jones, S. et al. 2006. Nucleic Acids Res. 34, D140-D144. "miRBase: microRNA sequences, targets and gene nomenclature."
Grillo, G. et al. 2003. Nucleic Acids Res. 31, 3608-3612. "PatSearch: a program for the detection of patterns and structural motifs in nucleotide sequences."
Grimson, A. et al. 2007. Molecular Cell 27, 91-105. "MicroRNA Targeting Specificity in Mammals: Determinants beyond Seed Pairing."
Heemskerk, J. et al. 2002. Nature Neuroscience Supplement 5, 1027-1029. "From chemical to drug: neurodegeneration drug screening and the ethics of clinical trials."
Heemskerk, J, et al. 2002. Trends Neurosci. 25, 494-496. "Teaching old drugs new tricks."
Heemskerk, J. et al. 2005. Chapter 16—"Therapeutics Development for Hereditary Disorders" in ed. Waxman, S. From Neuroscience to Neurology: Neuroscience, Molecular Medicine, and the Therapeutic Transformation of Neurology, pp. 285-291.
Hernandez-Imas, E. et al. 2015. PLoS One 10, e141735 (published online Oct. 28, 2015). "Functional Analysis of Mutations in Exon 9 of NF1 Revales the Presence of Several Elements Regulating Splicing."
Hodges, A. et al. 2006. Human Molecular Genetics 15, 965-977. "Regional and cellular gene expression changes in human Huntington's disease brain."
Hua et al. 2007. PLoS Biol 5, e73. Enhancement of SMN2 Exon 7 "Inclusion by Antisense Oligonucleotides Targeting the Exon."
Hua et al. 2008. American J. of Human Genetics 82, 834-848. "Antisense Masking of an hnRNP A1/A2 Intronic Splicing Silencer Corrects SMN2 Splicing in Transgenic Mice."
Hughes, A.C. et al. 2014. J. Mol. Biol. 426, 1428-1438. "Identification of Novel Alternative Splicing Events in the Huntingtin Gene and Assessment of the Functional Consequences Using Structural Protein Homology Modelling."
The Huntington's Disease Collaborative Research Group, 1993, Cell, 72, pp. 971-983 (1993). "A novel gene containing a trinucleotide repeat that is expanded and unstable on Huntington's Disease chromosomes."
Janas, A. M. 2015. "A Stem Cell Model of the Motor Circuit Reveals Distinct Requirements for SMN in Motor Neuron Survival and Function.", Columbia University Doctoral Thesis.
Jacobs, G.H. et al. 2006. Nucleic Acids Res. 34, suppl_1, D37-D40. "Transterm—extended search facilities and improved integration with other databases."
Kanadia, R.N. et al. 2003. Science 302, 1978-1980. "A Muscleblind Knockout Model for Myotonic Dystrophy."
Kaplan, A. et al. 2012. Prog. Neurobiol. 99(3), 262-280. "Therapeutic approaches to preventing cell death in Huntington disease."
Kim, D. et al. 2013. Genome Biology 14, Article No. R36. "TopHat2: accurate alignment of transcriptomes in the presence of insertions, deletions and gene fusions."
Kordasiewicz, H.B. et al. 2012. Neuron, 74, 1031-1044. "Sustained Therapeutic Reversal of Huntington's Disease by Transient Repression of Huntingtin Synthesis".
Kuhn, A. et al. 2007. Human Molecular Genetics 16, 1845-1861. "Mutant huntingtin's effects on striatal gene expression in mice recapitulate changes observed in human Huntington's disease brain and do not differ with mutant huntingtin length or wild-type huntingtin dosage."
Labadorf, A.T. et al. 2015. Plos One 10(10): e0141298 (published online Oct. 23, 2015). "Evidence of Extensive Alternative Splicing in Post Mortem Human Brain HTT Transcription by mRNA Sequencing." (including supplemental information).
Labadorf, A. et al. 2015. PLoS One 10(12): e0143563 (published online Dec. 4, 2015). "RNA Sequence Analysis of Human Huntington Disease Brain Reveals an Extensive Increase in Inflammatory and Developmental Gene Expression."
Labbadia, J. et al. 2013. Trends Biochem. Sci. 38, 378-385. "Huntington's disease: underlying molecular mechanisms and emerging concepts."
Landles, C. et al. 2010. J. Bio. Chem. 285, 8808-8823. "Protoelysis of Mutant Huntington Produces an Exon 1 Fragment That Accumulates as an Aggregated Protein in Neuronal Nuclei in Huntington Disease."
Lei, et al. 2005. Nucleic Acids Res 33, 3897-3909. "Exonization of AluYa5 in the human ACE gene requires mutations in both 3' and 5' splice sites and is facilitated by a conserved splicing enhancer."

(56) References Cited

OTHER PUBLICATIONS

Liang, Y. et al. 2009. Brain Res. 2009 1286, 221-229. "ATF3 plays a protective role against toxicity by N-terminal fragment of mutant huntingtin in stable PC12 cell line."
Love, M. I. et al. 2014. Genome Biology 15, 550. "Moderated estimation of fold change and dispersion for RNA-seq data with DESeq2."
Lunkes, A. et al. 2002. Molecular Cell 10, 259-269. "Proteases Acting on Mutant Huntingtin Generate Cleaved Products that Differentially Build Up Cytoplasmic and Nuclear Inclusions."
Macke, T.J. 2001. Nucleic Acids Res. 29, 4724-4735. "RNAMotif, an RNA secondary structure definition and search algorithm."
Mahmood, I. et al. 1996. Xenobiotica 26, 887-895. "Interspecies scaling: predicting clearance of drugs in humans. Three different approaches."
Mahmood, I. 2006. Pharm. Sci. 95, 1810-1821. "Prediction of human drug clearance from animal data: Application of the rule of exponents and 'fu corrected intercept method' (FCIM)."
Mahmoudi, S et al. 2010. PLoS Biology 8(11), e1000521. "WRAP53 is Essential for Cajal Body and for Targeting the Survival of Motor Neuron Complex to Cajal Bodies."
Mangiarini, L. 1996. Cell 87, 493-506. "Exon 1 of the HD Gene with an Expanded CAG Repeat Is Sufficient to Cause a Progressive Neurological Phenotype in Transgenic Mice."
Mantione, K.J. et al. 2014. Med. Sci. Monit. Basic Res. 20, 138-141. "Comparing Bioinformation Gene Expression Profiling Methods: Microarray and RNA-Seq."
Mendoza, L.G. et al. 1999. BioTechniques 27, 778-788. "Hight-Throughput Microarray-Based Enzyme-Linked Immunosorbent Assay (ELISA)."
Mielcarek, M. et al. 2014. PLOS Genetics 10: 8 e1004550. "Dysfunction of the CNS-Heart Axis in Mouse Models of Huntington's Disease."
Mignone, F. et al. 2005. Nucleic Acids Res. 33, D141-D146. "UTRdb and UTRsite: a collection of sequences and regulatory motifs of the untranslated regions of eukaryotic mRNAs."
Mort, M. et al. 2015. J. of Huntington's Disease 4(2 of 4), 161-171. "Huntingtin Exists as Multiple Splice Forms in Human Brain."
Neuder, A. et al. 2014. BMC Medical Genomics 7:60. "A common gene expression signature in Huntington's disease patient brain regions."
Paganetti, P. et al. 2009. ChemBioChem 10, 1678-1688. "Development of Method for the High-Throughput Quantification of Cellular Proteins."
Pouladi, M. et al. 2013. Nature Review Neuroscience 14, 709-721. "Choosing an animal model for the study of Huntington's disease."
Ratovitski, T. et al. 2012. Cell Cycle 11, 2006-2021. "Huntingtin protein interactions altered by polyglutamine expansion as determined by quantitative proteomic analysis."
Reiner, A. et al. 2011. International Review of Neurobiology 98, 325-372. "Genetics and neuropathology of Huntington's disease."
Ruzo, A. et al. 2015. PLoS One 10, e0127678 (published online May 26, 2015). "Discovery of Novel Isoforms of Huntingtin Reveals a New Hominid-Specific Exon."
Sadeghian, H. et al. 2011. Arch. Neurol. 68, 650-652. "Huntington Chorea Presenting with Motor Neuron Disease.".
Sathasivam, K. et al. 2013. Proc. Natl. Acad. Sci. 110, 2366-2370. "Aberrant splicing of HTT generates the pathogenic exon 1 protein in Huntington disease."
Schilling, G. et al. 2007. J Neuropathol. Exp. Neurol. 66, 313-320. "Characterization of Huntingtin Pathologic Fragments in Human Huntington Disease, Transgenic Mice, and Cell Models."
Schwab, C. et al. 2008. J. Neuropathol Exp Neurol 67, 1159-1165. "Colocalization of Transactivation-Responsive DNA-Binding Protein 43 and Huntingtin in Inclusions of Huntington Disease."
Shlyakhtenko, L.S. et al. 2007. Nanomedicine: Nanotech., Bio., and Med. 3, 192-197. "Single-molecule selection and recovery of structure-specific antibodies using atomic force microscopy."
Southwell, A.L. et al. 2013. Hum. Mol. Genet. 22, 18-34. "A fully humanized transgenic mouse model of Huntington disease."
Stanek, L.M. et al. 2014. Human Gene Therapy 25, 461-474. "Silencing Mutant Huntingtin by Adeno-Associated Virus-Mediated RNA Interference Ameliorates Disease Manifestations in the YAC128 Mouse Model of Huntington's Disease."
Stoilov, P. et al. 2008. Proc. Natl. Acad. Sci. 105, 11218-11223. "A high-throughput screening strategy identifies cardiotonic steroids as alternative splicing modulators."
Taylor et al. 1999. Nat. Biotechnol. 17, 1097-1100 "Induction of endogenous Bcl-xS through the control of Bcl-x pre-mRNA splicing by antisense oligonucleotides."
Van der Burg, J.M.M. et al. 2009. The Lancet (Neurology) 8, 765-774. "Beyond the brain: widespread pathology in Huntington's disease."
Varma, H. et al. 2008. Comb Chem High Throughput Screen 11, 238-248. "High Throughput Screening for Neurodegeneration and Complex Disease Phenotypes."
Vickers et al., 2006. J. Immunol. 176, 3652-3661 "Modification of MyD88 mRNA splicing and inhibition of IL-1beta signaling in cell culture and in mice with a 2'-O-methoxyethyl-modified oligonucleotide."
Wachter, A. 2014. Trends in Genetics 30, 172-181. "Gene regulation by structured mRNA elements."
Weiland, M. et al. 2012. Methods 56, 351-357. "Engineering of ribozyme-based riboswitches for mammalian cells."
Wild, E.J. et al. 2014. Movement Disorders 29, 1434-1445. "Targets for Future Clinical Trials in Huntington's Disease: What's in the Pipeline?".
Wilton et al. 1999. Neuromuscul. Disord. 9, 330-338. "Specific removal of the nonsense mutation from the mdx dystrophin mRNA using antisense oligonucleotides."
Xiong, H.Y. et al. 2015. Science 347, 1254806 (published online Dec. 18, 2014.) "The human splicing code reveals new insights into the genetic determinants of disease."
Yen, L. et al. 2004. Nature 431, 471-6. "Exogenous control of mammalian gene expression through modulation of RNA self-cleavage."
Yeo, G. et al. 2004. J. Comput. Biol. 11, 377-394. "Maximum entropy modeling of short sequence motifs with applications to RNA splicing signals."
Younis et al. 2010. Molecular and Cellular Biology 30, 1718-1728. "Rapid-Response Splicing Reporter Screens Identify Differential Regulators of Constitutive and Alternative Splicing."
Yu, S. et al. 2014. Trends in Pharmacological Sci. 35, 53-62. "Drugging unconventional targets: insights from Huntington's disease."
Zona, S. et al. 2014. Biochimica et Biophysica Acta 1839, 1316-1322. "FOXM1: An emerging master regulator of DNA damage response and genotoxic agent resistance."
Nair, A.B. et al. 2016. J. Basic and Clinical Pharmacy 7, 27-31. "A simple and practical guide for dose conversion between animals and human."
Neuder, A. et al. 2017. Scientific Reports 7, 1307 (published online May 2, 2017). "The pathogenic exon 1 HTT protein is produced by incomplete splicing in Huntington's disease patients."
Nopoulos, P. C. 2016. Dialogues Clin Neurosci 18, 91-98. "Huntington disease: a single-gene degenerative disorder of the striatum."
Ratni, H. et al. 2016. J. Med. Chem. 59, 6086-6100. "Specific Correction of Alternative Survival Motor Neuron 2 Splicing by Small Molecules: Discovery of a Potential Novel Medicine to Treat Spinal Muscular Atrophy."
Rüb, U. et al. 2016. Brain Pathol. 26, 726-740. "Huntington's disease (HD): the neuropathology of a multisystem neurodegenerative disorder of the human brain."
Saudou, F. et al. 2016. Neuron 89, 910-926. "The Biology of Huntingtin."
Wang, G. et al. 2016. Proc. Natl. Acad. Sci. 113, 3359-3364. "Ablation of huntingtin in adult neurons is nondeleterious but its depletion in young mice causes acute pancreatitis."
Woll, M.G. et al. 2016. J. Med. Chem. 59, 6070-6085. "Discovery and Optimization of Small Molecule Splicing Modifiers of Survival Motor Neuron 2 as a Treatment for Spinal Muscular Atrophy."
International Search Report for PCT/US20/32446, dated Jul. 7, 2020.

(56) References Cited

OTHER PUBLICATIONS

Written Opinion of the International Searching Authority in PCT/US20/32446, dated Jul. 7, 2020.
Chemical Abstracts Registry No. 2107242-04-04, indexed in the Registry file on STN CAS Online Aug. 2, 2017. (Year: 2017).
Daldin et al., "Polyglutamine expansion affects huntingtin conformation in multiple Huntington's disease models", Scientific Reports, vol. 7, 15 pages, 2017.
Gleave et al., "Synthesis and evaluation of 3-amino-6-aryl-pyridazines as selective CB2 agonists for the treatment of inflammatory pain", Bioorganic & Medicinal Chemistry Letters, vol. 20, pp. 465-468, 2010.
Kaida et al., "U1 snRNP protects pre-mRNAs from premature cleavage and polyadenylation"; Nature, vol. 468, pp. 664-669; Dec. 2, 2010.
Ross & Tabrizi, "Huntington's disease: from molecular pathogenesis to clinical treatment"; The Lancet Neurology, vol. 10, pp. 83-98, Jan. 2011.
Wang et al., "Mechanism of alternative splicing and its regulation (Review)", Biomedical Reports, vol. 3, pp. 152-158, 2015.
Berg, J.M., Tymoczko, J.L., & Stryer, L., *Biochemistry* ($5^{th}$ed.), p. 798, 2002.
Opposition in European Patent No. 3,386,511, dated Feb. 25, 2022, 29 pages.
Bhattacharyya et al., Small molecule splicing modifiers with systemic HTT-lowering activity Nature Communications 12(7299), 2021.
Boudreau et al., 2009. "Nonallele-Specific Silencing of Mutant and Wild-Type Huntingtin Demonstrates Therapeutic Efficacy in Huntington"s Disease Mice." Molecular Therapy: The Journal of the American Society of Gene Therapy 17 (6): 1053-63.
Campagne et al., 2019. "Structural Basis of a Small Molecule Targeting RNA for a Specific Splicing Correction." Nature Chemical Biology 15 (12): 1191-98, 2019.
Connelly et al., 2016. "The Emerging Role of RNA as a Therapeutic Target for Small Molecules." Cell Chemical Biology 23 (9): 1077-90.
Effenberger et al., 2016. "Modulating Splicing with Small Molecular Inhibitors of the Spliceosome." Wiley Interdisciplinary Reviews. RNA 8 (2). https://doi.org/10.1002/wrna.1381.
Holste et al., 2008. "Strategies for Identifying RNA Splicing Regulatory Motifs and Predicting Alternative Splicing Events." PLoS Computational Biology 4 (1): e21.
Marxreiter et al., 2020. "Huntington Lowering Strategies." International Journal of Molecular Sciences 21 (6). https://doi.org/10.3390/ijms21062146.
Mount et al., A catalogue of splice junction sequences Nucleic Acids Research 10(2):459-472 (Jan. 22, 1982).
Nishigaki et al., Syntheses of 9-Deazatheophyllines and 6-Deoxy-9-deazatheophyllines Chemical and Pharmaceutical Bulletin 28(5):1636-1641 (1980).
Ratni et al., Discovery of Risdiplam, a Selective Survival of Motor Neuron-2 (SMN2) Gene Splicing Modifier . . . , Journal of Medicinal Chemistry, 61(15), 6501-6517 (2018).
Ritz et al., Dose-Response Analysis Using R PLos ONE 10(12) (Dec. 30, 2015).
Romo et al., 2018. "A Fresh Look at Huntington mRNA Processing in Huntington"s Disease." Journal of Huntington"s Disease 7 (2): 101-8.
Schilling Judith, Meike Broemer, Ilian Atanassov, Yvonne Duernberger, Ina Vorberg, Christoph Dieterich, Alina Dagane, et al. 2019. "Deregulated Splicing Is a Major Mechanism of RNA-Induced Toxicity in Huntingtons Disease." Journal of Molecular Biology 431 (9): 1869-77.
Sibley et al., 2016. "Lessons from Non-Canonical Splicing." Nature Reviews. Genetics 17 (7): 407-21.
Sivaramakrishnan et al., Binding to SMN2 pre-mRNA-protein complex elicits specificity for small molecule splicing modifiers Nature Communications 8(1) (Nov. 2017).
Southwell et al., A novel humanized mouse model of Huntington disease for preclinical development . . . Human Molecular Genetics, 1115-1132, 11(19), (Jan. 19, 2017).
Southwell et al. 2018. "Huntingtin Suppression Restores Cognitive Function in a Mouse Model of Huntingtons Disease." Science Translational Medicine (10) 1-12.
Southwell Amber L., Niels H. Skotte, Erika B. Villanueva, Michael E. Østergaard, Xiaofeng Gu, Holly B. Kordasiewicz, Chris Kay, et al. 2017. "A Novel Humanized Mouse Model of Huntington Disease for Preclinical Development of Therapeutics Targeting Mutant Huntingtin Alleles." Human Molecular Genetics 26 (6): 1115-32.
Tabrizi et al., Huntington Lowering Strategies for Disease Modification in Huntington's Disease J. Neuron 101(5):801-819 (Mar. 6, 2019).
Wild et al., 2017. "Therapies Targeting DNA and RNA in Huntington"s Disease." Lancet Neurology 16 (10): 837-47.
International Search Report in PCT/US2021/059010, dated Apr. 26, 2022.
Written Opinion of the International Searching Authority in PCT/US2021/059010, dated Apr. 26, 2022.
Reply to Opposition in European Patent No. 3,386,511, dated Jul. 7, 2022, 427 pages.
EPO Board Communication in Opposition in European Patent No. 3,386,511, dated Oct. 18, 2022, 12 pages.
International Search Report in PCT/US2021/026316, dated Aug. 5, 2021.
Written Opinion of the International Searching Authority in PCT/US2021/026316, dated Aug. 5, 2021.
Burli et al., "Design, Synthesis, and Biological Evaluation of Potent and Selective Class IIa Histone Deacetylase (HDAC) Inhibitors as a Potential Therapy for Huntington's Disease", Journal of Medicinal Chemistry, vol. 56, pp. 9934-9954, 2013.
Chemical Abstracts Registry No. 1381103-87-2, indexed in the Registry file on STN CAS Online Jul. 4, 2012. (Year: 2012).
Chemical Abstracts Registry No. 1381109-95-0, indexed in the Registry file on STN CAS Online Jul. 4, 2012. (Year: 2012).
Chemical Abstracts Registry No. 1381103-06-5, indexed in the Registry file on STN CAS Online Jul. 4, 2012. (Year: 2012).
Chemical Abstracts Registry No. 1381085-12-6, indexed in the Registry file on STN CAS Online Jul. 4, 2012. (Year: 2012).
Chemical Abstracts Registry No. 1381084-38-3, indexed in the Registry file on STN CAS Online Jul. 4, 2012. (Year: 2012).
Chemical Abstracts Registry No. 1381084-19-0, indexed in the Registry file on STN CAS Online Jul. 4, 2012. (Year: 2012).
Chemical Abstracts Registry No. 1381069-02-8, indexed in the Registry file on STN CAS Online Jul. 4, 2012. (Year: 2012).
Chemical Abstracts Registry No. 1381060-23-6, indexed in the Registry file on STN CAS Online Jul. 4, 2012. (Year: 2012).
Chemical Abstracts Registry No. 1381036-73-2, indexed in the Registry file on STN CAS Online Jul. 4, 2012. (Year: 2012).
Chemical Abstracts Registry No. 1381033-11-9, indexed in the Registry file on STN CAS Online Jul. 4, 2012. (Year: 2012).
Chemical Abstracts Registry No. 1381016-89-2, indexed in the Registry file on STN CAS Online Jul. 4, 2012. (Year: 2012).
Chemical Abstracts Registry No. 1381016-41-6, indexed in the Registry file on STN CAS Online Jul. 4, 2012. (Year: 2012).
Chemical Abstracts Registry No. 1381013-97-3, indexed in the Registry file on STN CAS Online Jul. 4, 2012. (Year: 2012).
Chemical Abstracts Registry No. 1380991-96-7, indexed in the Registry file on STN CAS Online Jul. 4, 2012. (Year: 2012).
Chemical Abstracts Registry No. 1380991-09-2, indexed in the Registry file on STN CAS Online Jul. 4, 2012. (Year: 2012).
Chemical Abstracts Registry No. 1380955-66-7, indexed in the Registry file on STN CAS Online Jul. 4, 2012. (Year: 2012).
Chemical Abstracts Registry No. 1380889-28-0, indexed in the Registry file on STN CAS Online Jul. 3, 2012. (Year: 2012).
Chemical Abstracts Registry No. 1380857-75-9, indexed in the Registry file on STN CAS Online Jul. 3, 2012. (Year: 2012).
Chemical Abstracts Registry No. 1350420-68-6, indexed in the Registry file on STN CAS Online Dec. 7, 2011. (Year: 2011).
Chemical Abstracts Registry No. 1350191-80-8, indexed in the Registry file on STN CAS Online Dec. 7, 2011. (Year: 2011).

(56) References Cited

OTHER PUBLICATIONS

Chemical Abstracts Registry No. 919610-78-9, indexed in the Registry file on STN CAS Online Feb. 6, 2007. (Year: 2007).
Chemical Abstracts Registry No. 919610-77-8, indexed in the Registry file on STN CAS Online Feb. 6, 2007. (Year: 2007).
Chemical Abstracts Registry No. 919610-71-2, indexed in the Registry file on STN CAS Online Feb. 6, 2007. (Year: 2007).
Chemical Abstracts Registry No. 919610-70-1, indexed in the Registry file on STN CAS Online Feb. 6, 2007. (Year: 2007).
Chemical Abstracts Registry No. 919610-69-8, indexed in the Registry file on STN CAS Online Feb. 6, 2007. (Year: 2007).
Chemical Abstracts Registry No. 919494-40-9, indexed in the Registry file on STN CAS Online Feb. 6, 2007. (Year: 2007).
Chemical Abstracts Registry No. 919494-38-5, indexed in the Registry file on STN CAS Online Feb. 6, 2007. (Year: 2007).
Chemical Abstracts Registry No. 919494-22-7, indexed in the Registry file on STN CAS Online Feb. 6, 2007. (Year: 2007).
Chemical Abstracts Registry No. 1348577-48-9, indexed in the Registry file on STN CAS Online Dec. 4, 2011. (Year: 2011).
Chemical Abstracts Registry No. 1380990-95-3, indexed in the Registry file on STN CAS Online Jul. 4, 2012. (Year: 2012).
Chemical Abstracts Registry No. 1380944-26-2, indexed in the Registry file on STN CAS Online Jul. 4, 2012. (Year: 2012).
Chemical Abstracts Registry No. 1380879-49-1, indexed in the Registry file on STN CAS Online Jul. 3, 2012. (Year: 2012).
Chemical Abstracts Registry No. 1380858-18-3, indexed in the Registry file on STN CAS Online Jul. 3, 2012. (Year: 2012).
Chemical Abstracts Registry No. 1381109-36-9, indexed in the Registry file on STN CAS Online Jul. 4, 2012. (Year: 2012).
Chemical Abstracts Registry No. 1381106-70-2, indexed in the Registry file on STN CAS Online Jul. 4, 2012. (Year: 2012).
Chemical Abstracts Registry No. 1380864-49-2, indexed in the Registry file on STN CAS Online Jul. 3, 2012. (Year: 2012).
Chemical Abstracts Registry No. 1380859-62-0, indexed in the Registry file on STN CAS Online Jul. 3, 2012. (Year: 2012).
Chemical Abstracts Registry No. 1381035-24-0, indexed in the Registry file on STN CAS Online Jul. 4, 2012. (Year: 2012).
Chemical Abstracts Registry No. 2059673-20-8, indexed in the Registry file on STN CAS Online Jan. 26, 2017. (Year: 2017).
Chemical Abstracts Registry No. 2224380-48-5, indexed in the Registry file on STN CAS Online May 20, 2018.
Chemical Abstracts Registry No. 2055492-51-6, indexed in the Registry file on STN CAS Online Jan. 5, 2017.
Chemical Abstracts Registry No. 1608159-30-3, indexed in the Registry file on STN CAS Online May 22, 2014.
Chemical Abstracts Registry No. 1349790-59-5, indexed in the Registry file on STN CAS Online Dec. 6, 2011.
Chemical Abstracts Registry No. 1349075-20-2, indexed in the Registry file on STN CAS Online Dec. 5, 2011.
Chemical Abstracts Registry No. 1348522-09-7, indexed in the Registry file on STN CAS Online Dec. 4, 2011.
Chemical Abstracts Registry No. 1348048-78-1, indexed in the Registry file on STN CAS Online Dec. 4, 2011.
Chemical Abstracts Registry No. 1347905-79-6, indexed in the Registry file on STN CAS Online Dec. 4, 2011.
Chemical Abstracts Registry No. 1347641-28-4, indexed in the Registry file on STN CAS Online Dec. 2, 2011.
Chemical Abstracts Registry No. 1347614-67-8, indexed in the Registry file on STN CAS Online Dec. 2, 2011.
Chemical Abstracts Registry No. 1347467-65-5, indexed in the Registry file on STN CAS Online Dec. 2, 2011.
Chemical Abstracts Registry No. 2213453-82-6, indexed in the Registry file on STN CAS Online Apr. 16, 2018.
Chemical Abstracts Registry No. 2170880-44-9, indexed in the Registry file on STN CAS Online Jan. 24, 2018.
Chemical Abstracts Registry No. 2170880-30-3, indexed in the Registry file on STN CAS Online Jan. 24, 2018.
Chemical Abstracts Registry No. 2170880-29-0, indexed in the Registry file on STN CAS Online Jan. 24, 2018.
Chemical Abstracts Registry No. 2170876-00-1, indexed in the Registry file on STN CAS Online Jan. 24, 2018.
Chemical Abstracts Registry No. 2170875-99-5, indexed in the Registry file on STN CAS Online Jan. 24, 2018.
Chemical Abstracts Registry No. 2138484-61-2, indexed in the Registry file on STN CAS Online Nov. 3, 2017.
Chemical Abstracts Registry No. 2117679-02-2, indexed in the Registry file on STN CAS Online Aug. 21, 2017.
Chemical Abstracts Registry No. 2098833-57-7, indexed in the Registry file on STN CAS Online Jun. 21, 2017.
Chemical Abstracts Registry No. 2096985-34-9, indexed in the Registry file on STN CAS Online May 23, 2017.
Chemical Abstracts Registry No. 1957192-78-7, indexed in the Registry file on STN CAS Online Jul. 21, 2016.
Chemical Abstracts Registry No. 1579964-39-8, indexed in the Registry file on STN CAS Online Apr. 3, 2014.
Chemical Abstracts Registry No. 1381102-22-2, indexed in the Registry file on STN CAS Online Jul. 4, 2012.
Chemical Abstracts Registry No. 1381055-52-2, indexed in the Registry file on STN CAS Online Jul. 4, 2012.
Chemical Abstracts Registry No. 1380859-69-7, indexed in the Registry file on STN CAS Online Jul. 4, 2012.
Chemical Abstracts Registry No. 1283718-58-0, indexed in the Registry file on STN CAS Online Apr. 21, 2011.
Chemical Abstracts Registry No. 919610-72-3, indexed in the Registry file on STN CAS Online Feb. 6, 2007.
Chemical Abstracts Registry No. 919496-89-2, indexed in the Registry file on STN CAS Online Feb. 6, 2007.
Chemical Abstracts Registry No. 919494-45-4, indexed in the Registry file on STN CAS Online Feb. 6, 2007.
Chemical Abstracts Registry No. 919494-44-3, indexed in the Registry file on STN CAS Online Feb. 6, 2007.
Chemical Abstracts Registry No. 919494-39-6, indexed in the Registry file on STN CAS Online Feb. 6, 2007.
Chemical Abstracts Registry No. 919494-26-1, indexed in the Registry file on STN CAS Online Feb. 6, 2007.
Chemical Abstracts Registry No. 919494-23-8, indexed in the Registry file on STN CAS Online Feb. 6, 2007.
Chemical Abstracts Registry No. 919494-19-2, indexed in the Registry file on STN CAS Online Feb. 6, 2007.
Chemical Abstracts Registry No. 919493-72-4, indexed in the Registry file on STN CAS Online Feb. 6, 2007.
Chemical Abstracts Registry No. 919493-71-3, indexed in the Registry file on STN CAS Online Feb. 6, 2007.
Chemical Abstracts Registry No. 848953-00-4, indexed in the Registry file on STN CAS Online Apr. 21, 2005.
Chemical Abstracts Registry No. 848952-99-8, indexed in the Registry file on STN CAS Online Apr. 21, 2005.
Chemical Abstracts Registry No. 120821-79-6, indexed in the Registry file on STN CAS Online May 26, 1989.

\* cited by examiner

HETEROCYCLIC AND HETEROARYL COMPOUNDS FOR TREATING HUNTINGTON'S DISEASE

CROSS-REFERENCE TO RELATED APPLICATIONS

This application is a U.S. National Stage filing under 35 U.S.C. § 371 of International Application No. PCT/US2019/038889, filed Jun. 25, 2019, which in turn claims priority to U.S. Provisional Application No. 62/690,653, filed Jun. 27, 2018, the entire contents of which are incorporated by reference herein.

An aspect of the present description relates to compounds, forms, and pharmaceutical compositions thereof and methods of using such compounds, forms, or compositions thereof useful for treating or ameliorating Huntington's disease. In particular, another aspect of the present description relates to substituted bicyclic heterocyclic and heteroaryl compounds, forms and pharmaceutical compositions thereof and methods of using such compounds, forms, or compositions thereof for treating or ameliorating Huntington's disease.

BACKGROUND

Huntington's disease (HD) is a progressive, autosomal dominant neurodegenerative disorder of the brain, having symptoms characterized by involuntary movements, cognitive impairment, and mental deterioration. Death, typically caused by pneumonia or coronary artery disease, usually occurs 13 to 15 years after the onset of symptoms. The prevalence of HD is between three and seven individuals per 100,000 in populations of western European descent. In North America, an estimated 30,000 people have HD, while an additional 200,000 people are at risk of inheriting the disease from an affected parent. The disease is caused by an expansion of uninterrupted trinucleotide CAG repeats in the "mutant" huntingtin (Htt) gene, leading to production of HTT (Htt protein) with an expanded poly-glutamine (polyQ) stretch, also known as a "CAG repeat" sequence. There are no current small molecule therapies targeting the underlying cause of the disease, leaving a high unmet need for medications that can be used for treating or ameliorating HD. Consequently, there remains a need to identify and provide small molecule compounds for treating or ameliorating HD.

All other documents referred to herein are incorporated by reference into the present application as though fully set forth herein.

SUMMARY

An aspect of the present description relates to compounds comprising, a compound of Formula (I):

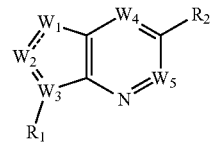

or a form thereof, wherein $R_1$, $R_2$, $W_1$, $W_2$, $W_3$, $W_4$ and $W_5$ are as defined herein.

An aspect of the present description also relates to a method for use of a compound of Formula (I) or a form or composition thereof to treat or ameliorate HD in a subject in need thereof comprising, administering to the subject an effective amount of the compound or a form or composition thereof.

An aspect of the present description further relates to a use of a compound of Formula (I) or a form thereof to treat or ameliorate HD in a subject in need thereof comprising, administering to the subject an effective amount of the compound or a form thereof.

An aspect of the present description further relates to a use of a compound of Formula (I) or a form thereof for the preparation of a medicament useful to treat or ameliorate HD in a subject in need thereof comprising, administering to the subject an effective amount of the medicament.

An aspect of the present description further relates to a use of a compound of Formula (I) or a form thereof used in combination with other agents useful for treating or ameliorating HD in a subject in need thereof comprising, administering to the subject an effective amount of a combination product for treating or ameliorating HD.

DETAILED DESCRIPTION

An aspect of the present description relates to compounds comprising, a compound of Formula (I):

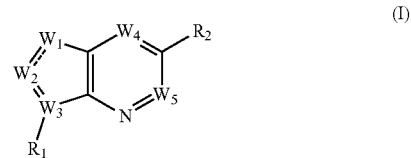

or a form thereof, wherein:
the dashed lines represent one or more double bonds optionally present where allowed by available valences;
$W_1$ is independently C—$R_a$, CH—$R_a$, N, N—$R_b$, O, or S where allowed by available valences;
$W_2$ is independently C—$R_a$, CH—$R_a$, N, or N—$R_b$ where allowed by available valences, and;
$W_3$ is independently C, CH, or N where allowed by available valences;
wherein at least one of $W_1$, $W_2$, or $W_3$ is N or N—$R_b$;
$W_4$ and $W_5$ are independently C—$R_a$ or N,
wherein when $W_1$ is S or O, $W_2$ is C—$R_a$, and $W_3$ is C;
$R_a$ is, in each instance, independently selected from hydrogen, cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, ($C_{1-6}$alkyl)$_2$-amino, amino-$C_{1-6}$alkyl, and hydroxy-$C_{1-6}$alkyl;
$R_b$ is selected from hydrogen and $C_{1-6}$alkyl;
$R_1$ is selected from $C_{3-10}$cycloalkyl and heterocyclyl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and
wherein, each instance of $C_{3-10}$cycloalkyl and heterocyclyl is optionally substituted with one, two or three $R_3$ substituents and optionally, with one additional $R_4$ substituent, or, wherein, alternatively, each instance of $C_{3-10}$cycloalkyl and heterocyclyl is optionally substituted with one, two, three, or four $R_3$ substituents;

$R_2$ is selected from phenyl, heterocyclyl, and heteroaryl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein, each instance of phenyl, heterocyclyl, and heteroaryl is optionally substituted with one, two, or three $R_5$ substituents, and optionally, with one additional $R_6$ substituent;

$R_3$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, and hydroxy-$C_{1-6}$alkyl;

$R_4$ is selected from $C_{3-10}$cycloalkyl, phenyl, heteroaryl, and heterocyclyl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein, each instance of $C_{3-10}$cycloalkyl, phenyl, heterocyclyl, and heteroaryl is optionally substituted with one, two, or three $R_7$ substituents;

$R_5$ is, in each instance, independently selected from halogen, hydroxy, cyano, nitro, $C_{1-6}$alkyl, deutero-$C_{1-4}$alkyl, halo-$C_{1-6}$alkyl, $C_{1-6}$alkoxy, halo-$C_{1-6}$alkoxy, oxime, amino, $C_{1-6}$alkyl-amino, $(C_{1-6}$alkyl$)_2$-amino, and $C_{1-6}$alkyl-thio;

$R_6$ is selected from phenyl and heteroaryl,
wherein heteroaryl is a 3-7 membered monocyclic or 6-10 membered bicyclic ring system having 1, 2, 3, or 4 heteroatom ring members independently selected from N, O, or S, and wherein, each instance of phenyl and heteroaryl is optionally substituted with one, two, three or four $R_8$ substituents;

$R_7$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, and $C_{3-10}$cycloalkyl; and $R_8$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, and $C_{3-10}$cycloalkyl;

wherein a form of the compound is selected from the group consisting of salt, hydrate, solvate, racemate, enantiomer, diastereomer, stereoisomer, and tautomer form thereof.

ASPECTS OF THE DESCRIPTION

One aspect of the present description includes a compound of Formula (I) comprising, a compound of Formula (I.1):

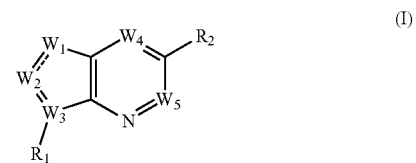

or a form thereof, wherein:
the dashed lines represent one or more double bonds optionally present where allowed by available valences;

$W_1$ is independently C—$R_a$, CH—$R_a$, N, N—$R_b$, O, or S where allowed by available valences;

$W_2$ is independently C—$R_a$, CH—$R_a$, N, or N—$R_b$ where allowed by available valences, and;

$W_3$ is independently C, CH, or N where allowed by available valences; wherein at least one of $W_1$, $W_2$, or $W_3$ is N or N—$R_b$;

$W_4$ and $W_5$ are independently C—$R_a$ or N,
wherein when $W_1$ is S or O, $W_2$ is C—$R_a$, and $W_3$ is C;

$R_a$ is, in each instance, independently selected from hydrogen, cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, and hydroxy-$C_{1-6}$alkyl;

$R_b$ is selected from hydrogen and $C_{1-6}$alkyl;

$R_1$ is selected from $C_{3-10}$cycloalkyl and heterocyclyl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein, each instance of $C_{3-10}$cycloalkyl and heterocyclyl is optionally substituted with one, two or three $R_3$ substituents and optionally, with one additional $R_4$ substituent, or, wherein, alternatively, each instance of $C_{3-10}$cycloalkyl and heterocyclyl is optionally substituted with one, two, three, or four $R_3$ substituents;

$R_2$ is selected from phenyl, heterocyclyl, and heteroaryl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein, each instance of phenyl, heterocyclyl, and heteroaryl is optionally substituted with one, two, or three $R_5$ substituents, and optionally, with one additional $R_6$ substituent;

$R_3$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, and hydroxy-$C_{1-6}$alkyl;

$R_4$ is selected from $C_{3-10}$cycloalkyl, phenyl, heteroaryl, and heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein heteroaryl is a 3-7 membered monocyclic or 6-10 membered bicyclic ring system having 1, 2, 3, or 4 heteroatom ring members independently selected from N, O, or S, and wherein, each instance of $C_{3-10}$cycloalkyl, phenyl, heterocyclyl, and heteroaryl is optionally substituted with one, two, or three $R_7$ substituents;

$R_5$ is, in each instance, independently selected from halogen, hydroxy, cyano, nitro, $C_{1-6}$alkyl, deutero-$C_{1-4}$alkyl, halo-$C_{1-6}$alkyl, $C_{1-6}$alkoxy, halo-$C_{1-6}$alkoxy, oxime, amino, $C_{1-6}$alkyl-amino, $(C_{1-6}$alkyl$)_2$-amino, and $C_{1-6}$alkyl-thio;

$R_6$ is selected from phenyl and heteroaryl, wherein heteroaryl is a 3-7 membered monocyclic or 6-10 membered bicyclic ring system having 1, 2, 3, or 4 heteroatom ring members independently selected from N, O, or S, and wherein, each instance of phenyl and heteroaryl is optionally substituted with one, two, three or four $R_8$ substituents;

$R_7$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, and $C_{3-10}$cycloalkyl;

$R_8$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, or $C_{3-10}$cycloalkyl.

One aspect includes a compound of Formula (I), wherein $W_1$ is N—$R_b$ and $W_4$ is N.

Another aspect includes a compound of Formula (I), wherein $W_1$ is N—$R_b$, $W_2$ is C—$R_a$, $W_3$ is C, $W_4$ is N and $W_5$ is C—$R_a$.

Another aspect includes a compound of Formula (I), wherein $W_1$ is N—$R_b$, $W_2$ is CH—$R_a$, $W_3$ is CH, $W_4$ is N and $W_5$ is C—$R_a$.

One aspect includes a compound of Formula (I), wherein $W_2$ is N—$R_b$ and $W_4$ is N.

Another aspect includes a compound of Formula (I), wherein $W_1$ is CH—$R_a$, $W_2$ is N—$R_b$, $W_3$ is CH, $W_4$ is N and $W_5$ is C—$R_a$.

One aspect includes a compound of Formula (I), wherein $W_3$ and $W_4$ are N.

Another aspect includes a compound of Formula (I), wherein $W_1$ is C—$R_a$, $W_2$ is C—$R_a$, $W_3$ is N, $W_4$ is N and $W_5$ is C—$R_a$.

Another aspect includes a compound of Formula (I), wherein $W_1$ is CH—$R_a$, $W_2$ is CH—$R_a$, $W_3$ is N, $W_4$ is N and $W_5$ is C—$R_a$.

One aspect includes a compound of Formula (I), wherein $W_1$, $W_2$ and $W_4$ are N.

Another aspect includes a compound of Formula (I), wherein $W_1$ is N, $W_2$ is N, $W_3$ is CH, $W_4$ is N and $W_5$ is C—$R_a$.

One aspect includes a compound of Formula (I), wherein $W_1$ and $W_2$ are N—$R_b$ and $W_4$ is N.

Another aspect includes a compound of Formula (I), wherein $W_1$ and $W_2$ are N—$R_b$, $W_3$ is CH, $W_4$ is N and $W_5$ is C—$R_a$.

One aspect includes a compound of Formula (I), wherein $W_1$, $W_3$ and $W_4$ are N.

Another aspect includes a compound of Formula (I), wherein $W_1$ is N, $W_2$ is C—$R_a$, $W_3$ is N, $W_4$ is N and $W_5$ is C—$R_a$.

One aspect includes a compound of Formula (I), wherein $W_1$ is N—$R_b$ and $W_3$ and $W_4$ are N.

Another aspect includes a compound of Formula (I), wherein $W_1$ is N—$R_b$, $W_2$ is CH—$R_a$, $W_3$ is N, $W_4$ is N and $W_5$ is C—$R_a$.

One aspect includes a compound of Formula (I), wherein $W_2$, $W_3$ and $W_4$ are N.

Another aspect includes a compound of Formula (I), wherein $W_1$ is C—$R_a$, $W_2$ is N, $W_3$ is N, $W_4$ is N and $W_5$ is C—$R_a$.

One aspect includes a compound of Formula (I), wherein $W_2$ is N—$R_b$ and $W_3$ and $W_4$ are N.

Another aspect includes a compound of Formula (I), wherein $W_1$ is CH—$R_a$, $W_2$ is N—$R_b$, $W_3$ is N, $W_4$ is N and $W_5$ is C—$R_a$.

One aspect includes a compound of Formula (I), wherein $W_1$, $W_2$, $W_3$ and $W_4$ are N.

Another aspect includes a compound of Formula (I), wherein $W_1$ is N, $W_2$ is N, $W_3$ is N, $W_4$ is N and $W_5$ is C—$R_a$.

One aspect includes a compound of Formula (I), wherein $W_1$ is S and $W_4$ is N.

Another aspect includes a compound of Formula (I), wherein $W_1$ is S, $W_2$ is C—$R_a$, $W_3$ is C, $W_4$ is N and $W_5$ is C—$R_a$.

One aspect includes a compound of Formula (I), wherein $W_1$ is O and $W_4$ is N.

Another aspect includes a compound of Formula (I), wherein $W_1$ is O, $W_2$ is C—$R_a$, $W_3$ is C, $W_4$ is N and $W_5$ is C—$R_a$.

One aspect includes a compound of Formula (I), wherein $W_1$ is N—$R_b$ and $W_5$ is N.

Another aspect includes a compound of Formula (I), wherein $W_1$ is N—$R_b$, $W_2$ is C—$R_a$, $W_3$ is C, $W_4$ is C—$R_a$ and $W_5$ is N.

Another aspect includes a compound of Formula (I), wherein $W_1$ is N—$R_b$, $W_2$ is CH—$R_a$, $W_3$ is CH, $W_4$ is C—$R_a$ and $W_5$ is N.

One aspect includes a compound of Formula (I), wherein $W_2$ is N—$R_b$ and $W_5$ is N.

Another aspect includes a compound of Formula (I), wherein $W_1$ is CH—$R_a$, $W_2$ is N—$R_b$, $W_3$ is CH, $W_4$ is C—$R_a$ and $W_5$ is N.

One aspect includes a compound of Formula (I), wherein $W_3$ and $W_5$ are N.

Another aspect includes a compound of Formula (I), wherein $W_1$ is C—$R_a$, $W_2$ is C—$R_a$, $W_3$ is N, $W_4$ is C—$R_a$ and $W_5$ is N.

Another aspect includes a compound of Formula (I), wherein $W_1$ is CH—$R_a$, $W_2$ is CH—$R_a$, $W_3$ is N, $W_4$ is C—$R_a$ and $W_5$ is N.

One aspect includes a compound of Formula (I), wherein $W_1$, $W_2$ and $W_5$ are N.

Another aspect includes a compound of Formula (I), wherein $W_1$ is N, $W_2$ is N, $W_3$ is CH, $W_4$ is C—$R_a$ and $W_5$ is N.

One aspect includes a compound of Formula (I), wherein $W_1$ and $W_2$ are N—$R_b$ and $W_5$ is N.

Another aspect includes a compound of Formula (I), wherein $W_1$ and $W_2$ are N—$R_b$, $W_3$ is CH, $W_4$ is C—$R_a$ and $W_5$ is N.

One aspect includes a compound of Formula (I), wherein $W_1$, $W_3$ and $W_5$ are N.

Another aspect includes a compound of Formula (I), wherein $W_1$ is N, $W_2$ is C—$R_a$, $W_3$ is N, $W_4$ is C—$R_a$ and $W_5$ is N.

One aspect includes a compound of Formula (I), wherein $W_1$ is N—$R_b$ and $W_3$ and $W_5$ are N.

Another aspect includes a compound of Formula (I), wherein $W_1$ is N—$R_b$, $W_2$ is CH—$R_a$, $W_3$ is N, $W_4$ is C—$R_a$ and $W_5$ is N.

One aspect includes a compound of Formula (I), wherein $W_2$, $W_3$ and $W_5$ are N.

Another aspect includes a compound of Formula (I), wherein $W_1$ is C—$R_a$, $W_2$ is N, $W_3$ is N, $W_4$ is C—$R_b$ and $W_5$ is N.

One aspect includes a compound of Formula (I), wherein $W_2$ is N—$R_b$ and $W_3$ and $W_5$ are N.

Another aspect includes a compound of Formula (I), wherein $W_1$ is CH—$R_a$, $W_2$ is N—$R_b$, $W_3$ is N, $W_4$ is C—$R_a$ and $W_5$ is N.

One aspect includes a compound of Formula (I), wherein $W_1$, $W_2$, $W_3$ and $W_5$ are N.

Another aspect includes a compound of Formula (I), wherein $W_1$ is N, $W_2$ is N, $W_3$ is N, $W_4$ is C—$R_a$ and $W_5$ is N.

One aspect includes a compound of Formula (I), wherein $W_1$ is S and $W_5$ is N.

Another aspect includes a compound of Formula (I), wherein $W_1$ is S, $W_2$ is C—$R_a$, $W_3$ is C, $W_4$ is C—$R_a$ and $W_5$ is N.

One aspect includes a compound of Formula (I), wherein $W_1$ is O and $W_5$ is N.

Another aspect includes a compound of Formula (I), wherein $W_1$ is O, $W_2$ is C—$R_a$, $W_3$ is C, $W_4$ is C—$R_a$ and $W_5$ is N.

One aspect includes a compound of Formula (I), wherein $W_1$ is N—$R_b$.

Another aspect includes a compound of Formula (I), wherein $W_1$ is N—$R_b$, $W_2$ is C—$R_a$, $W_3$ is C and $W_4$ and $W_5$ are C—$R_a$.

Another aspect includes a compound of Formula (I), wherein $W_1$ is N—$R_b$, $W_2$ is CH—$R_a$, $W_3$ is CH and $W_4$ and $W_5$ are C—$R_a$.

One aspect includes a compound of Formula (I), wherein $W_2$ is N—$R_b$.

Another aspect includes a compound of Formula (I), wherein $W_1$ is C—$R_a$, $W_2$ is N—$R_b$, $W_3$ is C and $W_4$ and $W_5$ are C—$R_a$.

Another aspect includes a compound of Formula (I), wherein $W_1$ is CH—$R_a$, $W_2$ is N—$R_b$, $W_3$ is CH and $W_4$ and $W_5$ are C—$R_a$.

One aspect includes a compound of Formula (I), wherein $W_3$ is N.

Another aspect includes a compound of Formula (I), wherein $W_1$ is C—$R_a$, $W_2$ is C—$R_a$, $W_3$ is N and $W_4$ and $W_5$ are C—$R_a$.

Another aspect includes a compound of Formula (I), wherein $W_1$ is CH—$R_a$, $W_2$ is CH—$R_a$, $W_3$ is N and $W_5$ are C—$R_a$.

One aspect includes a compound of Formula (I), wherein $W_1$ and $W_2$ are N.

Another aspect includes a compound of Formula (I), wherein $W_1$ is N, $W_2$ is N, $W_3$ is CH and $W_4$ and $W_5$ are C—$R_a$.

One aspect includes a compound of Formula (I), wherein $W_1$ and $W_2$ are N—$R_b$.

Another aspect includes a compound of Formula (I), wherein $W_1$ and $W_2$ are N—$R_b$, $W_3$ is CH and $W_4$ and $W_5$ are C—$R_a$.

One aspect includes a compound of Formula (I), wherein $W_1$ and $W_3$ are N.

Another aspect includes a compound of Formula (I), wherein $W_1$ is N, $W_2$ is C—$R_a$, $W_3$ is N and $W_4$ and $W_5$ are C—$R_a$.

One aspect includes a compound of Formula (I), wherein $W_1$ is N—$R_b$ and $W_3$ is N.

Another aspect includes a compound of Formula (I), wherein $W_1$ is N—$R_b$, $W_2$ is CH—$R_a$, $W_3$ is N and $W_4$ and $W_5$ are C—$R_a$.

One aspect includes a compound of Formula (I), wherein $W_2$ and $W_3$ are N.

Another aspect includes a compound of Formula (I), wherein $W_1$ is C—$R_a$, $W_2$ is N, $W_3$ is N and $W_4$ and $W_5$ are C—$R_a$.

One aspect includes a compound of Formula (I), wherein $W_2$ is N—$R_b$ and $W_3$ is are N.

Another aspect includes a compound of Formula (I), wherein $W_1$ is CH—$R_b$, $W_2$ is N—$R_b$, $W_3$ is N and $W_4$ and $W_5$ are C—$R_a$.

One aspect includes a compound of Formula (I), wherein $W_1$, $W_2$ and $W_3$ are N.

Another aspect includes a compound of Formula (I), wherein $W_1$ is N, $W_2$ is N, $W_3$ is N and $W_4$ and $W_5$ are C—$R_a$.

One aspect includes a compound of Formula (I), wherein $W_1$ is S.

Another aspect includes a compound of Formula (I), wherein $W_1$ is S, $W_2$ is C—$R_a$, $W_3$ is C and $W_4$ and $W_5$ are C—$R_a$.

One aspect includes a compound of Formula (I), wherein $W_1$ is O.

Another aspect includes a compound of Formula (I), wherein $W_1$ is O, $W_2$ is C—$R_a$, $W_3$ is C and $W_4$ and $W_5$ are C—$R_a$.

One aspect includes a compound of Formula (I), wherein $W_1$ is N—$R_b$ and $W_4$ and $W_5$ are N.

Another aspect includes a compound of Formula (I), wherein $W_1$ is N—$R_b$, $W_2$ is C—$R_a$, $W_3$ is C and $W_4$ and $W_5$ are N.

Another aspect includes a compound of Formula (I), wherein $W_1$ is N—$R_b$, $W_2$ is CH—$R_a$, $W_3$ is CH and $W_4$ and $W_5$ are N.

One aspect includes a compound of Formula (I), wherein $W_2$ is N—$R_b$ and $W_4$ and $W_5$ are N.

Another aspect includes a compound of Formula (I), wherein $W_1$ is CH—$R_a$, $W_2$ is N—$R_b$, $W_3$ is CH and $W_4$ and $W_5$ are N.

One aspect includes a compound of Formula (I), wherein $W_3$, $W_4$ and $W_5$ are N.

Another aspect includes a compound of Formula (I), wherein $W_1$ is C—$R_a$, $W_2$ is C—$R_a$, $W_3$ is N and $W_4$ and $W_5$ are N.

Another aspect includes a compound of Formula (I), wherein $W_1$ is CH—$R_a$, $W_2$ is CH—$R_a$, $W_3$ is N and $W_4$ and $W_5$ are N.

One aspect includes a compound of Formula (I), wherein $W_1$, $W_2$, $W_4$ and $W_5$ are N.

Another aspect includes a compound of Formula (I), wherein $W_1$ is N, $W_2$ is N, $W_3$ is CH and $W_4$ and $W_5$ are N.

One aspect includes a compound of Formula (I), wherein $W_1$ and $W_2$ are N—$R_b$ and $W_4$ and $W_5$ are N.

Another aspect includes a compound of Formula (I), wherein $W_1$ and $W_2$ are N—$R_b$, $W_3$ is CH and $W_4$ and $W_5$ are N.

One aspect includes a compound of Formula (I), wherein $W_1$, $W_3$, $W_4$ and $W_5$ are N.

Another aspect includes a compound of Formula (I), wherein $W_1$ is N, $W_2$ is C—$R_a$, $W_3$ is N and $W_4$ and $W_5$ are N.

One aspect includes a compound of Formula (I), wherein $W_1$ is N—$R_b$ and $W_3$, $W_4$ and $W_5$ are N.

Another aspect includes a compound of Formula (I), wherein $W_1$ is N—$R_b$, $W_2$ is CH—$R_a$, $W_3$ is N and $W_4$ and $W_5$ are N.

One aspect includes a compound of Formula (I), wherein $W_2$, $W_3$, $W_4$ and $W_5$ are N.

Another aspect includes a compound of Formula (I), wherein $W_1$ is C—$R_a$, $W_2$ is N, $W_3$ is N and $W_4$ and $W_5$ are N.

One aspect includes a compound of Formula (I), wherein $W_2$ is N—$R_b$ and $W_3$, $W_4$ and $W_5$ are N.

Another aspect includes a compound of Formula (I), wherein $W_1$ is CH—$R_a$, $W_2$ is N—$R_b$, $W_3$ is N and $W_4$ and $W_5$ are N.

One aspect includes a compound of Formula (I), wherein $W_1$, $W_2$, $W_3$, and $W_4$ and $W_5$ are N.

Another aspect includes a compound of Formula (I), wherein $W_1$ is N, $W_2$ is N, $W_3$ is N, and $W_4$ and $W_5$ are N.

One aspect includes a compound of Formula (I), wherein $W_1$ is S and $W_4$ and $W_5$ are N.

Another aspect includes a compound of Formula (I), wherein $W_1$ is S, $W_2$ is C—$R_a$, $W_3$ is C and $W_4$ and $W_5$ are N.

One aspect includes a compound of Formula (I), wherein $W_1$ is O and $W_4$ and $W_5$ are N.

Another aspect includes a compound of Formula (I), wherein $W_1$ is O, $W_2$ is C—$R_a$, $W_3$ is C and $W_4$ and $W_5$ are N.

One aspect includes a compound of Formula (I), wherein $R_a$ is, in each instance, independently selected from hydrogen, cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, ($C_{1-6}$alkyl)$_2$-amino, amino-$C_{1-6}$alkyl, and hydroxy-$C_{1-6}$alkyl.

Another aspect includes a compound of Formula (I), wherein $R_a$ is, in each instance, independently selected from hydrogen, hydroxy, $C_{1-6}$alkyl, $C_{1-6}$alkoxy, and $C_{1-6}$alkyl-amino.

Another aspect includes a compound of Formula (I), wherein $R_a$ is hydrogen.

Another aspect includes a compound of Formula (I), wherein $R_a$ is hydroxy.

Another aspect includes a compound of Formula (I), wherein $R_a$ is $C_{1-6}$alkyl selected from methyl, ethyl, propyl, isopropyl, and tert-butyl.

Another aspect includes a compound of Formula (I), wherein $R_a$ is methyl.

Another aspect includes a compound of Formula (I), wherein $R_a$ is $C_{1-6}$alkoxy selected from methoxy, ethoxy, propoxy, isopropoxy, and tert-butoxy.

Another aspect includes a compound of Formula (I), wherein $R_a$ is methoxy.

Another aspect includes a compound of Formula (I), wherein $R_a$ is $C_{1-6}$alkyl-amino wherein $C_{1-6}$alkyl is selected from methyl, ethyl, propyl, isopropyl, butyl, isobutyl, sec-butyl, and tert-butyl.

Another aspect includes a compound of Formula (I), wherein $R_a$ is $C_{1-6}$alkyl-amino selected from methylamino and ethylamino.

One aspect includes a compound of Formula (I), wherein $R_b$ is selected from hydrogen and $C_{1-6}$alkyl.

Another aspect includes a compound of Formula (I), wherein $R_b$ is hydrogen.

One aspect includes a compound of Formula (I), wherein $R_1$ is selected from $C_{3-10}$cycloalkyl and heterocyclyl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and
wherein, each instance of $C_{3-10}$cycloalkyl and heterocyclyl is optionally substituted with one, two or three $R_3$ substituents and optionally, with one additional $R_4$ substituent, or,
wherein, alternatively, each instance of $C_{3-10}$cycloalkyl and heterocyclyl is optionally substituted with one, two, three, or four $R_3$ substituents.

Another aspect includes a compound of Formula (I), wherein $R_1$ is $C_{3-10}$cycloalkyl, optionally substituted with one, two or three $R_3$ substituents and optionally, with one additional $R_4$ substituent, or alternatively, optionally substituted with one, two, three, or four $R_3$ substituents.

Another aspect includes a compound of Formula (I), wherein $R_1$ is $C_{3-10}$cycloalkyl selected from cyclopropyl, cylcobutyl, cyclopentyl, cyclohexyl, cycloheptyl, cyclooctyl, bicyclo[2.2.1]hexanyl, and adamantyl, optionally substituted with one, two or three $R_3$ substituents and optionally, with one additional $R_4$ substituent, or alternatively, optionally substituted with one, two, three, or four $R_3$ substituents.

Another aspect includes a compound of Formula (I), wherein $R_1$ is $C_{3-10}$cycloalkyl selected from cylcobutyl and cyclohexyl, optionally substituted with one, two or three $R_3$ substituents and optionally, with one additional $R_4$ substituent, or alternatively, optionally substituted with one, two, three, or four $R_3$ substituents.

Another aspect includes a compound of Formula (I), wherein $R_1$ is heterocyclyl selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, 3-azabicyclo[3.1.0]hexyl, (1R,5S)-3-azabicyclo [3.1.0]hexyl, 8-azabicyclo[3.2.1]octyl, (1R,5S)-8-azabicyclo[3.2.1]octyl, 8-azabicyclo[3.2.1]oct-2-en-yl, (1R,5S)-8-azabicyclo[3.2.1]oct-2-en-yl, 9-azabicyclo[3.3.1]nonyl, (1R,5S)-9-azabicyclo[3.3.1]nonyl, 3-oxa-9-azabicyclo[3.3.1]nonyl, and 3-oxa-9-azabicyclo[3.3.1]non-6-en-yl, optionally substituted with one, two or three $R_3$ substituents and optionally, with one additional $R_4$ substituent, or, alternatively, optionally substituted with one, two, three or four $R_3$ substituents.

Another aspect includes a compound of Formula (I), wherein $R_1$ is heterocyclyl selected from piperidinyl, piperazinyl, 1,2,3,6-tetrahydropyridinyl, 8-azabicyclo[3.2.1]octyl, (1R,5S)-8-azabicyclo[3.2.1]octyl, 8-azabicyclo[3.2.1]oct-2-en-yl, 3-oxa-9-azabicyclo[3.3.1]nonyl, and 3-oxa-9-azabicyclo[3.3.1]non-6-en-yl, optionally substituted with one, two or three $R_3$ substituents and optionally, with one additional $R_4$ substituent, or, alternatively, optionally substituted with one, two, three or four $R_3$ substituents.

Another aspect includes a compound of Formula (I), wherein $R_1$ is heterocyclyl selected from azetidin-1-yl, tetrahydrofuran-3-yl, pyrrolidin-1-yl, piperidin-1-yl, piperidin-4-yl, piperazin-1-yl, 1,4-diazepan-1-yl, 1,2,5,6-tetrahydropyridin-5-yl, 1,2,3,6-tetrahydropyridin-4-yl, 8-azabicyclo

[3.2.1]oct-3-yl, (1R,5S)-8-azabicyclo[3.2.1]oct-3-yl, 8-azabicyclo[3.2.1]oct-2-en-3-yl, (1R,5S)-8-azabicyclo[3.2.1]oct-2-en-3-yl, 9-azabicyclo[3.3.1]non-7-yl, (1R,5S)-9-azabicyclo[3.3.1]non-3-yl, 3-oxa-9-azabicyclo[3.3.1]non-7-yl, and 3-oxa-9-azabicyclo[3.3.1]non-6-en-7-yl, optionally substituted with one, two or three $R_3$ substituents and optionally, with one additional $R_4$ substituent, or, alternatively, optionally substituted with one, two, three or four $R_3$ substituents.

Another aspect includes a compound of Formula (I), wherein $R_1$ is heterocyclyl selected from piperidin-4-yl, piperazin-1-yl, 1,2,3,6-tetrahydropyridin-4-yl, 8-azabicyclo[3.2.1]oct-3-yl, (1R,5S)-8-azabicyclo[3.2.1]oct-3-yl, 8-azabicyclo[3.2.1]oct-2-en-3-yl, 3-oxa-9-azabicyclo[3.3.1]non-7-yl, and 3-oxa-9-azabicyclo[3.3.1]non-6-en-7-yl, optionally substituted with one, two or three $R_3$ substituents and optionally, with one additional $R_4$ substituent, or, alternatively, optionally substituted with one, two, three or four $R_3$ substituents.

One aspect includes a compound of Formula (I), wherein $R_2$ is selected from phenyl, heterocyclyl, and heteroaryl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S,
wherein heteroaryl is a 3-7 membered monocyclic or 6-10 membered bicyclic ring system having 1, 2, 3, or 4 heteroatom ring members independently selected from N, O, or S, and
wherein, each instance of phenyl, heterocyclyl, and heteroaryl is optionally substituted with one, two, or three $R_5$ substituents, and optionally with one additional $R_6$ substituent.

Another aspect includes a compound of Formula (I), wherein $R_2$ is phenyl, optionally substituted with one, two or three $R_5$ substituents and optionally, with one additional $R_6$ substituent.

Another aspect includes a compound of Formula (I), wherein $R_2$ is heterocyclyl selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, and 2,3-dihydro-1H-indenyl, optionally substituted with one, two or three $R_5$ substituents and optionally, with one additional $R_6$ substituent.

Another aspect includes a compound of Formula (I), wherein $R_2$ is 2,3-dihydro-1H-indenyl, optionally substituted with one, two or three $R_5$ substituents and optionally, with one additional $R_6$ substituent.

Another aspect includes a compound of Formula (I), wherein $R_2$ is heterocyclyl selected from azetidin-1-yl, tetrahydrofuran-3-yl, pyrrolidin-1-yl, piperidin-1-yl, piperidin-4-yl, piperazin-1-yl, 1,4-diazepan-1-yl, 1,2,5,6-tetrahydropyridin-5-yl, 1,2,3,6-tetrahydropyridin-4-yl, and 2,3-dihydro-1H-inden-5-yl, optionally substituted with one, two or three $R_5$ substituents and optionally, with one additional $R_6$ substituent.

Another aspect includes a compound of Formula (I), wherein $R_2$ is 2,3-dihydro-1H-inden-5-yl optionally substituted with one, two or three $R_5$ substituents and optionally, with one additional $R_6$ substituent.

Another aspect includes a compound of Formula (I), wherein $R_2$ is heteroaryl selected from furanyl, 1H-pyrrolyl, 1H-pyrazolyl, 1H-imidazolyl, 1,3-oxazolyl, pyridinyl, pyridazinyl, pyrimidinyl, pyrazinyl, 1H-indolyl, 1H-indazolyl, benzofuranyl, 1H-benzimidazolyl, 1H-benzotriazolyl, and quinolinyl, optionally substituted with one, two or three $R_5$ substituents and optionally, with one additional $R_6$ substituent.

Another aspect includes a compound of Formula (I), wherein $R_2$ is heteroaryl selected from pyridinyl, 1H-indazolyl, 1H-benzimidazolyl, 1H-benzotriazolyl, and quinolinyl, optionally substituted with one, two or three $R_5$ substituents and optionally, with one additional $R_6$ substituent.

Another aspect includes a compound of Formula (I), wherein $R_2$ is heteroaryl selected from furan-3-yl, 1H-pyrrol-3-yl, 1H-pyrazol-1-yl, 1H-pyrazol-3-yl, 1H-pyrazol-4-yl, 1H-imidazol-1-yl, 1H-imidazol-2-yl, 1H-imidazol-4-yl, 1,3-oxazol-4-yl, pyridin-2-yl, pyridin-3-yl, pyridin-4-yl, pyridazin-3-yl, pyridazin-4-yl, pyridazin-5-yl, pyrimidin-4-yl, pyrimidin-5-yl, pyrazin-2-yl, pyrazin-3-yl, 1H-indol-3-yl, 1H-indol-4-yl, 1H-indol-5-yl, 1H-indol-6-yl, 1H-indazol-5-yl, 1H-indazol-6-yl, benzofuran-2-yl, benzofuran-5-yl, 1H-benzimidazol-5-yl, 1H-benzimidazol-6-yl, 1H-benzotriazol-4-yl, 1H-benzotriazol-5-yl, 1H-benzotriazol-6-yl, 1H-benzotriazol-7-yl, and quinolin-7-yl, optionally substituted with one, two or three $R_5$ substituents and optionally, with one additional $R_6$ substituent.

Another aspect includes a compound of Formula (I), wherein $R_2$ is heteroaryl selected from pyridin-2-yl, 1H-indazol-6-yl, 1H-benzimidazol-6-yl, 1H-benzotriazol-7-yl, and quinolin-7-yl, optionally substituted with one, two or three $R_5$ substituents and optionally, with one additional $R_6$ substituent.

One aspect includes a compound of Formula (I), wherein $R_3$ is, in each instance, independently selected from cyano, halogen, hydroxy, $C_{1-6}$alkyl, deutero-$C_{1-4}$alkyl, halo-$C_{1-6}$alkyl, $C_{1-6}$alkoxy, halo-$C_{1-6}$alkoxy, $C_{1-6}$alkoxy-$C_{1-6}$alkyl, amino, $C_{1-6}$alkyl-amino, $(C_{1-6}$alkyl$)_2$-amino, amino-$C_{1-6}$alkyl, and hydroxy-$C_{1-6}$alkyl.

Another aspect includes a compound of Formula (I), wherein $R_3$ is, in each instance, independently selected from halogen, $C_{1-6}$alkyl, and $C_{1-6}$alkyl-amino.

Another aspect includes a compound of Formula (I), wherein $R_3$ is halogen selected from bromo, chloro, fluoro, and iodo.

Another aspect includes a compound of Formula (I), wherein $R_3$ is fluoro.

Another aspect includes a compound of Formula (I), wherein $R_3$ is $C_{1-6}$alkyl selected from methyl, ethyl, propyl, isopropyl, and tert-butyl.

Another aspect includes a compound of Formula (I), wherein $R_3$ is methyl.

Another aspect includes a compound of Formula (I), wherein $R_3$ is $C_{1-6}$alkyl-amino wherein $C_{1-6}$alkyl is selected from methyl, ethyl, propyl, isopropyl, butyl, isobutyl, sec-butyl, and tert-butyl.

Another aspect includes a compound of Formula (I), wherein $R_3$ is tert-butylamino.

One aspect includes a compound of Formula (I), wherein $R_4$ is selected from $C_{3-10}$cycloalkyl, phenyl, heteroaryl, and heterocyclyl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S,
wherein heteroaryl is a 3-7 membered monocyclic or 6-10 membered bicyclic ring system having 1, 2, 3, or 4 heteroatom ring members independently selected from N, O, or S, and wherein, each instance of $C_{3-10}$cycloalkyl, phenyl, heterocyclyl, and heteroaryl is optionally substituted with one, two, or three $R_7$ substituents.

One aspect includes a compound of Formula (I), wherein $R_5$ is, in each instance, independently selected from halogen, hydroxy, cyano, nitro, $C_{1-6}$alkyl, deutero-$C_{1-4}$alkyl, halo-$C_{1-6}$alkyl, $C_{1-6}$alkoxy, halo-$C_{1-6}$alkoxy, oxime, amino, $C_{1-6}$alkyl-amino, $(C_{1-6}$alkyl$)_2$-amino, and $C_{1-6}$alkyl-thio.

Another aspect includes a compound of Formula (I), wherein $R_5$ is, in each instance, independently selected from halogen, hydroxy, $C_{1-6}$alkyl, and oxime.

Another aspect includes a compound of Formula (I), wherein $R_5$ is halogen selected from bromo, chloro, fluoro, and iodo.

Another aspect includes a compound of Formula (I), wherein $R_5$ is halogen selected from chloro and fluoro.

Another aspect includes a compound of Formula (I), wherein $R_5$ is hydroxy.

Another aspect includes a compound of Formula (I), wherein $R_5$ is $C_{1-6}$alkyl selected from methyl, ethyl, propyl, isopropyl, and tert-butyl.

Another aspect includes a compound of Formula (I), wherein $R_5$ methyl.

Another aspect includes a compound of Formula (I), wherein $R_5$ is oxime.

One aspect includes a compound of Formula (I), wherein $R_6$ is selected from phenyl and heteroaryl,
wherein heteroaryl is a 3-7 membered monocyclic or 6-10 membered bicyclic ring system having 1, 2, 3, or 4 heteroatom ring members independently selected from N, O, or S, and
wherein, each instance of phenyl and heteroaryl is optionally substituted with one, two, three or four $R_8$ substituents.

Another aspect includes a compound of Formula (I), wherein $R_6$ is phenyl, optionally substituted with one, two, three or four $R_8$ substituents.

Another aspect includes a compound of Formula (I) wherein $R_6$ is heteroaryl selected from furanyl, thienyl, 1H-pyrrolyl, 1H-pyrazolyl, 1H-imidazolyl, 1H-1,2,3-triazolyl, 2H-1,2,3-triazolyl, 1H-1,2,4-triazolyl, 4H-1,2,4-triazolyl, 1,3-thiazolyl, 1,2-oxazolyl, 1,3-oxazolyl, 1,2,4-thiadiazolyl, 1,3,4-thiadiazol-yl, pyridinyl, pyridin-2(1H)-on-yl, pyridazinyl, pyrimidinyl, pyrimidin-4(3H)-on-yl, pyrazinyl, 1,3,5-triazinyl, 1H-indolyl, 1H-indazolyl, benzofuranyl, 1H-benzimidazolyl, 1H-benzotriazolyl, 1H-pyrrolo[2,3-b]pyridinyl, 1H-pyrrolo[2,3-c]pyridinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[1,5-a]pyridinyl, [1,2,3]triazolo[1,5-a]pyridinyl, 1H-[1,2,3]triazolo[4,5-b]pyridinyl, 3H-[1,2,3]triazolo[4,5-c]pyridinyl, 3H-[1,2,3]triazolo[4,5-c]pyridazinyl, [1,2,4]triazolo[1,5-a]pyridinyl, [1,2,4]triazolo[4,3-b]pyridazinyl, and quinolinyl, optionally substituted with one, two, three or four $R_8$ substituents.

Another aspect includes a compound of Formula (I) wherein $R_6$ is heteroaryl selected from furanyl, thienyl, 1H-pyrrolyl, 1H-pyrazolyl, 1H-imidazolyl, 1H-1,2,3-triazolyl, 2H-1,2,3-triazolyl, 1H-1,2,4-triazolyl, 4H-1,2,4-triazolyl, 1,3-thiazolyl, 1,2-oxazolyl, 1,3-oxazolyl, 1,2,4-thiadiazolyl, 1,3,4-thiadiazol-yl, pyridinyl, pyridin-2(1H)-on-yl, pyridazinyl, pyrimidinyl, pyrimidin-4(3H)-on-yl, pyrazinyl, 1,3,5-triazinyl, 1H-benzotriazolyl, 1H-pyrrolo[2,3-b]pyridinyl, imidazo[1,2-a]pyridinyl, imidazo[1,2-a]pyrimidinyl, imidazo[1,2-a]pyrazinyl, imidazo[1,5-a]pyridinyl, [1,2,3]triazolo[1,5-a]pyridinyl, 1H-[1,2,3]triazolo[4,5-b]pyridinyl, 3H-[1,2,3]triazolo[4,5-c]pyridinyl, [1,2,4]triazolo[1,5-a]pyridinyl, and [1,2,4]triazolo[4,3-b]pyridazinyl, optionally substituted with one, two, three or four $R_8$ substituents.

Another aspect includes a compound of Formula (I), wherein $R_6$ is heteroaryl selected from furan-2-yl, furan-3-yl, thien-2-yl, thien-3-yl, 1H-pyrrol-3-yl, 1H-pyrazol-1-yl, 1H-pyrazol-3-yl, 1H-pyrazol-4-yl, 1H-pyrazol-5-yl, 1H-imidazol-1-yl, 1H-imidazol-2-yl, 1H-imidazol-4-yl, 1H-1,2,3-triazol-1-yl, 1H-1,2,3-triazol-4-yl, 2H-1,2,3-triazol-2-yl, 2H-1,2,3-triazol-4-yl, 1H-1,2,4-triazol-1-yl, 4H-1,2,4-triazol-4-yl, 1,3-thiazol-2-yl, 1,3-thiazol-5-yl, 1,2-oxazol-4-yl, 1,3-oxazol-2-yl, 1,3-oxazol-3-yl, 1,3-oxazol-4-yl, 1,3-oxazol-5-yl, 1,2,4-thiadiazol-5-yl, 1,3,4-thiadiazol-2-yl, pyridin-2-yl, pyridin-3-yl, pyridin-4-yl, pyridin-2(1H)-on-4-yl, pyridazin-3-yl, pyridazin-4-yl, pyrimidin-4-yl, pyrimidin-5-yl, pyrimidin-4(3H)-on-6-yl, pyrazin-1-yl, pyrazin-2-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, benzofuran-2-yl, benzofuran-5-yl, 1H-benzimidazol-2-yl, 1H-benzimidazol-5-yl, 1H-benzimidazol-6-yl, 1H-benzotriazol-4-yl, 1H-benzotriazol-5-yl, 1H-benzotriazol-6-yl, 1H-benzotriazol-7-yl, 1H-pyrrolo[2,3-b]pyridin-4-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, 2H-pyrazolo[4,3-b]pyridin-5-yl, 2H-pyrazolo[4,3-c]pyridin-5-yl, pyrazolo[1,5-a]pyrazin-2-yl, imidazo[1,2-a]pyridin-2-yl, imidazo[1,2-a]pyridin-6-yl, imidazo[1,2-a]pyridin-7-yl, imidazo[1,2-a]pyrimidin-2-yl, imidazo[1,2-a]pyrimidin-6-yl, imidazo[1,2-c]pyrimidin-2-yl, imidazo[1,2-b]pyridazin-2-yl, imidazo[1,2-b]pyridazin-6-yl, imidazo[1,2-a]pyrazin-2-yl, imidazo[1,2-a]pyrazin-3-yl, imidazo[1,2-a]pyrazin-6-yl, imidazo[1,5-a]pyridine-6-yl, imidazo[1,5-a]pyridin-7-yl, [1,2,3]triazolo[1,5-a]pyridin-5-yl, [1,2,3]triazolo[1,5-a]pyridin-7-yl, 1H-[1,2,3]triazolo[4,5-b]pyridin-5-yl, 1H-[1,2,3]triazolo[4,5-b]pyridin-6-yl, 3H-[1,2,3]triazolo[4,5-c]pyridin-6-yl, 3H-[1,2,3]triazolo[4,5-c]pyridazin-6-yl, [1,2,4]triazolo[1,5-a]pyridin-7-yl, [1,2,4]triazolo[4,3-b]pyridazin-6-yl, quinolin-6-yl, quinolin-7-yl, and quinolin-8-yl, optionally substituted with one, two, three or four $R_8$ substituents.

Another aspect includes a compound of Formula (I), wherein $R_6$ is heteroaryl selected from furan-3-yl, thien-3-yl, 1H-pyrrol-3-yl, 1H-pyrazol-1-yl, 1H-pyrazol-3-yl, 1H-pyrazol-4-yl, 1H-pyrazol-5-yl, 1H-imidazol-1-yl, 1H-imidazol-2-yl, 1H-imidazol-4-yl, 1H-1,2,3-triazol-1-yl, 1H-1,2,3-triazol-4-yl, 2H-1,2,3-triazol-2-yl, 2H-1,2,3-triazol-4-yl, 1H-1,2,4-triazol-1-yl, 4H-1,2,4-triazol-4-yl, 1,3-thiazol-2-yl, 1,3-thiazol-5-yl, 1,2-oxazol-4-yl, 1,3-oxazol-2-yl, 1,3-oxazol-5-yl, 1,2,4-thiadiazol-5-yl, 1,3,4-thiadiazol-2-yl, pyridin-2-yl, pyridin-3-yl, pyridin-4-yl, pyridin-2(1H)-on-4-yl, pyridazin-3-yl, pyridazin-4-yl, pyrimidin-4-yl, pyrimidin-5-yl, pyrimidin-4(3H)-on-6-yl, pyrazin-2-yl, 1,3,5-triazin-2-yl, 1H-benzotriazol-6-yl, 1H-pyrrolo[2,3-b]pyridin-4-yl, 1H-pyrrolo[2,3-c]pyridin-4-yl, imidazo[1,2-a]pyridin-7-yl, imidazo[1,2-a]pyrimidin-6-yl, imidazo[1,2-b]pyridazin-6-yl, imidazo[1,2-a]pyrazin-3-yl, imidazo[1,2-a]pyrazin-6-ylimidazo[1,5-a]pyridin-7-yl, [1,2,3]triazolo[1,5-a]pyridin-5-yl, [1,2,3]triazolo[1,5-a]pyridin-7-yl, 1H-[1,2,3]triazolo[4,5-b]pyridin-5-yl, 1H-[1,2,3]triazolo[4,5-b]pyridin-6-yl, 3H-[1,2,3]triazolo[4,5-c]pyridin-6-yl, and [1,2,4]triazolo[4,3-b]pyridazin-6-yl, optionally substituted with one, two, three or four $R_8$ substituents.

One aspect includes a compound of Formula (I) wherein $R_7$ is, in each instance, independently selected from cyano, halogen, hydroxy, $C_{1-6}$alkyl, deutero-$C_{1-4}$alkyl, halo-$C_{1-6}$alkyl, C₁₋₆alkoxy, halo-C₁₋₆alkoxy, C₁₋₆alkoxy-C₁₋₆alkyl, amino, C₁₋₆alkyl-amino, (C₁₋₆alkyl)₂-amino, amino-C₁₋₆alkyl, and C₃₋₁₀cycloalkyl.

One aspect includes a compound of Formula (I) wherein R₈ is, in each instance, independently selected from cyano, halogen, hydroxy, C₁₋₆alkyl, deutero-C₁₋₄alkyl, halo-C₁₋₆alkyl, C₁₋₆alkoxy, halo-C₁₋₆alkoxy, C₁₋₆alkoxy-C₁₋₆alkyl, amino, C₁₋₆alkyl-amino, (C₁₋₆alkyl)₂-amino, amino-C₁₋₆alkyl, and C₃₋₁₀cycloalkyl.

One aspect includes a compound of Formula (I) wherein R₈ is, in each instance, independently selected from cyano, halogen, hydroxy, C₁₋₆alkyl, deutero-C₁₋₄alkyl, halo-C₁₋₆alkyl, C₁₋₆alkoxy, halo-C₁₋₆alkoxy, amino, C₁₋₆alkyl-amino, (C₁₋₆alkyl)₂-amino, and C₃₋₁₀cycloalkyl.

Another aspect includes a compound of Formula (I) wherein R₈ is cyano.

Another aspect includes a compound of Formula (I), wherein R₈ is halogen selected from bromo, chloro, fluoro, and iodo.

Another aspect includes a compound of Formula (I), wherein R₈ is halogen selected from bromo, chloro, and fluoro.

Another aspect includes a compound of Formula (I) wherein R₈ is hydroxy.

Another aspect includes a compound of Formula (I), wherein R₈ is C₁₋₆alkyl selected from methyl, ethyl, propyl, isopropyl, and tert-butyl.

Another aspect includes a compound of Formula (I), wherein R₈ is C₁₋₆alkyl selected from methyl, ethyl, and propyl.

Another aspect includes a compound of Formula (I) wherein R₈ is deutero-C₁₋₄alkyl wherein C₁₋₄alkyl is selected from methyl, ethyl, propyl, isopropyl, butyl, isobutyl, sec-butyl, and tert-butyl partially or completely substituted with one or more deuterium atoms where allowed by available valences.

Another aspect includes a compound of Formula (I) wherein R₈ is (²H₃)methyl.

Another aspect includes a compound of Formula (I), wherein R₈ is halo-C₁₋₆alkyl, wherein C₁₋₆alkyl is selected from methyl, ethyl, propyl, isopropyl, butyl, isobutyl, sec-butyl, and tert-butyl partially or completely substituted with one or more halogens selected from bromo, chloro, fluoro, and iodo where allowed by available valences.

Another aspect includes a compound of Formula (I), wherein R₈ is halo-C₁₋₆alkyl selected from trifluromethyl and difluoromethyl.

Another aspect includes a compound of Formula (I), wherein R₈ is C₁₋₆alkoxy selected from methoxy, ethoxy, propoxy, isopropoxy, and tert-butoxy.

Another aspect includes a compound of Formula (I), wherein R₈ is C₁₋₆alkoxy selected from methoxy and ethoxy.

Another aspect includes a compound of Formula (I), wherein R₈ is halo-C₁₋₆alkoxy,
  wherein C₁₋₆alkoxy is selected from methoxy, ethoxy, propoxy, isopropoxy, and tert-butoxy partially or completely substituted with one or more halogens selected from bromo, chloro, fluoro, and iodo where allowed by available valences.

Another aspect includes a compound of Formula (I), wherein R₈ is difluoromethoxy.

Another aspect includes a compound of Formula (I) wherein R₈ is amino.

Another aspect includes a compound of Formula (I), wherein R₈ is C₁₋₆alkyl-amino wherein C₁₋₆alkyl is selected from methyl, ethyl, propyl, isopropyl, butyl, isobutyl, sec-butyl, and tert-butyl.

Another aspect includes a compound of Formula (I), wherein R₈ is methylamino.

Another aspect includes a compound of Formula (I), wherein R₈ is (C₁₋₆alkyl)₂-amino wherein C₁₋₆alkyl is independently selected from methyl, ethyl, propyl, isopropyl, butyl, isobutyl, sec-butyl, and tert-butyl.

Another aspect includes a compound of Formula (I), wherein R₈ is dimethylamino.

Another aspect includes a compound of Formula (I), wherein R₈ is C₃₋₁₀cycloalkyl selected from cyclopropyl, cyclobutyl, cyclopentyl, cyclohexyl or cyclohexyl.

Another aspect includes a compound of Formula (I), wherein R₈ is cyclopropyl.

One aspect of the compound of Formula (I) includes a compound selected from Formula (Ia), Formula (Ib), Formula (Id), Formula (e), Formula (If), Formula (Ig), Formula (Ih), Formula (Ii), Formula (Ij), Formula (Ik), Formula (Il), Formula (Im), Formula (In), Formula (o), Formula (Ip), Formula (Iq), Formula (Is), Formula (It), Formula (Iu), Formula (Iv), Formula (Iw), Formula (Ix), Formula (Iy), Formula (Iz), Formula (Iaa), Formula (Ibb), Formula (Icc), Formula (Idd), Formula (ee), Formula (Iff), Formula (Igg), Formula (Ihh), Formula (Iii), Formula (Ijj), Formula (Ikk), Formula (Ill), Formula (Imm), Formula (Inn), Formula (oo), Formula (Ipp), Formula (Iqq), Formula (Irr), Formula (Iss), Formula (Itt), Formula (Iuu), Formula (Iww), Formula (Ixx), Formula (Iyy), Formula (Izz), Formula (Iaaa), Formula (Ibbb), Formula (Iccc), Formula (Iddd), Formula (Ieee), Formula (Ifff), Formula (Iggg), or Formula (Ihhh):

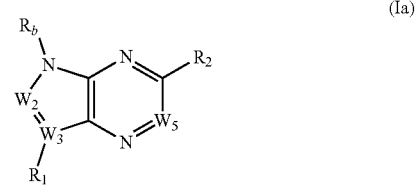

(Ia)

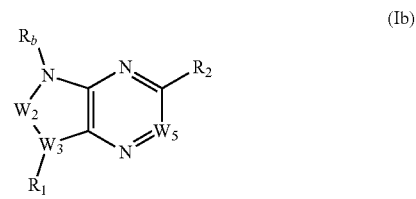

(Ib)

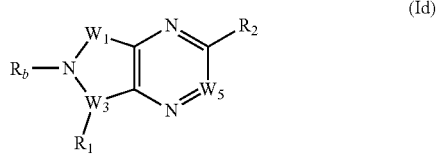

(Id)

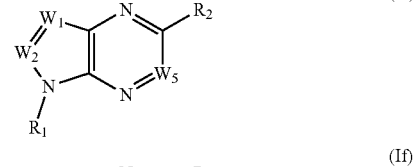

(Ie)

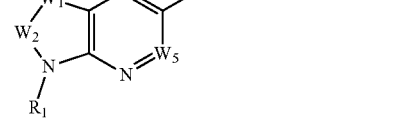

(If)

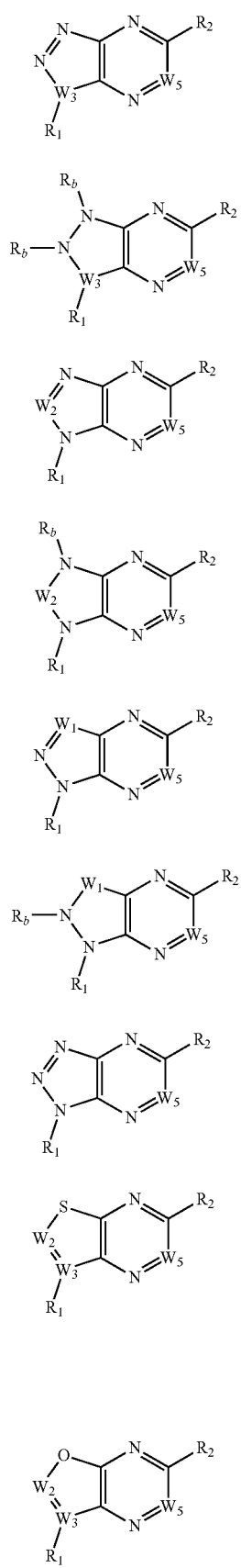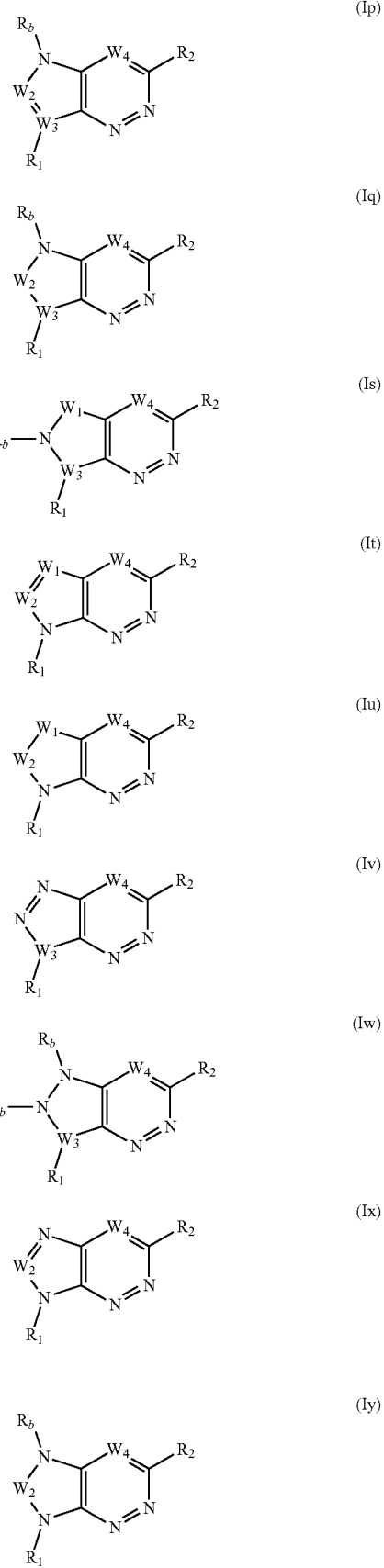

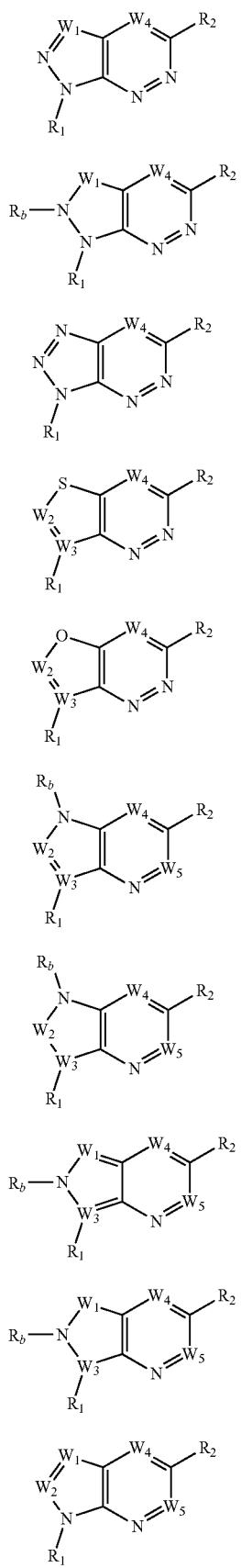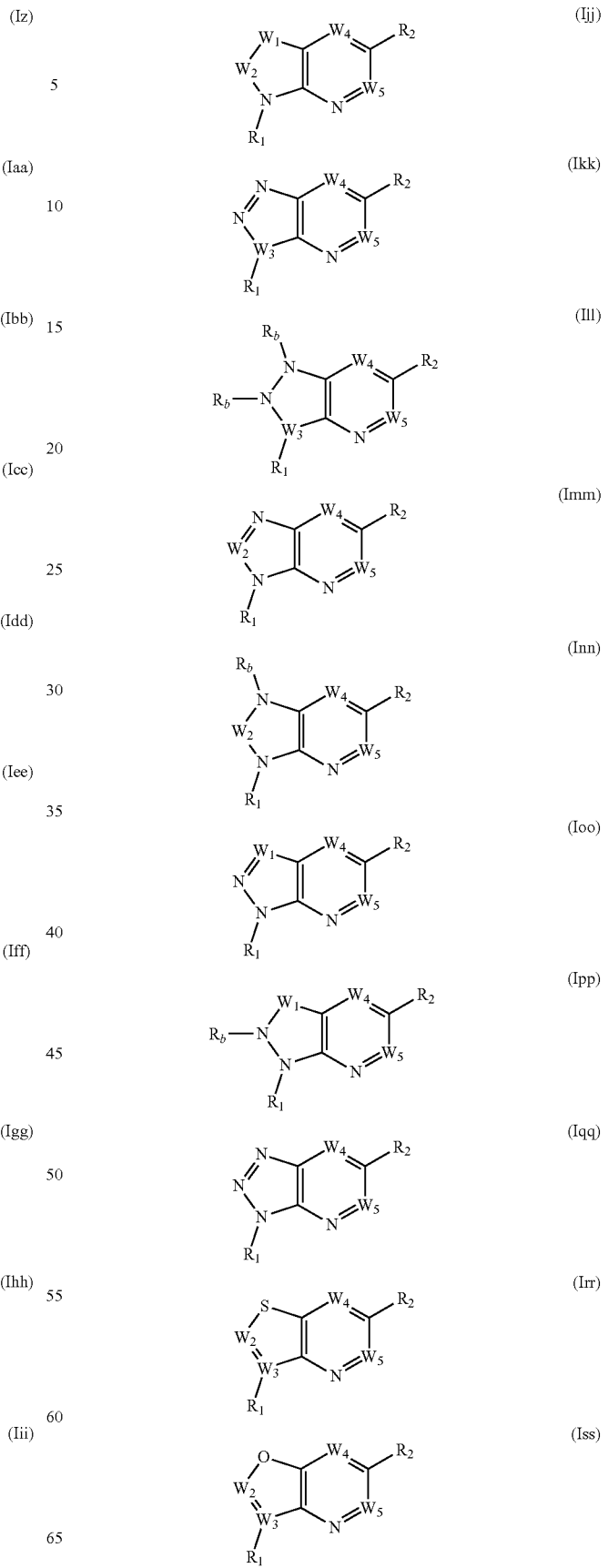

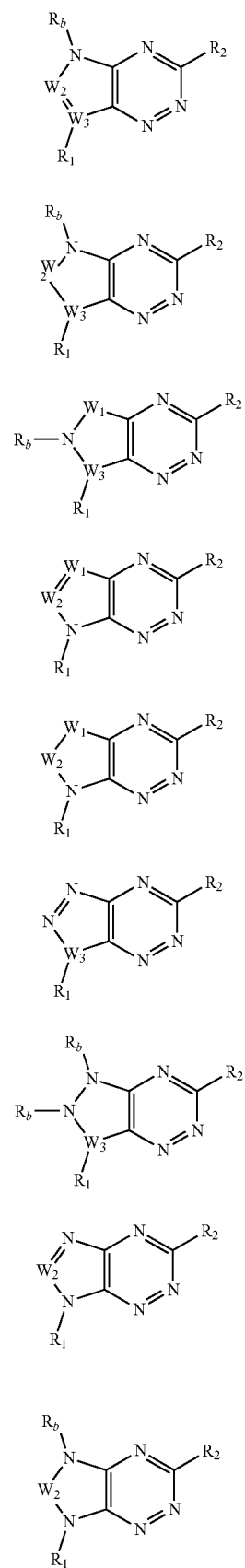
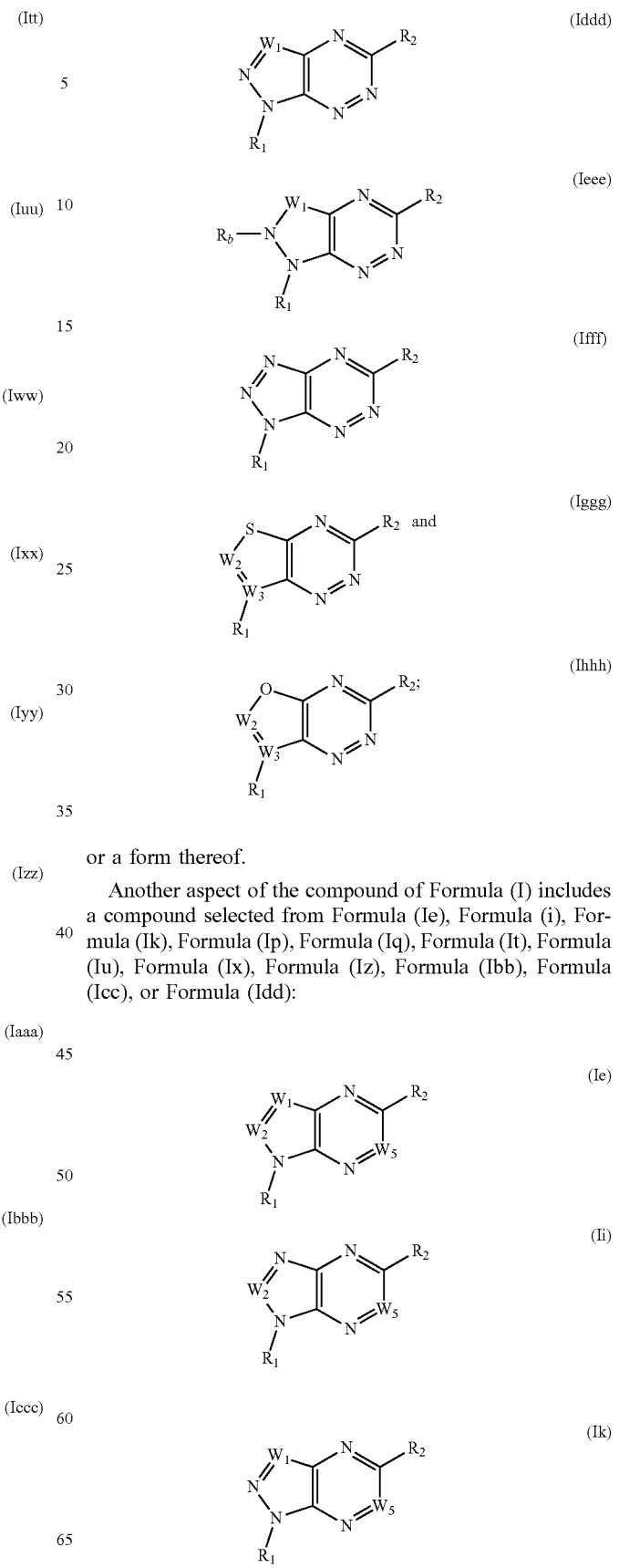
or a form thereof.
Another aspect of the compound of Formula (I) includes a compound selected from Formula (Ie), Formula (i), Formula (Ik), Formula (Ip), Formula (Iq), Formula (It), Formula (Iu), Formula (Ix), Formula (Iz), Formula (Ibb), Formula (Icc), or Formula (Idd):

-continued

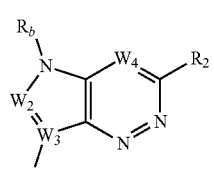 (Ip)

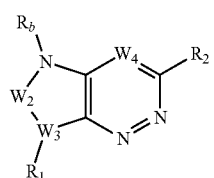 (Iq)

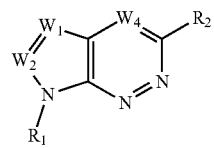 (It)

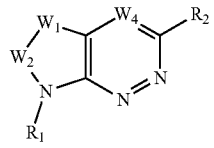 (Iu)

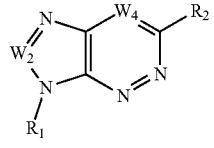 (Ix)

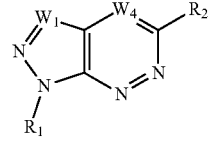 (Iz)

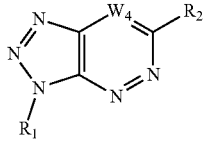 (Ibb)

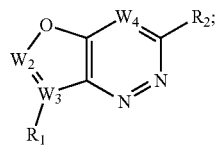 (Icc) and

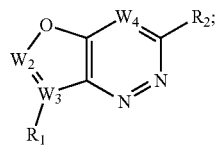 (Idd);

or a form thereof.

Another aspect of the compound of Formula (I) includes a compound selected from Formula (Ia1), Formula (I1), Formula (Id1), Formula (Ie1), Formula (If1), Formula (Ig1), Formula (Ih1), Formula (Ii1), Formula (I1j), Formula (Ik1), Formula (Il1), Formula (Im1), Formula (In1), Formula (Io1), Formula (Ip1), Formula (Iq1), Formula (Is1), Formula (It1), Formula (Iu1), Formula (Iv1), Formula (Iw 1), Formula (Ix1), Formula (Iy1), Formula (Iz1), Formula (Iaa1), Formula (Ibb1), Formula (Icc1), Formula (Idd1), Formula (Iee1), Formula (Iff1), Formula (Igg1), Formula (Ihh1), Formula (Iii1), Formula (Ijj1), Formula (Ikk1), Formula (Ill1), Formula (Imm1), Formula (Inn1), Formula (Ioo1), Formula (Ipp1), Formula (Iqq1), Formula (Irr1), Formula (Iss1), Formula (Itt1), Formula (Iuu1), Formula (Iww1), Formula (Ixx1), Formula (Iyy1), Formula (Izz1), Formula (Iaaa1), Formula (Ibbb1), Formula (Iccc1), Formula (Iddd1), Formula (Ieee1), Formula (Ifff1), Formula (Iggg1), or Formula (Ihhh1):

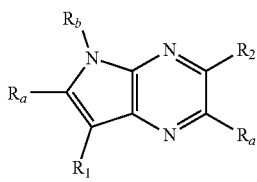 (Ia1)

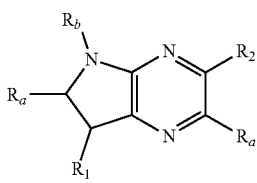 (Ib1)

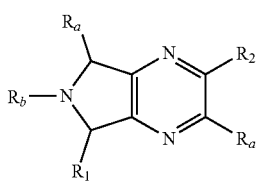 (Id1)

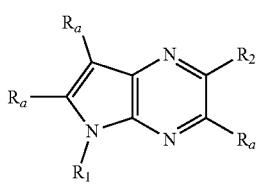 (Ie1)

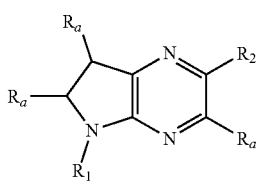 (If1)

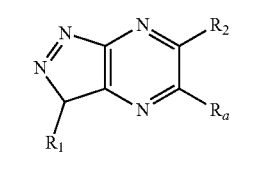 (Ig1)

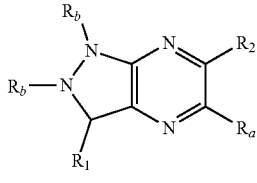 (Ih1)

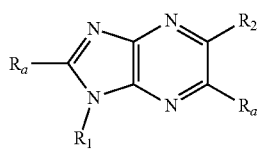 (Ii1)
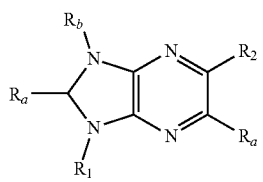 (Ij1)
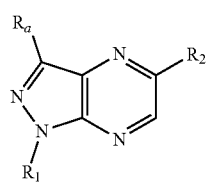 (Ik1)
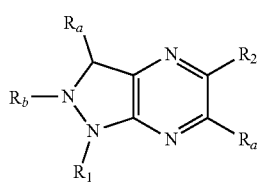 (Il1)
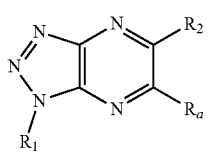 (Im1)
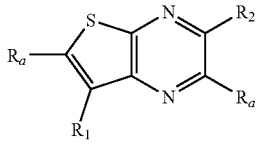 (In1)
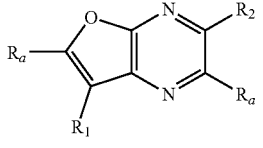 (Io1)
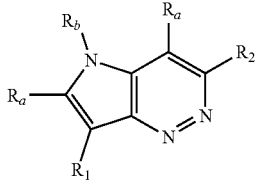 (Ip1)
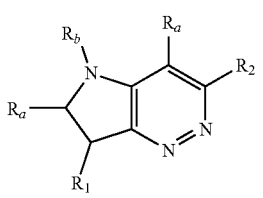 (Iq1)
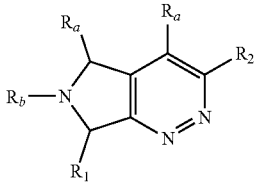 (Is1)
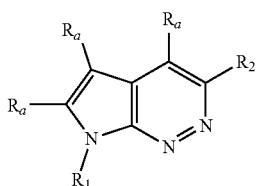 (It1)
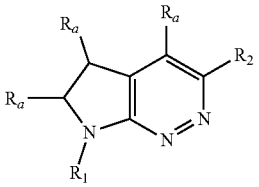 (Iu1)
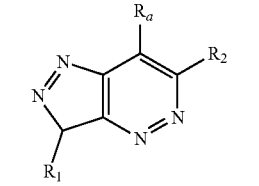 (Iv1)
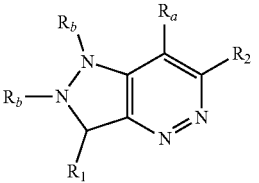 (Iw1)
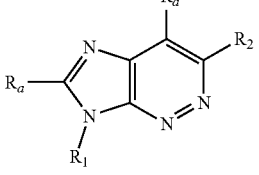 (Ix1)
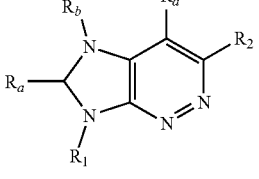 (Iy1)
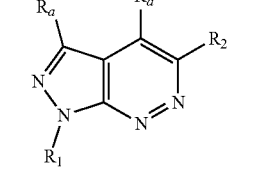 (Iz1)

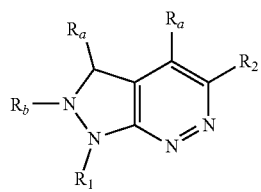 (Iaa1)
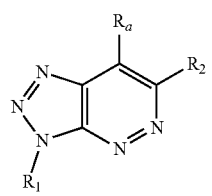 (Ibb1)
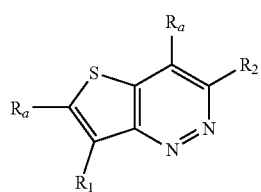 (Icc1)
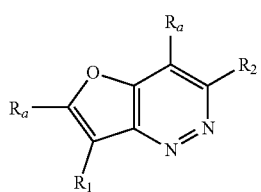 (Idd1)
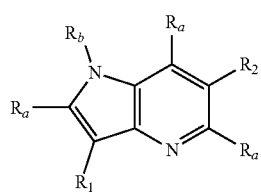 (Iee1)
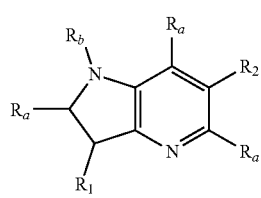 (Iff1)
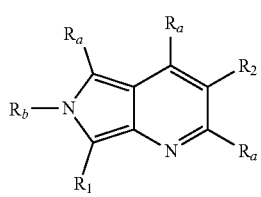 (Igg1)
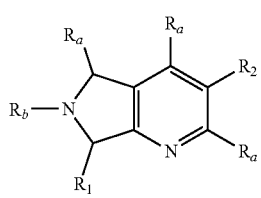 (Ihh1)
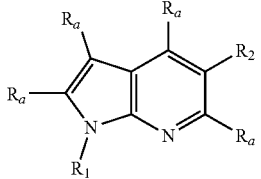 (Iii1)
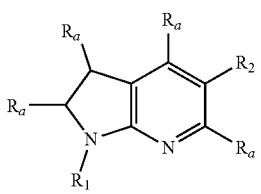 (Ijj1)
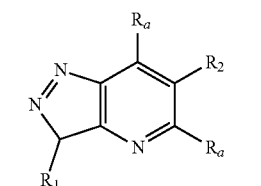 (Ikk1)
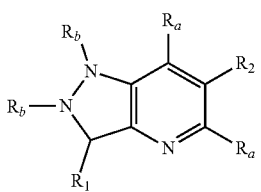 (Ill1)
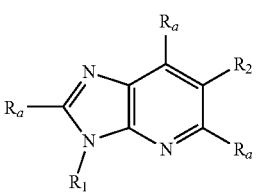 (Imm1)
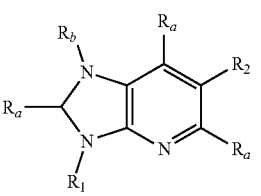 (Inn1)
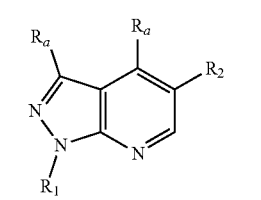 (Ioo1)
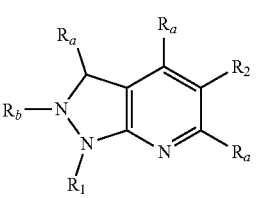 (Ipp1)

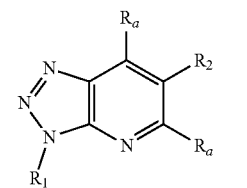 (Iqq1)
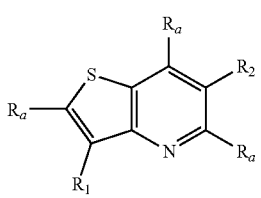 (Irr1)
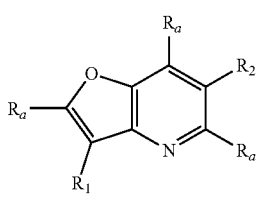 (Iss1)
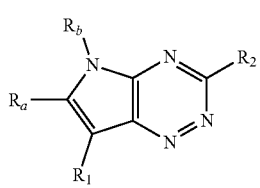 (Itt1)
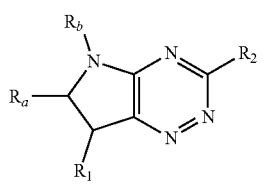 (Iuu1)
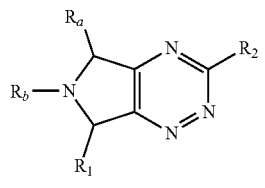 (Iww1)
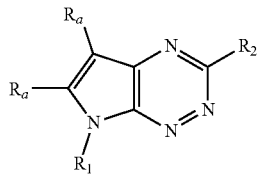 (Ixx1)
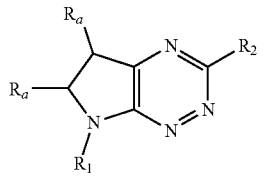 (Iyy1)
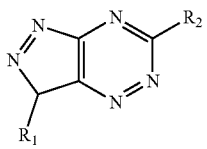 (Izz1)
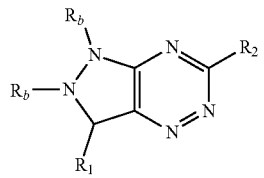 (Iaaa1)
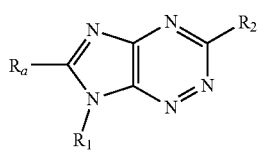 (Ibbb1)
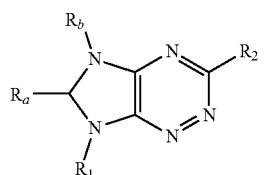 (Iccc1)
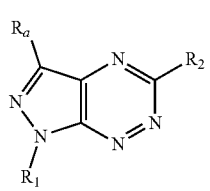 (Iddd1)
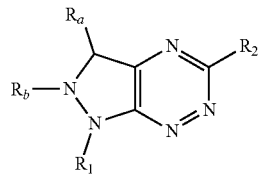 (Ieee1)
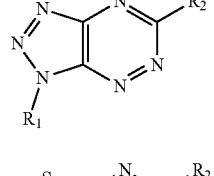 (Ifff1)
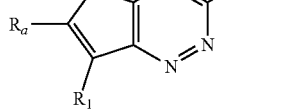 (Iggg1)
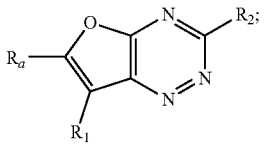 (Ihhh1)
or a form thereof.
Another aspect of the compound of Formula (I) includes a compound selected from Formula (Ie1), Formula (Ii1), Formula (Ik1), Formula (Ip1), Formula (Iq1), Formula (It1), Formula (Iu1), Formula (Ix1), Formula (Iz1), Formula (Ibb1), Formula (Icc1), or Formula (Idd1):
(Ie1)
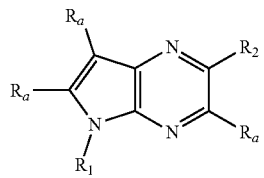
(Ii1)
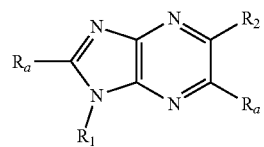
(Ik1)
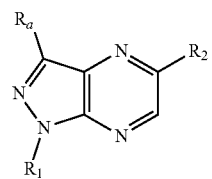
(Ip1)
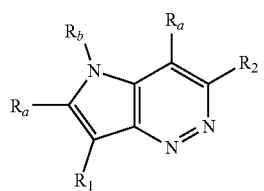
(Iq1)
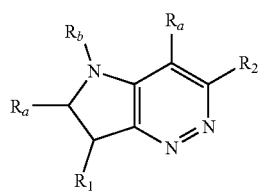
(It1)
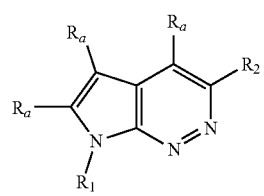
(Iu1)
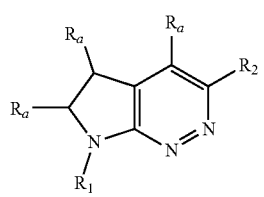
(Ix1)
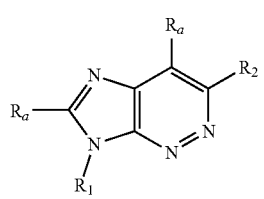
(Iz1)
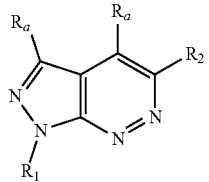
(Ibb1)
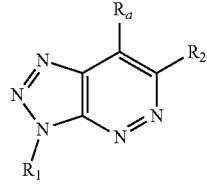
(Icc1)
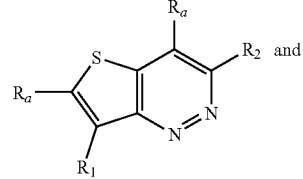
(Idd1)
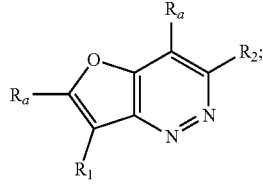
or a form thereof.
Another aspect of the compound of Formula (I) includes the compound of Formula (Ie1):
(Ie1)
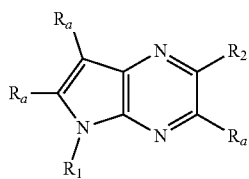
or a form thereof.
Another aspect of the compound of Formula (I) includes the compound of Formula (Ii1):
(Ii1)
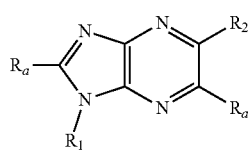
or a form thereof.

Another aspect of the compound of Formula (I) includes the compound of Formula (Ik1):

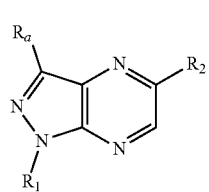
(Ik1)

or a form thereof.

Another aspect of the compound of Formula (I) includes the compound of Formula (Ip1):

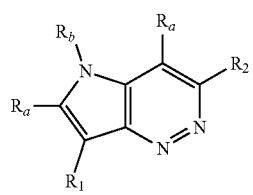
(Ip1)

or a form thereof.

Another aspect of the compound of Formula (I) includes the compound of Formula (Iq1):

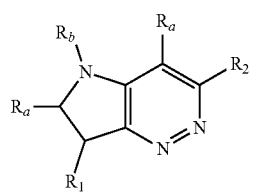
(Iq1)

or a form thereof.

Another aspect of the compound of Formula (I) includes the compound of Formula (It1):

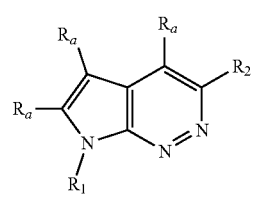
(It1)

or a form thereof.

Another aspect of the compound of Formula (I) includes the compound of Formula (Is1):

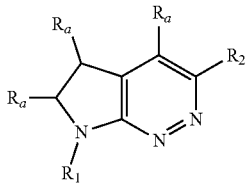
(Iu1)

or a form thereof.

Another aspect of the compound of Formula (I) includes the compound of Formula (Ix1):

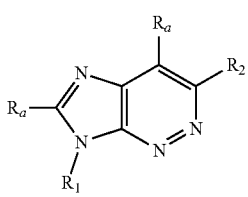
(Ix1)

or a form thereof.

Another aspect of the compound of Formula (I) includes the compound of Formula (Iz1):

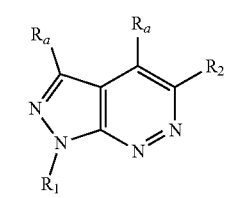
(Iz1)

or a form thereof.

Another aspect of the compound of Formula (I) includes the compound of Formula (Ibb1):

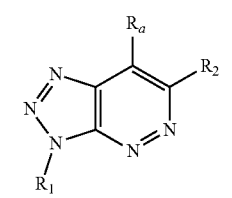
(Ibb1)

or a form thereof.

Another aspect of the compound of Formula (I) includes the compound of Formula (Icc1):
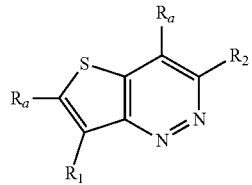
or a form thereof.
Another aspect of the compound of Formula (I) includes the compound of Formula (Idd1):
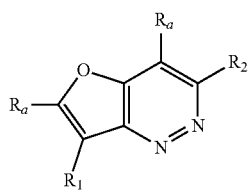
or a form thereof.
An aspect of the compound of Formula (I) or a form thereof includes a compound selected from the group consisting of:
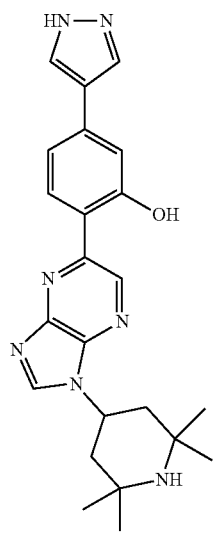
1
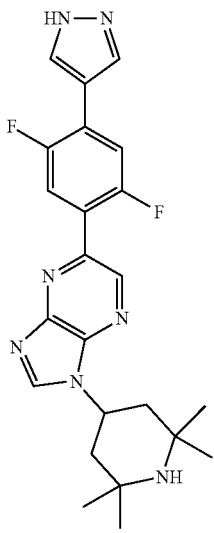
2
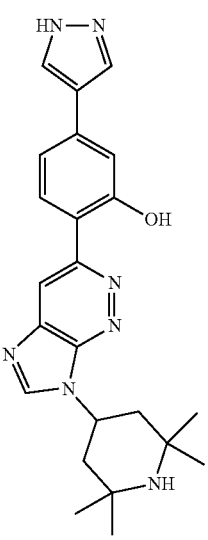
3
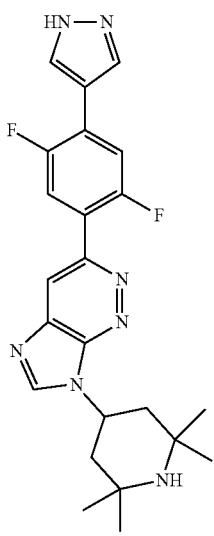
4

| 5 | 8 |
|---|---|
| 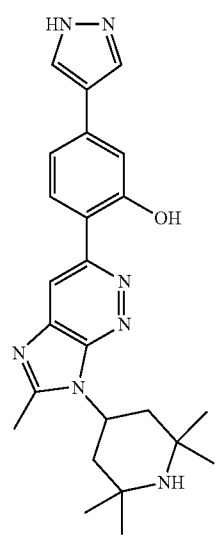 | 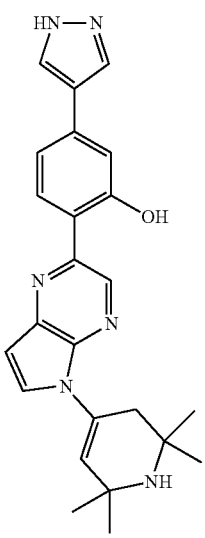 |
| 6 | 9 |
| 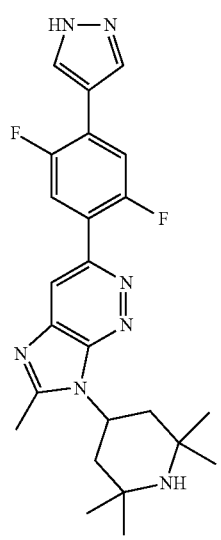 | 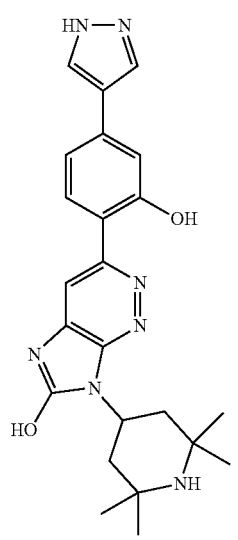 |
| 7 | 10 |
| 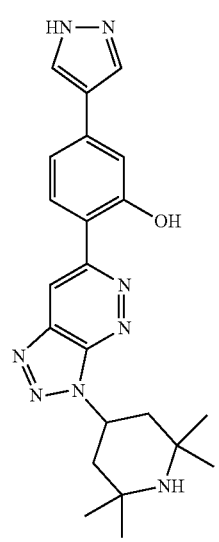 | 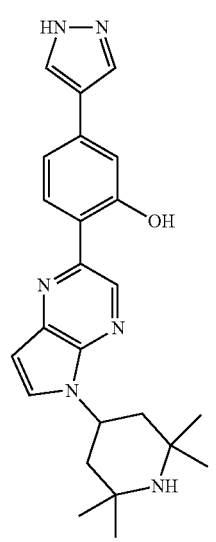 |

11
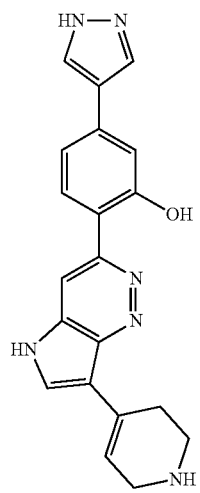
12
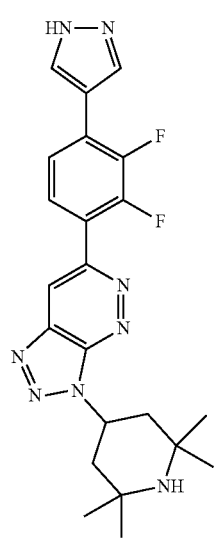
13
14
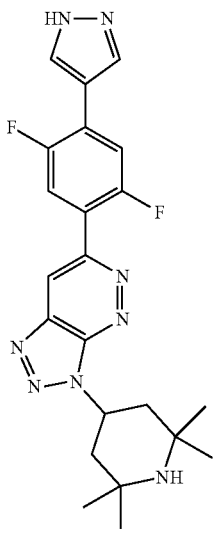
15
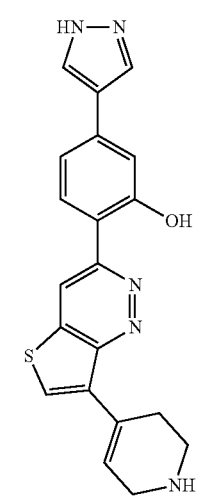
16

17
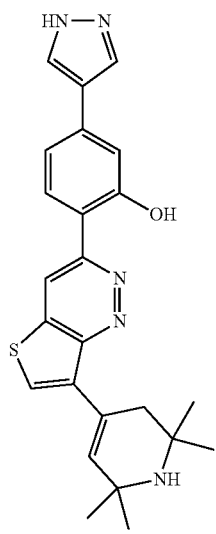
18
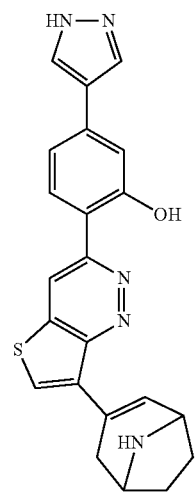
19
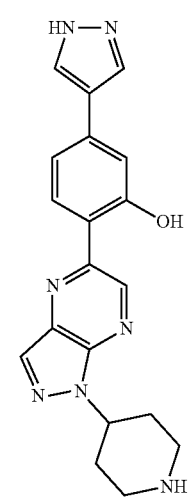
20
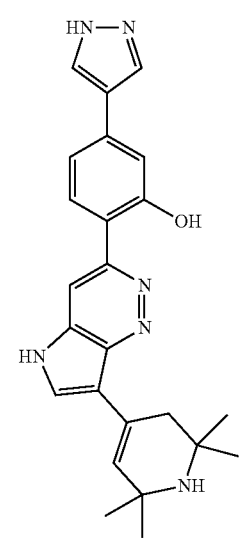
21
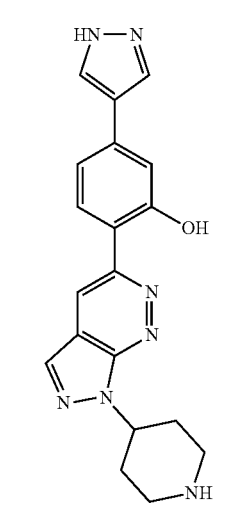
22
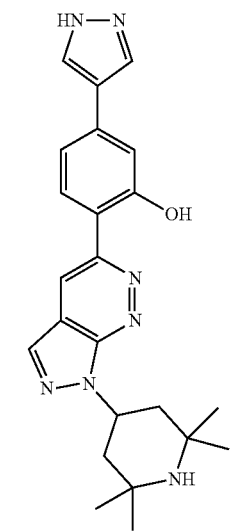

23
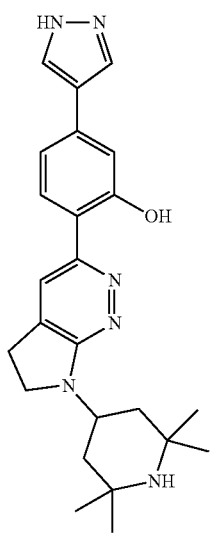
24
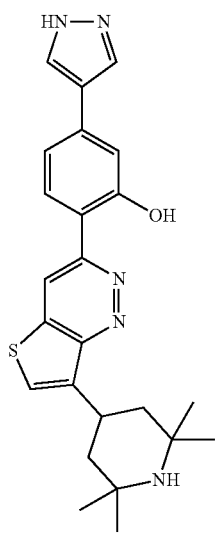
25
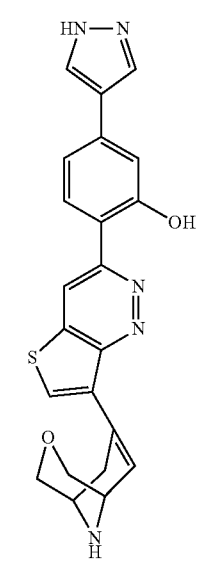
26
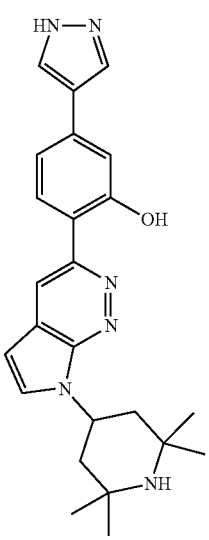
27
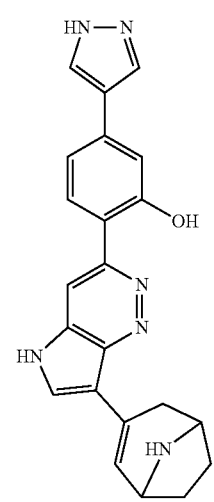
28
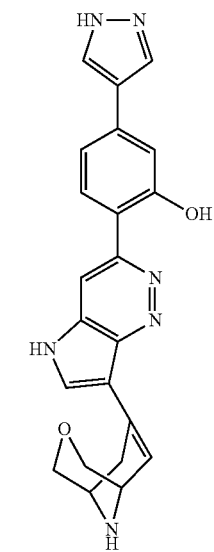

45
-continued
29
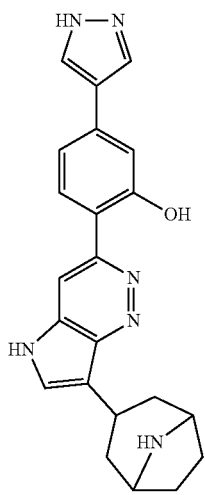
30
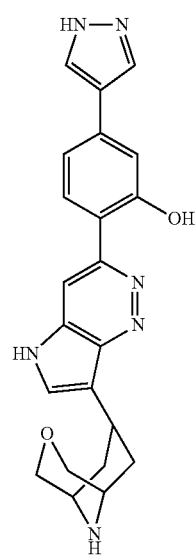
31
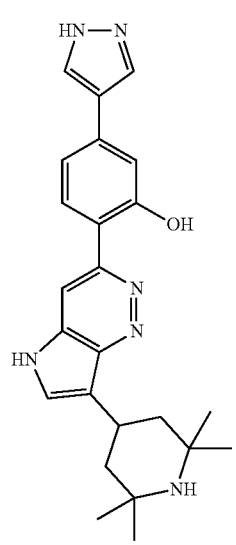
46
-continued
32
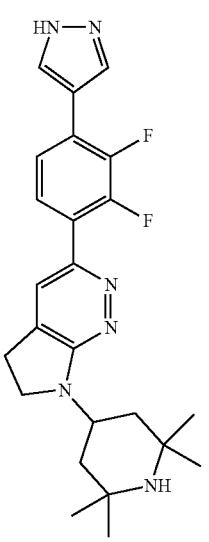
33
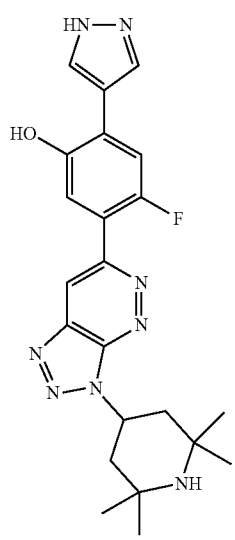
34
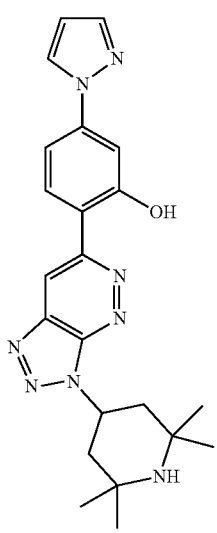

47
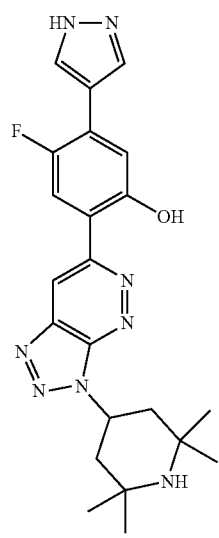
35
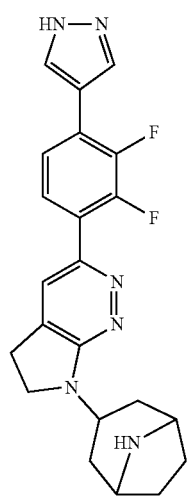
36
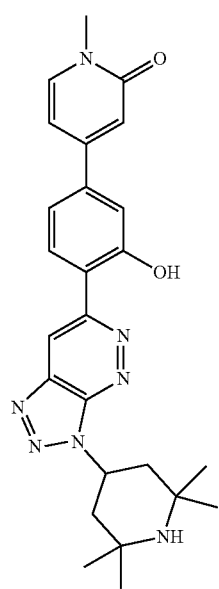
37
48
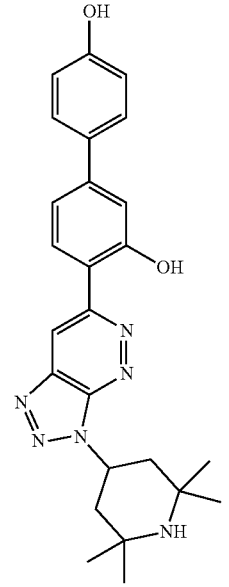
38
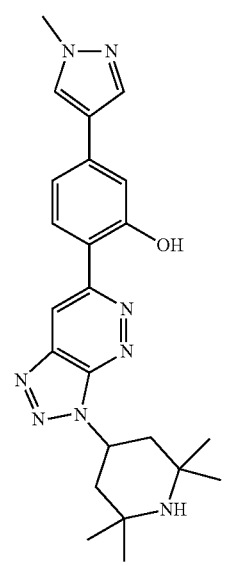
39
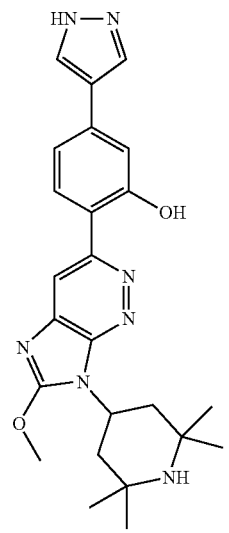
40

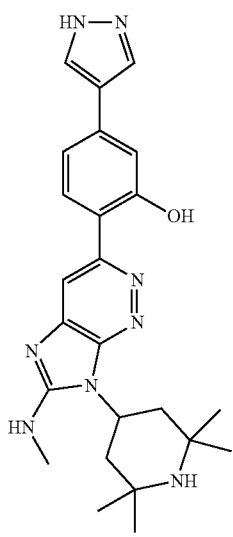
42
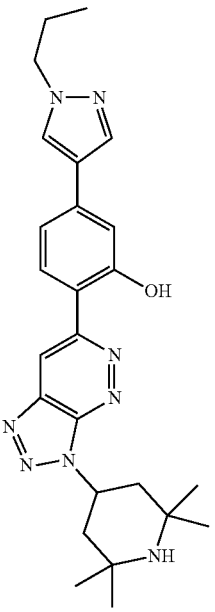
47
43
48
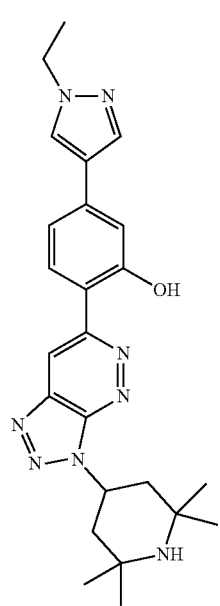
46
49

51
-continued
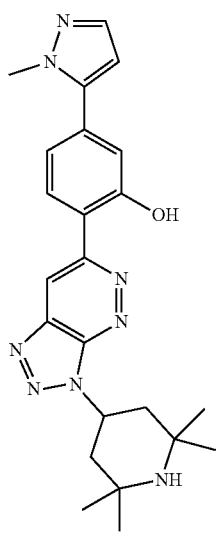
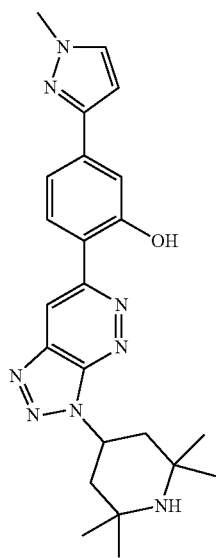
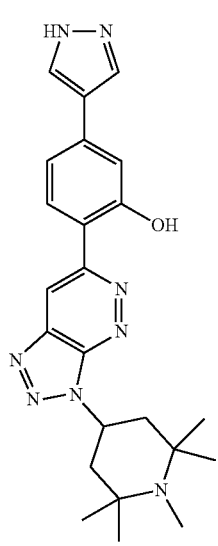
52
-continued
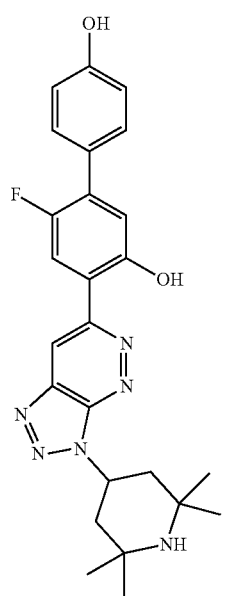
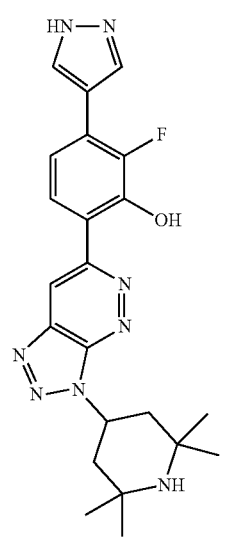

53
-continued
55
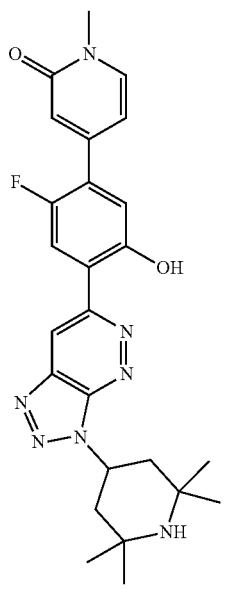
56
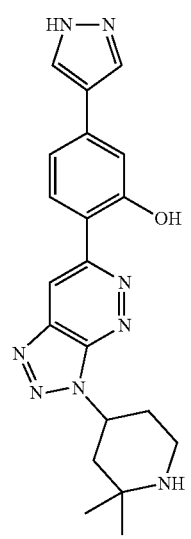
57
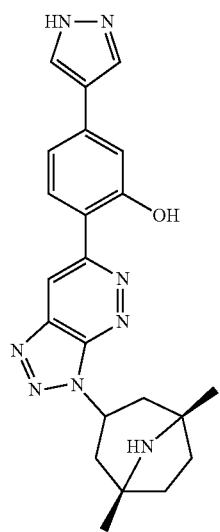
54
-continued
58
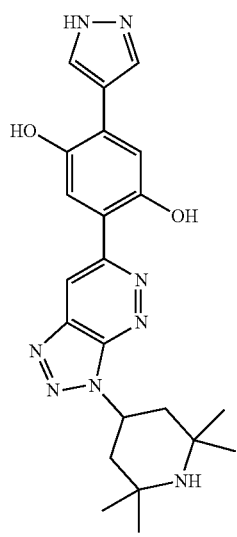
59
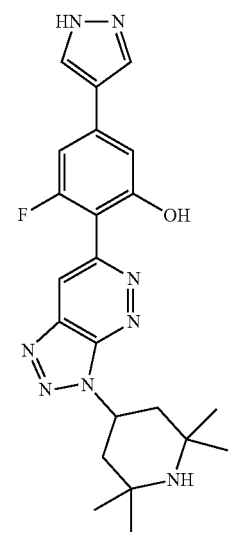
60
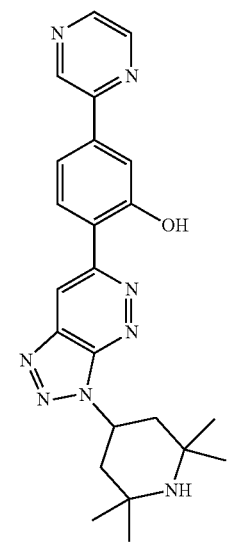

| 61 | 64 |
|---|---|
| 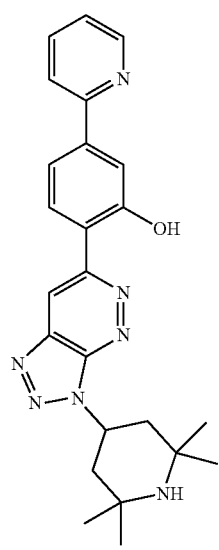 | 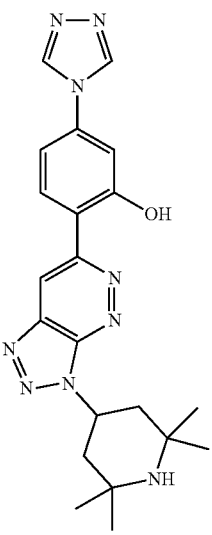 |
| 62 | 65 |
| 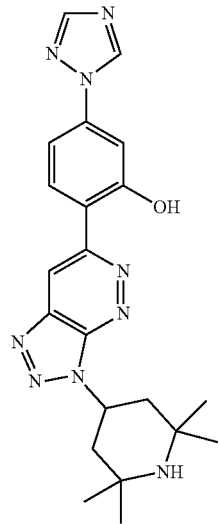 | 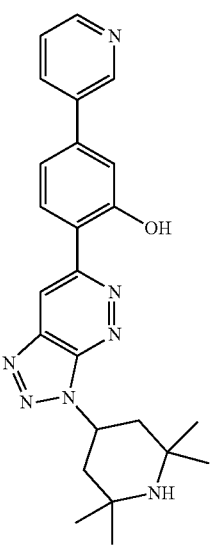 |
| 63 | 66 |
| | 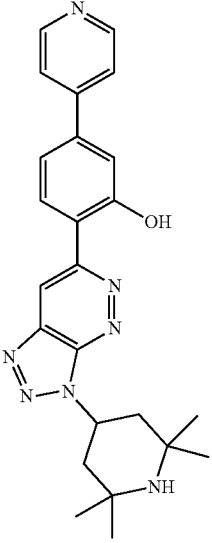 |

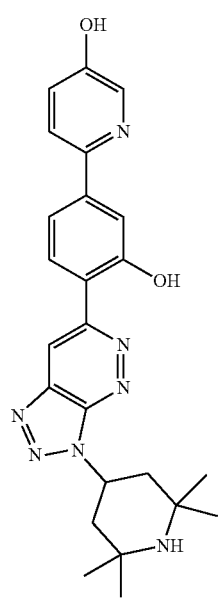
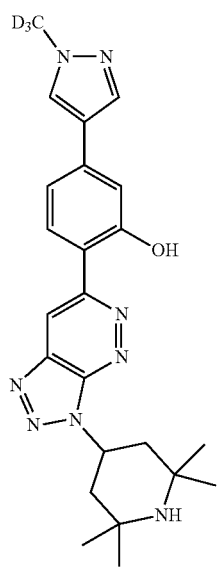

71
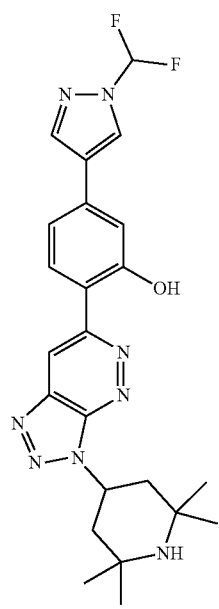
72
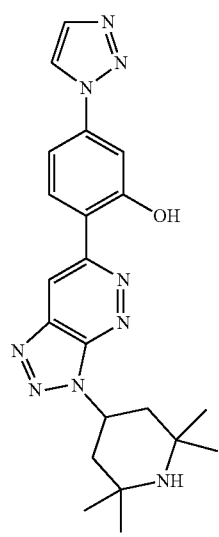
73
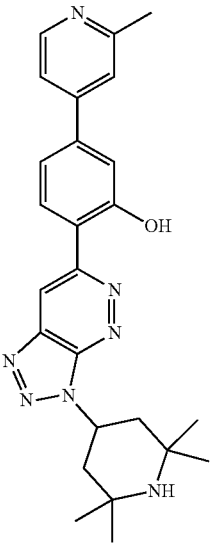
74
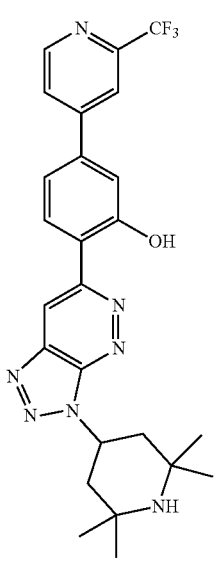
75
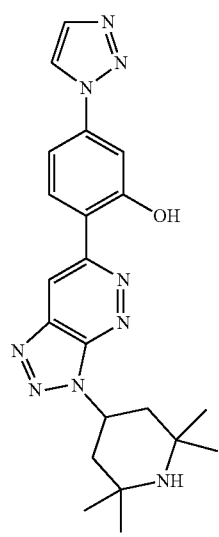

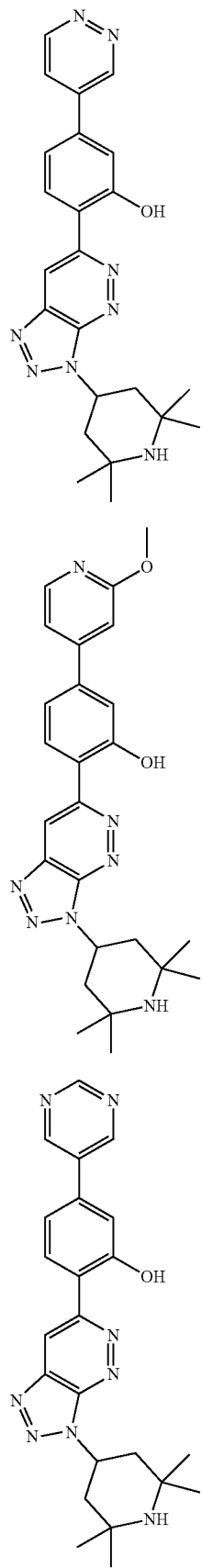
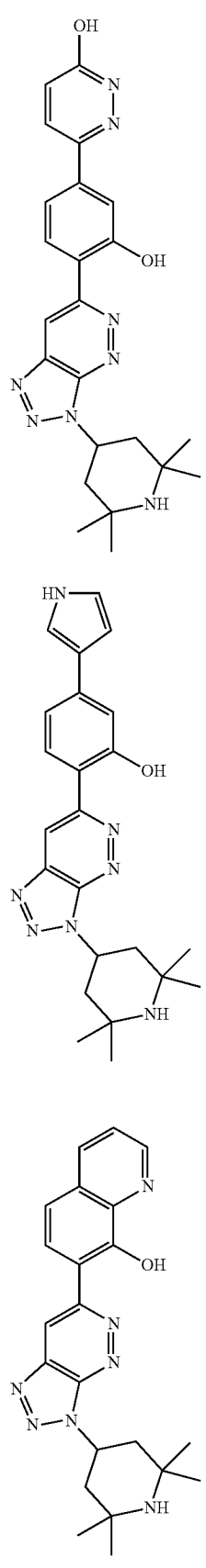

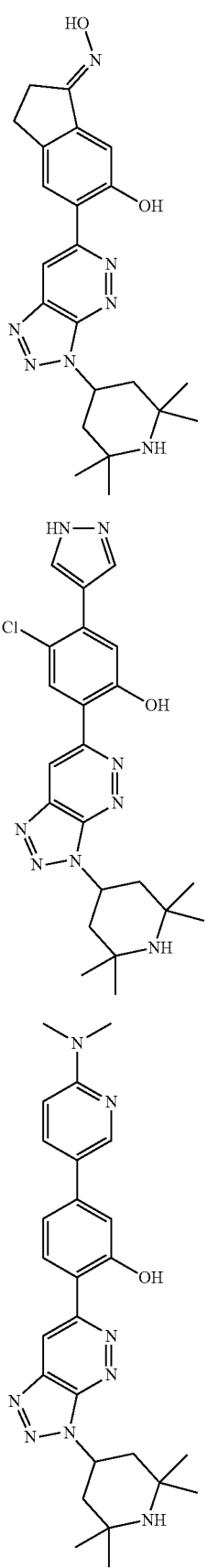

87
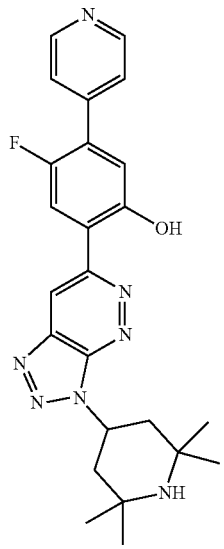
88
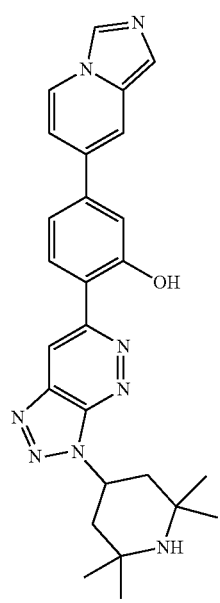
89
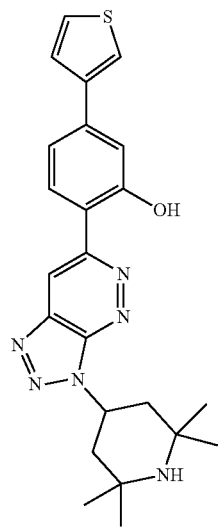
90
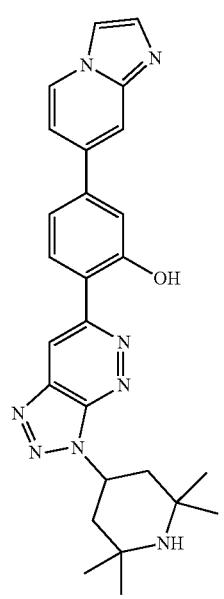
91
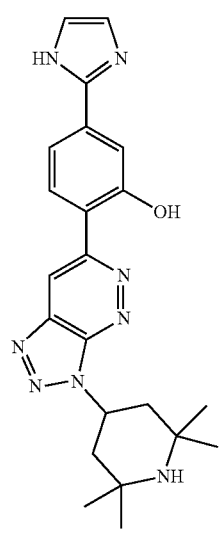
92
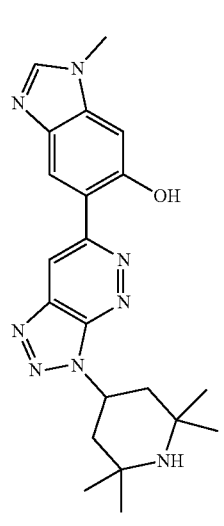

93
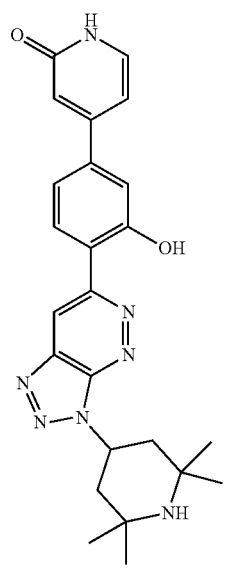
94
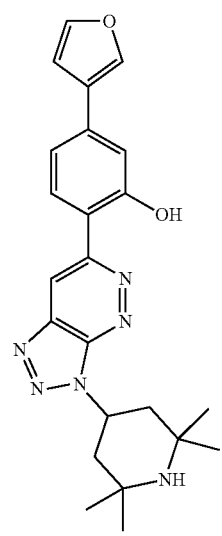
95
96
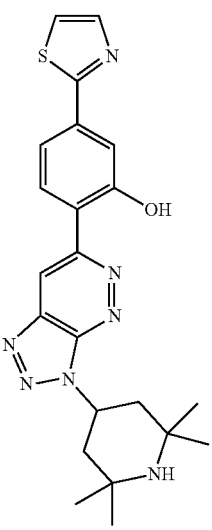
97
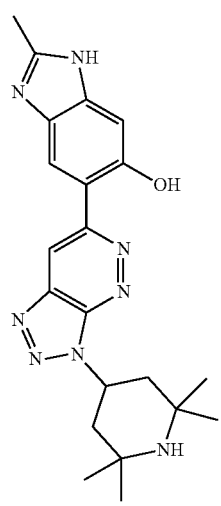
98
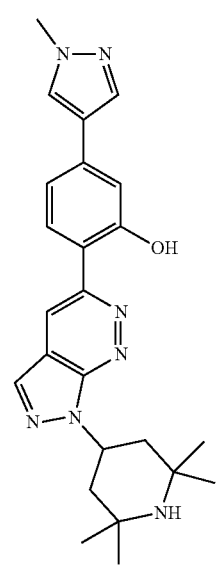

99
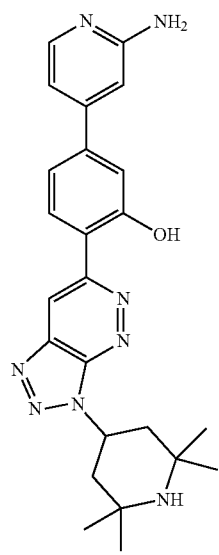
100
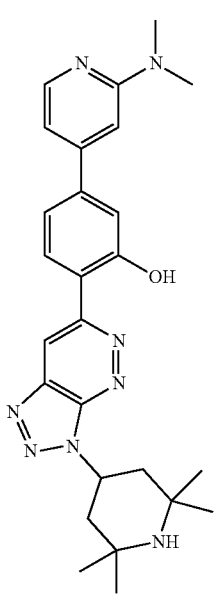
101
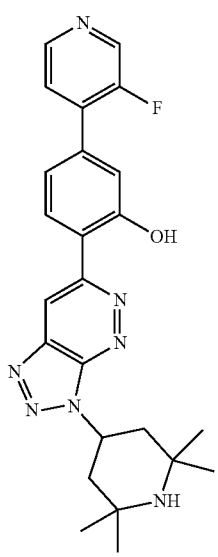
102
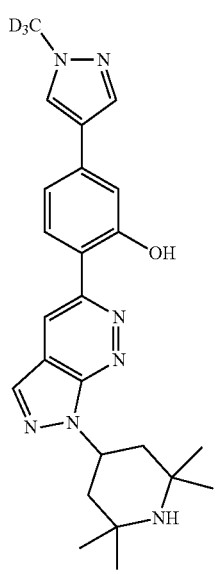

71
-continued
103
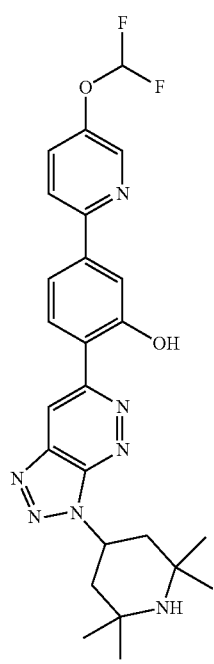
104
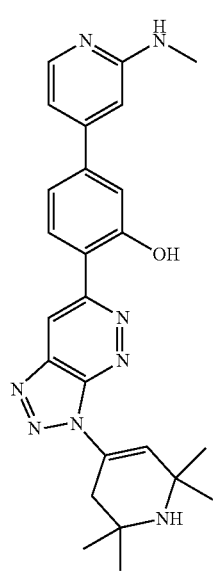
72
-continued
105
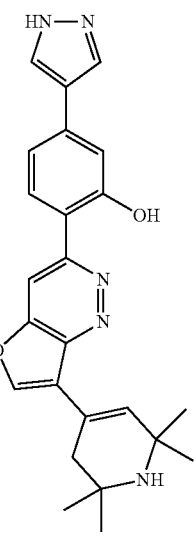
106
107

108 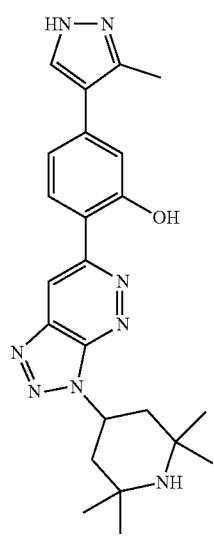
109 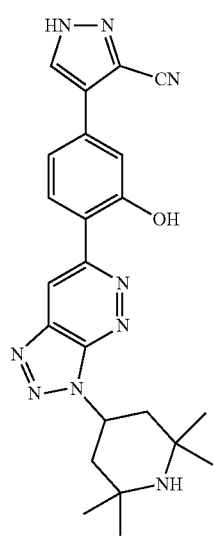
110 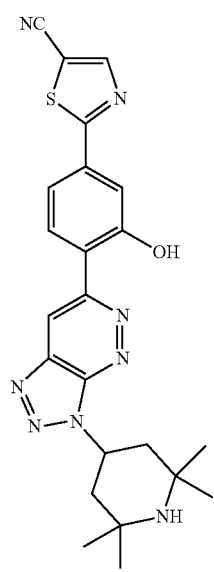
111 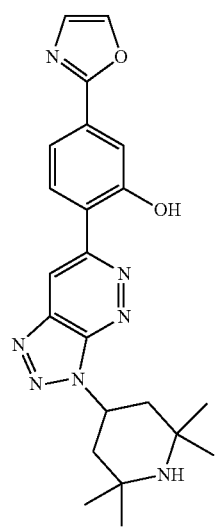
112 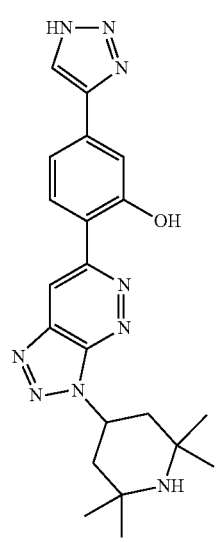
113 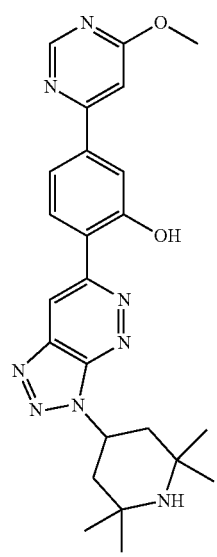

-continued

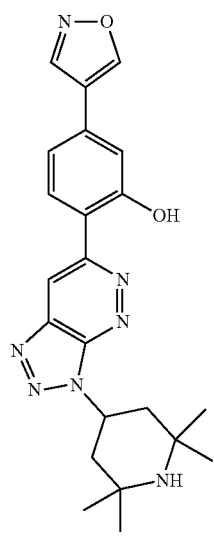
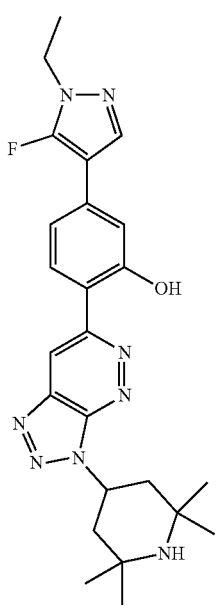

124
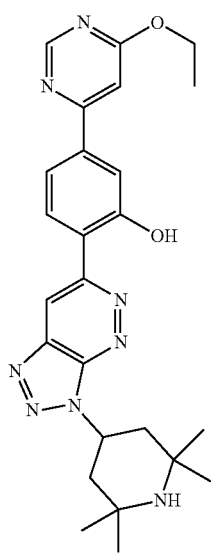
125
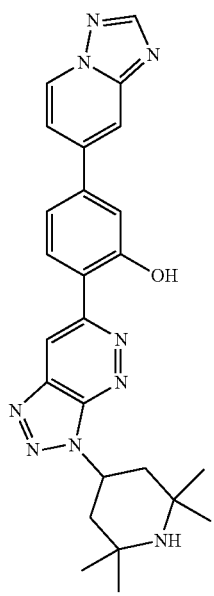
126
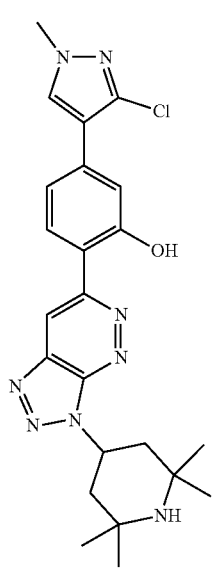
127

128 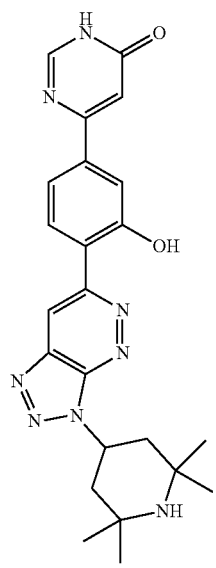
129 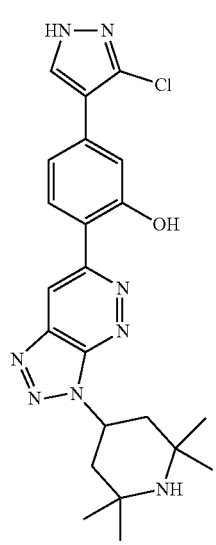
130 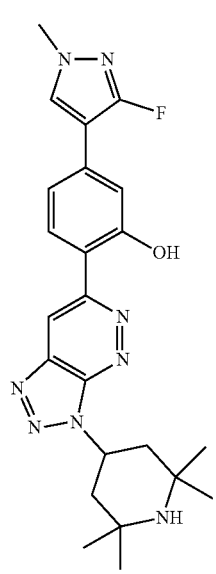
131 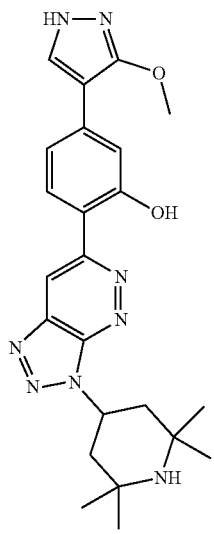
132 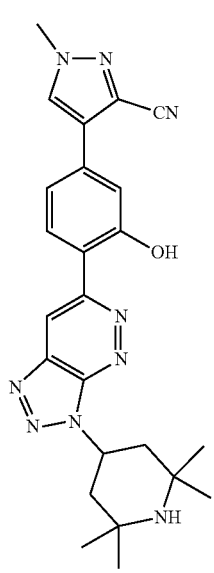
133 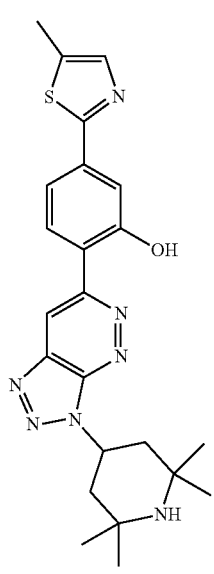

83
-continued
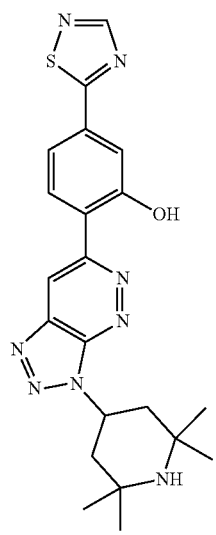
134
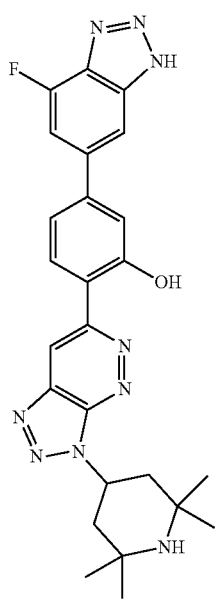
135
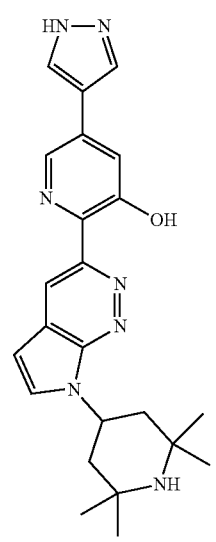
136
84
-continued
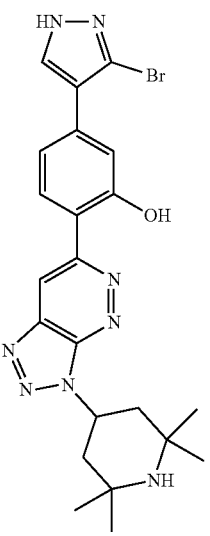
137
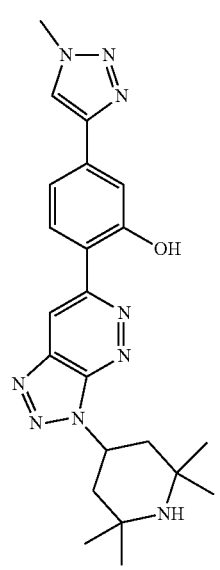
138
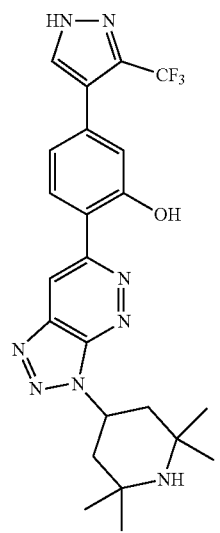
139

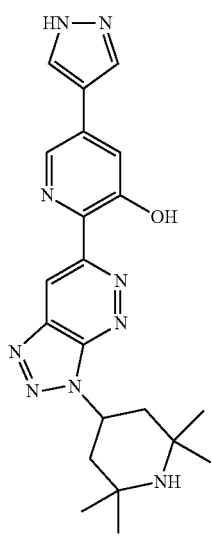
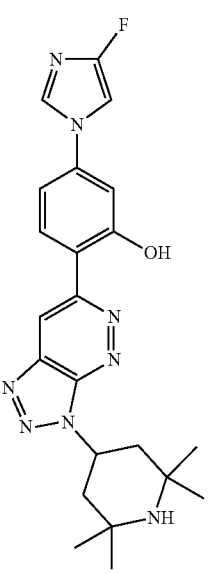

145
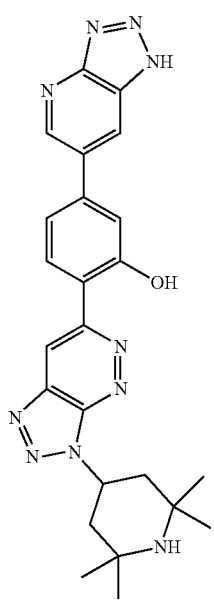
146
147
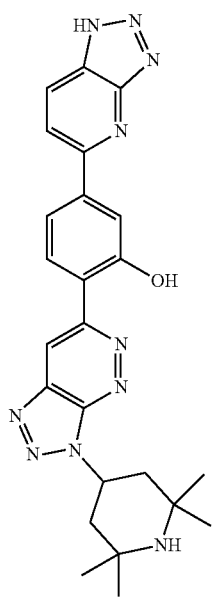
148

149
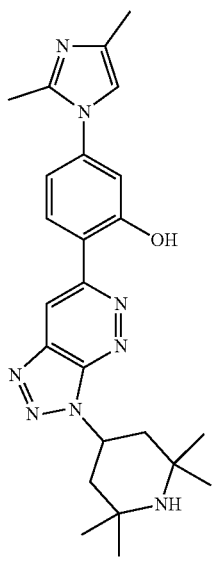
150
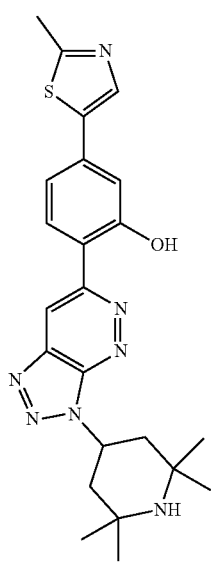
151
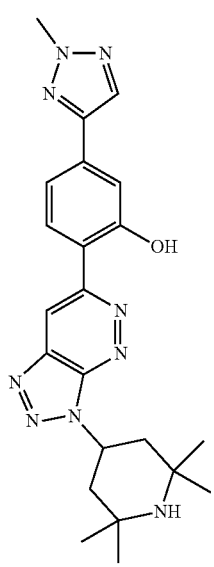
152
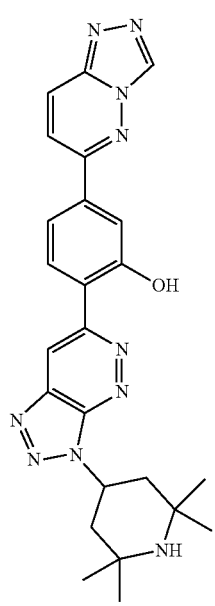
153
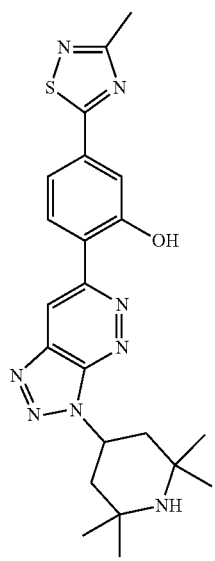

154 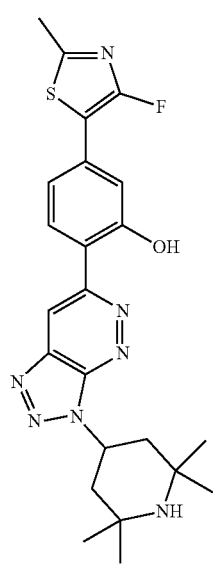
155 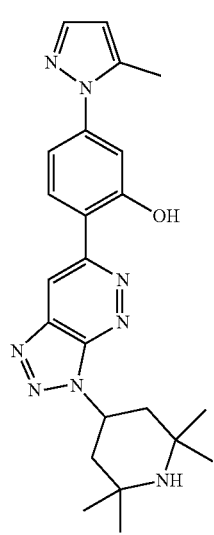
156 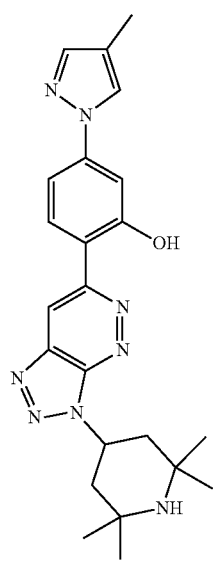
157 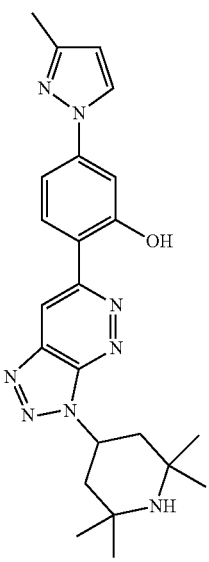
158 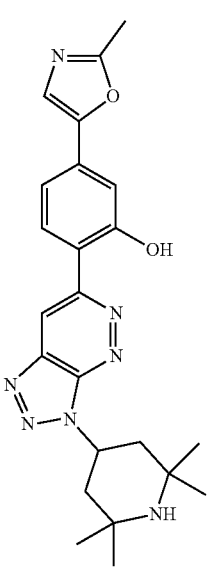
159 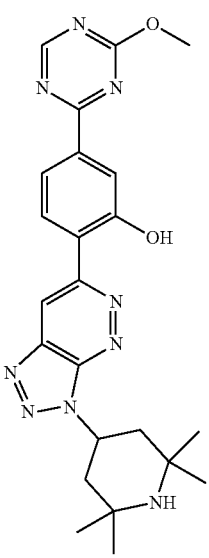

93
-continued
160
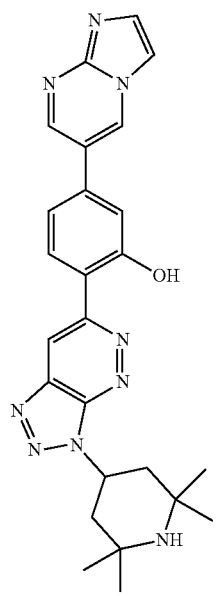
161
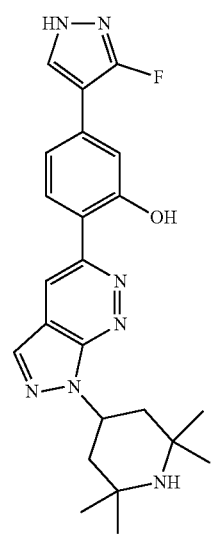
94
-continued
162
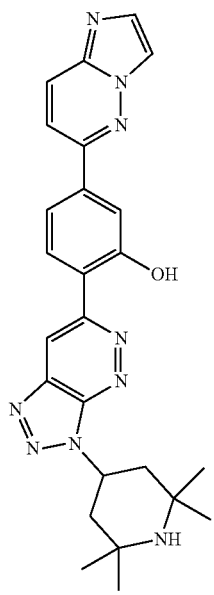
163
164

165 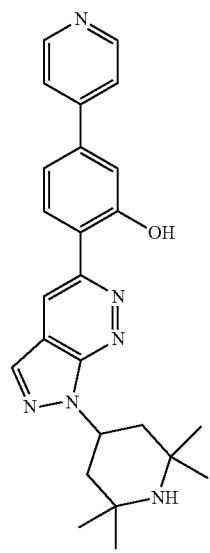
166 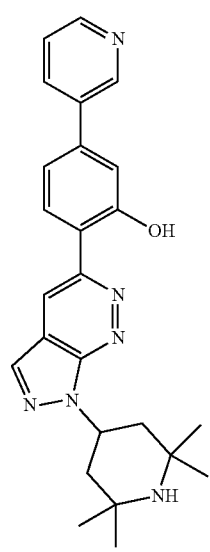
167 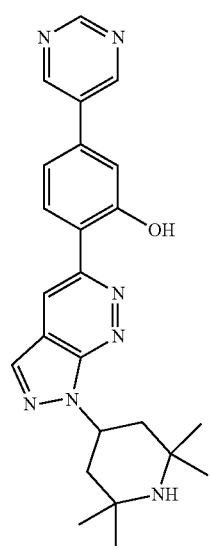
168 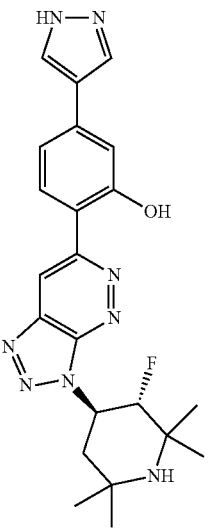
169 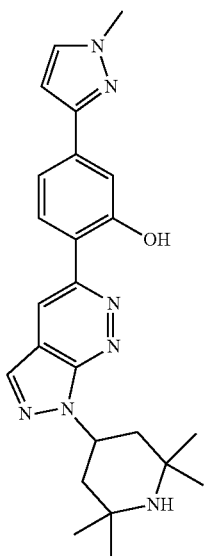
170 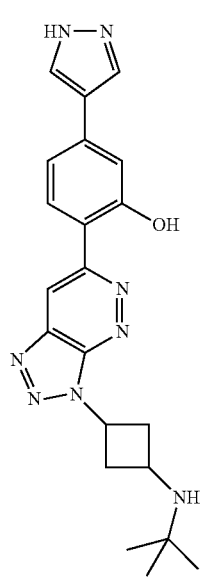

171
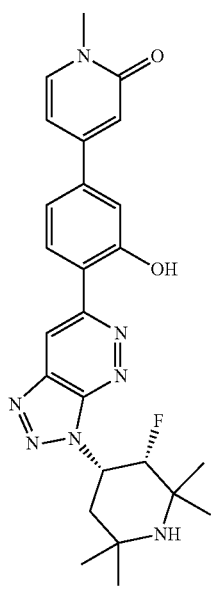
173
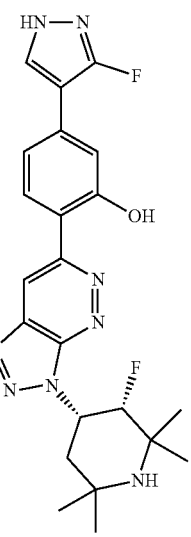
172
174
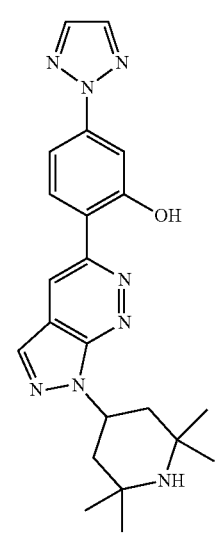

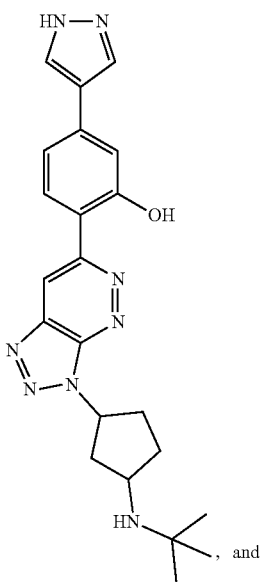
, and

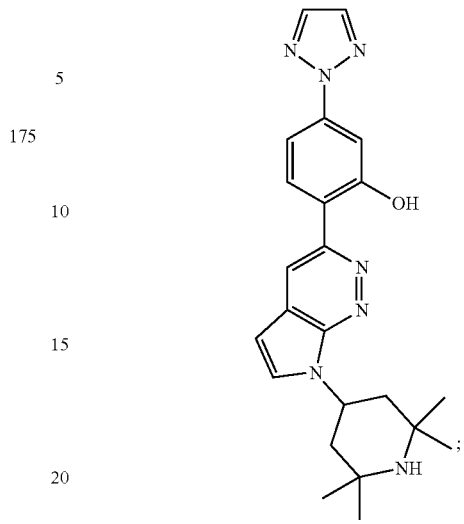
;

wherein the form of the compound is selected from the group consisting of a salt, hydrate, solvate, racemate, enantiomer, diastereomer, stereoisomer, and tautomer form thereof.

An aspect the compound of Formula (I) or a form thereof (wherein compound number (#[1]) indicates that the salt form was isolated) includes a compound selected from the group consisting of:

| Cpd | Name |
| --- | --- |
| 1[1] | 5-(1H-pyrazol-4-yl)-2-[1-(2,2,6,6-tetramethylpiperidin-4-yl)-1H-imidazo[4,5-b]pyrazin-5-yl]phenol |
| 2[1] | 5-[2,5-difluoro-4-(1H-pyrazol-4-yl)phenyl]-1-(2,2,6,6-tetramethylpiperidin-4-yl)-1H-imidazo[4,5-b]pyrazine |
| 3[1] | 5-(1H-pyrazol-4-yl)-2-[7-(2,2,6,6-tetramethylpiperidin-4-yl)-7H-imidazo[4,5-c]pyridazin-3-yl]phenol |
| 4[1] | 3-[2,5-difluoro-4-(1H-pyrazol-4-yl)phenyl]-7-(2,2,6,6-tetramethylpiperidin-4-yl)-7H-imidazo[4,5-c]pyridazine |
| 5[1] | 2-[6-methyl-7-(2,2,6,6-tetramethylpiperidin-4-yl)-7H-imidazo[4,5-c]pyridazin-3-yl]-5-(1H-pyrazol-4-yl)phenol |
| 6[1] | 3-[2,5-difluoro-4-(1H-pyrazol-4-yl)phenyl]-6-methyl-7-(2,2,6,6-tetramethylpiperidin-4-yl)-7H-imidazo[4,5-c]pyridazine |
| 7[1] | 5-(1H-pyrazol-4-yl)-2-[3-(2,2,6,6-tetramethylpiperidin-4-yl)-3H-[1,2,3]triazolo[4,5-c]pyridazin-6-yl]phenol |
| 8[1] | 5-(1H-pyrazol-4-yl)-2-[5-(2,2,6,6-tetramethyl-1,2,3,6-tetrahydropyridin-4-yl)-5H-pyrrolo[2,3-b]pyrazin-2-yl]phenol |
| 9[1] | 3-[2-hydroxy-4-(1H-pyrazol-4-yl)phenyl]-7-(2,2,6,6-tetramethylpiperidin-4-yl)-7H-imidazo[4,5-c]pyridazin-6-ol |
| 10[1] | 5-(1H-pyrazol-4-yl)-2-[5-(2,2,6,6-tetramethylpiperidin-4-yl)-5H-pyrrolo[2,3-b]pyrazin-2-yl]phenol |
| 11[1] | 5-(1H-pyrazol-4-yl)-2-[7-(1,2,3,6-tetrahydropyridin-4-yl)-5H-pyrrolo[3,2-c]pyridazin-3-yl]phenol |
| 12[1] | 2-[7-(piperidin-4-yl)-5H-pyrrolo[3,2-c]pyridazin-3-yl]-5-(1H-pyrazol-4-yl)phenol |
| 13[1] | 6-[2,3-difluoro-4-(1H-pyrazol-4-yl)phenyl]-3-(2,2,6,6-tetramethylpiperidin-4-yl)-3H-[1,2,3]triazolo[4,5-c]pyridazine |
| 14[1] | 6-[2,5-difluoro-4-(1H-pyrazol-4-yl)phenyl]-3-(2,2,6,6-tetramethylpiperidin-4-yl)-3H-[1,2,3]triazolo[4,5-c]pyridazine |
| 15[1] | 5-(1H-pyrazol-4-yl)-2-[7-(1,2,3,6-tetrahydropyridin-4-yl)thieno[3,2-c]pyridazin-3-yl]phenol |
| 16[1] | 2-[2,5-difluoro-4-(1H-pyrazol-4-yl)phenyl]-5-(2,2,6,6-tetramethylpiperidin-4-yl)-5H-pyrrolo[2,3-b]pyrazine |
| 17[1] | 5-(1H-pyrazol-4-yl)-2-[7-(2,2,6,6-tetramethyl-1,2,3,6-tetrahydropyridin-4-yl)thieno[3,2-c]pyridazin-3-yl]phenol |
| 18[1] | 2-[7-(8-azabicyclo[3.2.1]oct-2-en-3-yl)thieno[3,2-c]pyridazin-3-yl]-5-(1H-pyrazol-4-yl)phenol |
| 19[1] | 2-[1-(piperidin-4-yl)-1H-pyrazolo[3,4-b]pyrazin-5-yl]-5-(1H-pyrazol-4-yl)phenol |
| 20[1] | 5-(1H-pyrazol-4-yl)-2-[7-(2,2,6,6-tetramethyl-1,2,3,6-tetrahydropyridin-4-yl)-5H-pyrrolo[3,2-c]pyridazin-3-yl]phenol |

-continued

| Cpd | Name |
|---|---|
| 21[1] | 2-[1-(piperidin-4-yl)-1H-pyrazolo[3,4-c]pyridazin-5-yl]-5-(1H-pyrazol-4-yl)phenol |
| 22[1] | 5-(1H-pyrazol-4-yl)-2-[1-(2,2,6,6-tetramethylpiperidin-4-yl)-1H-pyrazolo[3,4-c]pyridazin-5-yl]phenol |
| 23[1] | 5-(1H-pyrazol-4-yl)-2-[7-(2,2,6,6-tetramethylpiperidin-4-yl)-6,7-dihydro-5H-pyrrolo[2,3-c]pyridazin-3-yl]phenol |
| 24[1] | 5-(1H-pyrazol-4-yl)-2-[7-(2,2,6,6-tetramethylpiperidin-4-yl)thieno[3,2-c]pyridazin-3-yl]phenol |
| 25[1] | 2-[7-(3-oxa-9-azabicyclo[3.3.1]non-6-en-7-yl)thieno[3,2-c]pyridazin-3-yl]-5-(1H-pyrazol-4-yl)phenol |
| 26[1] | 5-(1H-pyrazol-4-yl)-2-[7-(2,2,6,6-tetramethylpiperidin-4-yl)-7H-pyrrolo[2,3-c]pyridazin-3-yl]phenol |
| 27[1] | 2-[7-(8-azabicyclo[3.2.1]oct-2-en-3-yl)-5H-pyrrolo[3,2-c]pyridazin-3-yl]-5-(1H-pyrazol-4-yl)phenol |
| 28[1] | 2-[7-(3-oxa-9-azabicyclo[3.3.1]non-6-en-7-yl)-5H-pyrrolo[3,2-c]pyridazin-3-yl]-5-(1H-pyrazol-4-yl)phenol |
| 29[1] | 2-[7-(8-azabicyclo[3.2.1]oct-3-yl)-5H-pyrrolo[3,2-c]pyridazin-3-yl]-5-(1H-pyrazol-4-yl)phenol |
| 30[1] | 2-[7-(3-oxa-9-azabicyclo[3.3.1]non-7-yl)-5H-pyrrolo[3,2-c]pyridazin-3-yl]-5-(1H-pyrazol-4-yl)phenol |
| 31[1] | 5-(1H-pyrazol-4-yl)-2-[7-(2,2,6,6-tetramethylpiperidin-4-yl)-5H-pyrrolo[3,2-c]pyridazin-3-yl]phenol |
| 32[1] | 3-[2,3-difluoro-4-(1H-pyrazol-4-yl)phenyl]-7-(2,2,6,6-tetramethylpiperidin-4-yl)-6,7-dihydro-5H-pyrrolo[2,3-c]pyridazine |
| 33[1] | 4-fluoro-2-(1H-pyrazol-4-yl)-5-[3-(2,2,6,6-tetramethylpiperidin-4-yl)-3H-[1,2,3]triazolo[4,5-c]pyridazin-6-yl]phenol |
| 34 | 5-(1H-pyrazol-1-yl)-2-[3-(2,2,6,6-tetramethylpiperidin-4-yl)-3H-[1,2,3]triazolo[4,5-c]pyridazin-6-yl]phenol |
| 35[1] | 4-fluoro-5-(1H-pyrazol-4-yl)-2-[3-(2,2,6,6-tetramethylpiperidin-4-yl)-3H-[1,2,3]triazolo[4,5-c]pyridazin-6-yl]phenol |
| 36[1] | 7-[(3-exo)-8-azabicyclo[3.2.1]oct-3-yl]-3-[2,3-difluoro-4-(1H-pyrazol-4-yl)phenyl]-6,7-dihydro-5H-pyrrolo[2,3-c]pyridazine |
| 37 | 4-{3-hydroxy-4-[3-(2,2,6,6-tetramethylpiperidin-4-yl)-3H-[1,2,3]triazolo[4,5-c]pyridazin-6-yl]phenyl}-1-methylpyridin-2(1H)-one |
| 38[1] | 4-[3-(2,2,6,6-tetramethylpiperidin-4-yl)-3H-[1,2,3]triazolo[4,5-c]pyridazin-6-yl]biphenyl-3,4'-diol |
| 39[1] | 5-(1-methyl-1H-pyrazol-4-yl)-2-[3-(2,2,6,6-tetramethylpiperidin-4-yl)-3H-[1,2,3]triazolo[4,5-c]pyridazin-6-yl]phenol |
| 40[1] | 2-[6-methoxy-7-(2,2,6,6-tetramethylpiperidin-4-yl)-7H-imidazo[4,5-c]pyridazin-3-yl]-5-(1H-pyrazol-4-yl)phenol |
| 42[1] | 2-[6-(methylamino)-7-(2,2,6,6-tetramethylpiperidin-4-yl)-7H-imidazo[4,5-c]pyridazin-3-yl]-5-(1H-pyrazol-4-yl)phenol |
| 43 | 2-[7-(piperazin-1-yl)-5H-pyrrolo[3,2-c]pyridazin-3-yl]-5-(1H-pyrazol-4-yl)phenol |
| 46 | 5-(1-ethyl-1H-pyrazol-4-yl)-2-[3-(2,2,6,6-tetramethylpiperidin-4-yl)-3H-[1,2,3]triazolo[4,5-c]pyridazin-6-yl]phenol |
| 47 | 5-(1-propyl-1H-pyrazol-4-yl)-2-[3-(2,2,6,6-tetramethylpiperidin-4-yl)-3H-[1,2,3]triazolo[4,5-c]pyridazin-6-yl]phenol |
| 48 | 5-(1H-pyrazol-3-yl)-2-[3-(2,2,6,6-tetramethylpiperidin-4-yl)-3H-[1,2,3]triazolo[4,5-c]pyridazin-6-yl]phenol |
| 49[1] | 2-[6-(ethylamino)-7-(2,2,6,6-tetramethylpiperidin-4-yl)-7H-imidazo[4,5-c]pyridazin-3-yl]-5-(1H-pyrazol-4-yl)phenol |
| 50 | 5-(1-methyl-1H-pyrazol-5-yl)-2-[3-(2,2,6,6-tetramethylpiperidin-4-yl)-3H-[1,2,3]triazolo[4,5-c]pyridazin-6-yl]phenol |
| 51 | 5-(1-methyl-1H-pyrazol-3-yl)-2-[3-(2,2,6,6-tetramethylpiperidin-4-yl)-3H-[1,2,3]triazolo[4,5-c]pyridazin-6-yl]phenol |
| 52[1] | 2-[3-(1,2,2,6,6-pentamethylpiperidin-4-yl)-3H-[1,2,3]triazolo[4,5-c]pyridazin-6-yl]-5-(1H-pyrazol-4-yl)phenol |
| 53[1] | 6-fluoro-4-[3-(2,2,6,6-tetramethylpiperidin-4-yl)-3H-[1,2,3]triazolo[4,5-c]pyridazin-6-yl][1,1'-biphenyl]-3,4'-diol |
| 54[1] | 2-fluoro-3-(1H-pyrazol-4-yl)-6-[3-(2,2,6,6-tetramethylpiperidin-4-yl)-3H-[1,2,3]triazolo[4,5-c]pyridazin-6-yl]phenol |
| 55[1] | 4-{2-fluoro-5-hydroxy-4-[3-(2,2,6,6-tetramethylpiperidin-4-yl)-3H-[1,2,3]triazolo[4,5-c]pyridazin-6-yl]phenyl}-1-methylpyridin-2(1H)-one |
| 56[1] | 2-[3-(2,2-dimethylpiperidin-4-yl)-3H-[1,2,3]triazolo[4,5-c]pyridazin-6-yl]-5-(1H-pyrazol-4-yl)phenol |
| 57[1] | 2-{3-[(1R,5S)-1,5-dimethyl-8-azabicyclo[3.2.1]octan-3-yl]-3H-[1,2,3]triazolo[4,5-c]pyridazin-6-yl}-5-(1H-pyrazol-4-yl)phenol |
| 58[1] | 2-(1H-pyrazol-4-yl)-5-[3-(2,2,6,6-tetramethylpiperidin-4-yl)-3H-[1,2,3]triazolo[4,5-c]pyridazin-6-yl]benzene-1,4-diol |
| 59[1] | 3-fluoro-5-(1H-pyrazol-4-yl)-2-[3-(2,2,6,6-tetramethylpiperidin-4-yl)-3H-[1,2,3]triazolo[4,5-c]pyridazin-6-yl]phenol |
| 60[1] | 5-(pyrazin-2-yl)-2-[3-(2,2,6,6-tetramethylpiperidin-4-yl)-3H-[1,2,3]triazolo[4,5-c]pyridazin-6-yl]phenol |
| 61[1] | 5-(pyridin-2-yl)-2-[3-(2,2,6,6-tetramethylpiperidin-4-yl)-3H-[1,2,3]triazolo[4,5-c]pyridazin-6-yl]phenol |
| 62[1] | 4-fluoro-5-(1-methyl-1H-pyrazol-4-yl)-2-[3-(2,2,6,6-tetramethylpiperidin-4-yl)-3H-[1,2,3]triazolo[4,5-c]pyridazin-6-yl]phenol |

-continued

| Cpd | Name |
|---|---|
| 63[1] | 2-[3-(2,2,6,6-tetramethylpiperidin-4-yl)-3H-[1,2,3]triazolo[4,5-c]pyridazin-6-yl]-5-(1H-1,2,4-triazol-1-yl)phenol |
| 64[1] | 2-[3-(2,2,6,6-tetramethylpiperidin-4-yl)-3H-[1,2,3]triazolo[4,5-c]pyridazin-6-yl]-5-(4H-1,2,4-triazol-4-yl)phenol |
| 65[1] | 5-(pyridin-3-yl)-2-[3-(2,2,6,6-tetramethylpiperidin-4-yl)-3H-[1,2,3]triazolo[4,5-c]pyridazin-6-yl]phenol |
| 66[1] | 5-(pyridin-4-yl)-2-[3-(2,2,6,6-tetramethylpiperidin-4-yl)-3H-[1,2,3]triazolo[4,5-c]pyridazin-6-yl]phenol |
| 67[1] | 6-{3-hydroxy-4-[3-(2,2,6,6-tetramethylpiperidin-4-yl)-3H-[1,2,3]triazolo[4,5-c]pyridazin-6-yl]phenyl}pyridin-3-ol |
| 68[1] | 2-{3-hydroxy-4-[3-(2,2,6,6-tetramethylpiperidin-4-yl)-3H-[1,2,3]triazolo[4,5-c]pyridazin-6-yl]phenyl}pyrimidin-5-ol |
| 69[1] | 5-[1-($^2H_3$)methyl-1H-pyrazol-4-yl]-2-[3-(2,2,6,6-tetramethylpiperidin-4-yl)-3H-[1,2,3]triazolo[4,5-c]pyridazin-6-yl]phenol |
| 70[1] | 5-(1H-imidazol-1-yl)-2-[3-(2,2,6,6-tetramethylpiperidin-4-yl)-3H-[1,2,3]triazolo[4,5-c]pyridazin-6-yl]phenol |
| 71[1] | 5-[1-(difluoromethyl)-1H-pyrazol-4-yl]-2-[3-(2,2,6,6-tetramethylpiperidin-4-yl)-3H-[1,2,3]triazolo[4,5-c]pyridazin-6-yl]phenol |
| 72[1] | 2-[3-(2,2,6,6-tetramethylpiperidin-4-yl)-3H-[1,2,3]triazolo[4,5-c]pyridazin-6-yl]-5-(1H-1,2,3-triazol-1-yl)phenol |
| 73[1] | 5-(2-methylpyridin-4-yl)-2-[3-(2,2,6,6-tetramethylpiperidin-4-yl)-3H-[1,2,3]triazolo[4,5-c]pyridazin-6-yl]phenol |
| 74[1] | 2-[3-(2,2,6,6,-tetramethylpiperidin-4-yl)-3H-[1,2,3]triazolo[4,5-c]pyridazin-6-yl]-5-[2-(trifluoromethyl)pyridin-4-yl]phenol |
| 75[1] | 5-(pyrimidin-4-yl)-2-[3-(2,2,6,6-tetramethylpiperidin-4-yl)-3H-[1,2,3]triazolo[4,5-c]pyridazin-6-yl]phenol |
| 76[1] | 5-(pyridazin-4-yl)-2-[3-(2,2,6,6-tetramethylpiperidin-4-yl)-3H-[1,2,3]triazolo[4,5-c]pyridazin-6-yl]phenol |
| 77[1] | 5-(2-methoxypyridin-4-yl)-2-[3-(2,2,6,6-tetramethylpiperidin-4-yl)-3H-[1,2,3]triazolo[4,5-c]pyridazin-6-yl]phenol |
| 78 | 5-(pyrimidin-5-yl)-2-[3-(2,2,6,6-tetramethylpiperidin-4-yl)-3H-[1,2,3]triazolo[4,5-c]pyridazin-6-yl]phenol |
| 79[1] | 6-{3-hydroxy-4-[3-(2,2,6,6-tetramethylpiperidin-4-yl)-3H-[1,2,3]triazolo[4,5-c]pyridazin-6-yl]phenyl}pyridazin-3-ol |
| 80 | 5-(1H-pyrrol-3-yl)-2-[3-(2,2,6,6-tetramethylpiperidin-4-yl)-3H-[1,2,3]triazolo[4,5-c]pyridazin-6-yl]phenol |
| 81[1] | 6-[3-(2,2,6,6-tetramethylpiperidin-4-yl)-3H-[1,2,3]triazolo[4,5-c]pyridazin-6-yl]quinolin-7-ol |
| 82 | (3E)-3-(hydroxyimino)-6-[3-(2,2,6,6-tetramethylpiperidin-4-yl)-3H-[1,2,3]triazolo[4,5-c]pyridazin-6-yl]-2,3-dihydro-1H-inden-5-ol |
| 83[1] | 4-chloro-5-(1H-pyrazol-4-yl)-2-[3-(2,2,6,6-tetramethylpiperidin-4-yl)-3H-[1,2,3]triazolo[4,5-c]pyridazin-6-yl]phenol |
| 84 | 5-[6-(dimethylamino)pyridin-3-yl]-2-[3-(2,2,6,6-tetramethylpiperidin-4-yl)-3H-[1,2,3]triazolo[4,5-c]pyridazin-6-yl]phenol |
| 85 | 5-(imidazo[1,2-a]pyrazin-3-yl)-2-[3-(2,2,6,6-tetramethylpiperidin-4-yl)-3H-[1,2,3]triazolo[4,5-c]pyridazin-6-yl]phenol |
| 86 | 1-cyclopropyl-4-{3-hydroxy-4-[3-(2,2,6,6-tetramethylpiperidin-4-yl)-3H-[1,2,3]triazolo[4,5-c]pyridazin-6-yl]phenyl}pyridin-2(1H)-one |
| 87[1] | 4-fluoro-5-(pyridin-4-yl)-2-[3-(2,2,6,6-tetramethylpiperidin-4-yl)-3H-[1,2,3]triazolo[4,5-c]pyridazin-6-yl]phenol |
| 88 | 5-(imidazo[1,5-a]pyridin-7-yl)-2-[3-(2,2,6,6-tetramethylpiperidin-4-yl)-3H-[1,2,3]triazolo[4,5-c]pyridazin-6-yl]phenol |
| 89[1] | 2-[3-(2,2,6,6-tetramethylpiperidin-4-yl)-3H-[1,2,3]triazolo[4,5-c]pyridazin-6-yl]-5-(thiophen-3-yl)phenol |
| 90 | 5-(imidazo[1,2-a]pyridin-7-yl)-2-[3-(2,2,6,6-tetramethylpiperidin-4-yl)-3H-[1,2,3]triazolo[4,5-c]pyridazin-6-yl]phenol |
| 91 | 5-(1H-imidazol-2-yl)-2-[3-(2,2,6,6-tetramethylpiperidin-4-yl)-3H-[1,2,3]triazolo[4,5-c]pyridazin-6-yl]phenol |
| 92 | 1-methyl-5-[3-(2,2,6,6-tetramethylpiperidin-4-yl)-3H-[1,2,3]triazolo[4,5-c]pyridazin-6-yl]-1H-benzimidazol-6-ol |
| 93[1] | 4-{3-hydroxy-4-[3-(2,2,6,6-tetramethylpiperidin-4-yl)-3H-[1,2,3]triazolo[4,5-c]pyridazin-6-yl]phenyl}pyridin-2(1H)-one |
| 94 | 5-[3-(2,2,6,6-tetramethylpiperidin-4-yl)-3H-[1,2,3]triazolo[4,5-c]pyridazin-6-yl]-1H-indazol-6-ol |
| 95[1] | 5-(furan-3-yl)-2-[3-(2,2,6,6-tetramethylpiperidin-4-yl)-3H-[1,2,3]triazolo[4,5-c]pyridazin-6-yl]phenol |
| 96[1] | 2-[3-(2,2,6,6-tetramethylpiperidin-4-yl)-3H-[1,2,3]triazolo[4,5-c]pyridazin-6-yl]-5-(1,3-thiazol-2-yl)phenol |
| 97 | 2-methyl-5-[3-(2,2,6,6-tetramethylpiperidin-4-yl)-3H-[1,2,3]triazolo[4,5-c]pyridazin-6-yl]-1H-benzimidazol-6-ol |
| 98[1] | 5-(1-methyl-1H-pyrazol-4-yl)-2-[1-(2,2,6,6-tetramethylpiperidin-4-yl)-1H-pyrazolo[3,4-c]pyridazin-5-yl]phenol |
| 99 | 5-(2-aminopyridin-4-yl)-2-[3-(2,2,6,6-tetramethylpiperidin-4-yl)-3H-[1,2,3]triazolo[4,5-c]pyridazin-6-yl]phenol |

-continued

| Cpd | Name |
|---|---|
| 100 | 5-[2-(dimethylamino)pyridin-4-yl]-2-[3-(2,2,6,6-tetramethylpiperidin-4-yl)-3H-[1,2,3]triazolo[4,5-c]pyridazin-6-yl]phenol |
| 101 | 5-(3-fluoropyridin-4-yl)-2-[3-(2,2,6,6-tetramethylpiperidin-4-yl)-3H-[1,2,3]triazolo[4,5-c]pyridazin-6-yl]phenol |
| 102[1] | 5-[1-($^2$H$_3$)methyl-1H-pyrazol-4-yl]-2-[1-(2,2,6,6-tetramethylpiperidin-4-yl)-1H-pyrazolo[3,4-c]pyridazin-5-yl]phenol |
| 103[1] | 5-[5-(difluoromethoxy)pyridin-2-yl]-2-[3-(2,2,6,6-tetramethylpiperidin-4-yl)-3H-[1,2,3]triazolo[4,5-c]pyridazin-6-yl]phenol |
| 104 | 5-[2-(methylamino)pyridin-4-yl]-2-[3-(2,2,6,6-tetramethylpiperidin-4-yl)-3H-[1,2,3]triazolo[4,5-c]pyridazin-6-yl]phenol |
| 105[1] | 5-(1H-pyrazol-4-yl)-2-[7-(2,2,6,6-tetramethyl-1,2,3,6-tetrahydropyridin-4-yl)furo[3,2-c]pyridazin-3-yl]phenol |
| 106[1] | 5-(3-fluoro-1H-pyrazol-4-yl)-2-[3-(2,2,6,6-tetramethylpiperidin-4-yl)-3H-[1,2,3]triazolo[4,5-c]pyridazin-6-yl]phenol |
| 107[1] | 2-[3-(2,2,6,6-tetramethylpiperidin-4-yl)-3H-[1,2,3]triazolo[4,5-c]pyridazin-6-yl]-5-(1,3-thiazol-5-yl)phenol |
| 108[1] | 5-(3-methyl-1H-pyrazol-4-yl)-2-[3-(2,2,6,6-tetramethylpiperidin-4-yl)-3H-[1,2,3]triazolo[4,5-c]pyridazin-6-yl]phenol |
| 109[1] | 4-{3-hydroxy-4-[3-(2,2,6,6-tetramethylpiperidin-4-yl)-3H-[1,2,3]triazolo[4,5-c]pyridazin-6-yl]phenyl}-1H-pyrazole-3-carbonitrile |
| 110[1] | 2-{3-hydroxy-4-[3-(2,2,6,6-tetramethylpiperidin-4-yl)-3H-[1,2,3]triazolo[4,5-c]pyridazin-6-yl]phenyl}-1,3-thiazole-5-carbonitrile |
| 111[1] | 5-(1,3-oxazol-2-yl)-2-[3-(2,2,6,6-tetramethylpiperidin-4-yl)-3H-[1,2,3]triazolo[4,5-c]pyridazin-6-yl]phenol |
| 112 | 2-[3-(2,2,6,6-tetramethylpiperidin-4-yl)-3H-[1,2,3]triazolo[4,5-c]pyridazin-6-yl]-5-(1H-1,2,3-triazol-4-yl)phenol |
| 113 | 5-(6-methoxypyrimidin-4-yl)-2-[3-(2,2,6,6-tetramethylpiperidin-4-yl)-3H-[1,2,3]triazolo[4,5-c]pyridazin-6-yl]phenol |
| 114[1] | 5-[2-(difluoromethoxy)pyridin-4-yl]-2-[3-(2,2,6,6-tetramethylpiperidin-4-yl)-3H-[1,2,3]triazolo[4,5-c]pyridazin-6-yl]phenol |
| 115 | 5-(1H-imidazol-4-yl)-2-[3-(2,2,6,6-tetramethylpiperidin-4-yl)-3H-[1,2,3]triazolo[4,5-c]pyridazin-6-yl]phenol |
| 116[1] | 2-[3-(2,2,6,6-tetramethylpiperidin-4-yl)-3H-[1,2,3]triazolo[4,5-c]pyridazin-6-yl]-5-(1,3,4-thiadiazol-2-yl)phenol |
| 117[1] | 6-[4-(1H-pyrazol-4-yl)-1H-benzotriazol-7-yl]-3-(2,2,6,6-tetramethylpiperidin-4-yl)-3H-[1,2,3]triazolo[4,5-c]pyridazine |
| 118[1] | 5-(1H-pyrrolo[2,3-b]pyridin-4-yl)-2-[3-(2,2,6,6-tetramethylpiperidin-4-yl)-3H-[1,2,3]triazolo[4,5-c]pyridazin-6-yl]phenol |
| 119[1] | 5-(2-methoxypyrimidin-4-yl)-2-[3-(2,2,6,6-tetramethylpiperidin-4-yl)-3H-[1,2,3]triazolo[4,5-c]pyridazin-6-yl]phenol |
| 120[1] | 5-(1,2-oxazol-4-yl)-2-[3-(2,2,6,6-tetramethylpiperidin-4-yl)-3H-[1,2,3]triazolo[4,5-c]pyridazin-6-yl]phenol |
| 121[1] | 5-(5-fluoro-1-methyl-1H-pyrazol-4-yl)-2-[3-(2,2,6,6-tetramethylpiperidin-4-yl)-3H-[1,2,3]triazolo[4,5-c]pyridazin-6-yl]phenol |
| 122[1] | 5-(1-ethyl-5-fluoro-1H-pyrazol-4-yl)-2-[3-(2,2,6,6-tetramethylpiperidin-4-yl)-3H-[1,2,3]triazolo[4,5-c]pyridazin-6-yl]phenol |
| 123[1] | 5-(2-ethoxypyridin-4-yl)-2-[3-(2,2,6,6-tetramethylpiperidin-4-yl)-3H-[1,2,3]triazolo[4,5-c]pyridazin-6-yl]phenol |
| 124[1] | 5-(6-ethoxypyrimidin-4-yl)-2-[3-(2,2,6,6-tetramethylpiperidin-4-yl)-3H-[1,2,3]triazolo[4,5-c]pyridazin-6-yl]phenol |
| 125[1] | 2-[3-(2,2,6,6-tetramethylpiperidin-4-yl)-3H-[1,2,3]triazolo[4,5-c]pyridazin-6-yl]-5-([1,2,3]triazolo[1,5-a]pyridin-5-yl)phenol |
| 126[1] | 2-[3-(2,2,6,6-tetramethylpiperidin-4-yl)-3H-[1,2,3]triazolo[4,5-c]pyridazin-6-yl]-5-([1,2,4]triazolo[1,5-a]pyridin-7-yl)phenol |
| 127[1] | 5-(3-chloro-1-methyl-1H-pyrazol-4-yl)-2-[3-(2,2,6,6-tetramethylpiperidin-4-yl)-3H-[1,2,3]triazolo[4,5-c]pyridazin-6-yl]phenol |
| 128[1] | 6-{3-hydroxy-4-[3-(2,2,6,6-tetramethylpiperidin-4-yl)-3H-[1,2,3]triazolo[4,5-c]pyridazin-6-yl]phenyl}pyrimidin-4(3H)-one |
| 129[1] | 5-(3-chloro-1H-pyrazol-4-yl)-2-[3-(2,2,6,6-tetramethylpiperidin-4-yl)-3H-[1,2,3]triazolo[4,5-c]pyridazin-6-yl]phenol |
| 130[1] | 5-(3-fluoro-1-methyl-1H-pyrazol-4-yl)-2-[3-(2,2,6,6-tetramethylpiperidin-4-yl)-3H-[1,2,3]triazolo[4,5-c]pyridazin-6-yl]phenol |
| 131[1] | 5-(3-methoxy-1H-pyrazol-4-yl)-2-[3-(2,2,6,6-tetramethylpiperidin-4-yl)-3H-[1,2,3]triazolo[4,5-c]pyridazin-6-yl]phenol |
| 132[1] | 4-{3-hydroxy-4-[3-(2,2,6,6-tetramethylpiperidin-4-yl)-3H-[1,2,3]triazolo[4,5-c]pyridazin-6-yl]phenyl}-1-methyl-1H-pyrazole-3-carbonitrile |
| 133[1] | 5-(5-methyl-1,3-thiazol-2-yl)-2-[3-(2,2,6,6-tetramethylpiperidin-4-yl)-3H-[1,2,3]triazolo[4,5-c]pyridazin-6-yl]phenol |
| 134[1] | 2-[3-(2,2,6,6-tetramethylpiperidin-4-yl)-3H-[1,2,3]triazolo[4,5-c]pyridazin-6-yl]-5-(1,2,4-thiadiazol-5-yl)phenol |
| 135[1] | 5-(4-fluoro-1H-benzotriazol-6-yl)-2-[3-(2,2,6,6-tetramethylpiperidin-4-yl)-3H-[1,2,3]triazolo[4,5-c]pyridazin-6-yl]phenol |
| 136[1] | 5-(1H-pyrazol-4-yl)-2-[7-(2,2,6,6-tetramethylpiperidin-4-yl)-7H-pyrrolo[2,3-c]pyridazin-3-yl]pyridin-3-ol |
| 137[1] | 5-(3-bromo-1H-pyrazol-4-yl)-2-[3-(2,2,6,6-tetramethylpiperidin-4-yl)-3H-[1,2,3]triazolo[4,5-c]pyridazin-6-yl]phenol |

-continued

| Cpd | Name |
|---|---|
| 138[1] | 5-(1-methyl-1H-1,2,3-triazol-4-yl)-2-[3-(2,2,6,6-tetramethylpiperidin-4-yl)-3H-[1,2,3]triazolo[4,5-c]pyridazin-6-yl]phenol |
| 139[1] | 2-[3-(2,2,6,6-tetramethylpiperidin-4-yl)-3H-[1,2,3]triazolo[4,5-c]pyridazin-6-yl]-5-[3-(trifluoromethyl)-1H-pyrazol-4-yl]phenol |
| 140[1] | 5-(1H-pyrazol-4-yl)-2-[3-(2,2,6,6-tetramethylpiperidin-4-yl)-3H-[1,2,3]triazolo[4,5-c]pyridazin-6-yl]pyridin-3-ol |
| 141[1] | 5-(1H-pyrazol-4-yl)-2-[7-(2,2,6,6-tetramethylpiperidin-4-yl)-7H-imidazo[4,5-c]pyridazin-3-yl]pyridin-3-ol |
| 142[1] | 5-(imidazo[1,2-a]pyrazin-6-yl)-2-[3-(2,2,6,6-tetramethylpiperidin-4-yl)-3H-[1,2,3]triazolo[4,5-c]pyridazin-6-yl]phenol |
| 143[1] | 5-(4-fluoro-1H-imidazol-1-yl)-2-[3-(2,2,6,6-tetramethylpiperidin-4-yl)-3H-[1,2,3]triazolo[4,5-c]pyridazin-6-yl]phenol |
| 144[1] | 5-(4-methyl-1H-imidazol-1-yl)-2-[3-(2,2,6,6-tetramethylpiperidin-4-yl)-3H-[1,2,3]triazolo[4,5-c]pyridazin-6-yl]phenol |
| 145[1] | 2-[3-(2,2,6,6-tetramethylpiperidin-4-yl)-3H-[1,2,3]triazolo[4,5-c]pyridazin-6-yl]-5-(1H-[1,2,3]triazolo[4,5-b]pyridin-6-yl)phenol |
| 146[1] | 2-[3-(2,2,6,6-tetramethylpiperidin-4-yl)-3H-[1,2,3]triazolo[4,5-c]pyridazin-6-yl]-5-(3H-[1,2,3]triazolo[4,5-c]pyridin-6-yl)phenol |
| 147[1] | 2-[3-(2,2,6,6-tetramethylpiperidin-4-yl)-3H-[1,2,3]triazolo[4,5-c]pyridazin-6-yl]-5-(1H-[1,2,3]triazolo[4,5-b]pyridin-5-yl)phenol |
| 148 | 5-(3-fluoro-1-methyl-1H-pyrazol-4-yl)-2-[1-(2,2,6,6-tetramethylpiperidin-4-y])-1H-pyrazolo[3,4-c]pyridazin-5-yl]phenol |
| 149[1] | 5-(2,4-dimethyl-1H-imidazol-1-yl)-2-[3-(2,2,6,6-tetramethylpiperidin-4-yl)-3H-[1,2,3]triazolo[4,5-c]pyridazin-6-yl]phenol |
| 150[1] | 5-(2-methyl-1,3-thiazol-5-yl)-2-[3-(2,2,6,6-tetramethylpiperidin-4-yl)-3H-[1,2,3]triazolo[4,5-c]pyridazin-6-yl]phenol |
| 151[1] | 5-(2-methyl-2H-1,2,3-triazol-4-yl)-2-[3-(2,2,6,6-tetramethylpiperidin-4-yl)-3H-[1,2,3]triazolo[4,5-c]pyridazin-6-yl]phenol |
| 152[1] | 2-[3-(2,2,6,6-tetramethylpiperidin-4-yl)-3H-[1,2,3]triazolo[4,5-c]pyridazin-6-yl]-5-([1,2,4]triazolo[4,3-b]pyridazin-6-yl)phenol |
| 153[1] | 5-(3-methyl-1,2,4-thiadiazol-5-yl)-2-[3-(2,2,6,6-tetramethylpiperidin-4-yl)-3H-[1,2,3]triazolo[4,5-c]pyridazin-6-yl]phenol |
| 154 | 5-(4-fluoro-2-methyl-1,3-thiazol-5-yl)-2-[3-(2,2,6,6-tetramethylpiperidin-4-yl)-3H-[1,2,3]triazolo[4,5-c]pyridazin-6-yl]phenol |
| 155[1] | 5-(5-methyl-1H-pyrazol-1-yl)-2-[3-(2,2,6,6-tetramethylpiperidin-4-yl)-3H-[1,2,3]triazolo[4,5-c]pyridazin-6-yl]phenol |
| 156 | 5-(4-methyl-1H-pyrazol-1-yl)-2-(3-(2,2,6,6-tetramethylpiperidin-4-yl)-3H-[1,2,3]triazolo[4,5-c]pyridazin-6-yl)phenol |
| 157[1] | 5-(3-methyl-1H-pyrazol-1-yl)-2-(3-(2,2,6,6-tetramethylpiperidin-4-yl)-3H-[1,2,3]triazolo[4,5-c]pyridazin-6-yl)phenol |
| 158 | 5-(2-methyl-1,3-oxazol-5-yl)-2-[3-(2,2,6,6-tetramethylpiperidin-4-yl)-3H-[1,2,3]triazolo[4,5-c]pyridazin-6-yl]phenol |
| 159[1] | 5-(4-methoxy-1,3,5-triazin-2-yl)-2-(3-(2,2,6,6-tetramethylpiperidin-4-yl)-3H-[1,2,3]triazolo[4,5-c]pyridazin-6-yl)phenol |
| 160[1] | 5-(imidazo[1,2-a]pyrimidin-6-yl)-2-(3-(2,2,6,6-tetramethylpiperidin-4-yl)-3H-[1,2,3]triazolo[4,5-c]pyridazin-6-yl)phenol |
| 161[1] | 5-(3-fluoro-1H-pyrazol-4-yl)-2-(1-(2,2,6,6-tetramethylpiperidin-4-yl)-1H-pyrazolo[3,4-c]pyridazin-5-yl)phenol |
| 162[1] | 5-(imidazo[1,2-b]pyridazin-6-yl)-2-(3-(2,2,6,6-tetramethylpiperidin-4-yl)-3H-[1,2,3]triazolo[4,5-c]pyridazin-6-yl)phenol |
| 163[1] | 2-[3-(2,2,6,6-tetramethylpiperidin-4-yl)-3H-[1,2,3]triazolo[4,5-c]pyridazin-6-yl]-5-(2H-1,2,3-triazol-2-yl)phenol |
| 164[1] | 2-{3-[(3S,4S)-3-fluoro-2,2,6,6-tetramethylpiperidin-4-yl]-3H-[1,2,3]triazolo[4,5-c]pyridazin-6-yl}-5-(1H-pyrazol-4-yl)phenol |
| 165[1] | 5-(pyridin-4-yl)-2-[1-(2,2,6,6-tetramethylpiperidin-4-yl)-1H-pyrazolo[3,4-c]pyridazin-5-yl]phenol |
| 166[1] | 5-(pyridin-3-yl)-2-[1-(2,2,6,6-tetramethylpiperidin-4-yl)-1H-pyrazolo[3,4-c]pyridazin-5-yl]phenol |
| 167[1] | 5-(pyrimidin-5-yl)-2-[1-(2,2,6,6-tetramethylpiperidin-4-yl)-1H-pyrazolo[3,4-c]pyridazin-5-yl]phenol |
| 168[1] | 2-{3-[(3S,4R)-3-fluoro-2,2,6,6-tetramethylpiperidin-4-yl]-3H-[1,2,3]triazolo[4,5-c]pyridazin-6-yl}-5-(1H-pyrazol-4-yl)phenol |
| 169[1] | 5-(1-methyl-1H-pyrazol-3-yl)-2-[1-(2,2,6,6-tetramethylpiperidin-4-yl)-1H-pyrazolo[3,4-c]pyridazin-5-yl]phenol |
| 170[1] | 2-{3-[3-(tert-butylamino)cyclobutyl]-3H-[1,2,3]triazolo[4,5-c]pyridazin-6-yl}-5-(1H-pyrazol-4-yl)phenol |
| 171[1] | 4-(4-{3-[(3S,4S)-3-fluoro-2,2,6,6-tetramethylpiperidin-4-yl]-3H-[1,2,3]triazolo[4,5-c]pyridazin-6-yl}-3-hydroxyphenyl)-1-methylpyridin-2(1H)-one |
| 172[1] | 6-(4-{3-[(3S,4S)-3-fluoro-2,2,6,6-tetramethylpiperidin-4-yl]-3H-[1,2,3]triazolo[4,5-c]pyridazin-6-yl}-3-hydroxyphenyl)-3-methylpyrimidin-4(3H)-one |
| 173 | 5-(3-fluoro-1H-pyrazol-4-yl)-2-{3-[(3S,4S)-3-fluoro-2,2,6,6-tetramethylpiperidin-4-yl]-3H-[1,2,3]triazolo[4,5-c]pyridazin-6-yl}phenol |

-continued

| Cpd | Name |
|---|---|
| 174[1] | 2-[1-(2,2,6,6-tetramethylpiperidin-4-yl)-1H-pyrazolo[3,4-c]pyridazin-5-yl]-5-(2H-1,2,3-triazol-2-yl)phenol |
| 175[1] | 2-{3-[3-(tert-butylamino)cyclopentyl]-3H-[1,2,3]triazolo[4,5-c]pyridazin-6-yl}-5-(1H-pyrazol-4-yl)phenol, and |
| 176 | 2-[7-(2,2,6,6-tetramethylpiperidin-4-yl)-7H-pyrrolo[2,3-c]pyridazin-3-yl]-5-(2H-1,2,3-triazol-2-yl)phenol; | wherein the form of the compound is selected from the group consisting of a salt, hydrate, solvate, racemate, enantiomer, diastereomer, stereoisomer, and tautomer form thereof.

Another aspect of the compound of Formula (I) or a form thereof is a compound salt selected from the group consisting of:

| Cpd | Name |
|---|---|
| 1 | 5-(1H-pyrazol-4-yl)-2-[1-(2,2,6,6-tetramethylpiperidin-4-yl)-1H-imidazo[4,5-b]pyrazin-5-yl]phenol hydrochloride |
| 2 | 5-[2,5-difluoro-4-(1H-pyrazol-4-yl)phenyl]-1-(2,2,6,6-tetramethylpiperidin-4-yl)-1H-imidazo[4,5-b]pyrazine hydrochloride |
| 3 | 5-(1H-pyrazol-4-yl)-2-[7-(2,2,6,6-tetramethylpiperidin-4-yl)-7H-imidazo[4,5-c]pyridazin-3-yl]phenol hydrochloride |
| 4 | 3-[2,5-difluoro-4-(1H-pyrazol-4-yl)phenyl]-7-(2,2,6,6-tetramethylpiperidin-4-yl)-7H-imidazo[4,5-c]pyridazine hydrochloride |
| 5 | 2-[6-methyl-7-(2,2,6,6-tetramethylpiperidin-4-yl)-7H-imidazo[4,5-c]pyridazin-3-yl]-5-(1H-pyrazol-4-yl)phenol hydrochloride |
| 6 | 3-[2,5-difluoro-4-(1H-pyrazol-4-yl)phenyl]-6-methyl-7-(2,2,6,6-tetramethylpiperidin-4-yl)-7H-imidazo[4,5-c]pyridazine hydrochloride |
| 7 | 5-(1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 8 | 5-(1H-pyrazol-4-yl)-2-[5-(2,2,6,6-tetramethyl-1,2,3,6-tetrahydropyridin-4-yl)-5H-pyrrolo[2,3-b]pyrazin-2-yl]phenol hydrochloride |
| 9 | 3-[2-hydroxy-4-(1H-pyrazol-4-yl)phenyl]-7-(2,2,6,6-tetramethylpiperidin-4-yl)-7H-imidazo[4,5-c]pyridazin-6-ol hydrochloride |
| 10 | 5-(1H-pyrazol-4-yl)-2-[5-(2,2,6,6-tetramethylpiperidin-4-yl)-5H-pyrrolo[2,3-b]pyrazin-2-yl]phenol hydrochloride |
| 11 | 5-(1H-pyrazol-4-yl)-2-[7-(1,2,3,6-tetrahydropyridin-4-yl)-5H-pyrrolo[3,2-c]pyridazin-3-yl]phenol hydrochloride |
| 12 | 2-[7-(piperidin-4-yl)-5H-pyrrolo[3,2-c]pyridazin-3-yl]-5-(1H-pyrazol-4-yl)phenol hydrochloride |
| 13 | 6-[2,3-difluoro-4-(1H-pyrazol-4-yl)phenyl]-3-(2,2,6,6-tetramethylpiperidin-4-yl)-3H-[1,2,3]triazolo[4,5-c]pyridazine hydrochloride |
| 14 | 6-[2,5-difluoro-4-(1H-pyrazol-4-yl)phenyl]-3-(2,2,6,6-tetramethylpiperidin-4-yl)-3H-[1,2,3]triazolo[4,5-c]pyridazine hydrochloride |
| 15 | 5-(1H-pyrazol-4-yl)-2-[7-(1,2,3,6-tetrahydropyridin-4-yl)thieno[3,2-c]pyridazin-3-yl]phenol hydrochloride |
| 16 | 2-[2,5-difluoro-4-(1H-pyrazol-4-yl)phenyl]-5-(2,2,6,6-tetramethylpiperidin-4-yl)-5H-pyrrolo[2,3-b]pyrazine hydrochloride |
| 17 | 5-(1H-pyrazol-4-yl)-2-[7-(2,2,6,6-tetramethyl-1,2,3,6-tetrahydropyridin-4-yl)thieno[3,2-c]pyridazin-3-yl]phenol hydrochloride |
| 18 | 2-[7-(8-azabicyclo[3.2.1]oct-2-en-3-yl)thieno[3,2-c]pyridazin-3-yl]-5-(1H-pyrazol-4-yl)phenol hydrochloride |
| 19 | 2-[1-(piperidin-4-yl)-1H-pyrazolo[3,4-b]pyrazin-5-yl]-5-(1H-pyrazol-4-yl)phenol hydrochloride |
| 20 | 5-(1H-pyrazol-4-yl)-2-[7-(2,2,6,6-tetramethyl-1,2,3,6-tetrahydropyridin-4-yl)-5H-pyrrolo[3,2-c]pyridazin-3-yl]phenol hydrochloride |
| 21 | 2-[1-(piperidin-4-yl)-1H-pyrazolo[3,4-c]pyridazin-5-yl]-5-(1H-pyrazol-4-yl)phenol hydrochloride |
| 22 | 5-(1H-pyrazol-4-yl)-2-[1-(2,2,6,6-tetramethylpiperidin-4-yl)-1H-pyrazolo[3,4-c]pyridazin-5-yl]phenol hydrochloride |
| 23 | 5-(1H-pyrazol-4-yl)-2-[7-(2,2,6,6-tetramethylpiperidin-4-yl)-6,7-dihydro-5H-pyrrolo[2,3-c]pyridazin-3-yl]phenol hydrochloride |
| 24 | 5-(1H-pyrazol-4-yl)-2-[7-(2,2,6,6-tetramethylpiperidin-4-yl)thieno[3,2-c]pyridazin-3-yl]phenol hydrochloride |
| 25 | 2-[7-(3-oxa-9-azabicyclo[3.3.1]non-6-en-7-yl)thieno[3,2-c]pyridazin-3-yl]-5-(1H-pyrazol-4-yl)phenol hydrochloride |
| 26 | 5-(1H-pyrazol-4-yl)-2-[7-(2,2,6,6-tetramethylpiperidin-4-yl)-7H-pyrrolo[2,3-c]pyridazin-3-yl]phenol hydrochloride |
| 27 | 2-[7-(8-azabicyclo[3.2.1]oct-2-en-3-yl)-5H-pyrrolo[3,2-c]pyridazin-3-yl]-5-(1H-pyrazol-4-yl)phenol hydrochloride |
| 28 | 2-[7-(3-oxa-9-azabicyclo[3.3.1]non-6-en-7-yl)-5H-pyrrolo[3,2-c]pyridazin-3-yl]-5-(1H-pyrazol-4-yl)phenol hydrochloride |
| 29 | 2-[7-(8-azabicyclo[3.2.1]oct-3-y])-5H-pyrrolo[3,2-c]pyridazin-3-yl]-5-(1H-pyrazol-4-yl)phenol hydrochloride |
| 30 | 2-[7-(3-oxa-9-azabicyclo[3.3.1]non-7-yl)-5H-pyrrolo[3,2-c]pyridazin-3-yl]-5-(1H-pyrazol-4-yl)phenol hydrochloride |

-continued

| Cpd | Name |
|---|---|
| 31 | 5-(1H-pyrazol-4-yl)-2-[7-(2,2,6,6-tetramethylpiperidin-4-yl)-5H-pyrrolo[3,2-c]pyridazin-3-yl]phenol hydrochloride |
| 32 | 3-[2,3-difluoro-4-(1H-pyrazol-4-yl)phenyl]-7-(2,2,6,6-tetramethylpiperidin-4-yl)-6,7-dihydro-5H-pyrrolo[2,3-c]pyridazine hydrochloride |
| 33 | 4-fluoro-2-(1H-pyrazol-4-yl)-5-[3-(2,2,6,6-tetramethylpiperidin-4-yl)-3H-[1,2,3]triazolo[4,5-c]pyridazin-6-yl]phenol hydrochloride |
| 35 | 4-fluoro-5-(1H-pyrazol-4-yl)-2-[3-(2,2,6,6-tetramethylpiperidin-4-yl)-3H-[1,2,3]triazolo[4,5-c]pyridazin-6-yl]phenol hydrobromide |
| 36 | 7-[(3-exo)-8-azabicyclo[3.2.1]oct-3-yl]-3-[2,3-difluoro-4-(1H-pyrazol-4-yl)phenyl]-6,7-dihydro-5H-pyrrolo[2,3-c]pyridazine hydrochloride |
| 38 | 4-[3-(2,2,6,6-tetramethylpiperidin-4-yl)-3H-[1,2,3]triazolo[4,5-c]pyridazin-6-yl]biphenyl-3,4'-diol hydrobromide |
| 39 | 5-(1-methyl-1H-pyrazol-4-yl)-2-[3-(2,2,6,6-tetramethylpiperidin-4-yl)-3H-[1,2,3]triazolo[4,5-c]pyridazin-6-yl]phenol hydrobromide |
| 40 | 2-[6-methoxy-7-(2,2,6,6-tetramethylpiperidin-4-yl)-7H-imidazo[4,5-c]pyridazin-3-yl]-5-(1H-pyrazol-4-yl)phenol hydrochloride |
| 42 | 2-[6-(methylamino)-7-(2,2,6,6-tetramethylpiperidin-4-yl)-7H-imidazo[4,5-c]pyridazin-3-yl]-5-(1H-pyrazol-4-yl)phenol hydrochloride |
| 49 | 2-[6-(ethylamino)-7-(2,2,6,6-tetramethylpiperidin-4-yl)-7H-imidazo[4,5-c]pyridazin-3-yl]-5-(1H-pyrazol-4-yl)phenol hydrochloride |
| 52 | 2-[3-(1,2,2,6,6-pentamethylpiperidin-4-yl)-3H-[1,2,3]triazolo[4,5-c]pyridazin-6-yl]-5-(1H-pyrazol-4-yl)phenol dihydrochloride |
| 53 | 6-fluoro-4-[3-(2,2,6,6-tetramethylpiperidin-4-yl)-3H-[1,2,3]triazolo[4,5-c]pyridazin-6-yl][1,1'-biphenyl]-3,4'-diol hydrobromide |
| 54 | 2-fluoro-3-(1H-pyrazol-4-yl)-6-[3-(2,2,6,6-tetramethylpiperidin-4-yl)-3H-[1,2,3]triazolo[4,5-c]pyridazin-6-yl]phenol dihydrochloride |
| 55 | 4-{2-fluoro-5-hydroxy-4-[3-(2,2,6,6-tetramethylpiperidin-4-yl)-3H-[1,2,3]triazolo[4,5-c]pyridazin-6-yl]phenyl}-1-methylpyridin-2(1H)-one hydrochloride |
| 56 | 2-[3-(2,2-dimethylpiperidin-4-yl)-3H-[1,2,3]triazolo[4,5-c]pyridazin-6-yl]-5-(1H-pyrazol-4-yl)phenol hydrochloride |
| 57 | 2-{3-[(1R,5S)-1,5-dimethyl-8-azabicyclo[3.2.1]octan-3-yl]-3H-[1,2,3]triazolo[4,5-c]pyridazin-6-yl}-5-(1H-pyrazol-4-yl)phenol hydrochloride |
| 58 | 2-(1H-pyrazol-4-yl)-5-[3-(2,2,6,6-tetramethylpiperidin-4-yl)-3H-[1,2,3]triazolo[4,5-c]pyridazin-6-yl]benzene-1,4-diol dihydrochloride |
| 59 | 3-fluoro-5-(1H-pyrazol-4-yl)-2-[3-(2,2,6,6-tetramethylpiperidin-4-yl)-3H-[1,2,3]triazolo[4,5-c]pyridazin-6-yl]phenol dihydrochloride |
| 60 | 5-(pyrazin-2-yl)-2-[3-(2,2,6,6-tetramethylpiperidin-4-yl)-3H-[1,2,3]triazolo[4,5-c]pyridazin-6-yl]phenol dihydrochloride |
| 61 | 5-(pyridin-2-yl)-2-[3-(2,2,6,6-tetramethylpiperidin-4-yl)-3H-[1,2,3]triazolo[4,5-c]pyridazin-6-yl]phenol dihydrochloride |
| 62 | 4-fluoro-5-(1-methyl-1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 63 | 2-[3-(2,2,6,6-tetramethylpiperidin-4-yl)-3H-[1,2,3]triazolo[4,5-c]pyridazin-6-yl]-5-(1H-1,2,4-triazol-1-yl)phenol hydrochloride |
| 64 | 2-[3-(2,2,6,6-tetramethylpiperidin-4-yl)-3H-[1,2,3]triazolo[4,5-c]pyridazin-6-yl]-5-(4H-1,2,4-triazol-4-yl)phenol hydrochloride |
| 65 | 5-(pyridin-3-yl)-2-[3-(2,2,6,6-tetramethylpiperidin-4-yl)-3H-[1,2,3]triazolo[4,5-c]pyridazin-6-yl]phenol dihydrochloride |
| 66 | 5-(pyridin-4-yl)-2-[3-(2,2,6,6-tetramethylpiperidin-4-yl)-3H-[1,2,3]triazolo[4,5-c]pyridazin-6-yl]phenol dihydrochloride |
| 67 | 6-{3-hydroxy-4-[3-(2,2,6,6-tetramethylpiperidin-4-yl)-3H-[1,2,3]triazolo[4,5-c]pyridazin-6-yl]phenyl}pyridin-3-ol dihydrochloride |
| 68 | 2-{3-hydroxy-4-[3-(2,2,6,6-tetramethylpiperidin-4-yl)-3H-[1,2,3]triazolo[4,5-c]pyridazin-6-yl]phenyl}pyrimidin-5-ol dihydrochloride |
| 69 | 5-[1-($^{2}H_3$)methyl-1H-pyrazol-4-yl]-2-[3-(2,2,6,6-tetramethylpiperidin-4-yl)-3H-[1,2,3]triazolo[4,5-c]pyridazin-6-yl]phenol dihydrochloride |
| 70 | 5-(1H-imidazol-1-yl)-2-[3-(2,2,6,6-tetramethylpiperidin-4-yl)-3H-[1,2,3]triazolo[4,5-c]pyridazin-6-yl]phenol hydrochloride |
| 71 | 5-[1-(difluoromethyl)-1H-pyrazol-4-yl]-2-[3-(2,2,6,6-tetramethylpiperidin-4-yl)-3H-[1,2,3]triazolo[4,5-c]pyridazin-6-yl]phenol dihydrochloride |
| 72 | 2-[3-(2,2,6,6-tetramethylpiperidin-4-yl)-3H-[1,2,3]triazolo[4,5-c]pyridazin-6-yl]-5-(1H-1,2,3-triazol-1-yl)phenol hydrochloride |
| 73 | 5-(2-methylpyridin-4-yl)-2-[3-(2,2,6,6-tetramethylpiperidin-4-yl)-3H-[1,2,3]triazolo[4,5-c]pyridazin-6-yl]phenol hydrochloride |
| 74 | 2-[3-(2,2,6,6-tetramethylpiperidin-4-yl)-3H-[1,2,3]triazolo[4,5-c]pyridazin-6-yl]-5-[2-(trifluoromethyl)pyridin-4-yl]phenol dihydrochloride |
| 75 | 5-(pyrimidin-4-yl)-2-[3-(2,2,6,6-tetramethylpiperidin-4-yl)-3H-[1,2,3]triazolo[4,5-c]pyridazin-6-yl]phenol dihydrochloride |
| 76 | 5-(pyridazin-4-yl)-2-[3-(2,2,6,6-tetramethylpiperidin-4-yl)-3H-[1,2,3]triazolo[4,5-c]pyridazin-6-yl]phenol hydrochloride |
| 77 | 5-(2-methoxypyridin-4-yl)-2-[3-(2,2,6,6-tetramethylpiperidin-4-yl)-3H-[1,2,3]triazolo[4,5-c]pyridazin-6-yl]phenol dihydrochloride |
| 79 | 6-{3-hydroxy-4-[3-(2,2,6,6-tetramethylpiperidin-4-yl)-3H-[1,2,3]triazolo[4,5-c]pyridazin-6-yl]phenyl}pyridazin-3-ol hydrochloride |
| 81 | 6-[3-(2,2,6,6-tetramethylpiperidin-4-yl)-3H-[1,2,3]triazolo[4,5-c]pyridazin-6-yl]quinolin-7-ol hydrobromide |

| Cpd | Name |
|---|---|
| 83 | 4-chloro-5-(1H-pyrazol-4-yl)-2-[3-(2,2,6,6-tetramethylpiperidin-4-yl)-3H-[1,2,3]triazolo[4,5-c]pyridazin-6-yl]phenol dihydrobromide |
| 87 | 4-fluoro-5-(pyridin-4-yl)-2-[3-(2,2,6,6-tetramethylpiperidin-4-yl)-3H-[1,2,3]triazolo[4,5-c]pyridazin-6-yl]phenol dihydrobromide |
| 89 | 2-[3-(2,2,6,6-tetramethylpiperidin-4-yl)-3H-[1,2,3]triazolo[4,5-c]pyridazin-6-yl]-5-(thiophen-3-yl)phenol hydrochloride |
| 93 | 4-{3-hydroxy-4-[3-(2,2,6,6-tetramethylpiperidin-4-yl)-3H-[1,2,3]triazolo[4,5-c]pyridazin-6-yl]phenyl}pyridin-2(1H)-one hydrochloride |
| 95 | 5-(furan-3-yl)-2-[3-(2,2,6,6-tetramethylpiperidin-4-yl)-3H-[1,2,3]triazolo[4,5-c]pyridazin-6-yl]phenol hydrochloride |
| 96 | 2-[3-(2,2,6,6-tetramethylpiperidin-4-yl)-3H-[1,2,3]triazolo[4,5-c]pyridazin-6-yl]-5-(1,3-thiazol-2-yl)phenol hydrochloride |
| 98 | 5-(1-methyl-1H-pyrazol-4-yl)-2-[1-(2,2,6,6-tetramethylpiperidin-4-yl)-1H-pyrazolo[3,4-c]pyridazin-5-yl]phenol dihydrochloride |
| 102 | 5-[1-($^2$H$_3$)methyl-1H-pyrazol-4-yl]-2-[1-(2,2,6,6-tetramethylpiperidin-4-yl)-1H-pyrazolo[3,4-c]pyridazin-5-yl]phenol dihydrochloride |
| 103 | 5-[5-(difluoromethoxy)pyridin-2-yl]-2-[3-(2,2,6,6-tetramethylpiperidin-4-yl)-3H-[1,2,3]triazolo[4,5-c]pyridazin-6-yl]phenol formate |
| 105 | 5-(1H-pyrazol-4-yl)-2-[7-(2,2,6,6-tetramethyl-1,2,3,6-tetrahydropyridin-4-yl)furo[3,2-c]pyridazin-3-yl]phenol hydrochloride |
| 106 | 5-(3-fluoro-1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 107 | 2-[3-(2,2,6,6-tetramethylpiperidin-4-yl)-3H-[1,2,3]triazolo[4,5-c]pyridazin-6-yl]-5-(1,3-thiazol-5-yl)phenol hydrochloride |
| 108 | 5-(3-methyl-1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 109 | 4-{3-hydroxy-4-[3-(2,2,6,6-tetramethylpiperidin-4-yl)-3H-[1,2,3]triazolo[4,5-c]pyridazin-6-yl]phenyl}-1H-pyrazole-3-carbonitrile hydrochloride |
| 110 | 2-{3-hydroxy-4-[3-(2,2,6,6-tetramethylpiperidin-4-yl)-3H-[1,2,3]triazolo[4,5-c]pyridazin-6-yl]phenyl}-1,3-thiazole-5-carbonitrile hydrochloride |
| 111 | 5-(1,3-oxazol-2-yl)-2-[3-(2,2,6,6-tetramethylpiperidin-4-yl)-3H-[1,2,3]triazolo[4,5-c]pyridazin-6-yl]phenol formate |
| 114 | 5-[2-(difluoromethoxy)pyridin-4-yl]-2-[3-(2,2,6,6-tetramethylpiperidin-4-yl)-3H-[1,2,3]triazolo[4,5-c]pyridazin-6-yl]phenol hydrochloride |
| 116 | 2-[3-(2,2,6,6-tetramethylpiperidin-4-yl)-3H-[1,2,3]triazolo[4,5-c]pyridazin-6-yl]-5-(1,3,4-thiadiazol-2-yl)phenol hydrochloride |
| 117 | 6-[4-(1H-pyrazol-4-yl)-1H-benzotriazol-7-yl]-3-(2,2,6,6-tetramethylpiperidin-4-yl)-3H-[1,2,3]triazolo[4,5-c]pyridazine trifluoroacetate |
| 118 | 5-(1H-pyrrolo[2,3-b]pyridin-4-yl)-2-[3-(2,2,6,6-tetramethylpiperidin-4-yl)-3H-[1,2,3]triazolo[4,5-c]pyridazin-6-yl]phenol hydrochloride |
| 119 | 5-(2-methoxypyrimidin-4-yl)-2-[3-(2,2,6,6-tetramethylpiperidin-4-yl)-3H-[1,2,3]triazolo[4,5-c]pyridazin-6-yl]phenol hydrochloride |
| 120 | 5-(1,2-oxazol-4-yl)-2-[3-(2,2,6,6-tetramethylpiperidin-4-yl)-3H-[1,2,3]triazolo[4,5-c]pyridazin-6-yl]phenol hydrochloride |
| 121 | 5-(5-fluoro-1-methyl-1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 122 | 5-(1-ethyl-5-fluoro-1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 123 | 5-(2-ethoxypyridin-4-yl)-2-[3-(2,2,6,6-tetramethylpiperidin-4-yl)-3H-[1,2,3]triazolo[4,5-c]pyridazin-6-yl]phenol hydrochloride |
| 124 | 5-(6-ethoxypyrimidin-4-yl)-2-[3-(2,2,6,6-tetramethylpiperidin-4-yl)-3H-[1,2,3]triazolo[4,5-c]pyridazin-6-yl]phenol hydrochloride |
| 125 | 2-[3-(2,2,6,6-tetramethylpiperidin-4-yl)-3H-[1,2,3]triazolo[4,5-c]pyridazin-6-yl]-5-([1,2,3]triazolo[1,5-a]pyridin-5-yl)phenol hydrochloride |
| 126 | 2-[3-(2,2,6,6-tetramethylpiperidin-4-yl)-3H-[1,2,3]triazolo[4,5-c]pyridazin-6-yl]-5-([1,2,4]triazolo[1,5-a]pyridin-7-yl)phenol hydrochloride |
| 127 | 5-(3-chloro-1-methyl-1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 128 | 6-{3-hydroxy-4-[3-(2,2,6,6-tetramethylpiperidin-4-yl)-3H-[1,2,3]triazolo[4,5-c]pyridazin-6-yl]phenyl}pyrimidin-4(3H)-one hydrochloride |
| 129 | 5-(3-chloro-1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 130 | 5-(3-fluoro-1-methyl-1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 131 | 5-(3-methoxy-1H-pyrazol-4-yl)-2-[3-(2,2,6,6-tetramethylpiperidin-4-yl)-3H-[1,2,3]triazolo[4,5-c]pyridazin-6-yl]phenol hydrochlorid |
| 132 | 4-{3-hydroxy-4-[3-(2,2,6,6-tetramethylpiperidin-4-yl)-3H-[1,2,3]triazolo[4,5-c]pyridazin-6-yl]phenyl}-1-methyl-1H-pyrazole-3-carbonitrile hydrochloride |
| 133 | 5-(5-methyl-1,3-thiazol-2-yl)-2-[3-(2,2,6,6-tetramethylpiperidin-4-y])-3H-[1,2,3]triazolo[4,5-c]pyridazin-6-yl]phenol hydrochloride |
| 134 | 2-[3-(2,2,6,6-tetramethylpiperidin-4-yl)-3H-[1,2,3]triazolo[4,5-c]pyridazin-6-yl]-5-(1,2,4-thiadiazol-5-yl)phenol hydrochloride |
| 135 | 5-(4-fluoro-1H-benzotriazol-6-yl)-2-[3-(2,2,6,6-tetramethylpiperidin-4-yl)-3H-[1,2,3]triazolo[4,5-c]pyridazin-6-yl]phenol hydrochloride |
| 136 | 5-(1H-pyrazol-4-yl)-2-[7-(2,2,6,6-tetramethylpiperidin-4-yl)-7H-pyrrolo[2,3-c]pyridazin-3-yl]pyridin-3-ol dihydrochloride |

| Cpd | Name |
|---|---|
| 137 | 5-(3-bromo-1H-pyrazol-4-yl)-2-[3-(2,2,6,6-tetramethylpiperidin-4-yl)-3H-[1,2,3]triazolo[4,5-c]pyridazin-6-yl]phenol hydrochloride |
| 138 | 5-(1-methyl-1H-1,2,3-triazol-4-yl)-2-[3-(2,2,6,6-tetramethylpiperidin-4-yl)-3H-[1,2,3]triazolo[4,5-c]pyridazin-6-yl]phenol hydrochloride |
| 139 | 2-[3-(2,2,6,6-tetramethylpiperidin-4-yl)-3H-[1,2,3]triazolo[4,5-c]pyridazin-6-yl]-5-[3-(trifluoromethyl)-1H-pyrazol-4-yl]phenol hydrochloride |
| 140 | 5-(1H-pyrazol-4-yl)-2-[3-(2,2,6,6-tetramethylpiperidin-4-yl)-3H-[1,2,3]triazolo[4,5-c]pyridazin-6-yl]pyridin-3-ol hydrochloride |
| 141 | 5-(1H-pyrazol-4-yl)-2-[7-(2,2,6,6-tetramethylpiperidin-4-yl)-7H-imidazo[4,5-c]pyridazin-3-yl]pyridin-3-ol dihydrochloride |
| 142 | 5-(imidazo[1,2-a]pyrazin-6-yl)-2-[3-(2,2,6,6-tetramethylpiperidin-4-yl)-3H-[1,2,3]triazolo[4,5-c]pyridazin-6-yl]phenol hydrochloride |
| 143 | 5-(4-fluoro-1H-imidazol-1-yl)-2-[3-(2,2,6,6-tetramethylpiperidin-4-yl)-3H-[1,2,3]triazolo[4,5-c]pyridazin-6-yl]phenol dihydrochloride |
| 144 | 5-(4-methyl-1H-imidazol-1-yl)-2-[3-(2,2,6,6-tetramethylpiperidin-4-yl)-3H-[1,2,3]triazolo[4,5-c]pyridazin-6-yl]phenol dihydrochloride |
| 145 | 2-[3-(2,2,6,6-tetramethylpiperidin-4-yl)-3H-[1,2,3]triazolo[4,5-c]pyridazin-6-yl]-5-(1H-[1,2,3]triazolo[4,5-b]pyridin-6-yl)phenol dihydrochloride |
| 146 | 2-[3-(2,2,6,6-tetramethylpiperidin-4-yl)-3H-[1,2,3]triazolo[4,5-c]pyridazin-6-yl]-5-(3H-[1,2,3]triazolo[4,5-c]pyridin-6-yl)phenol dihydrochloride |
| 147 | 2-[3-(2,2,6,6-tetramethylpiperidin-4-yl)-3H-[1,2,3]triazolo[4,5-c]pyridazin-6-yl]-5-(1H-[1,2,3]triazolo[4,5-b]pyridin-5-yl)phenol dihydrochloride |
| 149 | 5-(2,4-dimethyl-1H-imidazol-1-yl)-2-[3-(2,2,6,6-tetramethylpiperidin-4-yl)-3H-[1,2,3]triazolo[4,5-c]pyridazin-6-yl]phenol dihydrochloride |
| 150 | 5-(2-methyl-1,3-thiazol-5-yl)-2-[3-(2,2,6,6-tetramethylpiperidin-4-yl)-3H-[1,2,3]triazolo[4,5-c]pyridazin-6-yl]phenol dihydrochloride |
| 151 | 5-(2-methyl-2H-1,2,3-triazol-4-yl)-2-[3-(2,2,6,6-tetramethylpiperidin-4-yl)-3H-[1,2,3]triazolo[4,5-c]pyridazin-6-yl]phenol hydrochloride |
| 152 | 2-[3-(2,2,6,6-tetramethylpiperidin-4-yl)-3H-[1,2,3]triazolo[4,5-c]pyridazin-6-yl]-5-([1,2,4]triazolo[4,3-b]pyridazin-6-yl)phenol hydrochloride |
| 153 | 5-(3-methyl-1,2,4-thiadiazol-5-yl)-2-[3-(2,2,6,6-tetramethylpiperidin-4-yl)-3H-[1,2,3]triazolo[4,5-c]pyridazin-6-yl]phenol hydrochloride |
| 155 | 5-(5-methyl-1H-pyrazol-1-yl)-2-[3-(2,2,6,6-tetramethylpiperidin-4-yl)-3H-[1,2,3]triazolo[4,5-c]pyridazin-6-yl]phenol dihydrochloride |
| 157 | 5-(3-methyl-1H-pyrazol-1-yl)-2-(3-(2,2,6,6-tetramethylpiperidin-4-yl)-3H-[1,2,3]triazolo[4,5-c]pyridazin-6-yl]phenol dihydrochloride |
| 159 | 5-(4-methoxy-1,3,5-triazin-2-yl)-2-(3-(2,2,6,6-tetramethylpiperidin-4-yl)-3H-[1,2,3]triazolo[4,5-c]pyridazin-6-yl]phenol dihydrochloride |
| 160 | 5-(imidazo[1,2-a]pyrimidin-6-yl)-2-(3-(2,2,6,6-tetramethylpiperidin-4-yl)-3H-[1,2,3]triazolo[4,5-c]pyridazin-6-yl]phenol hydrochloride |
| 161 | 5-(3-fluoro-1H-pyrazol-4-yl)-2-(1-(2,2,6,6-tetramethylpiperidin-4-yl)-1H-pyrazolo[3,4-c]pyridazin-5-yl)phenol hydrochloride |
| 162 | 5-(imidazo[1,2-b]pyridazin-6-yl)-2-(3-(2,2,6,6-tetramethylpiperidin-4-yl)-3H-[1,2,3]triazolo[4,5-c]pyridazin-6-yl]phenol hydrochloride |
| 163 | 2-[3-(2,2,6,6-tetramethylpiperidin-4-yl)-3H-[1,2,3]triazolo[4,5-c]pyridazin-6-yl]-5-(2H-1,2,3-triazol-2-yl)phenol hydrochloride |
| 164 | 2-{3-[(3S,4S)-3-fluoro-2,2,6,6-tetramethylpiperidin-4-yl]-3H-[1,2,3]triazolo[4,5-c]pyridazin-6-yl}-5-(1H-pyrazol-4-yl)phenol dihydrochloride |
| 165 | 5-(pyridin-4-yl)-2-[1-(2,2,6,6-tetramethylpiperidin-4-yl)-1H-pyrazolo[3,4-c]pyridazin-5-yl]phenol hydrochloride |
| 166 | 5-(pyridin-3-yl)-2-[1-(2,2,6,6-tetramethylpiperidin-4-yl)-1H-pyrazolo[3,4-c]pyridazin-5-yl]phenol hydrochloride |
| 167 | 5-(pyrimidin-5-yl)-2-[1-(2,2,6,6-tetramethylpiperidin-4-yl)-1H-pyrazolo[3,4-c]pyridazin-5-yl]phenol hydrochloride |
| 168 | 2-{3-[(3S,4R)-3-fluoro-2,2,6,6-tetramethylpiperidin-4-yl]-3H-[1,2,3]triazolo[4,5-c]pyridazin-6-yl}-5-(1H-pyrazol-4-yl)phenol dihydrochloride |
| 169 | 5-(1-methyl-1H-pyrazol-3-yl)-2-[1-(2,2,6,6-tetramethylpiperidin-4-yl)-1H-pyrazolo[3,4-c]pyridazin-5-yl]phenol hydrochloride |
| 170 | 2-{3-[3-(tert-butylamino)cyclobutyl]-3H-[1,2,3]triazolo[4,5-c]pyridazin-6-yl}-5-(1H-pyrazol-4-yl)phenol dihydrochloride |
| 171 | 4-(4-{3-[(3S,4S)-3-fluoro-2,2,6,6-tetramethylpiperidin-4-yl]-3H-[1,2,3]triazolo[4,5-c]pyridazin-6-yl}-3-hydroxyphenyl)-1-methylpyridin-2(1H)-one hydrochloride |
| 172 | 6-(4-{3-[(3S,4S)-3-fluoro-2,2,6,6-tetramethylpiperidin-4-yl]-3H-[1,2,3]triazolo[4,5-c]pyridazin-6-yl}-3-hydroxyphenyl)-3-methylpyrimidin-4(3H)-one dihydrochloride |
| 174 | 2-[1-(2,2,6,6-tetramethylpiperidin-4-yl)-1H-pyrazolo[3,4-c]pyridazin-5-yl]-5-(2H-1,2,3-triazol-2-yl)phenol hydrochloride, and |
| 175 | 2-{3-[3-(tert-butylamino)cyclopentyl]-3H-[1,2,3]triazolo[4,5-c]pyridazin-6-y]}-5-(1H-pyrazol-4-yl)phenol dihydrochloride; | wherein the form of the compound salt is selected from the group consisting of a hydrate, solvate, racemate, enantiomer, diastereomer, stereoisomer, and tautomer form thereof.

An aspect of the present description includes a method of use of a compound of Formula (I) or a form thereof for treating or ameliorating HD in a subject in need thereof, comprising administering an effective amount of the compound of Formula (I) or a form thereof to the subject.

Another aspect of the present description includes a method of use of the compound salt of Formula (I) or a form thereof for treating or ameliorating HD in a subject in need thereof, comprising administering an effective amount of the compound salt of Formula (I) or a form thereof to the subject.

An aspect of the present description includes a use of the compound of Formula (I) or a form thereof for treating or ameliorating HD in a subject in need thereof, comprising administering an effective amount of the compound of Formula (I) or a form thereof to the subject.

Another aspect of the present description includes a use of the compound salt of Formula (I) or a form thereof for treating or ameliorating HD in a subject in need thereof, comprising administering an effective amount of the compound salt of Formula (I) or a form thereof to the subject.

Chemical Definitions

The chemical terms used above and throughout the description herein, unless specifically defined otherwise, shall be understood by one of ordinary skill in the art to have the following indicated meanings.

As used herein, the term "$C_{1-6}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl), and the like. In certain aspects, $C_{1-6}$alkyl includes, but is not limited to $C_{1-4}$alkyl and the like. A $C_{1-6}$alkyl radical is optionally substituted with substituent species as described herein where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In certain aspects, $C_{2-8}$alkenyl includes, but is not limited to, $C_{2-6}$alkenyl, $C_{2-4}$alkenyl and the like. A $C_{2-8}$alkenyl radical is optionally substituted with substituent species as described herein where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl, butynyl and the like. In certain aspects, $C_{2-8}$alkynyl includes, but is not limited to, $C_{2-6}$alkynyl, $C_{2-4}$alkynyl and the like. A $C_{2-8}$alkynyl radical is optionally substituted with substituent species as described herein where allowed by available valences.

As used herein, the term "$C_{1-6}$alkoxy" generally refers to saturated hydrocarbon radicals having from one to eight carbon atoms in a straight or branched chain configuration of the formula: —O—$C_{1-6}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In certain aspects, $C_{1-6}$alkoxy includes, but is not limited to $C_{1-4}$alkoxy and the like. A $C_{1-6}$alkoxy radical is optionally substituted with substituent species as described herein where allowed by available valences.

As used herein, the term "$C_{3-10}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, 1H-indanyl, indenyl, tetrahydro-naphthalenyl and the like. In certain aspects, $C_{3-10}$cycloalkyl includes, but is not limited to $C_{3-8}$cycloalkyl, $C_{5-8}$cycloalkyl, $C_{3-10}$cycloalkyl and the like. A $C_{3-10}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl, thienyl, pyrrolyl, pyrazolyl, imidazolyl, isoxazolyl, isothiazolyl, oxazolyl, 1,3-thiazolyl, triazolyl, oxadiazolyl, thiadiazolyl, tetrazolyl, pyridinyl, pyrimidinyl, pyrazinyl, pyridazinyl, triazinyl, indolyl, indazolyl, indolizinyl, isoindolyl, benzofuranyl, benzothienyl, benzoimidazolyl, 1,3-benzothiazolyl, 1,3-benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

In certain aspects, the nomenclature for a heteroaryl radical may differ, such as in non-limiting examples where furanyl may also be referred to as furyl, thienyl may also be referred to as thiophenyl, pyridinyl may also be referred to as pyridyl, benzothienyl may also be referred to as benzothiophenyl and 1,3-benzoxazolyl may also be referred to as 1,3-benzooxazolyl.

In certain other aspects, the term for a heteroaryl radical may also include other regioisomers, such as in non-limiting examples where the term pyrrolyl may also include 2H-pyrrolyl, 3H-pyrrolyl and the like, the term pyrazolyl may also include 1H-pyrazolyl and the like, the term imidazolyl may also include 1H-imidazolyl and the like, the term triazolyl may also include 1H-1,2,3-triazolyl and the like, the term oxadiazolyl may also include 1,2,4-oxadiazolyl, 1,3,4-oxadiazolyl and the like, the term tetrazolyl may also include 1H-tetrazolyl, 2H-tetrazolyl and the like, the term indolyl may also include 1H-indolyl and the like, the term indazolyl may also include 1H-indazolyl, 2H-indazolyl and the like, the term benzoimidazolyl may also include 1H-benzoimidazolyl and the term purinyl may also include 9H-purinyl and the like.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl, 1,4-benzodioxanyl, 2,3-dihydro-1,4-benzodioxinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl, 6,9-diazaspiro[4.5]decyl and the like. A heterocyclyl radical is optionally substituted on a carbon or nitrogen atom ring member with substituent species as described herein where allowed by available valences.

In certain aspects, the nomenclature for a heterocyclyl radical may differ, such as in non-limiting examples where 1,3-benzodioxolyl may also be referred to as benzo[d][1,3]dioxolyl and 2,3-dihydro-1,4-benzodioxinyl may also be referred to as 2,3-dihydrobenzo[b][1,4]dioxinyl.

As used herein, the term "deutero-$C_{1-4}$alkyl," refers to a radical of the formula: —$C_{1-4}$alkyl-deutero, wherein $C_{1-4}$alkyl is partially or completely substituted with one or more deuterium atoms where allowed by available valences.

As used herein, the term "$C_{1-6}$alkoxy-$C_{1-6}$alkyl" refers to a radical of the formula: —$C_{1-6}$alkyl-O—$C_{1-6}$alkyl.

As used herein, the term "$C_{1-6}$alkyl-amino" refers to a radical of the formula: —NH—$C_{1-6}$alkyl.

As used herein, the term "($C_{1-6}$alkyl)$_2$-amino" refers to a radical of the formula: —N($C_{1-6}$alkyl)$_2$.

As used herein, the term "$C_{1-6}$alkyl-thio" refers to a radical of the formula: —S—$C_{1-6}$alkyl.

As used herein, the term "amino-$C_{1-6}$alkyl" refers to a radical of the formula: —$C_{1-6}$alkyl-NH$_2$.

As used herein, the term "halo" or "halogen" generally refers to a halogen atom radical, including fluoro, chloro, bromo and iodo.

As used herein, the term "halo-$C_{1-6}$alkoxy" refers to a radical of the formula: —O—$C_{1-6}$alkyl-halo, wherein $C_{1-6}$alkyl is partially or completely substituted with one or more halogen atoms where allowed by available valences.

As used herein, the term "halo-$C_{1-6}$alkyl" refers to a radical of the formula: —$C_{1-6}$alkyl-halo, wherein $C_{1-6}$alkyl is partially or completely substituted with one or more halogen atoms where allowed by available valences.

As used herein, the term "hydroxy" refers to a radical of the formula: —OH.

As used herein, the term "hydroxy-$C_{1-6}$alkyl" refers to a radical of the formula: —$C_{1-6}$alkyl-OH, wherein $C_{1-6}$alkyl is partially or completely substituted with one or more hydroxy radicals where allowed by available valences.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances one or more substituents having a double bond (e.g., "oxo" or "=O") as the point of attachment may be described, shown or listed herein within a substituent group, wherein the structure may only show a single bond as the point of attachment to the core structure of Formula (I). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) or a form thereof encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms "each instance of" or "in each instance, when present," when used preceding a phrase such as " . . . $C_{3-14}$cycloalkyl, $C_{3-14}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl," are intended to refer to the $C_{3-14}$cycloalkyl, aryl, heteroaryl and heterocyclyl ring systems when each are present either alone or as a substituent.

As used herein, the term "optionally substituted" means optional substitution with the specified substituent variables, groups, radicals or moieties.

Compound Forms

As used herein, the term "form" means a compound of Formula (I) having a form selected from the group consisting of a free acid, free base, salt, hydrate, solvate, racemate, enantiomer, diastereomer, stereoisomer, and tautomer form thereof.

In certain aspects described herein, the form of the compound of Formula (I) is a free acid, free base or salt thereof.

In certain aspects described herein, the form of the compound of Formula (I) is a salt thereof.

In certain aspects described herein, the form of the compound of Formula (I) is an isotopologue thereof.

In certain aspects described herein, the form of the compound of Formula (I) is a stereoisomer, racemate, enantiomer or diastereomer thereof.

In certain aspects described herein, the form of the compound of Formula (I) is a tautomer thereof.

In certain aspects described herein, the form of the compound of Formula (I) is a pharmaceutically acceptable form.

In certain aspects described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term "protected" means that a functional group in a compound of Formula (I) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as "prodrugs". All prodrugs of compounds described herein are included within the scope of the use described herein.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I) can form salts, which are intended to be included within the scope of this description. Reference to a compound of Formula (I) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) may be formed, for example, by reacting a compound of Formula (I) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Particular aspects of acid addition salts include, and are not limited to, acetate, ascorbate, benzoate, benzenesulfonate, bisulfate, bitartrate, borate, bromide, butyrate, chloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain particular aspects of acid addition salts include chloride, bromide or dichloride.

Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. *Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I) and forms thereof, may further exist in a tautomeric form. All such tautomeric forms are contemplated and intended to be included within the scope of the compounds of Formula (I) or a form thereof as described herein.

The compounds of Formula (I) or a form thereof may contain asymmetric or chiral centers, and, therefore, exist in different stereoisomeric forms. The present description is intended to include all stereoisomeric forms of the compounds of Formula (I) as well as mixtures thereof, including racemic mixtures.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one particular aspect, the compounds described herein are (S) isomers and may exist as enantiomerically pure compositions substantially comprising only the (S) isomer. In another particular aspect, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers.

Also, some of the compounds of Formula (I) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates or isotopologues of the instant compounds.

The term "isotopologue" refers to isotopically-enriched compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, $^{35}Cl$ and $^{36}Cl$, respectively, each of which are also within the scope of this description.

Certain isotopically-enriched compounds described herein (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances.

Polymorphic crystalline and amorphous forms of the compounds of Formula (I) and of the salts, solvates, hydrates, esters and prodrugs of the compounds of Formula (I) are further intended to be included in the present description.

Compound Uses

An aspect of the present description relates to a method of use of a compound of Formula (I) or a form thereof for treating or ameliorating HD in a subject in need thereof, comprising administering an effective amount of the compound or a form thereof to the subject.

Another aspect of the present description relates to use of the compound of Formula (I) or a form thereof for treating or ameliorating HD in a subject in need thereof.

Another aspect of the present description relates to use of the compound of Formula (I) or a form thereof having activity toward HD.

An aspect of the present description relates to use of the compound of Formula (I) or a form thereof in a combination therapy to provide additive or synergistic activity, thus enabling the development of a combination product for treating or ameliorating HD.

In addition to monotherapeutic use, the instant compounds are useful in a combination therapy with current standard of agents, having additive or synergistic activity with one or more known agents.

A combination therapy comprising compounds described herein in combination with one or more known drugs may be used to treat HD regardless of whether HD is responsive to the known drug.

Certain aspects of the present description include the use of a compound of Formula (I) or a form thereof in a combination therapy for treating or ameliorating HD in a subject in need thereof, comprising administering an effective amount of the compound of Formula (I) or a form thereof and an effective amount of one or more agent(s).

Certain particular aspects of the present description include the use of a compound of Formula (I) or a form thereof in a combination therapy for treating or ameliorating HD in a subject in need thereof, comprising administering an effective amount of the compound of Formula (I) or a form thereof and an effective amount of one or more agent(s).

In an aspect of a use or method provided herein, compounds of Formula (I) or a form thereof used in combination with one or more additional agents can be administered to a subject or contacted with a subject or patient cell(s) prior to, concurrently with, or subsequent to administering to the subject or patient or contacting the cell with an additional agent(s). A compound(s) of Formula (I) or a form thereof and an additional agent(s) can be administered to a subject or contacted with a cell in single composition or different compositions. In a specific aspect, a compound(s) of Formula (I) or a form thereof is used in combination with gene therapy to inhibit HTT expression (using, e.g., viral delivery vectors) or the administration of another small molecule HTT inhibitor. In another specific aspect, a compound(s) of Formula (I) or a form thereof are used in combination with cell replacement using differentiated non-mutant HTT stem cells. In another specific aspect, a compound(s) of Formula (I) or a form thereof are used in combination with cell replacement using differentiated HTT stem cells.

In one aspect, provided herein is the use of compounds of Formula (I) or a form thereof in combination with supportive standard of care therapies, including palliative care.

An aspect of the present description includes the use of a compound of Formula (I) or a form thereof in the preparation of a kit comprising the compound of Formula (I) or a form thereof and instructions for administering an effective amount of the compound of Formula (I) or a form thereof and an effective amount of one or more agent(s) in a combination therapy for treating or ameliorating HD in a subject in need thereof.

Accordingly, the present description relates to use of a compound of Formula (I) or a form thereof for treating or ameliorating HD. In accordance with the use of the present description, compounds that are useful in selectively treating or ameliorating HD, have been identified and use of these compounds for treating or ameliorating HD has been provided.

Another aspect of the use of the present description relates to use of a compound of Formula (I) or a form thereof for treating or ameliorating HD in a subject in need thereof, comprising administering an effective amount of the compound of Formula (I) or a form thereof to the subject.

Another aspect of the use of the present description relates to a method of use of a compound of Formula (I) or a form thereof for treating or ameliorating HD in a subject in need thereof, comprising administering an effective amount of the compound to the subject.

Another aspect of the use of the present description relates to a method of use of a compound of Formula (I) or a form thereof for treating or ameliorating HD in a subject in need thereof, comprising administering an effective amount of the compound to the subject.

Another aspect of the use of the present description relates to use of a compound of Formula (I) or a form thereof in the manufacture of a medicament for treating or ameliorating HD in a subject in need thereof, comprising administering an effective amount of the medicament to the subject.

Another aspect of the use of the present description relates to use of a compound of Formula (I) or a form thereof in the preparation of a kit comprising the compound of Formula (I) or a form thereof and instructions for administering the compound for treating or ameliorating HD in a subject in need thereof.

In one respect, for each of such aspects, the subject is treatment naive. In another respect, for each of such aspects, the subject is not treatment naive.

As used herein, the term "treating" refers to: (i) preventing a disease, disorder or condition from occurring in a subject that may be predisposed to the disease, disorder and/or condition but has not yet been diagnosed as having the disease, disorder and/or condition; (ii) inhibiting a disease, disorder or condition, i.e., arresting the development thereof; and/or (iii) relieving a disease, disorder or condition, i.e., causing regression of the disease, disorder and/or condition.

As used herein, the term "subject" refers to an animal or any living organism having sensation and the power of voluntary movement, and which requires oxygen and organic food. Nonlimiting examples include members of the human, primate, equine, porcine, bovine, murine, rattus, canine and feline specie. In certain aspects, the subject is a mammal or a warm-blooded vertebrate animal. In other aspects, the subject is a human. As used herein, the term "patient" may be used interchangeably with "subject" and "human".

As used herein, the terms "effective amount" or "therapeutically effective amount" mean an amount of compound of Formula (I) or a form, composition or medicament thereof that achieves a target plasma concentration that is effective in treating or ameliorating HD as described herein and thus producing the desired therapeutic, ameliorative, inhibitory or preventative effect in a subject in need thereof. In one aspect, the effective amount may be the amount required to treat HD in a subject or patient, more specifically, in a human.

In another aspect, the concentration-biological effect relationships observed with regard to a compound of Formula (I) or a form thereof indicate a target plasma concentration ranging from approximately 0.001 µg/mL to approximately 50 µg/mL, from approximately 0.01 µg/mL to approximately 20 µg/mL, from approximately 0.05 µg/mL to approximately 10 µg/mL, or from approximately 0.1 µg/mL to approximately 5 µg/mL. To achieve such plasma concentrations, the compounds described herein may be administered at doses that vary, such as, for example, without limitation, from 0.1 ng to 10,000 mg.

In one aspect, the dose administered to achieve an effective target plasma concentration may be administered based upon subject or patient specific factors, wherein the doses administered on a weight basis may be in the range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 200 mg/kg/day, or about 0.001 mg/kg/day to about 150 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 25 mg/kg/day, or about 0.001 mg/kg/day to about 10 mg/kg/day, or about 0.001 mg/kg/day to about 5 mg/kg/day, or about 0.001 mg/kg/day to about 1 mg/kg/day, or about 0.001 mg/kg/day to about 0.5 mg/kg/day, or about 0.001 mg/kg/day to about 0.1 mg/kg/day, or from about 0.01 mg/kg/day to about 3500 mg/kg/day, or about 0.01 mg/kg/day to about 3000 mg/kg/day, or about 0.01 mg/kg/day to about 2500 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 500 mg/kg/day, or about 0.01 mg/kg/day to about 250 mg/kg/day, or about 0.01 mg/kg/day to about 200 mg/kg/day, or about 0.01 mg/kg/day to about 150 mg/kg/day, or about 0.01 mg/kg/day to about 100 mg/kg/day, or about 0.01 mg/kg/day to about 75 mg/kg/day, or about 0.01 mg/kg/day to about 50 mg/kg/day, or about 0.01 mg/kg/day to about 25 mg/kg/day, or about 0.01 mg/kg/day to about 10 mg/kg/day, or about 0.01 mg/kg/day to about 5 mg/kg/day, or about 0.01 mg/kg/day to about 1 mg/kg/day, or about 0.01 mg/kg/day to about 0.5 mg/kg/day, or about 0.01 mg/kg/day to about 0.1 mg/kg/day, or from about 0.1 mg/kg/day to about 3500 mg/kg/day, or about 0.1 mg/kg/day to about 3000 mg/kg/day, or about 0.1 mg/kg/day to about 2500 mg/kg/day, or about 0.1 mg/kg/day to about 2000 mg/kg/day, or about 0.1 mg/kg/day to about 1500 mg/kg/day, or about 0.1 mg/kg/day to about 1000 mg/kg/day, or about 0.1 mg/kg/day to about 500 mg/kg/day, or about 0.1 mg/kg/day to about 250 mg/kg/day, or about 0.1 mg/kg/day to about 200 mg/kg/day, or about 0.1 mg/kg/day to about 150 mg/kg/day, or about 0.1 mg/kg/day to about 100 mg/kg/day, or about 0.1 mg/kg/day to about 75 mg/kg/day, or about 0.1 mg/kg/day to about 50 mg/kg/day, or about 0.1 mg/kg/day to about 25 mg/kg/day, or about 0.1 mg/kg/day to about 10 mg/kg/day, or about 0.1 mg/kg/day to about 5 mg/kg/day, or about 0.1 mg/kg/day to about 1 mg/kg/day, or about 0.1 mg/kg/day to about 0.5 mg/kg/day.

Effective amounts for a given subject may be determined by routine experimentation that is within the skill and judgment of a clinician or a practitioner skilled in the art in light of factors related to the subject. Dosage and administration may be adjusted to provide sufficient levels of the active agent(s) or to maintain the desired effect. Factors which may be taken into account include genetic screening, severity of the disease state, status of disease progression, general health of the subject, ethnicity, age, weight, gender, diet, time of day and frequency of administration, drug combination(s), reaction sensitivities, experience with other therapies, and tolerance/response to therapy.

The dose administered to achieve an effective target plasma concentration may be orally administered once (once in approximately a 24 hour period; i.e., "q.d."), twice (once in approximately a 12 hour period; i.e., "b.i.d." or "q.12h"), thrice (once in approximately an 8 hour period; i.e., "t.i.d." or "q.8h"), or four times (once in approximately a 6 hour period; i.e., "q.d.s.", "q.i.d." or "q.6h") daily.

In certain aspects, the dose administered to achieve an effective target plasma concentration may also be administered in a single, divided, or continuous dose for a patient or subject having a weight in a range of between about 40 to about 200 kg (which dose may be adjusted for patients or subjects above or below this range, particularly children under 40 kg).

The typical adult subject is expected to have a median weight in a range of about 70 kg. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intravenous (bolus and infusion), intracerebral, and pulmonary routes of administration.

In another aspect, the dose administered may be adjusted based upon a dosage form described herein formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400, 500, 1000, 1500, 2000, 2500, 3000 or 4000 mg/day.

For any compound, the effective amount can be estimated initially either in cell culture assays or in relevant animal models, such as a mouse, guinea pig, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In certain aspects, the effective amount is such that a large therapeutic index is achieved. In further particular aspects, the dosage is within a range of circulating concentrations that include an $ED_{50}$ with little or no toxicity. The dosage may vary within this range depending upon the dosage form employed, sensitivity of the patient, and the route of administration.

In one aspect, provided herein are methods for modulating the amount of HTT (huntingtin protein), comprising contacting a human cell with a compound of Formula (I) or a form thereof. In a specific aspect, provided herein are methods for modulating the amount of HTT, comprising contacting a human cell with a compound of Formula (I) or a form thereof that modulates the expression of HTT. The human cell can be contacted with a compound of Formula (I) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I).

In a specific aspect, provided herein is a method for enhancing the inhibition of mutant HTT transcribed from the Htt gene, comprising contacting a human cell with a compound of Formula (I) or a form thereof. The human cell can be contacted with a compound of Formula (I) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of wild-type "normal" HTT expression and/or function. In another aspect, the human cell is from a human with HD. In another aspect, the human cell is in a human with HD. In one aspect, the compound is a form of the compound of Formula (I).

In another aspect, provided herein is a method for modulating the inhibition of mutant HTT transcribed from the Htt gene, comprising administering to a non-human animal model for HD a compound of Formula (I) or a form thereof. In a specific aspect, provided herein is a method for modulating the inhibition of mutant HTT transcribed from the Htt gene, comprising administering to a non-human animal model for HD a compound of Formula (I) or a form thereof. In a specific aspect, the compound is a form of the compound of Formula (I).

In another aspect, provided herein is a method for decreasing the amount of mutant HTT, comprising contacting a human cell with a compound of Formula (I) or a form thereof. In a specific aspect, provided herein is a method for decreasing the amount of mutant HTT, comprising contacting a human cell with a compound of Formula (I) that inhibits the transcription of mutant HTT (huntingtin mRNA) from the Htt gene. In another specific aspect, provided herein is a method for decreasing the amount of HTT, comprising contacting a human cell with a compound of Formula (I) that inhibits the expression of mutant HTT transcribed from the Htt gene. The human cell can be contacted with a compound of Formula (I) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I).

In certain aspects, treating or ameliorating HD with a compound of Formula (I) or a form thereof (alone or in combination with an additional agent) has a therapeutic effect and/or beneficial effect. In a specific aspect, treating HD with a compound of Formula (I) or a form thereof (alone or in combination with an additional agent) results in one, two or more of the following effects: (i) reduces or ameliorates the severity of HD; (ii) delays onset of HD; (iii) inhibits the progression of HD; (iv) reduces hospitalization of a subject; (v) reduces hospitalization length for a subject; (vi) increases the survival of a subject; (vii) improves the quality of life for a subject; (viii) reduces the number of symptoms associated with HD; (ix) reduces or ameliorates the severity of a symptom(s) associated with HD; (x) reduces the duration of a symptom associated with HD; (xi) prevents the recurrence of a symptom associated with HD; (xii) inhibits the development or onset of a symptom of HD; and/or (xiii) inhibits of the progression of a symptom associated with HD.

Metabolites

Also included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled isotopologue (e.g., $^{14}C$ or $^{3}H$) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Pharmaceutical Compositions

Aspects of the present description include the use of a compound of Formula (I) or a form thereof in a pharmaceutical composition for treating or ameliorating HD in a subject in need thereof, comprising administering an effective amount of the compound of Formula (I) or a form thereof in admixture with one or more pharmaceutically acceptable excipient(s).

An aspect of the present description includes the use of a pharmaceutical composition of the compound of Formula (I) or a form thereof in the preparation of a kit comprising the pharmaceutical composition of the compound of Formula (I) or a form thereof and instructions for administering the compound for treating or ameliorating HD in a subject in need thereof.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In certain aspects, the pharmaceutical composition is formulated to achieve a pH of from about pH 3 to about pH 7. In other aspects, the pharmaceutical composition is formulated to achieve a pH of from about pH 5 to about pH 8.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions for the instant compounds described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive antibodies. Other exemplary excipients include antioxidants such as ascorbic acid; chelating agents such as EDTA; carbohydrates such as dextrin, hydroxyalkylcellulose, hydroxyalkylmethylcellulose (e.g., hydroxypropylmethylcellulose, also known as HPMC), stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended use described herein. Suitable formulations for oral administration include solids, liquid solutions, emulsions and suspensions, while suitable inhalable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents, and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid, or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate, or kaolin, or as soft gelatin capsules wherein the active ingredient is mixed with non-aqueous or oil medium, such as glycerin, propylene glycol, polyethylene glycol, peanut oil, liquid paraffin, or olive oil.

In other aspects, pharmaceutical compositions described herein may be formulated as suspensions comprising a compound of Formula (I) or a form thereof in admixture with one or more pharmaceutically acceptable excipient(s) suitable for the manufacture of a suspension. In yet other aspects, pharmaceutical compositions described herein may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propanediol. The sterile injectable preparation may also be prepared as a lyophilized powder. Among the acceptable vehicles and solvents that may be employed are water, Ringer's solution and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the description are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In certain aspects, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polysorbate 20 or 80 (also referred to as Tween® 20 or Tween® 80, respectively) or polyoxyl 40 hydrogenated castor oil.

In other aspects, the bioavailability of low solubility compounds may be enhanced using particle size optimization techniques including the preparation of nanoparticles or nanosuspensions using techniques known to those skilled in the art. The compound forms present in such preparations include amorphous, partially amorphous, partially crystalline or crystalline forms.

In alternative aspects, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In certain aspects, the pharmaceutical composition further comprises HPBC in a range of from about 0.1% to about 20%, from about 1% to about 15%, or from about 2.5% to about 10%. The amount of solubility enhancer employed may depend on the amount of the compound in the composition.

Preparation of Compounds

General Synthetic Methods

As disclosed herein, general methods for preparing the compounds of Formula (I) or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reaction steps of the synthetic schemes provided herein in isolation is contemplated.

Scheme A:

Compounds of Formula (I), wherein $R_1$ is $C_{3-10}$cycloalkyl or heterocyclyl ring systems and $R_2$ is phenyl, heterocyclyl, or heteroaryl ring systems, may be prepared as described in Scheme A below.

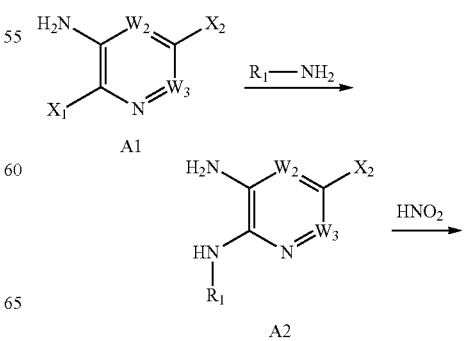

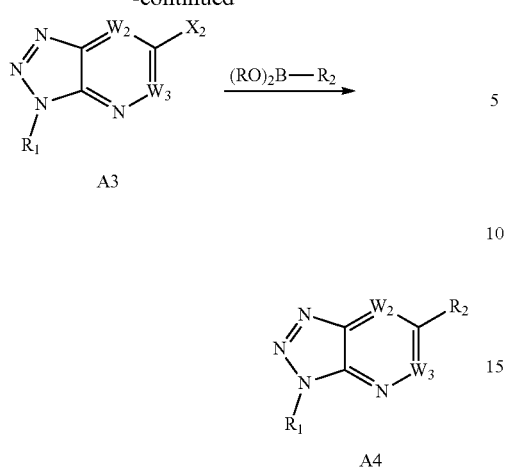

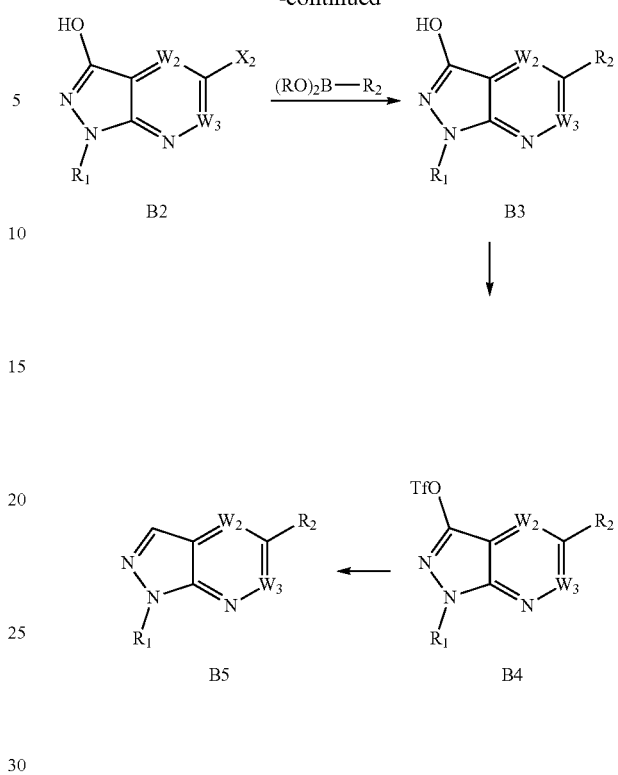

Compound A1 (where $X_1$ and $X_2$ are independently bromine, chlorine and the like; $W_2$ and $W_3$, are independently CH or N) is converted to Compound A2 by a nucleophilic substitution with a primary amine in the presence of a suitable base (such as $Et_3N$ and the like) in a suitable solvent (such as decanol and the like). Alternatively, Compound A1 is converted to Compound A2 via cross coupling with a primary amine in the presence of a suitable catalyst (such as RuPhos Pd G2 and the like) and base (such as sodium tert-butoxide and the like) in an appropriate solvent such as 1,4-dioxane and the like). Compound A2 is converted to Compound A3 by a diazotization/cyclization sequence upon treatment with an appropriate reagent (such as sodium nitrite and the like) in an appropriate solvent (such acetic acid and the like). Compound A3 is converted to Compound A4 by a Suzuki coupling with an aryl- or heteroaryl-boronic acid (or pinacol boronic ester) in the presence of a catalyst (such as $Pd(dppf)Cl_2$ and the like) and base (such as aqueous $K_2CO_3$ and the like) in a suitable solvent (such as 1,4-dioxane and the like). Alternatively, Compound A3 is converted to Compound A4 by a Stille coupling with an aryl- or heteroaryl-stannane in the presence of a catalyst (such as $Pd_2(dba)_3$ and the like), a ligand (such as X-Phos and the like) and a base (such as CsF and the like) in a suitable solvent (such as 1,4-dioxane and the like). Any protection groups on $R_1$ and $R_2$ are removed upon treatment with a suitable reagent (such as HCl in dioxane for a Boc protecting group and the like) in a suitable solvent (such as dioxane and the like).

Scheme B:

Compounds of Formula (I), wherein $R_1$ is $C_{3-10}$cycloalkyl or heterocyclyl ring systems and $R_2$ is phenyl, heterocyclyl, or heteroaryl ring systems, may be prepared as described in Scheme B below.

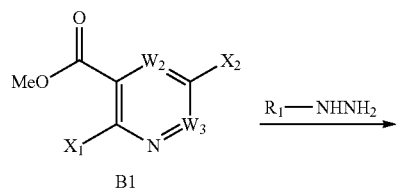

Compound B1 (where $X_1$ and $X_2$ are independently bromine, chlorine and the like; $W_2$ and $W_3$, are independently CH or N) is converted to Compound B2 through a nucleophilic substitution/cyclization sequence by treatment with hydrazine ($R_1NH_2NH_2$) and a suitable base (such as $Et_3N$ and the like) in a suitable solvent (such as methanol and the like). Compound B2 is converted to Compound B3 by a Suzuki coupling with an aryl- or heteroaryl-boronic acid (or pinacol boronic ester) in the presence of a catalyst (such as $Pd(dppf)Cl_2$ and the like) and base (such as aqueous $K_2CO_3$ and the like) in a suitable solvent (such as 1,4-dioxane and the like). Alternatively, Compound B2 is converted to Compound B3 by a Stille coupling with an aryl- or heteroaryl-stannane in the presence of a catalyst (such as $Pd_2(dba)_3$ and the like), a ligand (such as X-Phos and the like) and a base (such as CsF and the like) in a suitable solvent (such as 1,4-dioxane and the like). Compound B3 is converted to Compound B4 by treatment with an activated triflate (such as $Tf_2O$ or $Tf_2NPh$ and the like) in the presence of a suitable base (such as $Et_3N$ and the like) in a suitable solvent (such as dichloromethane and the like). Compound B4 is converted to Compound B5 by hydrogenation using an appropriate hydrogen source (such as ammonium formate and the like) in the presence of a suitable catalyst (such as Pd(dppf)$Cl_2$ and the like) in a suitable solvent (such as tetrahydrofuran and the like). Any protection groups on $R_1$ and $R_2$ are removed upon treatment with a suitable reagent (such as HCl in dioxane for a Boc protecting group and the like) in a suitable solvent (such as dioxane and the like).

Scheme C:

Compounds of Formula (I), wherein $R_1$ is $C_{3-10}$cycloalkyl or heterocyclyl ring systems and $R_2$ is phenyl, heterocyclyl, or heteroaryl ring systems, may be prepared as described in Scheme C below.

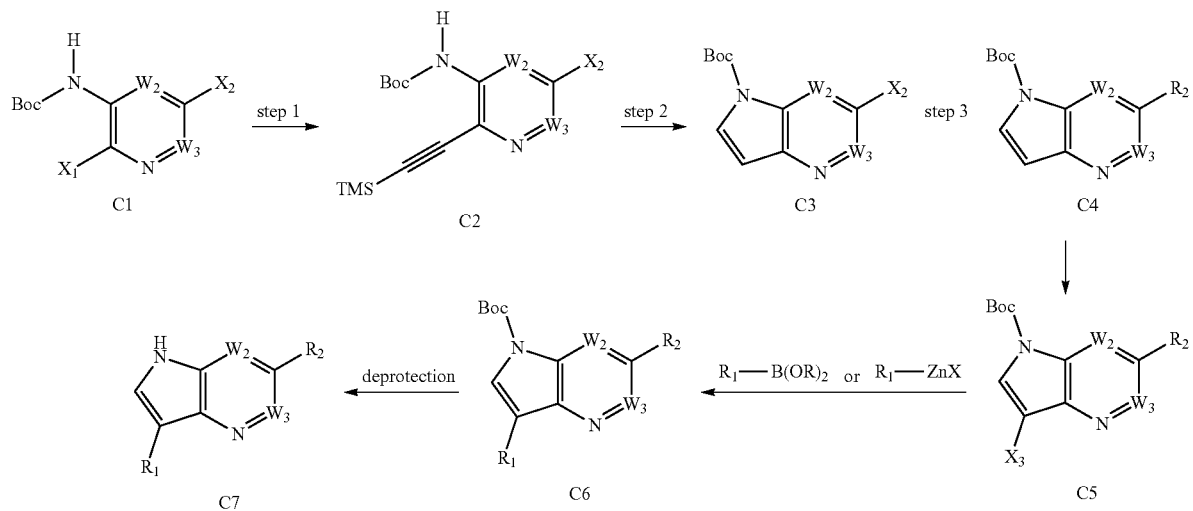

Compound C1 (where $X_1$ and $X_2$ are independently bromine, chlorine and the like; $W_2$ and $W_3$, are independently CH or N) is converted to Compound C2 by a Sonogashira coupling with a TMS protected acetylene in the presence of a suitable catalyst (such as $Pd(PPh_3)_2Cl_2$ and the like and CuI and the like) and suitable base (such as $Et_3N$ and the like) in a suitable solvent (such as acetonitrile and the like). Compound C2 is converted to Compound C3 by heating in a suitable solvent (such as DMF and the like) in the presence of a suitable base (such as $K_2CO_3$ and the like). Compound C3 is converted to Compound C4 by a Suzuki coupling with an aryl- or heteroaryl-boronic acid (or pinacol boronic ester) in the presence of a catalyst (such as $Pd(dppf)Cl_2$ and the like) and base (such as aqueous $K_2CO_3$ and the like) in a suitable solvent (such as 1,4-dioxane and the like). Alternatively, Compound C3 is converted to Compound C4 by a Stille coupling with an aryl- or heteroaryl-stannane in the presence of a catalyst (such as $Pd_2(dba)_3$ and the like), a ligand (such as X-Phos and the like) and a base (such as CsF and the like) in a suitable solvent (such as 1,4-dioxane and the like). Compound C4 is converted to Compound C5 (where $X_3$ is iodine, bromine and the like) by halogenation with a suitable reagent (such as NIS the like) in a suitable solvent (such as DMF and the like). Compound C5 is converted to Compound C6 by a Suzuki coupling with an optionally substituted and appropriately protected amino-containing cycloalkyl/cycloalkenyl pinacol boronic ester in the presence of a catalyst (such as $Pd(dppf)Cl_2$ and the like) and base (such as aqueous $K_2CO_3$ and the like) in a suitable solvent (such as 1,4-dioxane and the like). Alternatively, Compound C5 is converted to Compound C6 by a Negishi coupling with an optionally substituted and appropriately protected amino-containing cycloalkyl zinc halide in the presence of a catalyst (such as $Pd(dppf)Cl_2$ and the like) in a suitable solvent (such as 1,4-dioxane and the like). Upon treatment with a deprotecting agent appropriate for the protecting group (such as HCl in dioxane for a Boc protecting group and the like), Compound C6 is converted to Compound C7. In cases where unsaturation exists in the ring containing the basic amino group, the compound may be converted to the fully saturated analog under an atmosphere of $H_2$ in a suitable solvent (such as methanol and the like) and in the presence of catalyst (such as 10% Pd/C and the like).

Scheme D:

Compounds of Formula (I), wherein $R_1$ is $C_{3-10}$cycloalkyl or heterocyclyl ring systems and $R_2$ is phenyl, heterocyclyl, or heteroaryl ring systems, may be prepared as described in Scheme D below.

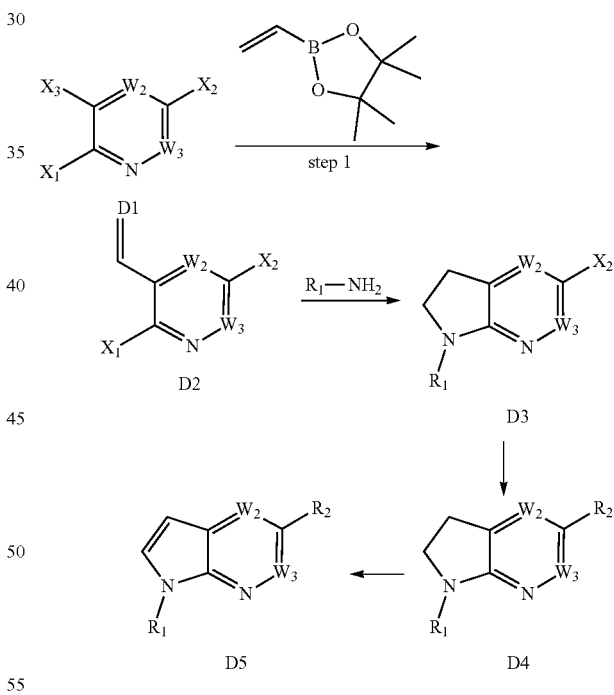

Compound D1 (where $X_1$, $X_2$ and $X_3$ are independently bromine, chlorine and the like; $W_2$ and $W_3$, are independently CH or N) is converted to Compound D2 by a Suzuki coupling with a vinyl pinacol boronic ester in the presence of a catalyst (such as $Pd(dppf)Cl_2$ and the like) and base (such as aqueous $K_2CO_3$ and the like) in a suitable solvent (such as 1,4-dioxane and the like). Compound D2 is converted to Compound D3 by heating with a primary amine ($R_1NH_2$) in a suitable solvent (such as acetonitrile and the like). Compound D3 is converted to Compound D4 by a Suzuki coupling with an aryl- or heteroaryl-boronic acid (or pinacol boronic ester) in the presence of a catalyst (such as Pd(dppf)Cl$_2$ and the like) and base (such as aqueous K$_2$CO$_3$ and the like) in a suitable solvent (such as 1,4-dioxane and the like). Alternatively, Compound D3 is converted to Compound D4 by a Stille coupling with an aryl- or heteroaryl-stannane in the presence of a catalyst (such as Pd$_2$(dba)$_3$ and the like), a ligand (such as X-Phos and the like) and a base (such as CsF and the like) in a suitable solvent (such as 1,4-dioxane and the like). Compound D4 is converted to Compound D5 by treating with a suitable oxidizing agent (such as manganese dioxide and the like) in a suitable solvent (such as toluene and the like). Any protection groups on R$_1$ and R$_2$ are removed upon treatment with a suitable reagent (such as HCl in dioxane for a Boc protecting group and the like) in a suitable solvent (such as dioxane and the like).

Scheme E:

Compounds of Formula (I), wherein R$_1$ is C$_{3-10}$cycloalkyl or heterocyclyl ring systems and R$_2$ is phenyl, heterocyclyl, or heteroaryl ring systems, may be prepared as described in Scheme E below.

Pd$_2$(dba)$_3$ and the like), a ligand (such as X-Phos and the like) and a base (such as CsF and the like) in a suitable solvent (such as 1,4-dioxane and the like). Compound E4 is converted to Compound E5 through hydrolysis of methyl ester in the presence of a suitable base (such as aqueous NaOH and the like) in a suitable solvent (such as methanol and the like) followed by decarboxylation of the resulting carboxylic acid upon heating in the appropriate solvent (such as DMSO and the like). Compound E5 is converted to Compound E6 by treatment with an activated triflate (such as Tf$_2$O or Tf$_2$NPh and the like) in presence of a suitable base (such as Et$_3$N and the like) in a suitable solvent (such as dichloromethane and the like). Compound E6 is converted to Compound E7 by a Suzuki coupling with an optionally substituted and appropriately protected amino-containing cycloalkyl/cycloalkenyl pinacol boronic ester in the presence of a catalyst (such as Pd(dppf)Cl$_2$ and the like) and base (such as aqueous K$_2$CO$_3$ and the like) in a suitable solvent (such as 1,4-dioxane and the like). Alternatively, Compound E6 is converted to Compound E7 by a Negishi coupling with an optionally substituted and appropriately

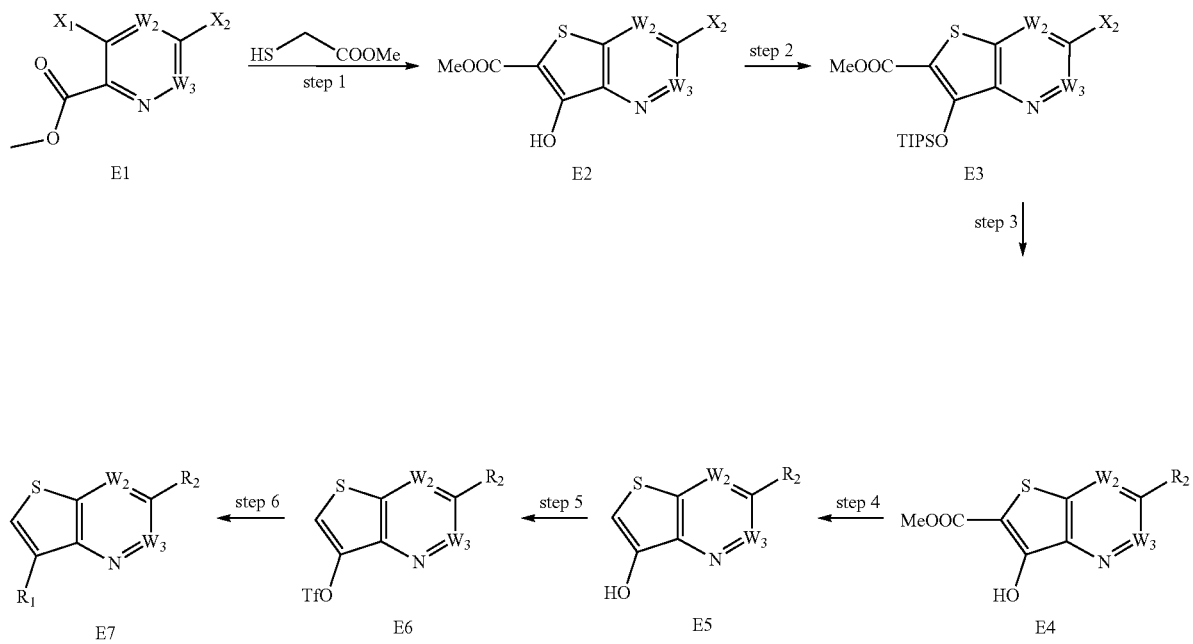

Compound E1 (where X$_1$ and X$_2$ are independently bromine, chlorine and the like; W$_2$ and W$_3$, are independently CH or N) is converted to Compound E2 through a condensation/cyclization sequence in the presence of a suitable base (such as Et$_3$N and the like) in a suitable solvent (such as acetonitrile and the like). Compound E2 is converted to Compound E3 by TIPS protection of the hydroxyl group by using an appropriate reagent (such as TIPSCl or TIPSOTf and the like) in the presence of a suitable base (such as imidazole and the like) in a suitable solvent (such as DMF and the like). Compound E3 is converted to Compound E4 by a Suzuki coupling with an aryl- or heteroaryl-boronic acid (or pinacol boronic ester) in the presence of a catalyst (such as Pd(dppf)Cl$_2$ and the like) and base (such as aqueous K$_2$CO$_3$ and the like) in a suitable solvent (such as 1,4-dioxane and the like). Alternatively, Compound E3 is converted to Compound E4 by a Stille coupling with an aryl- or heteroaryl-stannane in the presence of a catalyst (such as protected amino-containing cycloalkyl zinc halide in the presence of a catalyst (such as Pd(dppf)Cl$_2$ and the like) in a suitable solvent (such as 1,4-dioxane and the like). In cases where unsaturation exists in the ring containing the basic amino group, the compound may be converted to the fully saturated analog under an atmosphere of H$_2$ in a suitable solvent (such as methanol and the like) and in the presence of catalyst (such as 10% Pd/C and the like). Any protection groups on R$_1$ and R$_2$ are removed upon treatment with a suitable reagent (such as HCl in dioxane for a Boc protecting group and the like) in a suitable solvent (such as dioxane and the like).

Scheme F:

Compounds of Formula (I), wherein R$_1$ is C$_{3-10}$cycloalkyl or heterocyclyl ring systems and R$_2$ is phenyl, heterocyclyl, or heteroaryl ring systems, may be prepared as described in Scheme F below.

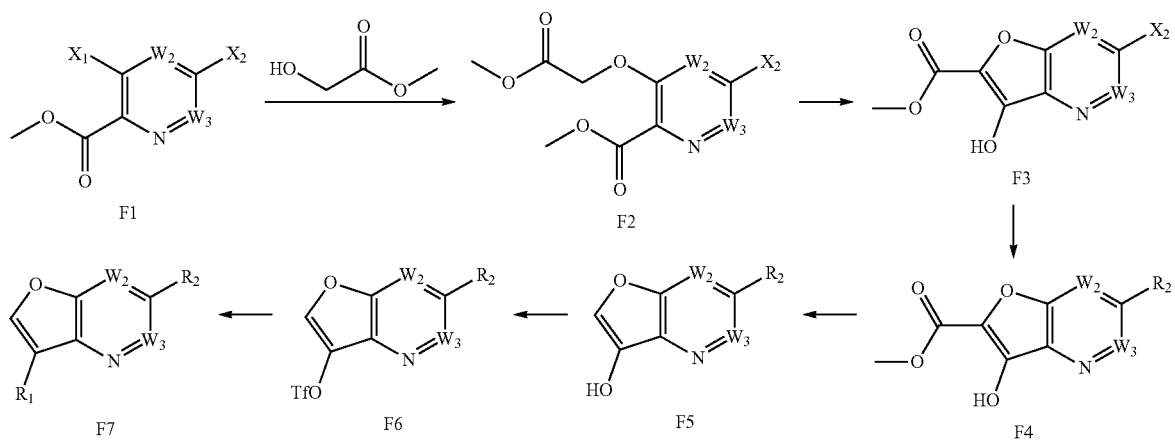

F1    F2    F3

F7    F6    F5    F4

Compound F1 (where $X_1$ and $X_2$ are independently bromine, chlorine and the like; $W_2$ and $W_3$, are independently CH or N) is converted to Compound F2 through nucleophilic substitution with methyl 2-hydroxyacetate in the presence of a suitable base (such as NaH and the like) in a suitable solvent (such as THF and the like). Compound F2 is converted to Compound F3 by cyclization upon treatment with an appropriate base (such as NaOMe and the like) in a suitable solvent (such as THF and the like). Compound F3 is converted to Compound F4 by a Suzuki coupling with an aryl- or heteroaryl-boronic acid (or pinacol boronic ester) in the presence of a catalyst (such as Pd(dppf)Cl$_2$ and the like) and base (such as aqueous K$_2$CO$_3$ and the like) in a suitable solvent (such as 1,4-dioxane and the like). Alternatively, Compound F3 is converted to Compound F4 by a Stille coupling with an aryl- or heteroaryl-stannane in the presence of a catalyst (such as Pd$_2$(dba)$_3$ and the like), a ligand (such as X-Phos and the like) and a base (such as CsF and the like) in a suitable solvent (such as 1,4-dioxane and the like). Compound F4 is converted to Compound F5 through a hydrolysis/decarboxylation sequence in the presence of a suitable base (such as aqueous NaOH and the like) in a suitable solvent (such as DMSO and the like). Compound F5 is converted to Compound F6 by treatment with an activated triflate (such as Tf$_2$ or Tf$_2$NPh and the like) in presence of a suitable base (such as Et$_3$N and the like) in a suitable solvent (such as dichloromethane and the like). Compound F6 is converted to Compound F7 by a Suzuki coupling with an optionally substituted and appropriately protected amino-containing cycloalkyl/cycloalkenyl pinacol boronic ester in the presence of a catalyst (such as Pd(dppf)Cl$_2$ and the like) and base (such as aqueous K$_2$CO$_3$ and the like) in a suitable solvent (such as 1,4-dioxane and the like). Alternatively, Compound F6 is converted to Compound F7 by a Negishi coupling with an optionally substituted and appropriately protected amino-containing cycloalkyl zinc halide in the presence of a catalyst (such as Pd(dppf)Cl$_2$ and the like) in a suitable solvent (such as 1,4-dioxane and the like). In cases where unsaturation exists in the ring containing the basic amino group, the compound may be converted to the fully saturated analog under an atmosphere of H$_2$ in a suitable solvent (such as methanol and the like) and in the presence of catalyst (such as 10% Pd/C and the like). Any protection groups on R$_1$ and R$_2$ are removed upon treatment with a suitable reagent (such as HCl in dioxane for a Boc protecting group and the like) in a suitable solvent (such as dioxane and the like).

Scheme G:

Compounds of Formula (I), wherein R$_1$ is C$_{3-10}$cycloalkyl or heterocyclyl ring systems and R$_2$ is phenyl, heterocyclyl, or heteroaryl ring systems, may be prepared as described in Scheme F below.

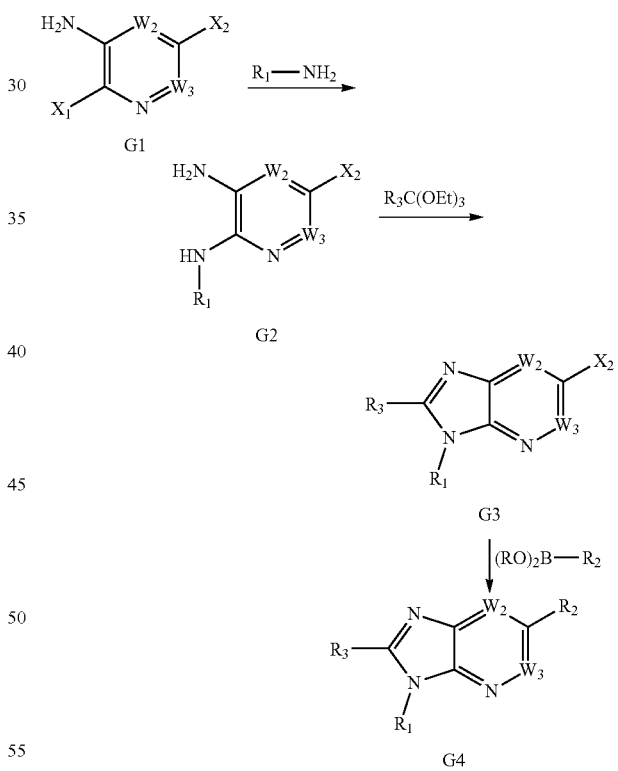

Compound G1 (where $X_1$ and $X_2$ are independently bromine, chlorine and the like; $W_2$ and $W_3$, are independently CH or N) is converted to Compound G2 by a nucleophilic substitution with a primary amine in the presence of a suitable base (such as Et$_3$N and the like) in a suitable solvent (such as decanol and the like). Alternatively, Compound G1 is converted to Compound G2 via cross coupling with a primary amine in the presence of a suitable catalyst (such as RuPhos Pd G2 and the like) and base (such as sodium tert-butoxide and the like) in an appropriate solvent such as 1,4-dioxane and the like). Compound G2 is converted to Compound G3 (where $R_3$ is H, Me, Et and the like) via cyclization using an appropriate reagent (such as triethylorthoformate and the like) in the presence of an appropriate catalyst (such as HCl and the like). Compound G3 is converted to Compound G4 by a Suzuki coupling with an aryl- or heteroaryl-boronic acid (or pinacol boronic ester) in the presence of a catalyst (such as Pd(dppf)Cl$_2$ and the like) and base (such as aqueous K$_2$CO$_3$ and the like) in a suitable solvent (such as 1,4-dioxane and the like). Alternatively, Compound G3 is converted to Compound G4 by a Stille coupling with an aryl- or heteroaryl-stannane in the presence of a catalyst (such as Pd$_2$(dba)$_3$ and the like), a ligand (such as X-Phos and the like) and a base (such as CsF and the like) in a suitable solvent (such as 1,4-dioxane and the like). Any protection groups on $R_1$ and $R_2$ are removed upon treatment with a suitable reagent (such as HCl in dioxane for a Boc protecting group and the like) in a suitable solvent (such as dioxane and the like).

Scheme H:

Compounds of Formula (I), wherein $R_1$ is alkyl, cycloalkyl, heterocyclyl, aryl or heteroaryl, $R_2$ is hydrogen, fluorine, chlorine, hydroxy, methoxy, aryl, or heteroaryl, and $R_3$ is monocyclic or bicyclic heterocyclyl or heteroaryl ring systems, may be prepared as described in Scheme H below.

Compound H1 (where $X_1$, $X_2$ and $X_3$ are independently bromine, chlorine and the like; $W_2$ and $W_3$, are independently CH or N) is converted to Compound H2 by a nucleophilic substitution with sodium benzenesulfinate in a suitable solvent (such as THF, DMSO and the like). Compound H2 is converted to Compound H3 by a nucleophilic substitution with a primary amine in the presence of a suitable base (such as K$_2$CO$_3$ and the like) in a suitable solvent (such as dioxane and the like). Alternatively, Compound H2 is converted to Compound H3 via cross coupling with a primary amine in the presence of a suitable catalyst (such as RuPhos Pd G2 and the like) and base (such as sodium tert-butoxide and the like) in an appropriate solvent such as 1,4-dioxane and the like). Compound H3 is converted to Compound H4 by treatment with sodium azide in an appropriate solvent (such as DMSO and the like). Compound H4 is converted to Compound H5 by a reduction upon treatment with an appropriate reagent (such as zinc metal and the like) in the presence of an appropriate acid (such as acetic acid and the like) in the appropriate solvent (such as CH$_2$Cl$_2$ and the like). Compound H5 is converted to Compound H6 via a diazotization/cyclization sequence upon treatment with an appropriate reagent (such as sodium nitrite and the like) in an appropriate solvent (such acetic acid and the like). Compound H6 is converted to Compound H8 by

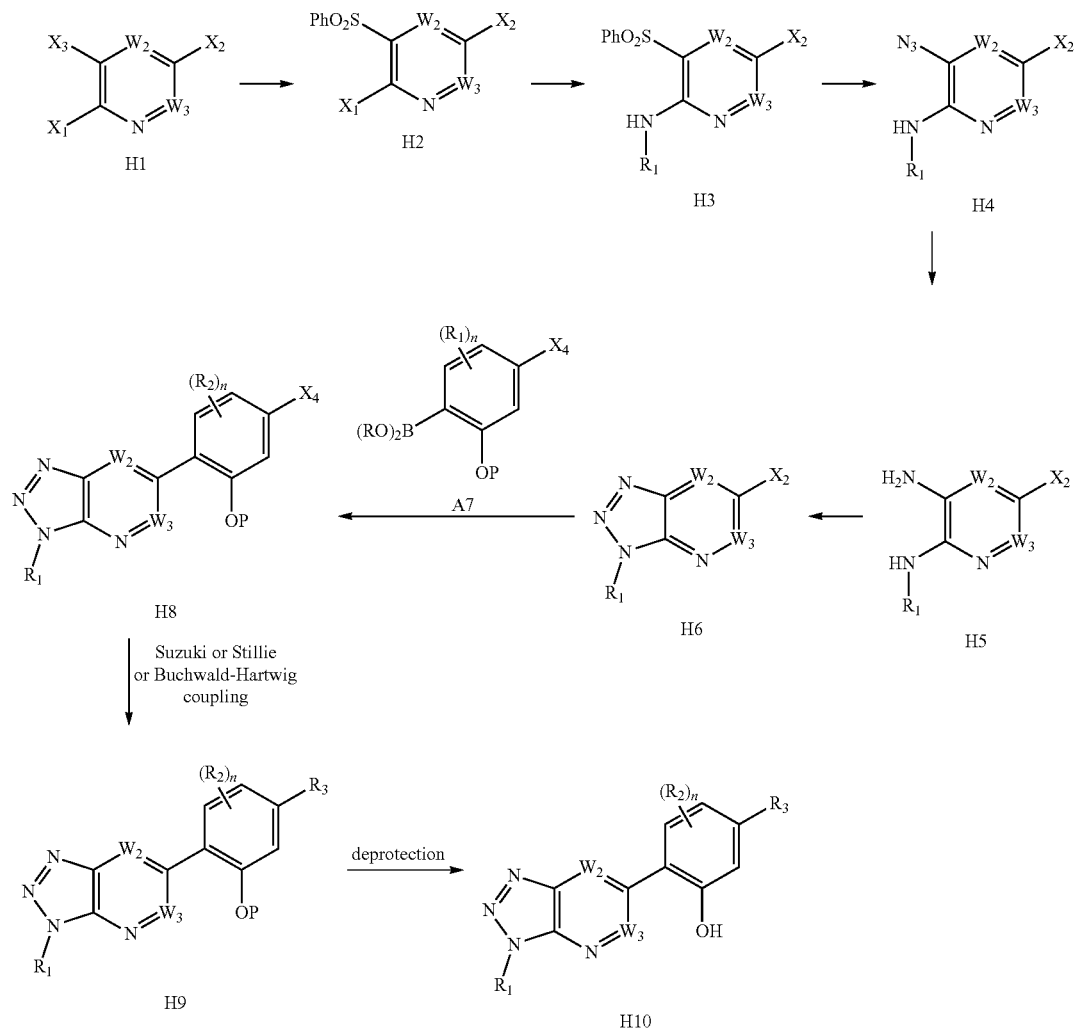

a Suzuki coupling with an aryl-boronic acid (or pinacol boronic ester) H7 (where $X_4$ is bromine, chlorine and the like; $R_2$ is hydrogen, fluorine, chlorine, hydroxy, methoxy, aryl or heteroaryl; and P is a protecting group such as MOM and the like) in the presence of a catalyst (such as Pd(dppf)$Cl_2$ and the like) and base (such as aqueous $K_2CO_3$ and the like) in a suitable solvent (such as 1,4-dioxane and the like). Compound H8 is converted to Compound H9 by a Suzuki coupling with an aryl- or heteroaryl-boronic acid (or pinacol boronic ester) in the presence of a catalyst (such as Pd(dppf)$Cl_2$ and the like) and a base (such as aqueous $K_2CO_3$ and the like) in a suitable solvent (such as 1,4-dioxane and the like). Alternatively, Compound H8 is converted to Compound H9 by a Stille coupling with an aryl- or heteroaryl-stannane in the presence of a catalyst (such as $Pd_2(dba)_3$ and the like), a ligand (such as X-Phos and the like) and a base (such as CsF and the like) in a suitable solvent (such as 1,4-dioxane and the like). Alternatively, Compound H8 is converted to Compound H9 by treatment with pinacolatodiboron and a base (such as KOAc and the like) in the presence of a catalyst (such as Pd(dppf)$Cl_2$ and the like) in an appropriate solvent (such as 1,4-dioxane and the like), followed by addition of an aryl- or heteroaryl-halide in the presence of a catalyst (such as Pd(dppf)$Cl_2$ and the like) and a base (such as aqueous $K_2CO_3$ and the like) in a suitable solvent (such as 1,4-dioxane and the like). Alternatively, Compound H8 is converted to Compound H9 by a Buchwald-Hartwig coupling with a heteroaryl or amine in the presence of a catalyst (such as $Pd_2(dba)_3$ and the like), a ligand (such as tBuX-Phos and the like) and a base (such as $K_3PO_4$ and the like) in a suitable solvent (such as 1,4-dioxane and the like). Compound H9 is converted to Compound H10 upon treatment with conditions appropriate to the removal of the protecting groups (such as HCl in dioxane for a MOM protecting group) in a suitable solvent (such as dioxane and the like).

SPECIFIC SYNTHETIC EXAMPLES

To describe in more detail and assist in understanding, the following non-limiting examples are offered to more fully illustrate the scope of compounds described herein and are not to be construed as specifically limiting the scope thereof. Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

Compound Examples

As used above, and throughout the present description, the following abbreviations, unless otherwise indicated, shall be understood to have the following meanings:

| Abbreviation | Meaning |
| --- | --- |
| Δ | heating (chemistry) or deletion (biology) |
| AcOH or HOAc | acetic acid |
| $Ac_2O$ | acetic anhydride |
| Ar | argon |
| ACN or $CH_3CN$ or MeCN | acetonitrile |
| atm | atmosphere(s) |
| $BBr_3$ | boron tribromide |
| BnOH | benzyl alcohol |
| Boc | tert-butoxy-carbonyl |
| $Boc_2O$ | di-tert-butyl dicarbonate |
| $B_2pin_2$ | bis(pinacolato)diboron |
| BuOH | n-butanol |
| $(t-Bu)_3P$ $HBF_4$ | Tri-t-butylphosphonium tetrafluoroborate |
| ° C. | degrees Centigrade |
| Celite ® or Celite | diatomaceous earth |
| $(COCl)_2$ | oxalyl chloride |
| CsCl | cesium chloride |
| $Cs_2CO_3$ | cesium carbonate |
| CsF | cesium fluoride |
| CuI | copper(I) iodide |
| d/h/hr/hrs/min/s | day(d)/hour(h, hr or hrs)/minute(min)/second(s) |
| DAST | (diethylamino)sulfur trifluoride |
| DCM or $CH_2Cl_2$ | dichloromethane |
| DIEA or DIPEA | N,N-diisopropylethylamine |
| DMA | dimethylacetamide |
| DMAP | 4-(dimethylamino)pyridine |
| DME | 1,2-dimethoxyethane |
| DMF | dimethylformamide |
| DMSO | dimethylsulfoxide |
| EtI | iodoethane |
| $Et_3N$ | triethylamine |
| EtOAc | ethyl acetate |
| EtOH | ethanol |
| $Et_2O$ | diethyl ether |
| $H_2$ | hydrogen |
| HCl | hydrochloric acid |
| $H_2SO_4$ | sulfuric acid |
| HCOOH | formic acid |
| $K_2CO_3$ | potassium carbonate |
| KOAc | potassium acetate |
| KOtBu | Potassium t-butoxide |
| KOH | potassium hydroxide |

| Abbreviation | Meaning |
|---|---|
| KSCN | potassium thiocyanate |
| LAH | lithium aluminum hydride |
| LC/MS, LCMS or LC-MS | liquid chromatographic mass spectroscopy |
| LDA | lithium diisopropylamine |
| LiOH | lithium hydroxide |
| MeOH | methanol |
| MeI | iodomethane |
| $MgSO_4$ | magnesium sulfate |
| MOM | methoxy methyl |
| MOMCl | chloromethyl methyl ether |
| MS | mass spectroscopy |
| NBS | N-bromosuccinimide |
| NCS | N-chlorosuccinimide |
| $NH_4Cl$ | ammonium chloride |
| $NH_4OAc$ | ammonium acetate |
| $NH_4OH$ | ammonium hydroxide or aqueous ammonia |
| $NH_2OH \cdot HCl$ | hydroxylamine hydrochloride |
| $NaBH_4$ | sodium borohydride |
| $Na_2CO_3$ | sodium carbonate |
| NaH | sodium hydride |
| $NaHCO_3$ | sodium bicarbonate |
| NaH | sodium hydride |
| NaOAc | sodium acetate |
| NaOH | sodium hydroxide |
| NaOMe | sodium methoxide |
| $Na_2SO_4$ | sodium sulfate |
| $N_2$ | nitrogen |
| $NH_4Cl$ | ammoniuim chloride |
| NMP | N-methylpyrrolidone |
| NMR | nuclear magnetic resonance |
| NOESY | Nuclear Overhauser Enhancement Spectroscopy |
| Pd | palladium |
| Pd/C | palladium on carbon |
| $Pd_2(dba)_3$ or $Pd_2dba_3$ | tris(dibenzylideneacetone)dipalladium(0) |
| $Pd(dppf)Cl_2$ or $Pd(dppf)Cl_2$—$CH_2Cl_2$ | [1,1'-bis(diphenylphosphino)ferrocene]dichloropalladium(II), complex with dichloromethane |
| $Pd(PPh_3)_4$ or $Pd(Ph_3P)_4$ | tetrakis(triphenylphosphine)palladium(0)) |
| $Pd(PPh_3)_2Cl_2$, $PdCl_2(PPh_3)_2$ or $PdCl_2(Ph_3P)_2$ | bis(triphenylphosphine)palladium(II) dichloride |

| Abbreviation | Meaning |
|---|---|
| PhMe | toluene |
| Psi | pounds per square inch pressure |
| $Pt_2O$ | platinum(IV) oxide |
| PyBOP | (benzotriazol-1-yloxy)tripyrrolidinophosphonium hexafluorophosphate |
| PyBroP ® | bromotripyrrolidinophosphonium hexafluorophosphate |
| RT | retention time |
| RuPhos Pd G2 | chloro(2-dicyclohexylphosphino-2',6'-diisopropoxy-1,1'-biphenyl)[2-(2'-amino-1,1'-biphenyl)]palladium(II) |
| $SOCl_2$ | thionly chloride |
| $SO_2Cl_2$ | sulfuryl chloride |
| TEA, $Et_3N$ or $NEt_3$ | triethylamine |
| TFA | trifluoroacetic acid |
| $Tf_2NPh$ | N-phenyl-bis(trifluoromethanesulfonimide) or 1,1,1-trifluoro-N-phenyl-N-[(trifluoromethyl)sulfonyl]methanesulfonamide or N,N-bis(trifluoromethylsulfonyl)aniline or N-phenyl-trifluoromethanesulfonimide |
| $Tf_2O$ | trifluoromethanesulfonic anhydride |
| THF | tetrahydrofuran |
| THP | tetrahydropyranyl |
| TIPS | tiisopropylsilane |
| TIPSCl | triisopropylsilyl chloride |
| TIPSOTf | triisopropylsilyl trifluoromethanesulfonate or trifluoromethanesulfonic acid triisopropylsilyl ester or triisopropylsilyl triflate |
| TLC | thin layer chromatography |
| TMEDA | tetramethylethylenediamine |
| TMS | trimethylsilane |
| TMSCl | trimethylchlorosilane or trimethylsilyl chloride |
| t-Bu | tert-butyl |
| UPLC | ultra performance liquid chromatography |

Example 1

Preparation of Compound 11

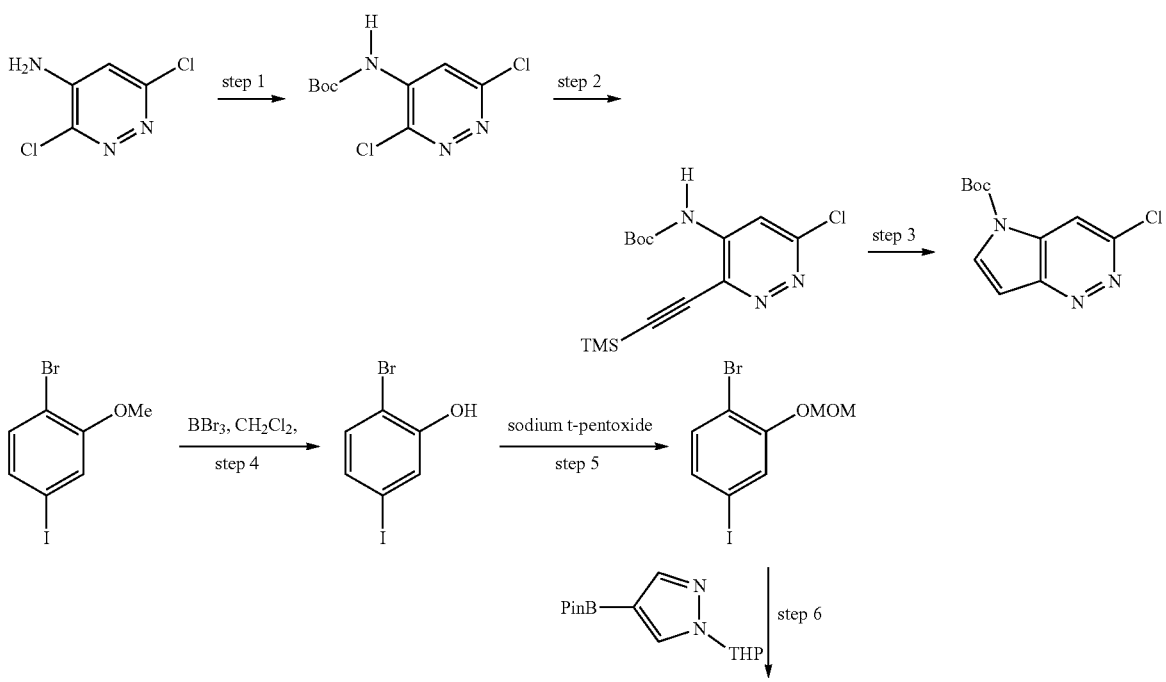

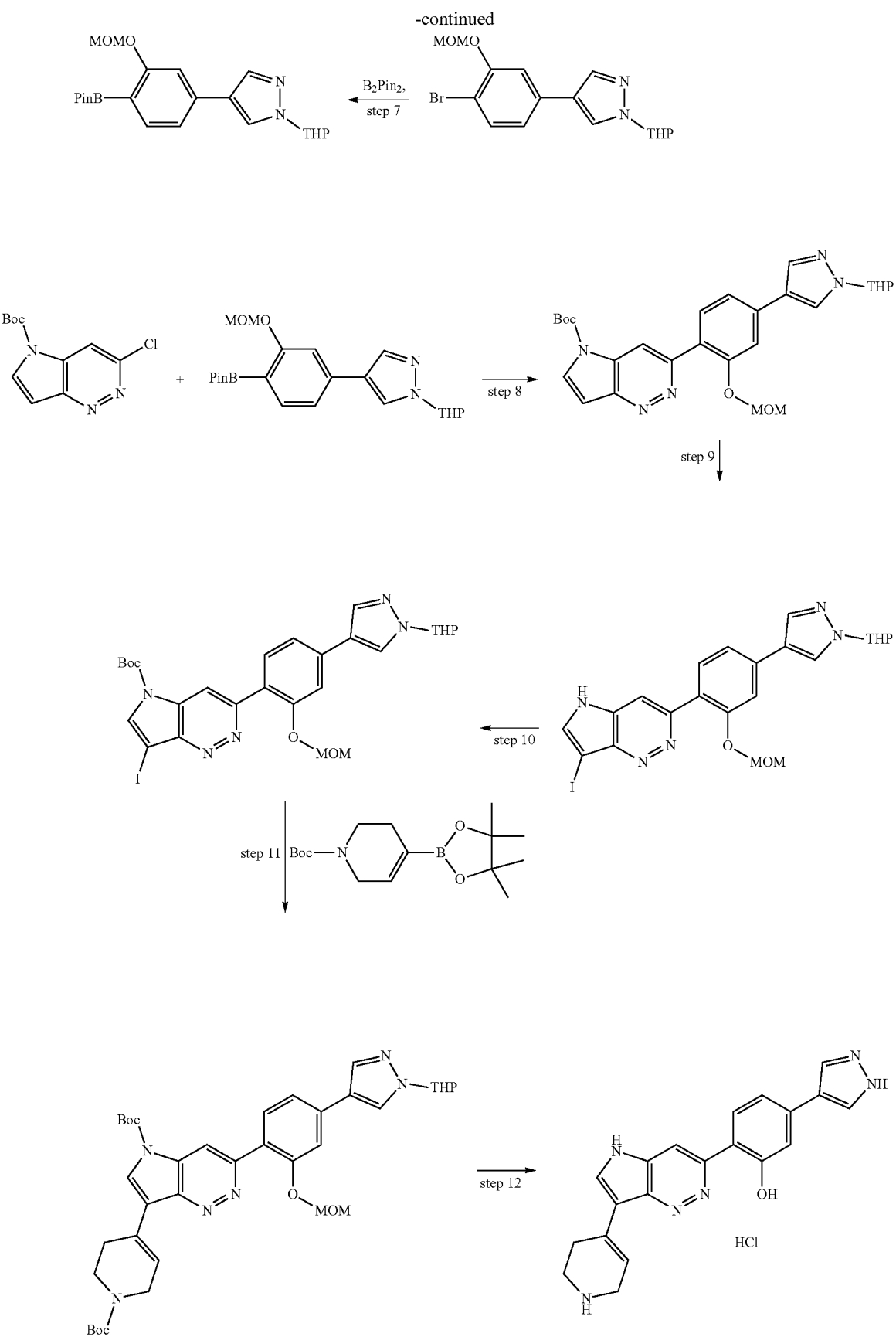

Step 1: To suspension of 3,6-dichloropyridazin-4-amine (1.48 g, 9.02 mmol) in $CH_2Cl_2$ (25 mL) was added di-tertbutyl dicarbonate (2.2 g, 10 mmol) in one portion followed by addition of a few crystals of DMAP. The reaction was stirred at room temperature for 4 h. Almost complete conversion was observed accompanied by formation of di-Boc material. The solvent was removed under reduced pressure and the product was isolated by silica gel column chromatography eluting with EtOAc/hexanes gradient (0-20% EtOAc) to afford tert-butyl N-(3,6-dichloropyridazin-4-yl)carbamate (1.71 g, 72%) as a white solid.

Step 2: To a mixture of tert-butyl N-(3,6-dichloropyridazin-4-yl)carbamate (1.71 g, 6.47 mmol), CuI (75 mg, 0.39 mmol) and $Pd(PPh_3)_2Cl_2$ (140 mg, 0.20 mmol) in $CH_3CN$ (25 mL) under an argon atmosphere was added $Et_3N$ (4.50 mL, 32.3 mmol) followed by ethynyl(trimethyl)silane (1.10 mL, 7.78 mmol). The mixture was heated under an argon atmosphere for 1 h, after which, no starting material was detected by UPLC. The solvent was concentrated and the residue was treated with EtOAc. The solid was filtered, washed well with EtOAc and discarded. The mother liquor was concentrated and the residue was purified by silica gel column chromatography eluting with EtOAc/hexanes gradient (0-20% EtOAc) to afford tert-butyl N-[6-chloro-3-(2-trimethylsilylethynyl)pyridazin-4-yl]carbamate (1.12 g, 53%) as an oil which solidified on standing.

Step 3: To a solution of tert-butyl N-[6-chloro-3-(2-trimethylsilylethynyl)pyridazin-4-yl]carbamate (1.1 g, 3.4 mmol) in DMF (10 mL) was added powdered $K_2CO_3$ (1.00 g, 7.24 mmol). The mixture was heated at 60° C. for 30 min. The reaction was then diluted with water and extracted with EtOAc. Upon drying of the organic phase over $Na_2SO_4$ and concentration of the solvent, the residue was purified by silica gel column chromatography eluting with EtOAc/hexanes gradient (0-50% EtOAc) to afford tert-butyl 3-chloropyrrolo[3,2-c]pyridazine-5-carboxylate (0.600 g, 70%) as a white solid. MS m/z 254.3 $[M+H]^+$.

Step 4: 1-Bromo-4-iodo-2-methoxybenzene (50 g, 160 mmol) was suspended in dichloromethane (75 mL) at −10° C. 1 N $BBr_3$ in $CH_2Cl_2$ (250 mL, 250 mmol) was cannulated in over 30 minutes, with the internal temperature remaining below 0° C. throughout the addition. After the addition, the mixture was stirred at 0° C. for 1 h, and then at room temperature for an additional 16 h. The mixture was cooled in an ice bath. 10% Aqueous $Na_2CO_3$ (250 mL) was added in portions. The mixture was then partitioned between $H_2O$ and dichloromethane. The dichloromethane layer was dried over $MgSO_4$ and then filtered. 2-Bromo-5-iodophenol (46 g, 96%) was obtained from the filtrate as a pinkish-white solid.

$^1$H NMR (acetone-$d_6$) δ: 9.24 (br s, 1H), 7.38 (d, J=2 Hz, 1H), 7.31 (d, J=8.5 Hz, 1H), 7.17 (dd, J=8.5 Hz, 2 Hz, 1H).

Step 5: 2-Bromo-5-iodophenol (54.9 g, 184 mmol), was dissolved in DMF (240 mL) at 0° C. 2.5 M Sodium tert-pentoxide in THF (90 mL, 230 mmol) was then added dropwise. The reaction was stirred at 0° C. for 15 minutes after the addition was complete. Chloromethyl methyl ether (18 mL, 225 mmol) was added dropwise over 30 minutes. The mixture was warmed to ambient temperature and was stirred for 16 h. The mixture was diluted with $H_2O$ (1500 mL) and was extracted into EtOAc (2×400 mL). The combined organic layers were washed with $H_2O$ (300 mL), and then with brine. The organic layer was dried over $MgSO_4$, filtered, and concentrated under vacuum. The crude product was flushed through a silica plug using $CH_2Cl_2$ in hexanes (0-10%) to yield 1-bromo-4-iodo-2-(methoxymethoxy)benzene (61 g, 97%) as a clear liquid.

$^1$H NMR (acetone-$d_6$) δ: 7.56 (d, J=2 Hz, 1H), 7.38 (d, J=8 Hz, 1H), 7.33 (dd, J=8 Hz, 2 Hz, 1H), 5.35 (s, 2H), 3.50 (s, 3H).

Step 6: 1-Bromo-4-iodo-2-(methoxymethoxy)benzene (49 g, 143 mmol), 1-(tetrahydro-2H-pyran-2-yl)-4-(4,4,5,5-tetramethyl-1,3,2-dioxaborolan-2-yl)-1H-pyrazole (48.4 g, 174 mmol), $PdCl_2$(dppf)-dichloromethane adduct (3.1 g, 3.6 mmol), dioxane (500 mL), and aqueous 1 N $K_2CO_3$ (350 mL, 350 mmol) were heated at 90° C. for 2 h. The reaction mixture was then partitioned between $H_2O$ and EtOAc. The organic layer was dried over $MgSO_4$, filtered, and concentrated under vacuum. Purification by silica gel chromatography (EtOAc in hexanes, 20-50%), followed by trituration with hexanes, yielded 4-(4-bromo-3-(methoxymethoxy)phenyl)-1-(tetrahydro-2H-pyran-2-yl)-1H-pyrazole (40.4 g, 77%) as an off-white solid.

$^1$H NMR (acetone-$d_6$) δ: 8.22 (s, 1H), 7.88 (s, 1H), 7.55 (d, J=8.5 Hz, 1H), 7.47 (d, J=2 Hz, 1H), 7.23 (dd, J=8.5 Hz, 2 Hz, 1H), 5.44 (dd, J=9.5 Hz, 2.5 Hz, 1H), 5.38 (S, 2H), 4.01 (m, 1H), 3.72 (m, 1H), 3.51 (s, 3H), 2.1-2.23 (m, 1H), 2.0-2.1 (m, 2H), 1.7-1.8 (m, 1H), 1.6-1.7 (m, 2H).

Step 7: Potassium acetate (22 g, 224 mmol) was pumped dry at 180° C. for 2 h, and then the flask was filled with argon. 4-(4-Bromo-3-(methoxymethoxy)phenyl)-1-(tetrahydro-2H-pyran-2-yl)-1H-pyrazole (20 g, 54.5 mmol), $PdCl_2$(dppf)-dichloromethane adduct (1.22 g, 1.47 mmol), bis(pinacolato)diboron (20.8 g, 81.9 mmol), and dry toluene (200 mL) was added. This mixture was heated at 110° C. for 2 days. The mixture was filtered through Celite®, eluting with ether. The filtrate was concentrated under vacuum, re-dissolved in ether, and was filtered again through Celite® to remove solid impurities. Purification by silica gel chromatography (EtOAc in hexanes, 20-50%) yielded crude product (12 g) that was mostly free of protodeboronated by-product. This was dissolved in ether (100 mL) and washed with aqueous $NaHCO_3$ (2×1.5 L) and brine, then dried over $MgSO_4$, and then filtered. The filtrate was concentrated to provide pure product (7.05 g, 32%) as a glassy semi-solid.

$^1$H NMR (500 MHz, acetone-$d_6$): δ 8.24 (s, 1H), 7.90 (s, 1H), 7.65 (d, J=8 Hz, 1H), 7.33 (d, J=1.5 Hz, 1H), 7.29 (dd, J=8 Hz, 1.5 Hz, 1H), 5.45 (dd, J=10 Hz, 2.5 Hz, 1H), 5.25 (s, 2H), 4.01 (m, 1H), 3.69-3.74 (m, 1H), 3.52 (s, 3H), 2.15-2.2 (m, 1H), 2.0-2.1 (m, 2H), 1.7-1.8 (m, 1H), 1.6-1.68 (m, 2H), 1.35 (s, 12H).

Step 8: A mixture of tert-butyl 3-chloropyrrolo[3,2-c]pyridazine-5-carboxylate (150 mg, 0.59 mmol), 4-[3-(methoxymethoxy)-4-(4,4,5,5-tetramethyl-1,3,2-dioxaborolan-2-yl)phenyl]-1-tetrahydropyran-2-yl-pyrazole (0.300 g, 0.724 mmol), [1,1'-bis(diphenylphosphino)ferrocene]dichloropalladium(I) (25 mg, 0.033 mmol) and $K_2CO_3$ (250 mg, 1.81 mmol) in a vial was evacuated and backfilled with argon. 1,4-Dioxane (2 mL) and water (0.5 mL) were added to the mixture and it was heated at 90° C. for 5 h. The mixture was cooled to room temperature, diluted with water, and the product was extracted with $CH_2Cl_2$ (3 times). The combined organic layers were dried over $Na_2SO_4$ and concentrated. The residue was purified by silica gel column chromatography eluting with EtOAc/hexanes gradient (70-100% EtOAc) to afford tert-butyl 3-[2-(methoxymethoxy)-4-(1-tetrahydropyran-2-ylpyrazol-4-yl)phenyl]pyrrolo[3,2-c]pyridazine-5-carboxylate (0.15 g, 0.297 mmol, 100 mass %, 50.2%) as a white solid.

MS m/z 506.6 $[M+H]^+$; $^1$H NMR (acetone-$d_6$) δ: 8.67 (s, 1H), 8.30 (d, J=0.9 Hz, 1H), 8.10 (d, J=4.1 Hz, 1H), 8.02 (d, J=8.2 Hz, 1H), 7.97 (d, J=0.9 Hz, 1H), 7.58 (d, J=1.6 Hz, 1H), 7.48 (dd, J=7.9, 1.6 Hz, 1H), 7.08 (dd, J=3.8, 0.9 Hz, 1H), 5.49 (dd, J=9.8, 2.5 Hz, 1H), 5.40 (s, 2H), 3.98-4.06 (m, 1H), 3.70-3.79 (m, 1H), 3.45 (s, 3H), 2.17-2.26 (m, 1H), 2.03-2.09 (m, 2H), 1.81 (s, 1H), 1.74 (s, 9H), 1.57-1.68 (m, 2H).

Step 9: A mixture of tert-butyl 3-[2-(methoxymethoxy)-4-(1-tetrahydropyran-2-ylpyrazol-4-yl)phenyl]pyrrolo[3,2-c]pyridazine-5-carboxylate (140 mg, 0.28 mmol) in diphenyl ether (1.6 mL) was heated at 200° C. for 15 min and monitored by UPLC. Once complete, the reaction was cooled to room temperature and a precipitate was formed. The mixture was then diluted with pentane. The solid was filtered and washed with additional pentane. After drying, 3-[2-(methoxymethoxy)-4-(1-tetrahydropyran-2-ylpyrazol-4-yl)phenyl]-5H-pyrrolo[3,2-c]pyridazine (110 mg, 0.27 mmol) was dissolved in DMF (1.5 mL) and N-iodosuccinimide (68 mg, 0.30 mmol) was added. The reaction was stirred at room temperature for 15 min and a product precipitated out of the solution. The reaction was diluted with water and the solid was filtered and washed with water and dried. 7-Iodo-3-[2-(methoxymethoxy)-4-(1-tetrahydropyran-2-ylpyrazol-4-yl)phenyl]-5H-pyrrolo[3,2-c]pyridazine (140 mg, 97%) was obtained as tan solid. MS m/z 532.4 [M+H]$^+$;

Step 10: 7-Iodo-3-[2-(methoxymethoxy)-4-(1-tetrahydropyran-2-ylpyrazol-4-yl)phenyl]-5H-pyrrolo[3,2-c]pyridazine (140 mg, 0.26 mmol) was suspended in $CH_2Cl_2$ (2 mL) and di-tertbutyl dicarbonate (80 mg, 0.37 mmol) was added followed by few crystals of DMAP. The reaction was stirred at room temperature and monitored by UPLC until complete consumption of the starting material was observed (20 min). The solvent was removed under reduce pressure and the residue was purified by silica gel column chromatography (60-100% EtOAc in hexanes) to afford tert-butyl 7-iodo-3-[2-(methoxymethoxy)-4-(1-tetrahydropyran-2-ylpyrazol-4-yl)phenyl]pyrrolo[3,2-c]pyridazine-5-carboxylate (122 mg, 71%) as a pale yellow foam.

MS m/z 632.5 [M+H]$^+$; $^1$H NMR (acetone-d$_6$) δ: 8.66 (s, 1H), 8.31 (d, J=0.6 Hz, 1H), 8.27 (s, 1H), 8.03 (d, J=7.9 Hz, 1H), 7.98 (d, J=0.9 Hz, 1H), 7.58 (d, J=1.6 Hz, 1H), 7.49 (dd, J=7.9, 1.6 Hz, 1H), 5.49 (dd, J=9.8, 2.5 Hz, 1H), 5.41 (s, 2H), 3.98-4.06 (m, 1H), 3.69-3.80 (m, 1H), 3.45 (s, 3H), 2.14-2.28 (m, 1H), 2.02-2.08 (m, 2H), 1.77-1.84 (m, 1H), 1.75 (s, 9H), 1.60-1.69 (m, 2H).

Step 11: An oven-dried flask was equipped with a magnetic stir bar and charged with tert-butyl 7-iodo-3-[2-(methoxymethoxy)-4-(1-tetrahydropyran-2-ylpyrazol-4-yl)phenyl]pyrrolo[3,2-c]pyridazine-5-carboxylate (122 mg, 0.19 mmol), tert-butyl 4-(4,4,5,5-tetramethyl-1,3,2-dioxaborolan-2-yl)-3,6-dihydro-2H-pyridine-1-carboxylate (75 mg, 0.24 mmol), Pd(PPh$_3$)$_4$ (25 mg, 0.022 mmol) and K$_2$CO$_3$ (80 mg, 0.58 mmol). The flask was sealed with a rubber septum, and then evacuated and backfilled with argon (3×). 1,4-Dioxane (1.2 mL) and water (0.3 mL) were added and the reaction was heated to 90° C. for 6 h. The reaction was cooled to room temperature, diluted with water (5 mL), and then extracted with CH$_2$Cl$_2$ (3×). The combined organic layers were dried over Na$_2$SO$_4$ and concentrated under reduced pressure. The residue was purified by silica gel column chromatography eluting with EtOAc/hexanes gradient (60-100% EtOAc) to afford tert-butyl 7-(1-tert-butoxycarbonyl-3,6-dihydro-2H-pyridin-4-yl)-3-[2-(methoxymethoxy)-4-(1-tetrahydropyran-2-ylpyrazol-4-yl)phenyl]pyrrolo[3,2-c]pyridazine-5-carboxylate (38 mg, 29%) and tert-butyl 4-[3-[2-(methoxymethoxy)-4-(1-tetrahydropyran-2-ylpyrazol-4-yl)phenyl]-5H-pyrrolo[3,2-c]pyridazin-7-yl]-3,6-dihydro-2H-pyridine-1-carboxylate (25 mg, 22%).

Step 12: To tert-butyl 7-(1-tert-butoxycarbonyl-3,6-dihydro-2H-pyridin-4-yl)-3-[2-(methoxymethoxy)-4-(1-tetrahydropyran-2-ylpyrazol-4-yl)phenyl]pyrrolo[3,2-c]pyridazine-5-carboxylate (38 mg, 0.055 mmol) was added 4N HCl in dioxane (1 mL, 4.0 mmol) followed by MeOH (1 mL). The reaction was heated at 55° C. for 8 h. The solvents were removed under reduced pressure and the residue was triturated in Et$_2$O. The resultant solid was filtered, washed well with excess Et$_2$O and dried under a nitrogen flow to afford 5-(1H-pyrazol-4-yl)-2-[7-(1,2,3,6-tetrahydropyridin-1-ium-4-yl)-5H-pyrrolo[3,2-c]pyridazin-3-yl]phenol hydrochloride (15 mg, 71%) as a bright yellow solid.

MS m/z 359.3 [M+H]$^+$; $^1$H NMR (DMSO-d$_6$) δ:13.26 (br s, 1H), 9.49 (s, 2H), 8.60 (s, 1H), 8.50 (br. s., 1H), 8.20 (s, 2H), 7.82 (d, J=8.5 Hz, 1H), 7.41 (td, J=4.3, 1.9 Hz, 2H), 6.97-7.16 (m, 1H), 3.81-4.00 (m, 2H), 3.35-3.55 (m, 2H), 2.77-2.97 (m, 2H); 1H not observed (NH or OH).

Using the procedure described for Example 1, above, additional compounds described herein were prepared by substituting the appropriate starting materials, suitable reagents and reaction conditions, obtaining compounds such as those selected from:

| Cpd | Data |
|---|---|
| 20 | MS m/z 415.5 [M + H]$^+$; $^1$H NMR (methanol-d$_4$) δ: 8.61 (s, 1H), 8.45 (s, 1H), 8.26 (s, 2H), 7.77 (d, J = 7.9 Hz, 1H), 7.45 (dd, J = 7.9, 1.6 Hz, 1H), 7.36 (d, J = 1.6 Hz, 1H), 7.06 (s, 1H), 3.73-3.79 (m, J = 6.6 Hz, 1H), 3.57-3.63 (m, J = 5.0 Hz, 1H), 1.71 (s, 6H), 1.64 (s, 6H); 4 Hs not observed (3 NHs and OH). |
| 27 | MS m/z 385.4 [M + H]$^+$; $^1$H NMR (methanol-d$_4$) δ: 8.60 (s, 1H), 8.42-8.49 (m, J = 2.5 Hz, 2H), 8.39 (s, 1H), 7.78 (d, J = 8.2 Hz, 1H), 7.48 (dd, J = 8.0, 1.7 Hz, 1H), 7.40 (d, J = 1.6 Hz, 1H), 7.35 (d, J = 5.7 Hz, 1H), 4.54 (dd, J = 6.3, 5.4 Hz, 1H), 4.43 (dd, J = 7.3, 4.1 Hz, 1H), 3.35-3.41 (m, 1H), 2.87 (d, J = 18.0 Hz, 1H), 2.42-2.52 (m, 1H), 2.37-2.42 (m, 1H), 2.25-2.36 (m, 1H), 2.03-2.16 (m, 1H); 4 Hs not observed (3 NHs and OH). |
| 28 | MS m/z 401.4 [M + H]$^+$; $^1$H NMR (methanol-d$_4$) δ: 8.62 (s, 1H), 8.50 (s, 2H), 8.47 (s, 1H), 7.79 (d, J = 7.9 Hz, 1H), 7.49 (dd, J = 8.2, 1.6 Hz, 1H), 7.41 (d, J = 1.6 Hz, 1H), 7.25 (d, J = 5.7 Hz, 1H), 4.33 (d, J = 6.0 Hz, 1H), 4.11-4.15 (m, 2H), 4.06 (dd, J = 12.6, 1.9 Hz, 1H), 3.97 (d, J = 7.3 Hz, 1H), 3.93 (d, J = 12.6 Hz, 1H), 3.39 (dd, J = 18.6, 8.2 Hz, 1H), 3.10 (dd, J = 18.3, 1.6 Hz, 1H); 4 Hs not observed (3 NHs and OH). |

Example 2

Preparation of Compound 30

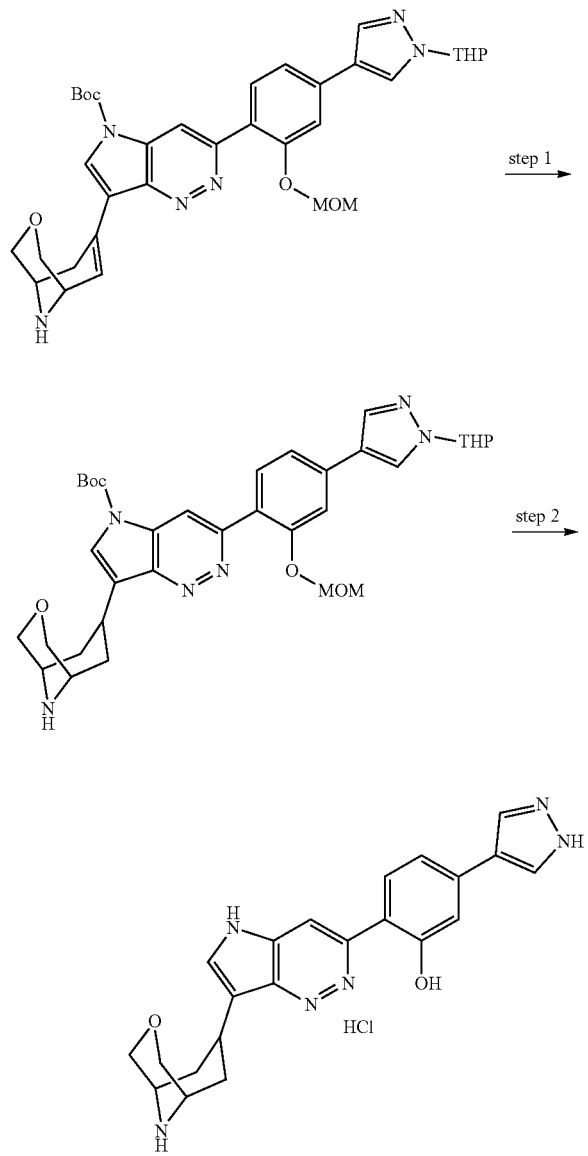

Step 1: A solution of tert-butyl 7-[5-tert-butoxycarbonyl-3-[2-(methoxymethoxy)-4-(1-tetrahydropyran-2-ylpyrazol-4-yl)phenyl]pyrrolo[3,2-c]pyridazin-7-yl]-3-oxa-9-azabicyclo[3.3.1]non-6-ene-9-carboxylate (prepared following the method described in Example 1, step 11) (100 mg, 0.14 mmol) in MeOH (2 mL) and EtOAc (0.2 mL) was hydrogenated over 10% Pd/C (20 mg, 0.02 mmol, 10 mass %) and 10% Pd(OH)$_2$/C (20 mg, 0.014 mmol, 10 mass %) in a Parr shaker at 50 psi of H$_2$ over 72 h. The catalysts were filtered and washed with MeOH. The mother liquor was concentrated and the residue was purified by silica gel column chromatography eluting with a MeOH/CH$_2$Cl$_2$ gradient (0-10% MeOH) to afford tert-butyl 7-[5-tert-butoxycarbonyl-3-[2-(methoxymethoxy)-4-(1-tetrahydropyran-2-ylpyrazol-4-yl)phenyl]pyrrolo[3,2-c]pyridazin-7-yl]-3-oxa-9-azabicyclo[3.3.1]nonane-9-carboxylate (46 mg, 46%) as a pale yellow foam. MS m/z 631.4 [M+H]$^+$.

Step 2: To tert-butyl 7-[5-tert-butoxycarbonyl-3-[2-(methoxymethoxy)-4-(1-tetrahydropyran-2-ylpyrazol-4-yl)phenyl]pyrrolo[3,2-c]pyridazin-7-yl]-3-oxa-9-azabicyclo[3.3.1]nonane-9-carboxylate (46 mg, 0.063 mmol) was added 4N HCl in dioxane (0.5 mL, 2 mmol) followed by MeOH (1 mL). The reaction was stirred at 50° C. for 16 h. Volatiles were then removed under reduced pressure, the residue was then triturated with Et$_2$O, and the solid was filtered and dried in a nitrogen flow to afford 2-[7-(3-oxa-9-azoniabicyclo[3.3.1]nonan-7-yl)-5H-pyrrolo[3,2-c]pyridazin-3-yl]-5-(1H-pyrazol-4-yl)phenol hydrochloride (16 mg, 58%) as a yellow solid. Stereochemistry was assigned based on NOESY data.

MS m/z 403.4 [M+H]$^+$; $^1$H NMR (methanol-d$_4$) δ: 8.53 (s, 1H), 8.46 (s, 2H), 8.26 (d, J=0.6 Hz, 1H), 7.75 (d, J=8.2 Hz, 1H), 7.47 (dd, J=8.2, 1.9 Hz, 1H), 7.39 (d, J=1.9 Hz, 1H), 3.96 (dd, J=12.6, 1.9 Hz, 2H), 3.90 (d, J=12.6 Hz, 2H), 3.85 (dd, J=9.4, 3.2 Hz, 2H), 3.66-3.78 (m, 1H), 2.82 (ddd, J=14.5, 9.4, 6.0 Hz, 2H), 2.51 (ddd, J=14.5, 11.4, 3.2 Hz, 2H); 4 Hs not observed (3 NHs and OH).

Using the procedure described for Example 2, above, additional compounds described herein were prepared by substituting the appropriate starting materials, suitable reagents and reaction conditions, obtaining compounds such as those selected from:

| Cpd | Data |
|---|---|
| 12 | MS m/z 361.3 [M + H]$^+$ |
| 29 | MS m/z 387.4 [M + H]$^+$; $^1$H NMR (methanol-d$_4$) δ: 8.53 (s, 1H), 8.49 (s, 2H), 8.20 (d, J = 0.9 Hz, 1H), 7.77 (d, J = 8.2 Hz, 1H), 7.48 (dd, J = 8.2, 1.6 Hz, 1H), 7.40 (d, J = 1.6 Hz, 1H), 4.20-4.27 (m, 2H), 3.74-3.84 (m, 1H), 3.66-3.71 (m, 2H), 2.33-2.41 (m, J = 2.5 Hz, 3H), 2.25-2.32 (m, 3H); 4 Hs not observed (3 NHs and OH). |
| 31 | MS m/z 417.5 [M + H]$^+$; $^1$H NMR (D$_2$O) δ: 8.15 (s, 1H), 7.89 (s, 2H), 7.72 (s, 1H), 7.41 (d, J = 8.2 Hz, 1H), 6.99 (d, J = 8.8 Hz, 1H), 6.81-6.92 (m, 1H), 3.60-3.70 (m, 1H), 2.01 (dd, J = 14.2, 2.8 Hz, 2H), 1.70 (t, J = 14.2 2H), 1.54 (s, 6H), 1.40 (s, 6H); 4 Hs not observed (3 NHs and OH). |

Example 3

Preparation of Compound 43

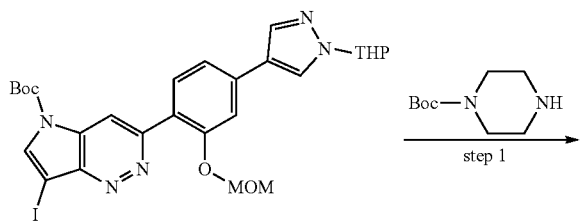

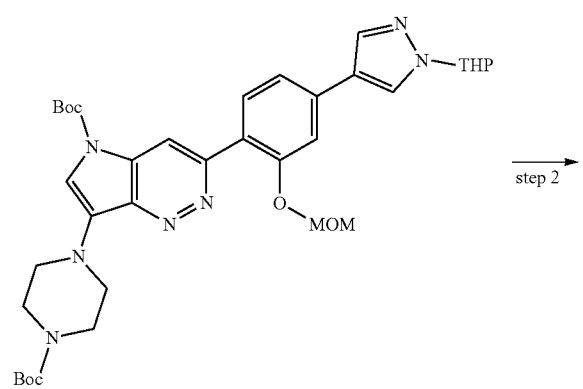

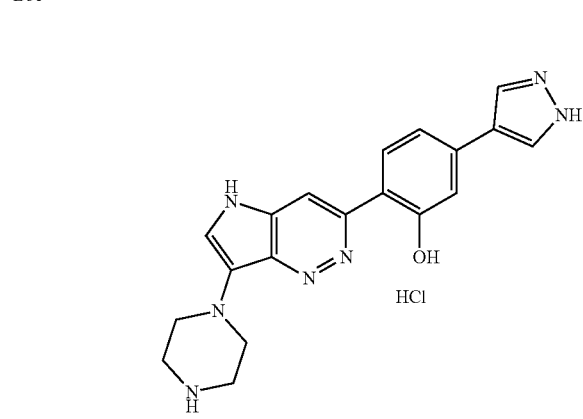

Step 1: An oven-dried flask was equipped with a magnetic stir bar and charged with tert-butyl 7-iodo-3-[2-(methoxymethoxy)-4-(1-tetrahydropyran-2-ylpyrazol-4-yl)phenyl]pyrrolo[3,2-c]pyridazine-5-carboxylate (43 mg, 0.07 mmol), tert-butyl piperazine-1-carboxylate (15 mg, 0.08 mmol), tris(dibenzylideneacetone)dipalladium(0) (6.3 mg, 0.007 mmol), S-Phos (5.7 mg, 0.014 mmol) and $Cs_2CO_3$ (45 mg, 0.14 mmol). The flask was sealed with a rubber septum, and then evacuated and backfilled with argon (repeated a total of 3×). DME (3 mL) was added and the reaction was heated to 80° C. for 2 h. The reaction was cooled to room temperature, filtered through Celite, and then concentrated under reduced pressure. The residue was purified by silica gel column chromatography eluting with EtOAc/hexanes gradient (40-80% EtOAc) to afford tert-butyl 7-(4-(tert-butoxycarbonyl)piperazin-1-yl)-3-(2-(methoxymethoxy)-4-(1-(tetrahydro-2H-pyran-2-yl)-1H-pyrazol-4-yl)phenyl)-5H-pyrrolo[3,2-c]pyridazine-5-carboxylate (18 mg, 38%) as a brownish solid. MS m/z 690.4 [M+H]⁺.

Step 2: To a solution of tert-butyl 7-(4-tert-butoxycarbonylpiperazin-1-yl)-3-[2-(methoxymethoxy)-4-(1-tetrahydropyran-2-ylpyrazol-4-yl)phenyl]pyrrolo[3,2-c]pyridazine-5-carboxylate (18 mg, 0.026 mmol) in $CH_2Cl_2$ (0.5 mL) plus 1 drop of MeOH was added 4M HCl in 1,4-dioxane (0.03 mL, 0.12 mmol) and the reaction mixture was stirred for 16 h at room temperature. The reaction was concentrated under reduced pressure. The residue was purified by silica gel column chromatography eluting with MeOH/$CH_2Cl_2$ (0% to 30% MeOH) to provide 2-(7-piperazin-1-yl-5H-pyrrolo[3,2-c]pyridazin-3-yl)-5-(1H-pyrazol-4-yl)phenol (5 mg, 53%) as an orange solid.

MS m/z 362.0 [M+H]⁺; ¹H NMR (methanol-$d_4$) δ: 8.45 (s, 1H), 8.15 (br s, 2H), 7.80 (s, 1H), 7.70 (d, J=8.0 Hz, 1H), 7.42 (dd, J=8.0, 1.9 Hz, 1H), 7.33 (d, J=1.9 Hz, 1H), 3.69-3.76 (m, 4H), 3.50-3.56 (m, 4H); 4 Hs not observed (3 NHs and OH).

Example 4

Preparation of Compound 8

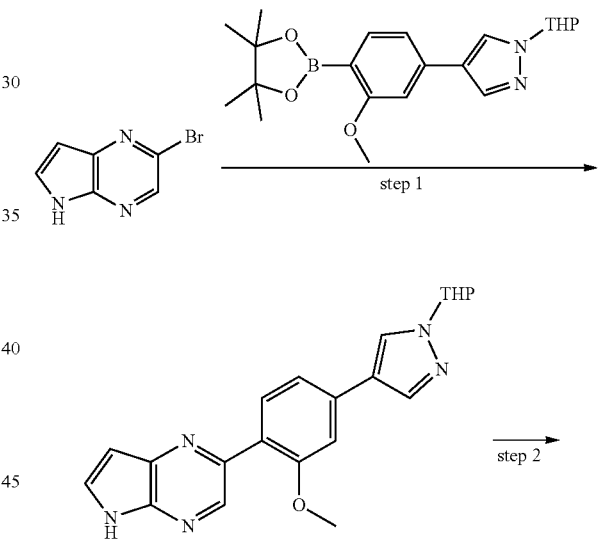

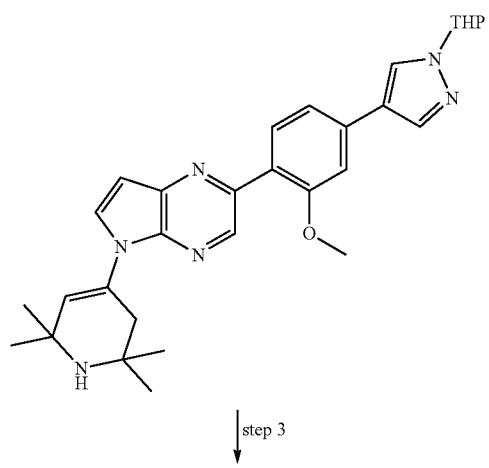

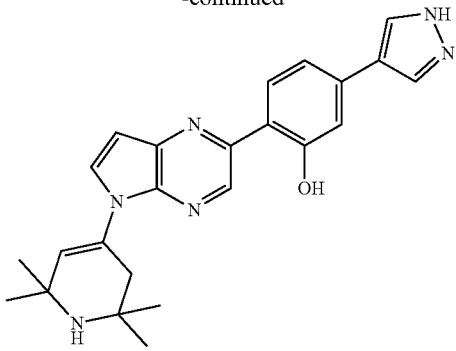

Step 1: A mixture of 2-bromo-5H-pyrrolo[2,3-b]pyrazine (50 mg, 0.25 mmol), 4-[3-methoxy-4-(4,4,5,5-tetramethyl-1,3,2-dioxaborolan-2-yl)phenyl]-1-tetrahydropyran-2-yl-pyrazole (107 mg, 0.28 mmol), [1,1'-bis(diphenylphosphino)ferrocene] dichloropalladium(II) (19 mg, 0.025 mmol) was purged with argon. 1,4-Dioxane (2 mL) and aqueous 2 M K₂CO₃ (0.35 mL, 0.7 mmol) were added and the reaction was heated at 90° C. for 16 h. The reaction mixture was then cooled to room temperature and diluted with water. The aqueous layer was extracted with EtOAc (3×). The combined organic layers were dried over Na₂SO₄ and concentrated under reduced pressure. The residue was purified using silica gel chromatography, eluting with a EtOAc/hexanes gradient (50-100% EtOAc) to afford 2-[2-methoxy-4-(1-tetrahydropyran-2-ylpyrazol-4-yl)phenyl]-5H-pyrrolo[2,3-b]pyrazine (76 mg, 80%) as a yellow foam.

MS m/z 376.3 [M+H]⁺; ¹H NMR (DMSO-d₆) δ: 8.67 (s, 1H), 8.51 (s, 1H), 8.06 (s, 1H), 7.82-7.88 (m, 1H), 7.71-7.76 (m, 1H), 7.39-7.44 (m, 1H), 7.32-7.38 (m, 1H), 6.63-6.69 (m, 1H), 5.41-5.46 (m, 1H), 3.94-4.00 (m, 1H), 3.93 (s, 3H), 3.63-3.71 (m, 1H), 2.10-2.20 (m, 2H), 1.94-1.98 (m, 2H), 1.52-1.60 (m, 2H).

Step 2: A mixture of 2-[2-methoxy-4-(1-tetrahydropyran-2-ylpyrazol-4-yl)phenyl]-5H-pyrrolo[2,3-b]pyrazine (76 mg, 0.20 mmol), (2,2,6,6-tetramethyl-1,3-dihydropyridin-4-yl) trifluoromethanesulfonate (120 mg, 0.42 mmol), aqueous 1 M K₃PO₄ (0.1 mL, 0.1 mmol), XPhos (18 mg, 0.04 mmol), tris(dibenzylideneacetone)dipalladium(0) (19 mg, 0.02 mmol), and 1,4-dioxane (2 mL) were heated under an argon atmosphere at 90° C. for 16 h. The reaction mixture was cooled to room temperature and diluted with water. The aqueous layer was extracted with CH₂Cl₂ (3×). The combined organic layers were dried over Na₂SO₄, filtered, and concentrated under reduced pressure. The residue was purified using silica gel chromatography, eluting with a MeOH/EtOAc gradient (0-10% MeOH) to afford 5-[2-methoxy-4-(1-tetrahydropyran-2-ylpyrazol-4-yl)phenyl]-1-(2,2,6,6-tetramethyl-1,3-dihydropyridin-4-yl)pyrrolo[3,2-b] pyridine (40 mg, 39%) as an orange foam.

MS m/z 513.3 [M+H]⁺; ¹H NMR (CDCl₃) δ: 8.73 (s, 1H), 7.87 (s, 1H), 7.81 (d, J=0.8 Hz, 1H), 7.75 (d, J=7.9 Hz, 1H), 7.51 (d, J=3.7 Hz, 1H), 7.18 (dd, J=7.9, 1.6 Hz, 1H), 7.06 (d, J=1.5 Hz, 1H), 6.69 (d, J=3.7 Hz, 1H), 6.06 (t, J=1.5 Hz, 1H), 5.37 (dd, J=9.1, 3.3 Hz, 1H), 4.02-4.05 (m, 2H), 3.85 (s, 3H), 3.63-3.73 (m, 1H), 2.56 (d, J=1.4 Hz, 2H), 2.00-2.16 (m, 3H), 1.54-1.71 (m, 3H), 1.29 (s, 6H), 1.26 (s, 6H).

Step 3: A solution of 2-[2-methoxy-4-(1-tetrahydropyran-2-ylpyrazol-4-yl)phenyl]-5-(2,2,6,6-tetramethyl-1,3-dihydropyridin-4-yl)pyrrolo[2,3-b]pyrazine (40 mg, 0.08 mmol) and NaSEt (85 mg, 0.8 mmol) in NMP (2 mL) was heated to 180° C. in the microwave for 30 min. The reaction mixture was then cooled to room temperature and diluted with CH₂Cl₂ (10 mL). The precipitate was filtered by vacuum filtration. The filtrate was concentrated and used without further purification.

A mixture of crude 5-(1-tetrahydropyran-2-ylpyrazol-4-yl)-2-[5-(2,2,6,6-tetramethyl-1,3-dihydropyridin-4-yl)pyrrolo[2,3-b]pyrazin-2-yl]phenol (0.039 g, 0.08 mmol) and 4 M HCl in dioxane (0.5 mL, 2 mmol) was stirred at room temperature for 1 h. The precipitate formed was collected by vacuum filtration and rinsed with CH₂Cl₂ (10 mL) to afford 5-(1H-pyrazol-4-yl)-2-[5-(2,2,6,6-tetramethyl-1,3-dihydropyridin-4-yl)pyrrolo[2,3-b]pyrazin-2-yl]phenol hydrochloride (7 mg, 43%) as a yellow solid.

MS m/z 415.4 [M+H]⁺; ¹H NMR (DMSO-d₆) δ: 9.15-9.25 (m, 2H), 8.16-8.20 (m, 1H), 8.13-8.16 (m, 2H), 8.08-8.12 (m, 1H), 7.22-7.27 (m, 2H), 6.92-6.97 (m, 1H), 6.40-6.46 (m, 1H), 3.02-3.06 (m, 2H), 1.63 (s, 6H), 1.56 (s, 6H).

Example 5

Preparation of Compound 10

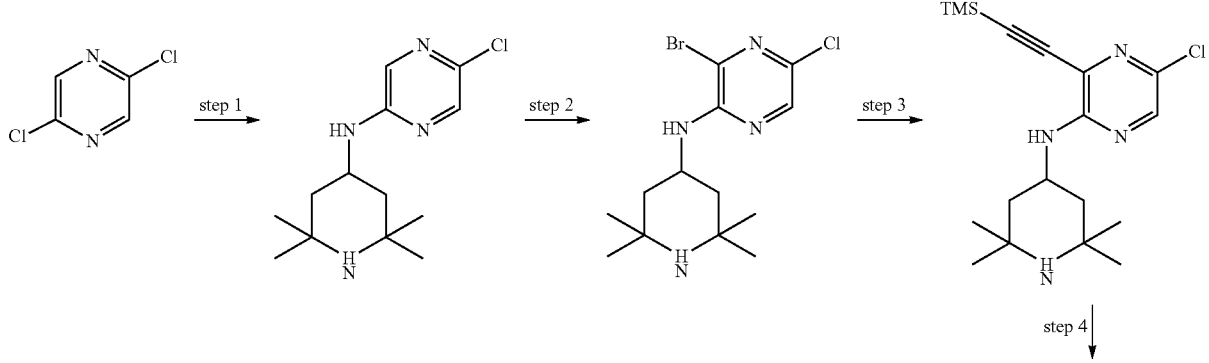

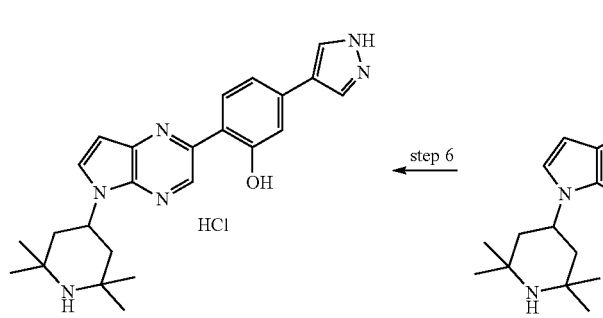 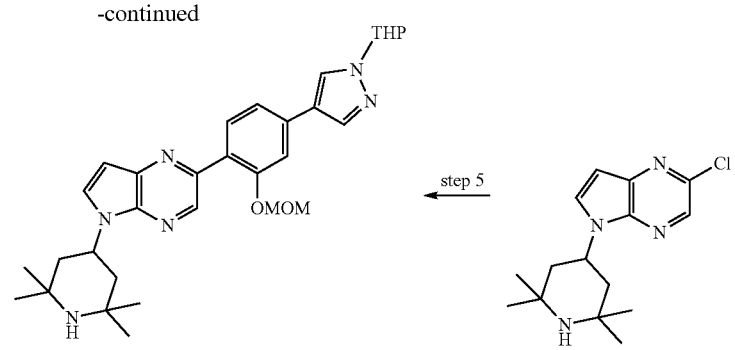

Step 1: To a mixture of 2,2,6,6-tetramethylpiperidin-4-amine (4.2 g, 27 mmol) in acetonitrile (10 mL) was added 2,5-dichloropyrazine (4.0 g, 27 mmol). The reaction mixture was stirred at 120° C. for 16 h. The reaction mixture was then allowed to cooled to room temperature and the precipitate was collected by vacuum filtration to afford 5-chloro-N-(2,2,6,6-tetramethylpiperidin-4-yl)pyrazin-2-amine as a light yellow solid (3.1 g, 43%).

MS m/z 269.3 [M+H]$^+$; $^1$H NMR (DMSO-d$_6$) δ: 8.02 (d, J=1.3 Hz, 1H), 7.68 (d, J=1.3 Hz, 1H), 7.09 (d, J=7.7 Hz, 1H), 4.09 (dd, J=7.7, 3.7 Hz, 1H), 1.77 (dd, J=12.4, 3.7 Hz, 2H), 1.16 (s, 6H), 1.03 (s, 6H), 0.95-0.99 (m, 2H).

Step 2: To a suspension of 5-chloro-N-(2,2,6,6-tetramethyl-4-piperidyl)pyrazin-2-amine (0.7 g, 3 mmol) in acetic acid (5 mL) at room temperature was added NBS (0.5 g, 3 mmol). After stirring for 30 min, a yellow precipitate formed. The precipitate was collected by vacuum filtration to afford 3-bromo-5-chloro-N-(2,2,6,6-tetramethyl-4-piperidyl)pyrazin-2-amine (0.7 g, 80%) as a yellow solid.

MS m/z 347.2, 349.2 [M+H]$^+$; $^1$H NMR (DMSO-d$_6$) δ: 8.19 (s, 1H), 6.91-6.95 (m, 1H), 4.31-4.36 (m, 1H), 1.90-1.96 (m, 2H), 1.72-1.76 (m, 2H), 1.39-1.45 (m, 12H).

Step 3: A mixture of 3-bromo-5-chloro-N-(2,2,6,6-tetramethyl-4-piperidyl)pyrazin-2-amine (1.4 g, 4.0 mmol), CuI (0.05 g, 0.3 mmol), and PdCl$_2$(PPh$_3$)$_2$ (0.17 g, 0.24 mmol) was purged with argon. THF (20 mL), Et$_3$N (2.2 mL, 16 mmol) and ethynyl(trimethyl)silane (0.8 mL, 6 mmol) were added sequentially. The resulting mixture was stirred under an argon atmosphere at 60° C. for 1 h. The reaction mixture was then cooled to room temperature and concentrated. The crude residue was purified using silica gel chromatography eluting with a MeOH/CH$_2$Cl$_2$ gradient (0-10% MeOH) to afford 5-chloro-N-(2,2,6,6-tetramethyl-4-piperidyl)-3-(2-trimethylsilylethynyl)pyrazin-2-amine (1.42 g, 97%) as a dark yellow solid.

MS m/z 365.3 [M+H]$^+$; $^1$H NMR (DMSO-d$_6$) δ: 8.19 (s, 1H), 4.32-4.37 (m, 1H), 1.98-2.03 (m, 2H), 1.63-1.67 (m, 2H), 1.43 (s, 6H), 1.40 (s, 6H), 0.26 (s, 9H).

Step 4: To a solution of 5-chloro-N-(2,2,6,6-tetramethyl-4-piperidyl)-3-(2-trimethylsilylethynyl)pyrazin-2-amine (1.42 g, 3.89 mmol) in THF (20 mL) was added 1M TBAF solution in THF (12 mL). The reaction mixture was stirred under argon at 60° C. for 2 h, then cooled to room temperature, and concentrated. The crude residue was purified using silica gel chromatography eluting with a MeOH/CH$_2$Cl$_2$ gradient (0-10% MeOH) to afford 2-chloro-5-(2,2,6,6-tetramethyl-4-piperidyl)pyrrolo[2,3-b]pyrazine (450 mg, 56%) as a dark red oil.

MS m/z 293.3 [M+H]$^+$; $^1$H NMR (DMSO-d$_6$) δ: 8.36 (s, 1H), 8.16-8.19 (m, 1H), 6.64-6.68 (m, 1H), 5.07-5.12 (m, 1H), 1.72-1.81 (m, 4H), 1.26 (s, 6H), 1.11 (s, 6H).

Step 5: A mixture of 2-chloro-5-(2,2,6,6-tetramethyl-4-piperidyl)pyrrolo[2,3-b]pyrazine (50 mg, 0.1708 mmol), 4-[3-(methoxymethoxy)-4-(4,4,5,5-tetramethyl-1,3,2-dioxaborolan-2-yl)phenyl]-1-tetrahydropyran-2-yl-pyrazole (85 mg, 0.2052 mmol), PdCl$_2$(dppf) (13 mg, 0.01741 mmol) was purged with argon. Aqueous 2 N K$_2$CO$_3$ (0.5 mL, 1 mmol), and 1,4-dioxane (2 mL) were added and the reaction was heated under argon at 100° C. for 16 h. The reaction mixture was then cooled to room temperature and diluted with CH$_2$Cl$_2$ and then filtered through a phase separation column and then concentrated. The crude residue was purified using silica gel chromatography eluting with a MeOH/CH$_2$Cl$_2$ gradient (0-10% MeOH) to afford 2-[2-(methoxymethoxy)-4-(1-tetrahydropyran-2-ylpyrazol-4-yl)phenyl]-5-(2,2,6,6-tetramethyl-4-piperidyl)pyrrolo[2,3-b]pyrazine (25 mg, 59%) as a dark brown oil contaminated with ~20% of 2-chloro-5-(2,2,6,6-tetramethyl-4-piperidyl)pyrrolo[2,3-b]pyrazine. MS m/z 545.5 [M+H]$^+$.

Step 6: To a solution of 2-[2-(methoxymethoxy)-4-(1-tetrahydropyran-2-ylpyrazol-4-yl)phenyl]-5-(2,2,6,6-tetramethyl-4-piperidyl)pyrrolo[2,3-b]pyrazine (55 mg, 0.10 mmol) in CH$_2$Cl$_2$ (1 mL) was added 4N HCl in dioxane (0.5 mL, 2 mmol) and the reaction was stirred at room temperature for 1 h. The yellow solid that precipitated was collected by vacuum filtration, rinsed with CH$_2$Cl$_2$ and dried to afford 5-(1H-pyrazol-4-yl)-2-(5-(2,2,6,6-tetramethylpiperidin-4-yl)-5H-pyrrolo[2,3-b]pyrazin-2-yl)phenol hydrochloride (18 mg, 23%).

MS m/z 417.4 [M+H]$^+$; $^1$H NMR (DMSO-d$_6$) δ: 9.10 (s, 1H), 8.06-8.19 (m, 4H), 7.20-7.27 (m, 2H), 6.81-6.85 (m, 1H), 5.20-5.24 (m, 1H), 2.33-2.45 (m, 2H), 2.12-2.17 (m, 2H), 1.59 (s, 6H), 1.50 (s, 6H).

Using the procedure described for Example 5, above, additional compounds described herein were prepared by substituting the appropriate starting materials, suitable reagents and reaction conditions, obtaining compounds such as those selected from:

| Cpd | Data |
|---|---|
| 16 | MS m/z 437.2 [M + H]$^+$, $^1$H NMR (methanol-d$_4$) δ: 8.82 (d, J = 2.2 Hz, 1H), 8.50 (d, J = 1.3 Hz, 2H), 8.11 (d, J = 3.8 Hz, 1H), 7.88 (dd, J = 11.3, 6.3 Hz, 1H), 7.78 (dd, J = 11.3, 6.6 Hz, 1H), 6.84 (d, J = 3.8 Hz, 1H), 5.34-5.46 (m, 1H), 2.49 (t, J = 13.9 Hz, 2H), 2.29 (dd, J = 13.9, 3.8 Hz, 2H), 1.70 (s, 6H), 1.58 (s, 6H); 2 Hs not observed (2 NHs). |

Example 6

Preparation of Compound 23

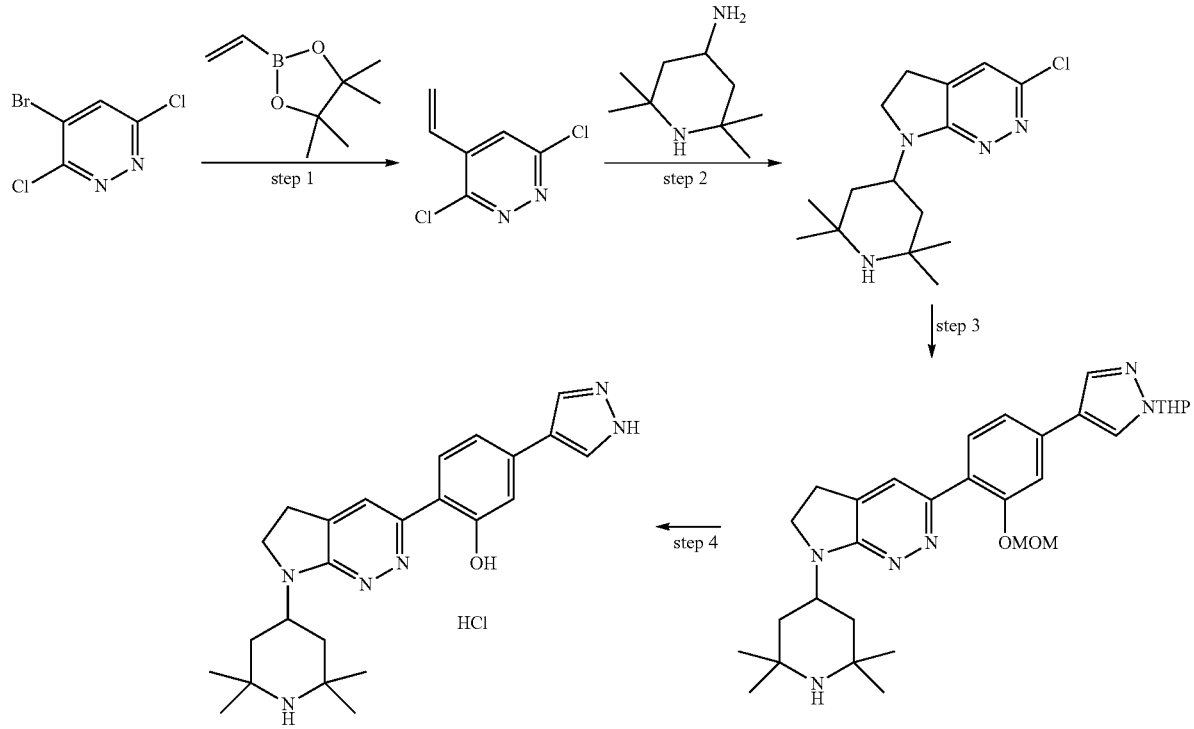

Step 1: An oven-dried flask was equipped with a magnetic stir bar and charged with 4-bromo-3,6-dichloropyridazine (0.227 g, 1.0 mmol), [1,1'-bis(diphenylphosphino)ferrocene]dichloropalladium(II) (75.0 mg, 0.1 mmol), and 4 4,4,5,5-tetramethyl-2-vinyl-1,3,2-dioxaborolane (0.171 mL, 1.0 mmol). The flask was sealed with a rubber septum, and then evacuated and backfilled with argon (repeated a total of 3×). Dioxane (6 mL) and 2N aq. $K_2CO_3$ (1.5 mL, 3.0 mmol) were added and the reaction was heated to 50° C. for 3 h. The reaction was cooled to room temperature, diluted with water (2 mL) and extracted with EtOAc (3×). The combined organic layers were dried over $Na_2SO_4$, concentrated under reduced pressure, and purified by column chromatography, eluting with a EtOAc/hexanes gradient (0-50% EtOAc) to provide 3,6-dichloro-4-vinylpyridazine (0.145 g, 82%).

Step 2: A mixture of 3,6-dichloro-4-vinylpyridazine (0.34 g, 1.94 mmol) and 2,2,6,6-tetramethylpiperidin-4-amine (0.72 mL, 4.6 mmol) was dissolved in acetonitrile (5 mL) and the resulting solution was heated to 90° C. for 16 h. The reaction mixture was concentrated and the residue was purified by silica gel column chromatography eluting with a EtOAc/hexanes gradient (0-50% EtOAc) to provide 3-chloro-7-(2,2,6,6-tetramethylpiperidin-4-yl)-6,7-dihydro-5H-pyrrolo[2,3-c]pyridazine (0.29 g, 62%). MS m/z 295.4 [M+H]$^+$.

Step 3: An oven-dried flask was equipped with a magnetic stir bar and charged with 3-chloro-7-(2,2,6,6-tetramethylpiperidin-4-yl)-6,7-dihydro-5H-pyrrolo[2,3-c]pyridazine (0.15 g, 0.5 mmol), 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole (0.32 mg, 0.76 mmol, prepared in Example 1, step 7), tetrakis(triphenylphosphine)palladium(0) (58 mg, 0.05 mmol), and $Na_2CO_3$ (160 mg, 1.5 mmol).

The flask was sealed with a rubber septum, and then evacuated and backfilled with argon (repeated a total of 3×). 1,4-Dioxane (10 mL) and water (1.5 mL) were added and the reaction was heated to 90° C. for 16 h. The reaction was cooled to room temperature, diluted with water (2 mL), and extracted with EtOAc (3×). The combined organic layers were dried over $Na_2SO_4$, concentrated under reduced pressure, and purified by column chromatography, eluting with a MeOH/$CH_2Cl_2$ gradient (0-20% MeOH) to afford 3-(2-(methoxymethoxy)-4-(1-(tetrahydro-2H-pyran-2-yl)-1H-pyrazol-4-yl)phenyl)-7-(2,2,6,6-tetramethylpiperidin-4-yl)-6,7-dihydro-5H-pyrrolo[2,3-c]pyridazine (0.145 mg, 52%) as an orange solid. MS m/z 547.3 [M+H]$^+$.

Step 4: 3-(2-(Methoxymethoxy)-4-(1-(tetrahydro-2H-pyran-2-yl)-1H-pyrazol-4-yl)phenyl)-7-(2,2,6,6-tetramethylpiperidin-4-yl)-6,7-dihydro-5H-pyrrolo[2,3-c]pyridazine (20 mg, 0.037 mmol) was dissolved in 1 mL of methanol, then 4 N HCl in 1,4-dioxane (0.5 mL, 2 mmol) was added and the reaction stirred at room temperature for 2 h. The reaction was concentrated and then triturated with 20% MeOH/ether. The precipitate was filtered and dried to afford 5-(1H-pyrazol-4-yl)-2-(7-(2,2,6,6-tetramethylpiperidin-4-yl)-6,7-dihydro-5H-pyrrolo[2,3-c]pyridazin-3-yl)phenol hydrochloride (10 mg, 66%) as a yellow solid.

MS m/z 419.5 [M+H]$^+$; $^1$H NMR (methanol-$d_4$) δ: 8.17 (s, 2H), 8.07 (s, 1H), 7.66 (d, J=8.2 Hz, 1H), 7.36 (dd, J=8.2, 1.6 Hz, 1H), 7.27 (d, J=1.6 Hz, 1H), 4.49-4.58 (m, 1H), 3.94 (t, J=7.9 Hz, 2H), 3.42 (dd, J=8.5, 7.3 Hz, 2H), 2.12 (dd, J=13.9, 3.5 Hz, 2H), 2.00 (t, J=13.9 Hz, 2H), 1.61 (s, 6H), 1.55 (s, 6H); 3 Hs not observed (1 OH and 2 NHs).

Using the procedure described for Example 6, above, additional compounds described herein were prepared by substituting the appropriate starting materials, suitable reagents and reaction conditions, obtaining compounds such as those selected from:

| Cpd | Data |
|---|---|
| 32 | MS m/z 439.5 [M + H]⁺; ¹H NMR (methanol-d₄) δ: 8.23 (s, 2H), 7.93 (s, 1H), 7.69-7.76 (m, 1H), 7.55-7.64 (m, 1H), 4.55-4.67 (m, 1H), 4.01-4.07 (m, 2H), 3.44 (br s, 2H), 2.12-2.19 (m, 2H), 2.02-2.08 (m, 2H), 1.64 (s, 6H), 1.57 (s, 6H); 2 Hs not observed (2 NHs). |
| 36 | MS m/z 409.3 [M + H]⁺; ¹H NMR (methanol-d₄) δ: 8.17 (s, 2H), 7.89 (d, J = 1.9 Hz, 1H), 7.66-7.74 (m, 1H), 7.55-7.61 (m, 1H), 4.48-4.58 (m, 1H), 4.21-4.26 (m, 2H), 3.99 (t, J = 7.6 Hz, 2H), 3.39-3.43 (m, 2H), 2.22-2.31 (m, 6H), 2.08-2.16 (m, 2H); 2 Hs not observed (2 NHs). |

Example 7

Preparation of Compound 26

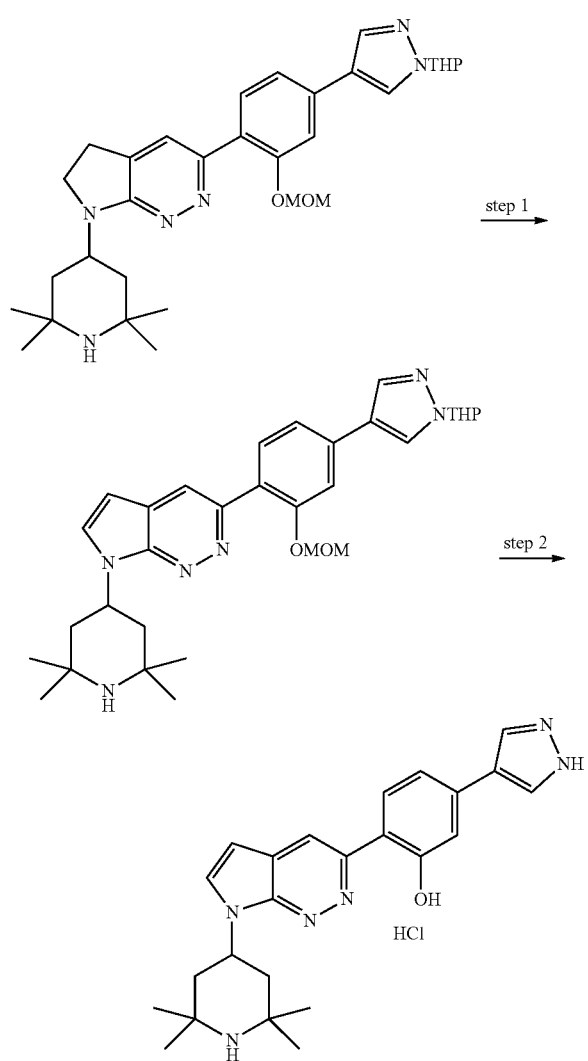

Step 1: A mixture of 3-(2-(methoxymethoxy)-4-(1-(tetrahydro-2H-pyran-2-yl)-1H-pyrazol-4-yl)phenyl)-7-(2,2,6,6-tetramethylpiperidin-4-yl)-6,7-dihydro-5H-pyrrolo[2,3-c]pyridazine (0.28 g, 0.49 mmol, prepared in Example 6, step 3) and manganese dioxide (0.28 g, 3.21 mmol) in toluene (10 mL) was heated at 125° C. in a sealed tube for 24 h. The reaction mixture was cooled to room temperature, filtered over a small pad of Celite and concentrated. The crude compound was purified by column chromatography, eluting with a MeOH/CH₂Cl₂ gradient (0-20% MeOH) to provide 3-(2-(methoxymethoxy)-4-(1-(tetrahydro-2H-pyran-2-yl)-1H-pyrazol-4-yl)phenyl)-7-(2,2,6,6-tetramethylpiperidin-4-yl)-7H-pyrrolo[2,3-c]pyridazine (0.2 g, 71%) as a tan solid. MS m/z 545.4 [M+H]⁺.

Step 2: To a solution of 3-(2-(methoxymethoxy)-4-(1-(tetrahydro-2H-pyran-2-yl)-1H-pyrazol-4-yl)phenyl)-7-(2,2,6,6-tetramethylpiperidin-4-yl)-7H-pyrrolo[2,3-c]pyridazine (0.2 g, 0.36 mmol) in 1,4-dioxane (4 mL) was added 4 N HCl in 1,4-dioxane (0.5 mL, 2 mmol) and the reaction was stirred at room temperature for 2 h. The reaction mixture was concentrated, triturated with 20% MeOH/ether, and the precipitate was filtered and dried to afford 5-(1H-pyrazol-4-yl)-2-(7-(2,2,6,6-tetramethylpiperidin-4-yl)-7H-pyrrolo[2,3-c]pyridazin-3-yl)phenol hydrochloride (120 mg, 78%) as an orange solid.

MS m/z 417.4 [M+H]⁺; ¹H NMR (methanol-d₄) δ: 8.84 (s, 1H), 8.68 (d, J=3.5 Hz, 1H), 8.39 (br s, 2H), 7.74 (d, J=7.9 Hz, 1H), 7.45 (d, J=8.2 Hz, 1H), 7.33-7.39 (m, 1H), 7.14 (d, J=3.5 Hz, 1H), 5.42-5.58 (m, 1H), 2.53 (t, J=13.6 Hz, 2H), 2.42 (dd, J=13.6, 3.2 Hz, 2H), 1.72 (s, 6H), 1.63 (s, 6H); 3 Hs not observed (1 OH and 2 NHs).

Using the procedure described for Example 7, above, additional compounds described herein were prepared by substituting the appropriate starting materials, suitable reagents and reaction conditions, obtaining compounds such as those selected from:

| Cpd | Data |
|---|---|
| 176 | MS m/z 418.5 [M + H]⁺; ¹H NMR (methanol-d₄) δ: 8.64 (s, 1H), 8.09-8.19 (m, 1H), 8.02-8.06 (m, 1H), 7.97 (s, 2H), 7.70-7.76 (m, 2H), 6.79 (d, J = 1.8 Hz, 1H), 5.47-5.60 (m, 1H), 2.51-2.59 (m, 2H), 2.37 (br d, J = 13.7 Hz, 2H), 1.74 (s,6H), 1.60 (s, 6H); 2 Hs not observed (NH and OH). |

Example 8

Preparation of Compound 17

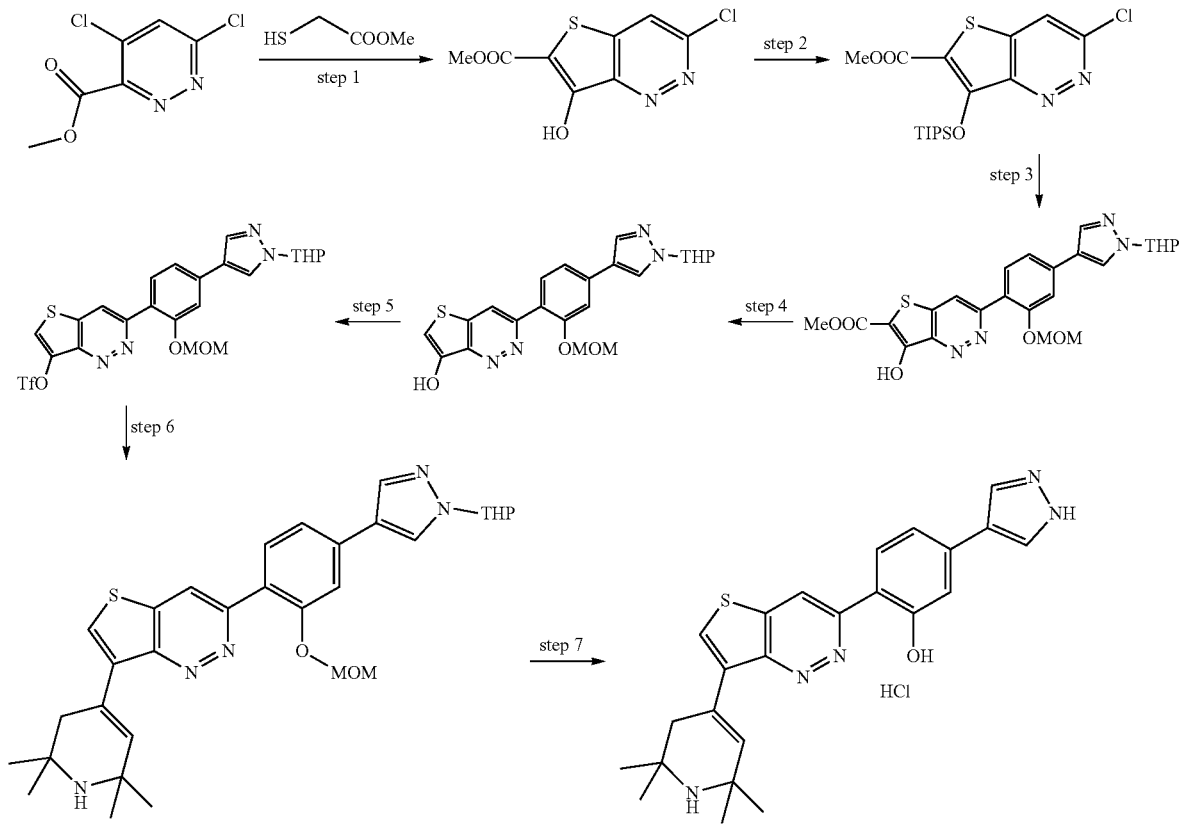

Step 1: To a solution of methyl 4,6-dichloropyridazine-3-carboxylate (2.05 g, 9.9 mmol) in CH$_3$CN (26 mL) was added a solution of methyl 2-sulfanylacetate (0.90 mL, 10.0 mmol) in CH$_3$CN (8.5 mL) dropwise at 0° C. Upon completion of addition, Et$_3$N (1.40 mL, 10.0 mmol) was added dropwise. The reaction stirred at 0° C. for 15 min. After 15 min, an additional portion of Et$_3$N (1.40 mL, 10.0 mmol) was added and the mixture was allowed to warm to room temperature and stirred overnight. The reaction was diluted with water and concentrated. The mixture was acidified with 4N HCl to pH 3 and the bright yellow solution turned colorless and a white precipitate was formed. The solid was collected by filtration and washed with water to afford methyl 3-chloro-7-hydroxy-thieno[3,2-c]pyridazine-6-carboxylate (2.26 g, 93.1% yield) as white solid. MS m/z 245.1 [M+H]$^+$.

Step 2: To a solution of methyl 3-chloro-7-hydroxy-thieno[3,2-c]pyridazine-6-carboxylate (2.26 g, 9.24 mmol) in DMF (30 mL) were added imidazole (1.0 g, 15 mmol) and TIPSCl (2.25 mL, 10 mmol). The mixture was stirred at room temperature for 15 min and then heated to 50° C. for 24 h. Upon completion, the reaction was cooled to room temperature and was then diluted with water and the product was extracted with EtOAc. The combined organic phases were dried over Na$_2$SO$_4$, concentrated and the residue was purified by silica gel column chromatography, eluting with a EtOAc/CH$_2$Cl$_2$ gradient (0-5% EtOAc), to provide methyl 3-chloro-7-triisopropylsilyloxy-thieno[3,2-c]pyridazine-6-carboxylate (2.04 g, 55.1% yield) as an off-white solid.

Step 3: A mixture of methyl 3-chloro-7-triisopropylsilyloxy-thieno[3,2-c]pyridazine-6-carboxylate (800 mg, 1.9 mmol), 4-[3-(methoxymethoxy)-4-(4,4,5,5-tetramethyl-1,3,2-dioxaborolan-2-yl)phenyl]-1-tetrahydropyran-2-yl-pyrazole (prepared in example 1, step 7, 1.00 g, 2.4 mmol), [1,1'-bis(diphenylphosphino)ferrocene] dichloropalladium (II) complex with dichloromethane (85 mg, 0.10 mmol) and K$_2$CO$_3$ (830 mg, 6.0 mmol) in a vial was evacuated and backfilled with N2 (repeated 3×), 1,4-dioxane (7 mL) and water (1.8 mL) were added and the mixture was heated at 90° C. for 16 h. The reaction was cooled to room temperature, diluted with water and acidified with 4N HCl. The product was extracted with CH$_2$Cl$_2$ (3×). The organic phases were combined, dried over Na$_2$SO$_4$ and concentrated. Crude methyl 7-hydroxy-3-[2-(methoxymethoxy)-4-(1-tetrahydropyran-2-ylpyrazol-4-yl)phenyl]thieno[3,2-c]pyridazine-6-carboxylate was used directly in the next step without purification.

Step 4: Crude methyl 7-hydroxy-3-[2-(methoxymethoxy)-4-(1-tetrahydropyran-2-ylpyrazol-4-yl)phenyl]thieno[3,2-c]pyridazine-6-carboxylate obtained above was mixed with 5 N NaOH (3 mL, 15 mmol) and MeOH (15 mL) and heated at 95° C. until complete hydrolysis was observed (6 h). Once complete, the reaction was cooled to room temperature and carefully acidified with 4N HCl to pH 3-4. The intermediate carboxylic acid was extracted with CH$_2$Cl$_2$/MeOH. The organic phase was dried over Na$_2$SO$_4$. Volatiles were removed under reduced pressure and the residue was dissolved in DMSO (10 mL). The mixture was heated at 80° C. for 60 min after which complete decarboxylation of the intermediate α-ketoacid was observed. Upon cooling to room temperature, the mixture was diluted with water and the product was extracted with EtOAc. The organic phase was dried over Na₂SO₄ and the solvent was removed. The residue was purified by silica gel column chromatography eluting with a MeOH/CH₂Cl₂ gradient (0-5% MeOH) to afford 3-[2-(methoxymethoxy)-4-(1-tetrahydropyran-2-ylpyrazol-4-yl)phenyl]thieno[3,2-c]pyridazin-7-ol (0.64 g, 76% yield) as a yellow solid. MS m/z 439.4 [M+H]⁺.

Step 5: To a solution of 3-[2-(methoxymethoxy)-4-(1-tetrahydropyran-2-ylpyrazol-4-yl)phenyl]thieno[3,2-c]pyridazin-7-ol (204 mg, 0.47 mmol) in CH₂Cl₂ (2.5 mL) was added DIPEA (0.16 mL, 0.92 mmol). The reaction was cooled to 0° C. and triflic anhydride (0.09 mL, 0.53 mmol) was added dropwise. The reaction was stirred at 0° C. for 30 min, then diluted with water and the products were extracted with CH₂Cl₂. The organic phase was dried over Na₂SO₄, the volatiles were removed under reduced pressure and the residue was purified by silica gel column chromatography eluting with a MeOH/EtOAc gradient (0-5% MeOH) to afford [3-[2-(methoxymethoxy)-4-(1-tetrahydropyran-2-ylpyrazol-4-yl)phenyl]thieno[3,2-c]pyridazin-7-yl]trifluoromethanesulfonate (0.13 g, 48% yield) as white foam. MS m/z 571.3 [M+H]⁺.

Step 6: An oven-dried flask was equipped with a magnetic stir bar and charged with [3-[2-(methoxymethoxy)-4-(1-tetrahydropyran-2-ylpyrazol-4-yl)phenyl]thieno[3,2-c]pyridazin-7-yl]trifluoromethanesulfonate (127 mg, 0.22 mmol), 2,2,6,6-tetramethyl-4-(4,4,5,5-tetramethyl-1,3,2-dioxaborolan-2-yl)-1,3-dihydropyridine (64 mg, 0.24 mmol), [1,1'-bis(diphenylphosphino)ferrocene] dichloropalladium (II) and (18 mg, 0.02 mmol), K₂CO₃ (100 mg, 0.72 mmol). The flask was sealed with a rubber septum, and then evacuated and backfilled with argon (repeated a total of 3×). Dioxane (1.2 mL) and water (0.8 mL) were added and the reaction was heated to 90° C. for 16 h. The reaction was cooled to room temperature, diluted with water (5 mL), and then extracted with EtOAc (3×). The combined organic layers were dried over Na₂SO₄ and concentrated under reduced pressure. The residue was purified by silica gel column chromatography eluting with a MeOH (with 2.5% NH₄OH)/CH₂Cl₂ gradient (0 to 10% MeOH/NH₄OH) to afford 3-(2-(methoxymethoxy)-4-(1-(tetrahydro-2H-pyran-2-yl)-1H-pyrazol-4-yl)phenyl)-7-(2,2,6,6-tetramethyl-1,2,3,6-tetrahydropyridin-4-yl)thieno[3,2-c]pyridazine (55.6 mg, 45% yield) as brownish foam. MS m/z 560.5 [M+H]⁺.

Step 7: To 3-[2-(methoxymethoxy)-4-(1-tetrahydropyran-2-ylpyrazol-4-yl)phenyl]-7-(2,2,6,6-tetramethyl-1,3-dihydropyridin-4-yl)thieno[3,2-c]pyridazine (13.8 mg, 0.025 mmol) was added 4 N HCl in dioxane (0.5 mL, 2 mmol) and MeOH (0.5 mL). The reaction was stirred at room temperature for 30 min and then ~2 h at 50° C. The volatiles were then removed under reduced pressure, the residue was triturated with Et₂O, and the solid was filtered and dried to afford 5-(1H-pyrazol-4-yl)-2-[7-(2,2,6,6-tetramethyl-1,3-dihydropyridin-4-yl)thieno[3,2-c]pyridazin-3-yl]phenol hydrochloride (7 mg, 60% yield) as a yellow solid.

MS m/z 432.4 [M+H]⁺; ¹H NMR (methanol-d₄) δ: 9.37 (s, 1H), 8.49 (s, 1H), 8.22 (s, 2H), 7.93 (d, J=8.2 Hz, 1H), 7.42 (dd, J=8.2, 1.6 Hz, 1H), 7.36 (d, J=1.6 Hz, 1H), 7.20 (s, 1H), 3.56-3.77 (m, 2H), 1.72 (s, 6H), 1.65 (s, 6H); 3 Hs not observed (2 NHs and OH).

Using the procedure described for Example 8, above, additional compounds described herein may be prepared by substituting the appropriate starting materials, suitable reagents and reaction conditions, obtaining compounds such as those selected from:

| Cpd | Data |
|---|---|
| 15 | MS m/z 376.3 [M + H]⁺; ¹H NMR (DMSO-d₆) δ: 9.41 (br s, 2H), 9.38 (s, 1H), 8.40 (s, 1H), 8.26 (s, 2H), 8.11 (d, J = 9.1 Hz, 1H), 7.58-7.68 (m, 1H), 7.40 (d, J = 1.9 Hz, 1H), 7.37-7.39 (m, 1H), 3.84-4.03 (m, 2H), 3.41-3.51 (m, 2H), 2.87-3.02 (m, 2H); 1H not observed (NH or OH). |
| 18 | MS m/z 402.3 [M + H]⁺; ¹H NMR (methanol-d₄) δ: 9.47 (s, 1H), 8.55 (s, 1H), 8.36 (s, 2H), 7.91 (d, J = 8.2 Hz, 1H), 7.59 (dt, J = 6.3, 1.6 Hz, 1H), 7.48 (dd, J = 8.2, 1.6 Hz, 1H), 7.40 (d, J = 1.6 Hz, 1H), 4.57 (dd, J = 6.6, 6.0 Hz, 1H), 4.45 (dd, J = 6.6, 5.0 Hz, 1H), 3.38-3.46 (m, 1H), 2.84-3.01 (m, 1H), 2.40-2.53 (m, 2H), 2.24-2.37 (m, 1H), 2.06-2.19 (m, 1H); 3 Hs not observed (2 NHs and OH). |
| 25 | MS m/z 418.4 [M + H]⁺; ¹H NMR (methanol-d₄) δ: 9.51 (s, 1H), 8.66 (s, 1H), 8.43 (s, 2H), 7.91 (d, J = 8.2 Hz, 1H), 7.49 (dd, J = 8.2, 1.6 Hz, 1H), 7.44-7.47 (m, 1H), 7.41 (d, J = 1.6 Hz, 1H), 4.37 (d, J = 5.7 Hz, 1H), 4.16 (d, J = 12.6 Hz, 1H), 4.12 (dd, J = 12.6, 1.9 Hz, 1H), 4.07 (dd, J = 12.6, 1.9 Hz, 1H), 3.98 (s, 2H), 3.39-3.48 (m, 1H), 3.18 (dd, J = 18.3, 1.9 Hz, 1H); 3 Hs not observed (2 NHs and OH). |

Example 9

Preparation of Compound 24

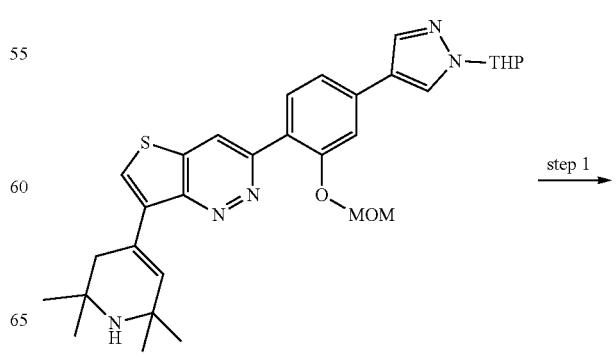

step 1

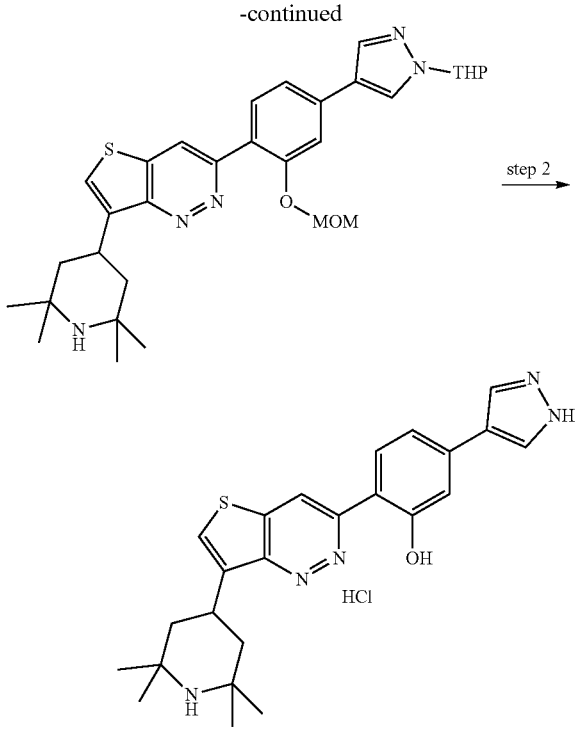

Step 1: A solution of 3-[2-(methoxymethoxy)-4-(1-tetrahydropyran-2-ylpyrazol-4-yl)phenyl]-7-(2,2,6,6-tetramethyl-1,3-dihydropyridin-4-yl)thieno[3,2-c]pyridazine (50 mg, 0.089 mmol, from Example 8, step 6) in MeOH (3 mL) was hydrogenated in a Parr shaker over Pt$_2$O (100 mg, 0.44 mmol) for 72 h at 50 psi of H$_2$. The catalyst was then filtered and washed with MeOH. The mother liquor was concentrated and the residue, crude 3-[2-(methoxymethoxy)-4-(1-tetrahydropyran-2-ylpyrazol-4-yl)phenyl]-7-(2,2,6,6-tetramethyl-4-piperidyl)thieno[3,2-c]pyridazine, was taken directly into the next step.

Step 2: A solution of crude 3-[2-(methoxymethoxy)-4-(1-tetrahydropyran-2-ylpyrazol-4-yl)phenyl]-7-(2,2,6,6-tetramethyl-4-piperidyl)thieno[3,2-c]pyridazine obtained from step 1 above in MeOH (1 mL) was treated with 4N HCl in dioxane (0.5 mL, 2 mmol). The reaction was stirred at room temperature for 30 min and then ~2 h at 50° C. The volatiles were then removed under reduced pressure, the residue was triturated with Et$_2$O, and the solid was filtered and washed with Et$_2$O. The crude product was purified by prep HPLC using the polar method (20-65% CH$_3$CN/H$_2$O). Upon concentration of the desired fractions and treatment of the residue with 4N HCl in dioxane (0.5 mL, 2 mmol), 5-(1H-pyrazol-4-yl)-2-(7-(2,2,6,6-tetramethylpiperidin-4-yl)thieno[3,2-c]pyridazin-3-yl)phenol dihydrochloride (2.4 mg, 6% yield) was obtained as a yellow solid.

MS m/z 434.3 [M+H]$^+$; $^1$H NMR (DMSO-d$_6$) δ: 9.32 (br s 1H), 9.30 (s, 1H), 8.19 (s, 2H), 8.15 (br. s, 1H), 8.12 (s, 1H), 8.05 (d, J=8.8 Hz, 1H), 7.27-7.36 (m, 2H), 3.91-4.00 (m, 1H), 2.18 (dd, J=12.3, 2.5 Hz, 2H), 1.89-2.07 (m, 2H), 1.60 (s, 6H), 1.50 (s, 6H); 1H not observed (NH or OH).

Example 10

Preparation of Compound 98

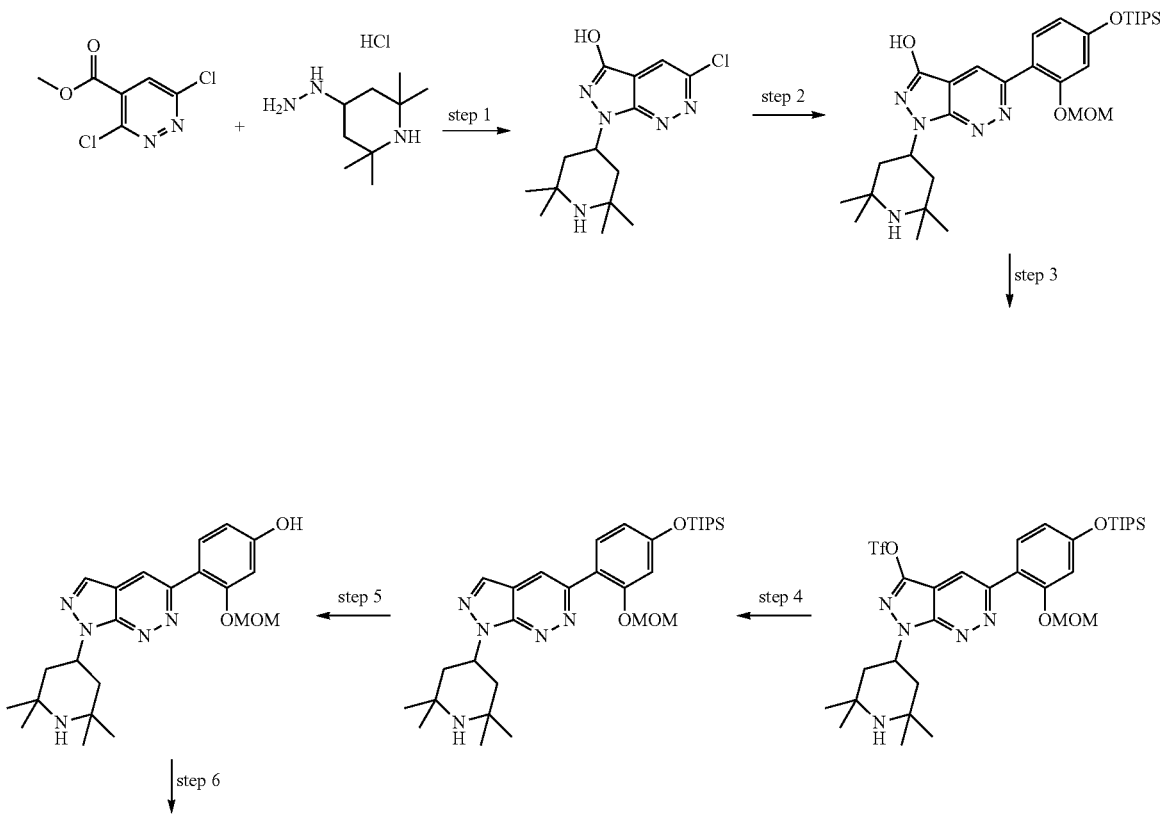

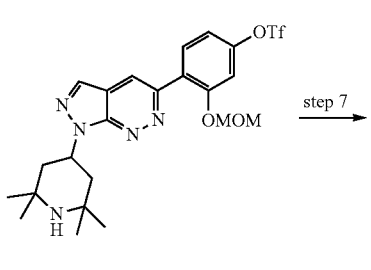 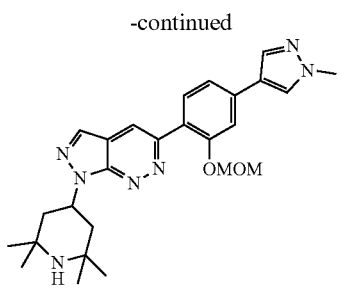 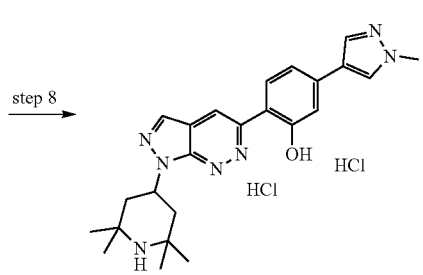

Step 1: Methyl 3,6-dichloropyridazine-4-carboxylate (500 mg, 2.42 mmol), (2,2,6,6-tetramethyl-4-piperidyl)hydrazine dihydrochloride (590 mg, 2.84 mmol), and DIPEA (1.3 mL, 7.26 mmol) were mixed in MeOH (2 mL) and heated to 70° C. overnight. UPLC showed 2 peaks with the desired mass in an approximately 2:3 ratio. The solvent was removed under reduced pressure and the residue was purified using silica gel chromatography eluting with a MeOH/CH$_2$Cl$_2$ gradient (0% to 30%) to provide 5-chloro-2-(2,2,6,6-tetramethyl-4-piperidyl)pyrazolo[3,4-c]pyridazin-3-ol (230 mg, 31%) as dark violet solid and 5-chloro-1-(2,2,6,6-tetramethyl-4-piperidyl)pyrazolo[3,4-c]pyridazin-3-ol (200 mg, 13.4%) as a brownish-orange solid.

MS m/z 310.8 [M+H]$^+$; $^1$H NMR (methanol-d$_4$) δ: 7.84 (s, 1H), 5.24 (tt, J=12.3, 3.8 Hz, 1H), 2.30 (dd, J=14.2, 12.3 Hz, 2H), 2.05 (dd, J=14.2, 3.8 Hz, 2H), 1.66 (s, 6H), 1.54 (s, 6H); 2 Hs not observed (NH and OH).

Step 2: An oven-dried flask was equipped with a magnetic stir bar and charged with 5-chloro-1-(2,2,6,6-tetramethyl-4-piperidyl)pyrazolo[3,4-c]pyridazin-3-ol (500 mg, 1.61 mmol), triisopropyl-[3-(methoxymethoxy)-4-(4,4,5,5-tetramethyl-1,3,2-dioxaborolan-2-yl)phenoxy]silane (775 mg, 1.78 mmol), [1,1'-bis(diphenylphosphino)ferrocene] dichloropalladium(II) (121 mg, 0.16 mmol) and K$_2$CO$_3$ (451 mg, 3.23 mmol). The flask was sealed with a rubber septum, and then evacuated and backfilled with argon (repeated a total of 3×). Dioxane (2 mL) and water (0.5 mL) were added and the reaction was heated to 90° C. for 16 h. The reaction was cooled to room temperature, diluted with water, and extracted with EtOAc (3×). The combined organic layers were dried over Na$_2$SO$_4$, concentrated under reduced pressure, and the residue was purified by column chromatography on silica gel, eluting with a MeOH/CH$_2$Cl$_2$ gradient (0% to 30% MeOH) to provided 5-[2-(methoxymethoxy)-4-triisopropylsilyloxy-phenyl]-1-(2,2,6,6-tetramethyl-4-piperidyl)pyrazolo[3,4-c]pyridazin-3-ol (200 mg, 21%) as a brownish solid. MS m/z 584.4 [M+H]$^+$.

Step 3: To a suspension of 5-[2-(methoxymethoxy)-4-triisopropylsilyloxy-phenyl]-1-(2,2,6,6-tetramethyl-4-piperidyl)pyrazolo[3,4-c]pyridazin-3-ol (200 mg, 0.34 mmol) in CH$_2$Cl$_2$ (4 mL) were added N,N-bis(trifluoromethylsulfonyl)aniline (247 mg, 0.69 mmol) and Et$_3$N (0.15 mL, 1.03 mmol) and the reaction was stirred at room temperature for 16 h. The reaction was concentrated under reduced pressure, and the residue was purified by column chromatography on silica gel, eluting with a MeOH/CH$_2$Cl$_2$ gradient (0% to 30% MeOH) to provide [5-[2-(methoxymethoxy)-4-triisopropylsilyloxy-phenyl]-1-(2,2,6,6-tetramethyl-4-piperidyl)pyrazolo[3,4-c]pyridazin-3-yl] trifluoromethanesulfonate (236 mg, 96%) as a tan solid.

MS m/z 716.6 [M+H]$^+$.

Step 4: To a mixture of [5-[2-(methoxymethoxy)-4-triisopropylsilyloxy-phenyl]-1-(2,2,6,6-tetramethyl-4-piperidyl)pyrazolo[3,4-c]pyridazin-3-yl] trifluoromethanesulfonate (236 mg, 0.33 mmol), dppf (38 mg, 0.066 mmol), [1,1'-bis(diphenylphosphino)ferrocene] dichloropalladium(II) (49 mg, 0.066 mmol), and ammonium formate (104 mg, 1.65 mmol) in dry THF (4 ml) was added Et$_3$N (0.23 mL, 1.65 mmol). The mixture was purged with argon and then heated at 60° C. for 6 h in a sealed tube. The reaction was cooled to room temperature, diluted with water, and extracted with EtOAc (3×). The combined organic layers were dried over Na$_2$SO$_4$ and concentrated under reduced pressure. The residue was purified by column chromatography on silica gel, eluting with a MeOH/CH$_2$Cl$_2$ gradient (0% to 15% MeOH) to provide triisopropyl-[3-(methoxymethoxy)-4-[1-(2,2,6,6-tetramethyl-4-piperidyl)pyrazolo[3,4-c]pyridazin-5-yl]phenoxy]silane (170 mg, 91%) as a grey solid.

MS m/z 568.5 [M+H]$^+$; $^1$H NMR (methanol-d$_4$) δ: 8.45 (s, 1H), 8.32 (s, 1H), 7.67 (d, J=8.2 Hz, 1H), 6.96 (d, J=2.5 Hz, 1H), 6.77 (dd, J=8.8, 2.5 Hz, 1H), 5.74 (tt, J=12.6, 3.8 Hz, 1H), 5.22 (s, 2H), 3.42 (s, 3H), 2.06-2.33 (m, 4H), 1.56 (s, 6H), 1.39 (s, 6H), 1.35 (spt, J=7.6 Hz, 3H), 1.19 (d, J=7.6 Hz, 18H); 1H not observed (NH).

Step 5: To a solution of triisopropyl-[3-(methoxymethoxy)-4-[1-(2,2,6,6-tetramethyl-4-piperidyl)pyrazolo[3,4-c]pyridazin-5-yl]phenoxy]silane (273 mg, 0.48 mmol) in THF (4 mL) was added 1.0 M TBAF in THF (0.53 mmol, 0.53 mL) and the reaction was stirred at room temperature for 30 min. The solvent was removed under reduced pressure, and the residue was purified by column chromatography on silica gel, eluting with a MeOH/CH$_2$Cl$_2$ gradient (0% to 30% MeOH) to provide 3-(methoxymethoxy)-4-[1-(2,2,6,6-tetramethyl-4-piperidyl)pyrazolo[3,4-c]pyridazin-5-yl]phenol (101 mg, 51%) as a clear solid. MS m/z 412.4 [M+H]$^+$.

Step 6: To a suspension of 3-(methoxymethoxy)-4-[1-(2,2,6,6-tetramethyl-4-piperidyl)pyrazolo[3,4-c]pyridazin-5-yl]phenol (101 mg, 0.25 mmol) in CH$_2$Cl$_2$ (2 mL) were added N,N-bis(trifluoromethylsulfonyl)aniline (133 mg, 0.37 mmol) and Et$_3$N (0.104 mL, 0.74 mmol). The reaction mixture was stirred at room temperature for 16 h. UPLC showed complete conversion. The solvent was removed under reduced pressure and the residue was purified by column chromatography on silica gel, eluting with a EtOAc/hexanes gradient (20 to 100% EtOAc) to provide [3-(methoxymethoxy)-4-[1-(2,2,6,6-tetramethyl-4-piperidyl)pyrazolo[3,4-c]pyridazin-5-yl]phenyl] trifluoromethanesulfonate (121 mg, 91%) as a clear solid.

MS m/z 544.4 [M+H]$^+$; $^1$H NMR (methanol-d$_4$) δ: 8.53 (s, 1H), 8.38 (s, 1H), 7.94 (d, J=8.5 Hz, 1H), 7.40 (d, J=2.5 Hz, 1H), 7.24 (dd, J=8.5, 2.5 Hz, 1H), 5.79 (tt, J=12.6, 3.8 Hz, 1H), 5.31 (s, 2H), 3.44 (s, 3H), 2.39 (t, J=13.6 Hz, 2H), 2.28 (dd, J=13.6, 3.8 Hz, 2H), 1.66 (s, 6H), 1.50 (s, 6H); 1H not observed (NH).

Step 7: An oven-dried flask was equipped with a magnetic stir bar and charged with [3-(methoxymethoxy)-4-[1-(2,2,6,6-tetramethyl-4-piperidyl)pyrazolo[3,4-c]pyridazin-5-yl]phenyl]trifluoromethanesulfonate (51 mg, 0.094 mmol), 1-methyl-4-(4,4,5,5-tetramethyl-1,3,2-dioxaborolan-2-yl)pyrazole (23 mg, 0.11 mmol), [1,1'-bis(diphenylphosphino)ferrocene]dichloropalladium(I) (7 mg, 0.009 mmol), and $K_2CO_3$ (26 mg, 0.19 mmol). The flask was sealed with a rubber septum, and then evacuated and backfilled with argon (repeated a total of 3×). 1,4-Dioxane (1 mL) and water (0.25 mL) were added and the reaction was heated to 90° C. for 16 h. The reaction was cooled to room temperature, diluted with water, and extracted with EtOAc (3×). The combined organic layers were dried over $Na_2SO_4$, concentrated under reduced pressure, and the residue was purified by column chromatography on silica gel, eluting with a $MeOH/CH_2Cl_2$ gradient (0% to 30% MeOH) to provide 5-[2-(methoxymethoxy)-4-(1-methylpyrazol-4-yl)phenyl]-1-(2,2,6,6-tetramethyl-4-piperidyl)pyrazolo[3,4-c]pyridazine (40 mg, 89%) as an orange solid. MS m/z 476.5 $[M+H]^+$.

Step 8: To a solution of 5-[2-(methoxymethoxy)-4-(1-methylpyrazol-4-yl)phenyl]-1-(2,2,6,6-tetramethyl-4-piperidyl)pyrazolo[3,4-c]pyridazine (40 mg, 0.084 mmol) in 1 mL of $CH_2Cl_2$ and 2 drops of MeOH was added 4 N HCl in 1,4-dioxane (42 µL, 0.17 mmol) and the reaction was stirred for 5 h until UPLC showed complete consumption of the starting material. The solvent was removed under reduced pressure and the residue was triturated in $Et_2O$, and the precipitate was collected by filtration. The solid was further washed with diethyl ether and dried to afford 5-(1-methylpyrazol-4-yl)-2-[1-(2,2,6,6-tetramethyl-4-piperidyl)pyrazolo[3,4-c]pyridazin-5-yl]phenol dihydrochloride (32 mg, 75%) as a yellow solid.

MS m/z 432.5 $[M+H]^+$; $^1H$ NMR (methanol-$d_4$) δ: 9.11 (s, 1H), 8.66 (s, 1H), 8.16 (s, 1H), 7.99 (s, 1H), 7.86 (d, J=7.9 Hz, 1H), 7.35 (dd, J=8.2, 1.5 Hz, 1H), 7.29 (d, J=1.5 Hz, 1H), 5.74 (tt, J=12.6, 4.0 Hz, 1H), 4.00 (s, 3H), 2.52 (t, J=13.8 Hz, 2H), 2.44 (dd, J=13.8, 4.0 Hz, 2H), 1.76 (s, 6H), 1.62 (s, 6H); 2 NH not observed (NH and OH).

Using the procedure described for Example 10, above, additional compounds described herein were prepared by substituting the appropriate starting materials, suitable reagents and reaction conditions, obtaining compounds such as those selected from:

| Cpd | Data |
|---|---|
| 21 | MS m/z 362.4 $[M + H]^+$; $^1H$ NMR (methanol-$d_4$) δ: 9.12 (s, 1H), 8.68 (s, 1H), 8.42 (s, 2H), 7.89 (d, J = 8.2 Hz, 1H), 7.44 (dd, J = 8.2, 1.9 Hz, 1H), 7.38 (d, J = 1.6 Hz, 1H), 5.52 (tt, J = 10.4, 4.4 Hz, 1H), 3.67-3.72 (m, 2H), 3.43 (td, J = 12.3, 3.2 Hz, 2H), 2.58-2.70 (m, 2H), 2.46-2.55 (m, 2H); 3 Hs not observed (2 NHs and OH). |
| 102 | MS m/z 435.5 $[M + H]^+$; $^1H$ NMR (methanol-$d_4$) δ: 8.84 (s, 1H), 8.43 (s, 1H), 8.05 (s, 1H), 7.97 (d, J = 8.2 Hz, 1H), 7.89 (s, 1H), 7.25 (d, J = 8.2 Hz, 1H), 7.23 (s, 1H), 5.78 (tt, J = 12.4, 3.4 Hz, 1H), 2.51 (t, J = 13.7 Hz, 2H), 2.40 (dd, J = 13.7, 3.4 Hz, 2H), 1.76 (s, 6H), 1.60 (s, 6H); 2 Hs not observed (NH and OH). |
| 148 | MS m/z 450.4 $[M + H]^+$; $^1H$ NMR (methanol-$d_4$) δ: 8.81 (s, 1H), 8.40 (s, 1H), 7.77-7.86 (m, 2H), 7.25-7.32 (m, 1H), 6.91-7.00 (m, 1H), 5.56-5.72 (m, 1H), 3.26 (s, 3H), 2.42 (t, J = 13.4 Hz, 2H), 2.28 (dd, J = 13.4, 2.8 Hz, 2H), 1.65 (s, 6H), 1.50 (s, 6H); 2 Hs not observed (OH and NH). |
| 161 | MS m/z 436.5 $[M + H]^+$; $^1H$ NMR (methanol-$d_4$) δ: 8.81 (d, J = 8.5 Hz, 1H), 8.38 (s, 1H), 7.86-8.07 (m, 2H), 7.23-7.31 (m, 1H), 7.04 (d, J = 8.6 Hz, 1H), 5.61-5.74 (m, 1H), 1.98-2.18 (m, 4H), 1.48 (s, 6H), 1.30 (s, 6H), 3 Hs not observed (2 NHs and OH). |

Example 11

Preparation of Compound 22

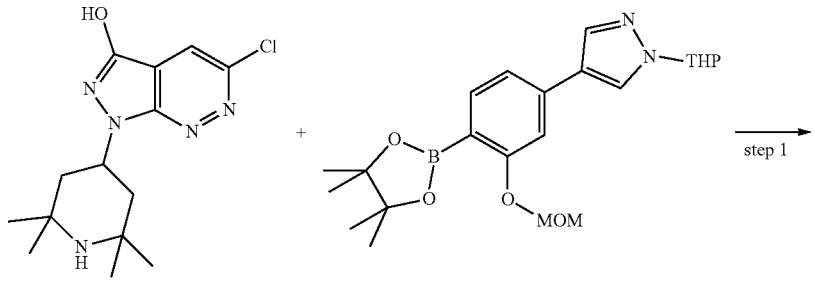

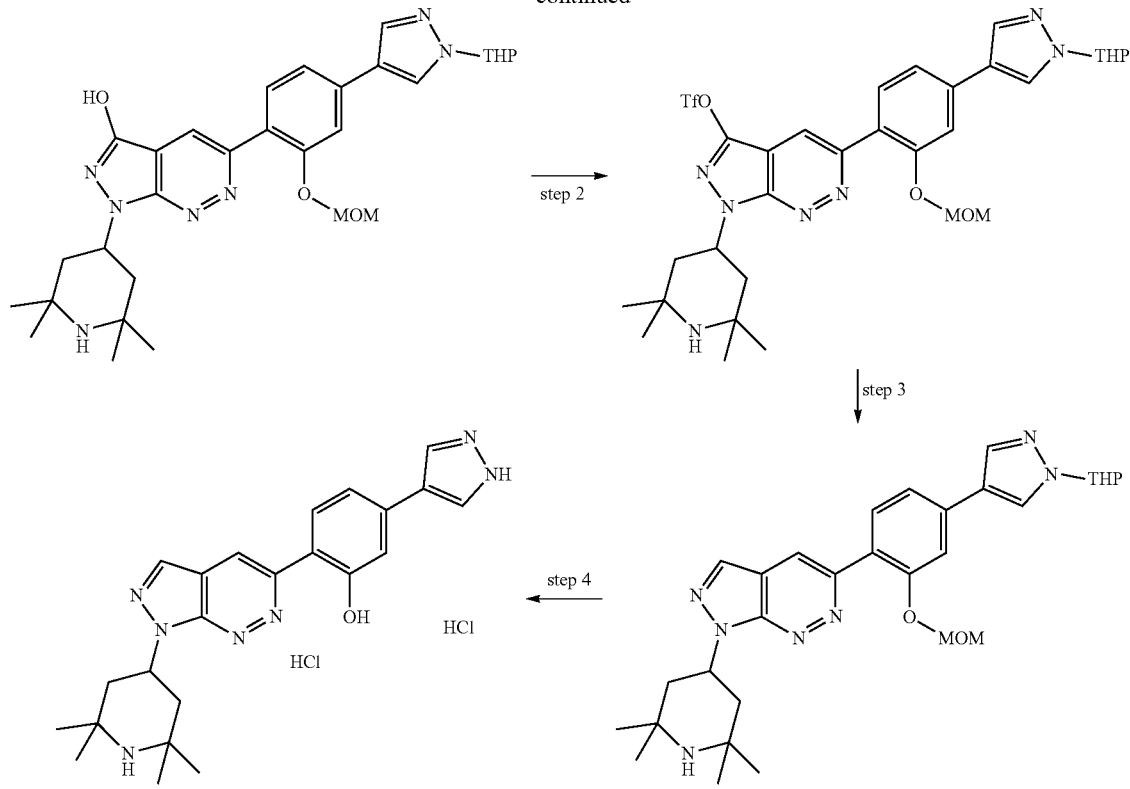

Step 1: An oven-dried flask was equipped with a magnetic stir bar and charged with 5-chloro-1-(2,2,6,6-tetramethyl-4-piperidyl)pyrazolo[3,4-c]pyridazin-3-ol (186 mg, 0.60 mmol), 4-[3-(methoxymethoxy)-4-(4,4,5,5-tetramethyl-1,3,2-dioxaborolan-2-yl)phenyl]-1-tetrahydropyran-2-yl-pyrazole (prepared in example 1, step 7, 298.5 mg, 0.72 mmol), [1,1-bis(diphenylphosphino)ferrocene] dichloropalladium (II) (45 mg, 0.06 mmol), and $K_2CO_3$ (252 mg, 1.80 mmol). The flask was sealed with a rubber septum, and then evacuated and backfilled with argon (repeated a total of 3×). 1,4-Dioxane (2 mL) and water (0.5 mL) were added and the reaction was heated to 90° C. for 16 h. The reaction was cooled to room temperature, diluted with water, and extracted with EtOAc (3×). The combined organic phases were dried over $Na_2SO_4$, concentrated under reduced pressure, and purified by column chromatography, eluting with a MeOH/$CH_2Cl_2$ gradient (0-30% MeOH) to provide 5-(2-(methoxymethoxy)-4-(1-(tetrahydro-2H-pyran-2-yl)-1H-pyrazol-4-yl)phenyl)-1-(2,2,6,6-tetramethylpiperidin-4-yl)-1H-pyrazolo[3,4-c]pyridazin-3-ol (229 mg, 68%) as a dark yellow solid. MS m/z 562.5 [M+H]$^+$.

Step 2: To a solution of 5-[2-(methoxymethoxy)-4-(1-tetrahydropyran-2-ylpyrazol-4-yl)phenyl]-1-(2,2,6,6-tetramethyl-4-piperidyl)pyrazolo[3,4-c]pyridazin-3-ol (229 mg, 0.41 mmol) in $CH_2Cl_2$ (4 mL) was added N,N-bis(trifluoromethylsulfonyl)aniline (294 mg, 0.82 mmol) and $Et_3N$ (0.17 mL, 1.22 mmol) and the reaction was stirred at room temperature for 16 h. The reaction was cooled to room temperature, diluted with water, and extracted with $CH_2Cl_2$ (3×). The combined organic phases were dried over $Na_2SO_4$, concentrated under reduced pressure and purified by column chromatography, eluting with a MeOH/$CH_2Cl_2$ gradient (0-25% MeOH) to provide 5-(2-(methoxymethoxy)-4-(1-(tetrahydro-2H-pyran-2-yl)-1H-pyrazol-4-yl)phenyl)-1-(2,2,6,6-tetramethylpiperidin-4-yl)-1H-pyrazolo[3,4-c]pyridazin-3-yl trifluoromethanesulfonate (166 mg, 59%) as a clear solid.

MS m/z 694.3 [M+H]$^+$; $^1$H NMR (acetone-$d_6$) δ: 8.50 (s, 1H), 8.17 (d, J=0.6 Hz, 1H), 7.91 (d, J=8.2 Hz, 1H), 7.83 (d, J=0.6 Hz, 1H), 7.47 (d, J=1.6 Hz, 1H), 7.37 (dd, J=8.2, 1.6 Hz, 1H), 5.73 (tt, J=12.3, 4.0 Hz, 1H), 5.34 (dd, J=9.8, 2.5 Hz, 1H), 5.27 (s, 2H), 3.85-3.92 (m, 1H), 3.54-3.64 (m, 1H), 3.30 (s, 3H), 2.15-2.27 (m, 4H), 1.60-1.68 (m, 2H), 1.54 (s, 6H), 1.45-1.52 (m, 4H), 1.37 (s, 6H), 1H not observed (NH).

Step 3: To a solution of 5-(2-(methoxymethoxy)-4-(1-(tetrahydro-2H-pyran-2-yl)-1H-pyrazol-4-yl)phenyl)-1-(2,2,6,6-tetramethylpiperidin-4-yl)-1H-pyrazolo[3,4-c]pyridazin-3-yl trifluoromethanesulfonate (166 mg, 0.24 mmol), Pd(OAc)$_2$ (11 mg, 0.048 mmol), dppf (27 mg, 0.048 mmol), and $Et_3N$ (0.17 mL, 1.2 mmol) in dry THF (0.5 ml) was added ammonium formate (77 mg, 1.2 mmol). The mixture was purged with argon and heated at 60° C. for 2.5 h in a sealed tube. The reaction was cooled to room temperature, diluted with water, and extracted with EtOAc (3×). The combined organic phases were dried over $Na_2SO_4$, concentrated under reduced pressure, and the residue was purified by column chromatography on silica gel, eluting with a MeOH/$CH_2Cl_2$ gradient (0% to 20% MeOH) to provide 5-(2-(methoxymethoxy)-4-(1-(tetrahydro-2H-pyran-2-yl)-1H-pyrazol-4-yl)phenyl)-1-(2,2,6,6-tetramethylpiperidin-4-yl)-1H-pyrazolo[3,4-c]pyridazine (115 mg, 88%) as a clear foam. MS m/z 546.5 [M+H]$^+$.

Step 4: To a solution of 5-(2-(methoxymethoxy)-4-(1-(tetrahydro-2H-pyran-2-yl)-1H-pyrazol-4-yl)phenyl)-1-(2,2,6,6-tetramethylpiperidin-4-yl)-1H-pyrazolo[3,4-c]pyridazine (115 mg, 0.21 mmol) in 1 ml $CH_2Cl_2$ and 1 drop of MeOH was added 4N HCl in dioxane (0.11 mL, 0.44 mmol) and the reaction was stirred at room temperature for 2 h. The yellow solid that precipitated was collected by vacuum filtration, rinsed with CH₂Cl₂, Et₂O and dried to afford 5-(1H-pyrazol-4-yl)-2-(1-(2,2,6,6-tetramethylpiperidin-4-yl)-1H-pyrazolo[3,4-c]pyridazin-5-yl)phenol hydrochloride (78 mg, 89%) as a yellow solid:

MS m/z 418.5 [M+H]⁺; ¹H NMR (methanol-d4) δ: 9.20 (s, 1H), 8.75 (s, 1H), 8.62 (s, 2H), 7.91 (d, J=8.2 Hz, 1H), 7.49 (dd, J=8.2, 1.9 Hz, 1H), 7.43 (d, J=1.6 Hz, 1H), 5.75 (tt, J=12.0, 4.1 Hz, 1H), 2.53 (t, J=14.2 Hz, 2H), 2.46 (dd, J=14.2, 4.1 Hz, 2H), 1.76 (s, 6H), 1.63 (s, 6H); 3 Hs not observed (2 NHs and OH).

Using the procedure described for Example 11, above, additional compounds described herein were prepared by substituting the appropriate starting materials, suitable reagents and reaction conditions, obtaining compounds such as those selected from:

late dihydrochloride (412 mg, 1.28 mmol) were mixed in DMF (3 mL) and stirred at room temperature for 5 min. The reaction mixture was partitioned between EtOAc and water. The combined organic phases were dried over Na₂SO₄, concentrated under reduced pressure, and the residue was purified by column chromatography on silica gel, eluting with a EtOAc/hexanes gradient (0% to 30% EtOAc) to provide benzyl 4-[(2E)-2-[(3,6-dibromopyrazin-2-yl)methylene]hydrazino]piperidine-1-carboxylate (550 mg, 87%) as a yellow solid.

MS m/z 496.0, 498.0, 500.0 [M+H]⁺; ¹H NMR (acetone-d₆) δ: 8.27-8.33 (m, 1H), 8.17 (d, J=4.7 Hz, 1H), 7.90 (s, 1H), 7.36-7.45 (m, 4H), 7.29-7.36 (m, 1H), 5.14 (s, 2H), 4.05-4.15 (m, 2H), 3.64-3.74 (m, 1H), 2.08-2.10 (m, 2H), 2.01-2.05 (m, 2H), 1.49-1.64 (m, 2H).

| Cpd | Data |
|---|---|
| 165 | MS m/z 429.3 [M + H]⁺; ¹H NMR (methanol-d₄) δ: 8.90 (s, 1H), 8.61 (d, J = 4.6 Hz, 2H), 8.41 (s, 1H), 8.06 (d, J = 8.5 Hz, 1H), 7.79 (br d, J = 4.9 Hz, 2H), 7.39 (s, 1H), 7.35 (d, J = 8.2 Hz, 1H), 5.61-5.75 (m, 1H), 1.94-2.16 (m, 4H), 1.45 (s, 6H),1.26 (s, 6H); 2 Hs not observed (NH and OH). |
| 166 | MS m/z 429.3 [M + H]⁺; ¹H NMR (methanol-d₄) δ: 9.31 (br s, 1H), 9.01-9.10 (m, 2H), 8.92 (br d, J = 3.1 Hz, 1H), 8.57 (s, 1H), 8.17-8.31 (m, 2H), 7.56 (br s, 2H), 5.71-5.88 (m, 1H), 2.49-2.60 (m, 2H), 2.35-2.48 (m, 2H), 1.77 (s, 6H), 1.63 (s, 6H); 2 Hs not observed (NH and OH). |
| 167 | MS m/z 430.3 [M + H]⁺; ¹H NMR (methanol-d₄) δ: 9.19 (s, 1H), 9.16 (br s, 2H), 8.93 (s, 1H), 8.46 (s, 1H), 8.17 (d, J = 8.5 Hz, 1H), 7.35-7.50 (m, 2H), 5.76-5.89 (m, 1H), 2.49-2.56 (m, 2H), 2.42 (br dd, J = 13.6, 3.2 Hz, 2H), 1.77 (s, 6H), 1.61 (s, 6H); 2 Hs not observed (NH and OH). |
| 169 | MS m/z 432.4 [M + H]⁺; ¹H NMR (methanol-d₄) δ: 8.83 (s, 1H), 8.39 (s, 1H), 7.93-8.05 (m, 1H), 7.65 (s, 1H), 7.35-7.54 (m, 2H),6.65-6.78 (m, 1H), 5.54-5.83 (m, 1H), 3.95 (s, 3H), 2.12-2.46 (m, 4H), 1.61 (br s, 6H), 1.44 (br s, 6H); 2 Hs not observed (NH and OH). |
| 174 | MS m/z 419.4 [M + H]⁺; ¹H NMR (methanol-d₄) δ: 8.77-8.95 (m, 1H), 8.38 (br s, 1H), 8.01-8.14 (m, 1H), 7.97 (s, 2H), 7.55-7.78 (m, 2H), 5.58-5.73 (m, 1H), 1.94-2.22 (m, 4H), 1.46 (s, 6H), 1.26 (s, 6H); 2Hs not observed (NH and OH). |

Example 12

Preparation of Compound 19

Step 2: A solution of benzyl 4-[(2E)-2-[(3,6-dibromopyrazin-2-yl)methylene]hydrazino]piperidine-1-carboxylate (550 mg, 1.11 mmol) in CH₃CN (2 mL) was heated in a microwave at 200° C. for 1 h. The solvent was removed

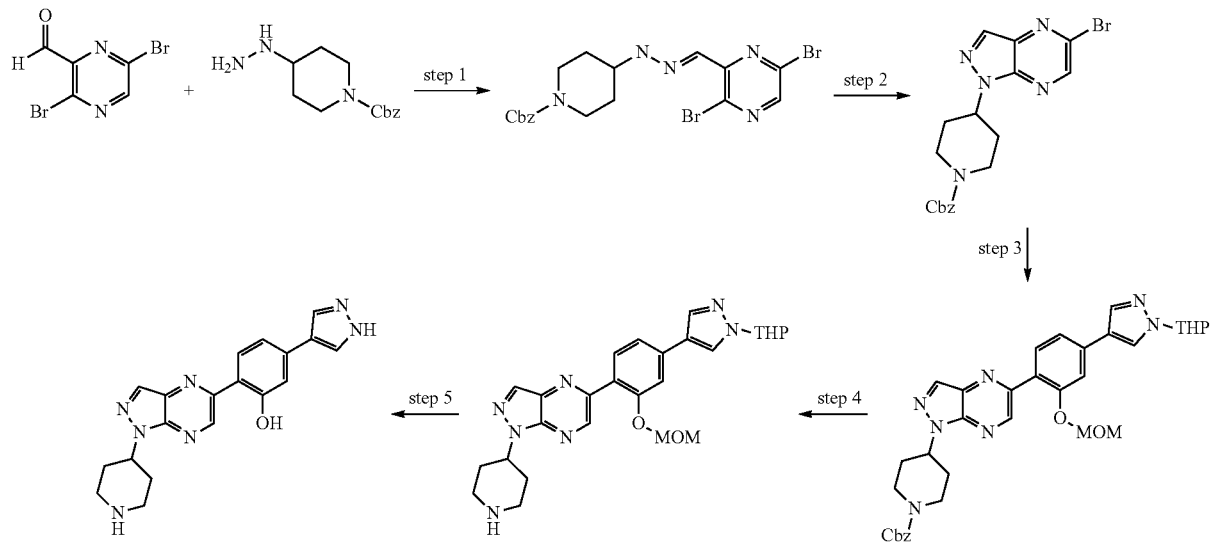

Step 1: 3,6-Dibromopyrazine-2-carbaldehyde (340 mg, 1.28 mmol) and benzyl 4-hydrazinopiperidine-1-carboxyunder reduced pressure and the residue was purified by column chromatography on silica gel, eluting with a EtOAc/

CH$_2$Cl$_2$ gradient (0% to 60% EtOAc) to provide benzyl 4-(5-bromo-1H-pyrazolo[3,4-b]pyrazin-1-yl)piperidine-1-carboxylate (78 mg, 16%). MS m/z 416.0, 418.0 [M+H]$^+$.

Step 3: An oven-dried flask was equipped with a magnetic stir bar and charged with benzyl 4-(5-bromopyrazolo[3,4-b]pyrazin-1-yl)piperidine-1-carboxylate (78 mg, 0.19 mmol), 4-[3-(methoxymethoxy)-4-(4,4,5,5-tetramethyl-1,3,2-dioxaborolan-2-yl)phenyl]-1-tetrahydropyran-2-yl-pyrazole (prepared in Example 1, step 7, 93 mg, 0.23 mmol), [1,1'-bis(diphenylphosphino)ferrocene] dichloropalladium (I) (14 mg, 0.019 mmol) and K$_2$CO$_3$ (78 mg, 0.56 mmol). The flask was sealed with a rubber septum, and then evacuated and backfilled with argon (repeated a total of 3×). 1,4-Dioxane (2 mL) and water (0.5 mL) were added and the reaction was heated to 90° C. for 16 h. The reaction was cooled to room temperature, diluted with water, and extracted with EtOAc (3×). The combined organic layers were dried over Na$_2$SO$_4$, concentrated under reduced pressure, and purified by column chromatography, eluting with a EtOAc/CH$_2$Cl$_2$ gradient (0-60% EtOAc) to provide benzyl 4-(5-(2-(methoxymethoxy)-4-(1-(tetrahydro-2H-pyran-2-yl)-1H-pyrazol-4-yl)phenyl)-1H-pyrazolo[3,4-b]pyrazin-1-yl)piperidine-1-carboxylate (69 mg, 59%) as brownish solid. MS m/z 624.3 [M+H]$^+$;

Step 4: To a solution of benzyl 4-[5-[2-(methoxymethoxy)-4-(1-tetrahydropyran-2-ylpyrazol-4-yl)phenyl]pyrazolo[3,4-b]pyrazin-1-yl]piperidine-1-carboxylate (69 mg, 0.11 mmol) in EtOH (3 mL) was added 10% Pd/C (10 mg) and the reaction mixture was hydrogenated under 1 atm of H$_2$ for 16 h. The catalyst was removed by filtration, the solvent was evaporated under reduced pressure, and the residue was purified by column chromatography, eluting with a MeOH/CH$_2$Cl$_2$ gradient (0-30% MeOH). 5-[2-(Methoxymethoxy)-4-(1-tetrahydropyran-2-ylpyrazol-4-yl)phenyl]-1-(4-piperidyl)pyrazolo[3,4-b]pyrazine (15 mg, 28%) was obtained as a white solid. MS m/z 490.4 [M+H]$^+$;

Step 5: To a solution of 5-[2-(methoxymethoxy)-4-(1-tetrahydropyran-2-ylpyrazol-4-yl)phenyl]-1-(4-piperidyl)pyrazolo[3,4-b]pyrazine (15 mg, 0.031 mmol) in CH$_2$Cl$_2$ (1 mL, with one drop of MeOH) was added 4 N HCl in 1,4-dioxane (15 μL, 0.06 mmol) and the reaction was stirred at room temperature for 2 h. The precipitate was collected by filtration, washed with Et$_2$O (3×) and dried to provide 2-[1-(4-piperidyl)pyrazolo[3,4-b]pyrazin-5-yl]-5-(1H-pyrazol-4-yl)phenol; hydrochloride (8 mg, 66%) as a yellow solid.

MS m/z 362.3 [M+H]$^+$; $^1$H NMR (DMSO-d$_6$) δ:11.68 (br s, 1H), 10.09 (br s, 1H), 9.38 (d, J=1.6 Hz, 1H), 8.95 (br s, 1H), 8.68 (br s, 1H), 8.56 (s, 1H), 8.14 (br s, 1H), 8.05 (dd, J=8.8, 1.6 Hz, 1H), 7.27 (s, 2H), 5.18-5.28 (m, 1H), 3.58-3.66 (m, 1H), 3.42-3.53 (m, 1H), 3.17-3.39 (m, 2H), 2.76-2.88 (m, 1H), 2.34-2.45 (m, 1H), 2.14-2.31 (m, 2H).

Example 13

Preparation of Compound 80

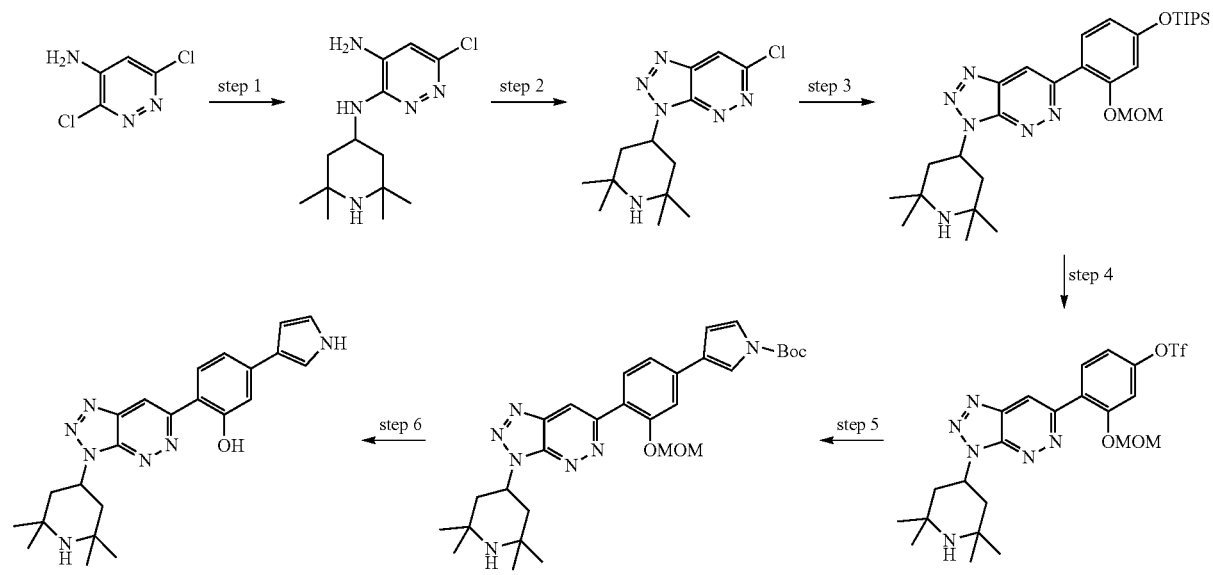

Step 1: To a suspension of 3,6-dichloropyridazin-4-amine (2.0 g, 12.2 mmol) in 1-decanol (3.5 mL) were added 2,2,6,6-tetramethylpiperidin-4-amine (2.3 mL, 1.1 equiv.) and N,N-diisopropylethylamine (3 mL, 1.4 equiv.) in a 60 mL sealed screw-cap tube. The reaction was stirred at 150° C. for 72 h after which the partially solidified reaction mixture was transferred to a round-bottom flask with the aid of methanol. The organic components were concentrated to afford a thick oil, which was rinsed with hexanes to remove 1-decanol (this may lead to solidification). The crude product was purified by column chromatography, eluting with a MeOH (with 2.5% NH$_4$OH)/CH$_2$Cl$_2$ gradient (5 to 30% MeOH/NH$_4$OH). The first compound to elute was unreacted starting material 3,6-dichloropyridazin-4-amine. Then, a mixture of 6-chloro-N3-(2,2,6,6-tetramethylpiperidin-4-yl)pyridazine-3,4-diamine and 6-chloro-N3-(2,2,6,6-tetramethylpiperidin-4-yl)pyridazine-3,5-diamine elute (they co-elute), followed by N3,N6-bis(2,2,6,6-tetramethylpiperidin-4-yl)pyridazine-3,4,6-triamine. Column chromatography generally results in a 50-60% yield of 6-chloro-N3-(2,2,6,6-tetramethylpiperidin-4-yl)pyridazine-3,4-diamine and 6-chloro-N3-(2,2,6,6-tetramethylpiperidin-4-yl)pyridazine-3,5-diamine (2:1 ratio). The mixture of 6-chloro-N3-(2,2,6,6-tetramethylpiperidin-4-yl)pyridazine-3,4-diamine and 6-chloro-N3-(2,2,6,6-tetramethylpiperidin-4-yl)pyridazine-3,5-diamine (2.7 g, 77%) obtained after chromatography was used in the next step without further purification.

Step 2: To a solution of a mixture of 6-chloro-N3-(2,2,6,6-tetramethyl-4-piperidyl)pyridazine-3,4-diamine and 6-chloro-N3-(2,2,6,6-tetramethyl-4-piperidyl)pyridazine-3,5-diamine (2.7 g, 9.5 mmol) in AcOH (8 mL) was added NaNO$_2$ (1.3 g, 19 mmol) in portions and the mixture was stirred at room temperature for 1 h. The reaction was quenched by the addition of saturated aqueous sodium bicarbonate slowly until reaching pH~7. The aqueous layer was extracted with ethyl acetate three times. The organic layer was dried over Na$_2$SO$_4$, filtered, and concentrated in vacuo. The crude product was purified by column chromatography on silica gel, eluting with a MeOH/CH$_2$Cl$_2$ gradient (0-20% MeOH) to yield 6-chloro-3-(2,2,6,6-tetramethyl-4-piperidyl)triazolo[4,5-c]pyridazine (1.22 g, 43%) as brownish solid:

MS m/z 295.8 [M+H]$^+$; $^1$H NMR (500 MHz, methanol-d$_4$) δ: 8.56 (s, 1H), 5.76 (tt, J=12.6, 4.1 Hz, 1H), 2.30 (dd, J=12.6, 4.1 Hz, 2H), 2.23 (t, J=12.6 Hz, 2H), 1.47 (s, 6H), 1.32 (s, 6H).

Step 3: An oven-dried flask was equipped with a magnetic stir bar and charged with 6-chloro-3-(2,2,6,6-tetramethyl-4-piperidyl)triazolo[4,5-c]pyridazine (1.11 g, 3.77 mmol), tri-isopropyl(3-(methoxymethoxy)-4-(4,4,5,5-tetramethyl-1,3,2-dioxaborolan-2-yl)phenoxy)silane (1.81 g, 4.15 mmol), [1,1'-bis(diphenylphosphino)ferrocene] dichloropalladium (II) (138 mg, 0.19 mmol) and K$_2$CO$_3$ (1.56 g, 11.31 mmol). The flask was sealed with a rubber septum, and then evacuated and backfilled with argon (repeated a total of 3x). 1,4-Dioxane (18 mL) and water (4 mL) were added and the reaction was heated to 90° C. for 16 h. The reaction was cooled to room temperature, diluted with water (5 mL) and extracted with EtOAc (3x). The combined organic layers were dried over Na$_2$SO$_4$ and concentrated under reduced pressure, to provide crude 6-(2-(methoxymethoxy)-4-((triisopropylsilyl)oxy)phenyl)-3-(2,2,6,6-tetramethylpiperidin-4-yl)-3H-[1,2,3]triazolo[4,5-c]pyridazine (1.67 g, 78%) as a brown solid which was used in the next step without further purification.

Step 4: To a solution of 6-(2-(methoxymethoxy)-4-((triisopropylsilyl)oxy)phenyl)-3-(2,2,6,6-tetramethylpiperidin-4-yl)-3H-[1,2,3]triazolo[4,5-c]pyridazine (1.67 g, 2.94 mmol) in THF (10 mL) was added 1.0 M TBAF in THF (3.1 mL, 3.1 mmol). The reaction mixture was stirred at room temperature for 1 h until TLC showed complete consumption of the starting material. The solvent was removed under reduced pressure and the crude product was purified by column chromatography on silica gel, eluting with a EtOAc/hexanes gradient (10-80% EtOAc) to yield 3-(methoxymethoxy)-4-(3-(2,2,6,6-tetramethylpiperidin-4-yl)-3H-[1,2,3]triazolo[4,5-c]pyridazin-6-yl)phenol (985 mg, 81%) as a tan oil. To a solution of 3-(methoxymethoxy)-4-(3-(2,2,6,6-tetramethylpiperidin-4-yl)-3H-[1,2,3]triazolo[4,5-c]pyridazin-6-yl)phenol (985 mg, 2.39 mmol) in CH$_2$Cl$_2$ (8 mL) was added N,N-bis(trifluoromethylsulfonyl)aniline (1.71 g, 4.78 mmol) and Et$_3$N (1.0 mL, 7.2 mmol). The reaction was stirred for 5 h until UPLC showed complete conversion.

The solvent was removed under reduced pressure and the residue was purified by column chromatography on silica gel, eluting with a EtOAc/hexanes gradient (0-60% EtOAc) to give 3-(methoxymethoxy)-4-(3-(2,2,6,6-tetramethylpiperidin-4-yl)-3H-[1,2,3]triazolo[4,5-c]pyridazin-6-yl)phenyl trifluoromethanesulfonate (20 mg, 71%).

MS m/z 545.6 [M+H]$^+$; $^1$H NMR (acetone-d$_6$) δ: 8.68 (s, 1H), 8.04 (d, J=8.5 Hz, 1H), 7.35 (d, J=2.5 Hz, 1H), 7.21 (dd, J=8.8, 2.5 Hz, 1H), 5.67 (tt, J=11.2, 5.4 Hz, 1H), 5.31 (s, 2H), 3.35 (s, 3H), 2.04-2.27 (m, 4H), 1.36 (s, 6H), 1.16 (s, 6H), 1H not observed (NH).

Step 5: An oven-dried flask was equipped with a magnetic stir bar and charged with [3-(methoxymethoxy)-4-[3-(2,2,6,6-tetramethyl-4-piperidyl)triazolo[4,5-c]pyridazin-6-yl]phenyl]trifluoromethanesulfonate (50 mg, 0.092 mmol), tert-butyl 3-(4,4,5,5-tetramethyl-1,3,2-dioxaborolan-2-yl)pyrrole-1-carboxylate (32 mg, 0.11 mmol), [1,1'-bis(diphenylphosphino)ferrocene] dichloropalladium(I) (7 mg, 0.009 mmol) and K$_2$CO$_3$ (26 mg, 0.18 mmol). The flask was sealed with a rubber septum, and then evacuated and backfilled with argon (repeated a total of 3x). 1,4-Dioxane (18 mL) and water (4 mL) were added and the reaction was heated to 90° C. for 16 h. The reaction was cooled to room temperature, diluted with water (5 mL), and extracted with EtOAc (3x). The combined organic layers were dried over Na$_2$SO$_4$, concentrated under reduced pressure, and purified using silica gel chromatography eluting with a MeOH/CH$_2$Cl$_2$ gradient (0% to 30% MeOH) to provide tert-butyl 3-[3-(methoxymethoxy)-4-[3-(2,2,6,6-tetramethyl-4-piperidyl)triazolo[4,5-c]pyridazin-6-yl]phenyl]pyrrole-1-carboxylate (40 mg, 78%) as an orange solid. MS m/z 562.3 [M+H]$^+$.

Step 6: To a solution of tert-butyl 3-[3-(methoxymethoxy)-4-[3-(2,2,6,6-tetramethyl-4-piperidyl)triazolo[4,5-c]pyridazin-6-yl]phenyl]pyrrole-1-carboxylate (40 mg, 0.071 mmol) in CH$_2$Cl$_2$ (2 mL) plus 2 drops of MeOH was added 4 N HCl in 1,4-dioxane (36 μL). The reaction was stirred for 5 h until UPLC showed complete consumption of the starting material. The solvents were removed under reduced pressure and the product was purified by column chromatography, eluting with a MeOH/CH$_2$Cl$_2$ gradient (with 2.5% NH$_4$OH) (5 to 30% MeOH/NH$_4$OH) to provide 5-(1H-pyrrol-3-yl)-2-(3-(2,2,6,6-tetramethylpiperidin-4-yl)-3H-[1,2,3]triazolo[4,5-c]pyridazin-6-yl)phenol (22 mg, 74%) as an orange solid.

MS m/z 418.5 [M+H]$^+$; $^1$H NMR (methanol-d4) δ: 9.00 (s, 1H), 7.95 (d, J=8.2 Hz, 1H), 7.25 (d, J=1.6 Hz, 1H), 7.22-7.24 (m, 1H), 7.18 (d, J=1.6 Hz, 1H), 6.83 (dd, J=2.8, 1.9 Hz, 1H), 6.52 (dd, J=2.8, 1.6 Hz, 1H), 5.89 (tt, J=10.4, 5.5 Hz, 1H), 2.47-2.68 (m, 4H), 1.72 (s, 6H), 1.57 (s, 6H); 3 Hs not observed (2 NHs and OH).

Using the procedure described for Example 13, above, additional compounds described herein were prepared by substituting the appropriate starting materials, suitable reagents and reaction conditions, obtaining compounds such as those selected from:

| Cpd | Data |
|---|---|
| 37 | MS m/z 460.6 [M + H]$^+$; $^1$H NMR (methanol-d$_4$) δ: 9.15 (s, 1H), 8.20 (d, J = 8.2 Hz, 1H), 7.82 (d, J = 6.9 Hz, 1H), 7.41 (dd, J = 8.2, 1.9 Hz, 1H), 7.39 (d, J = 1.9 Hz, 1H), 6.91 (d, J = 2.2 Hz, 1H), 6.84 (dd, J = 6.9, 2.2 Hz, 1H), 5.99 (tt, J = 10.4, 4.7 Hz, 1H), 3.67 (s, 3H), 2.64-2.74 (m, 4H), 1.79 (s, 6H), 1.64 (s, 6H); 2 Hs not observed (NH and OH). |

-continued

| Cpd | Data |
|---|---|
| 38 | MS m/z 445.5 [M + H]⁺; ¹H NMR (DMSO-d₆) δ: 9.17 (s, 1H), 8.97-9.06 (m, 1H), 8.15 (br. s, 1H), 8.12 (d, J = 8.2 Hz, 1H), 7.49-7.61 (m, 2H), 7.29 (d, J = 1.6 Hz, 1H), 7.27 (s, 1H), 6.80-6.96 (m, 2H), 5.93 (tt, J = 12.0, 4.4 Hz, 1H), 2.53-2.67 (m, 4H), 1.66 (s, 6H), 1.53 (s, 6H); 1H not observed (NH). |
| 39 | MS m/z 433.5 [M + H]⁺; ¹H NMR (methanol-d₄) δ: 9.11 (s, 1H), 8.14 (s, 1H), 8.08 (d, J = 7.9 Hz, 1H), 8.00 (s, 1H), 7.31 (dd, J = 8.8, 1.9 Hz, 1H), 7.28 (d, J = 1.9 Hz, 1H), 5.97 (tt, J = 12.3, 4.0 Hz, 1H), 4.01 (s, 3H), 2.56-2.76 (m, 4H), 1.79 (s, 6H), 1.64 (s, 6H), 2 Hs not observed (NH and OH). |
| 46 | MS m/z 447.6 [M + H]⁺; ¹H NMR (methanol-d₄) δ: 9.11 (s, 1H), 8.21 (d, J = 0.9 Hz, 1H), 8.07 (d, J = 8.2 Hz, 1H), 8.02 (s, 1H), 7.32 (dd, J = 8.2, 1.9 Hz, 1H), 7.29 (d, J = 1.9 Hz, 1H), 5.97 (tt, J = 10.1, 6.3 Hz, 1H), 4.30 (q, J = 7.3 Hz, 2H), 2.55-2.76 (m, 4H), 1.79 (s, 6H), 1.64 (s, 6H), 1.55 (t, J = 7.3 Hz, 3H), 2 Hs not observed (NH and OH). |
| 47 | MS m/z 461.6 [M + H]⁺; ¹H NMR (methanol-d₄) δ: 9.03 (s, 1H), 8.11 (d, J = 0.9 Hz, 1H), 8.05 (d, J = 8.5 Hz, 1H), 7.92 (d, J = 0.9 Hz, 1H), 7.29 (dd, J = 8.2, 1.9 Hz, 1H), 7.26 (d, J = 1.9 Hz, 1H), 5.82 (tt, J = 12.3, 4.6 Hz, 1H), 4.19 (t, J = 7.3 Hz, 2H), 2.23-2.45 (m, 4H), 1.95 (sxt, J = 7.3 Hz, 2H), 1.54 (s, 6H), 1.38 (s, 6H), 0.97 (t, J = 7.3 Hz, 3H), 2 Hs not observed (NH and OH). |
| 48 | MS m/z 419.5 [M + H]⁺; ¹H NMR (methanol-d₄) δ: 9.15 (s, 1H), 8.20 (d, J = 8.8 Hz, 1H), 8.04 (s, 1H), 7.45-7.57 (m, 2H), 7.00 (s, 1H), 5.97 (tt, J = 12.1, 4.7 Hz, 1H), 2.59-2.76 (m, 4H), 1.79 (s, 6H), 1.65 (s, 6H), 3 Hs not observed (2 NHs and OH). |
| 50 | MS m/z 433.5 [M + H]⁺; ¹H NMR (methanol-d₄) δ: 9.19 (s, 1H), 8.26 (d, J = 8.8 Hz, 1H), 7.95-8.06 (m, 1H), 7.21-7.37 (m, 2H), 6.72-6.81 (m, 1H), 5.99 (tt, J = 11.3, 5.5 Hz, 1H), 4.11 (s, 3H), 2.59-2.76 (m, 4H), 1.80 (s, 6H), 1.65 (s, 6H); 2 Hs not observed (NH and OH). |
| 51 | MS m/z 433.5 [M + H]⁺; ¹H NMR (methanol-d₄) δ: 9.20 (s, 1H), 8.14 (dd, J = 7.6, 0.9 Hz, 1H), 7.91 (d, J = 2.5 Hz, 1H), 7.54 (d, J = 1.9 Hz, 1H), 7.52 (s, 1H), 6.90 (d, J = 2.5 Hz, 1H), 5.98 (tt, J = 10.7, 5.7 Hz, 1H), 4.09 (s, 3H), 2.59-2.78 (m, 4H), 1.79 (s, 6H), 1.66 (s, 6H), 2 Hs not observed (NH and OH). |
| 65 | MS m/z 430.5 [M + H]⁺; ¹H NMR (methanol-d₄) δ: 9.29 (s, 1H), 9.18 (s, 1H), 9.03 (s, 1H), 8.90 (s, 1H), 8.30 (s, 1H), 8.23 (s, 1H), 7.54 (s, 2H), 5.96 (s, 1H), 2.52-2.68 (m, 4H), 1.78 (s, 6H), 1.64 (s, 6H); 2 Hs not observed (NH and OH). |
| 66 | MS m/z 430.4 [M + H]⁺; ¹H NMR (methanol-d₄) δ: 9.11 (s, 1H), 8.82 (d, J = 6.9 Hz, 2H), 8.38 (d, J = 6.9 Hz, 2H), 8.24 (d, J = 7.9 Hz, 1H), 7.56-7.65 (m, 2H), 5.88-6.02 (m, 1H), 2.53-2.63 (m, 4H), 1.68 (s, 6H), 1.54 (s, 6H); 2 Hs not observed (NH and OH). |
| 69 | MS m/z 436.5 [M + H]⁺; ¹H NMR (methanol-d₄) δ: 9.11 (s, 1H), 8.17 (d, J = 0.6 Hz, 1H), 8.07 (d, J = 8.2 Hz, 1H), 8.03 (d, J = 0.6 Hz, 1H), 7.31 (dd, J = 8.2, 1.9 Hz, 1H), 7.28 (d, J = 1.9 Hz, 1H), 5.97 (tt, J = 11.0, 5.7 Hz, 1H), 2.61-2.74 (m, 4H), 1.79 (s, 6H), 1.64 (s, 6H), 2 Hs not observed (NH and OH). |
| 71 | MS m/z 469.5 [M + H]⁺; ¹H NMR (methanol-d₄) δ: 9.11 (s, 1H), 8.53 (s, 1H), 8.18 (s, 1H), 8.11 (d, J = 8.2 Hz, 1H), 7.55 (t, J = 59.9 Hz, 1H), 7.37 (dd, J = 8.2, 1.6 Hz, 1H), 7.34 (d, J = 1.6 Hz, 1H), 5.97 (tt, J = 10.1, 6.3 Hz, 1H), 2.56-2.73 (m, 4H), 1.78 (s, 6H), 1.64 (s, 6H), 2Hs not observed (NH and OH). |
| 77 | MS m/z 460.5 [M + H]⁺; ¹H NMR (methanol-d₄) δ: 9.22 (s, 1H), 8.40 (d, J = 6.3 Hz, 1H), 8.32 (d, J = 7.9 Hz, 1H), 7.79 (dd, J = 6.3, 1.6 Hz, 1H), 7.75 (d, J = 0.9 Hz, 1H), 7.60-7.65 (m, 2H), 5.97-6.02 (m, 1H), 4.31 (s, 3H), 2.62-2.78 (m, 4H), 1.80 (s, 6H), 1.65 (s, 6H); 2 Hs not observed (NH and OH). |
| 93 | MS m/z 446.4 [M + H]⁺; ¹H NMR (methanol-d₄) δ: 9.17 (s, 1H), 8.24 (d, J = 7.9 Hz, 1H), 7.83 (d, J = 6.3 Hz, 1H), 7.40-7.50 (m, 2H), 7.14 (d, J = 8.8 Hz, 1H), 7.08 (br s, 1H), 5.89-6.05 (m, 1H), 2.58-2.76 (m, 4H), 1.79 (s, 6H), 1.65 (s, 6H); 3 Hs not observed (NH and 2 OHs). |

Example 14

Preparation of Compound 67

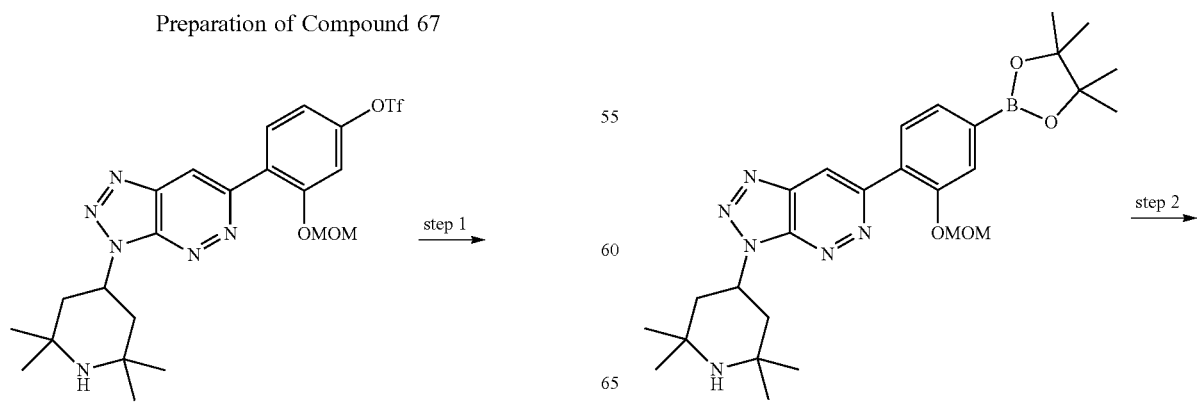

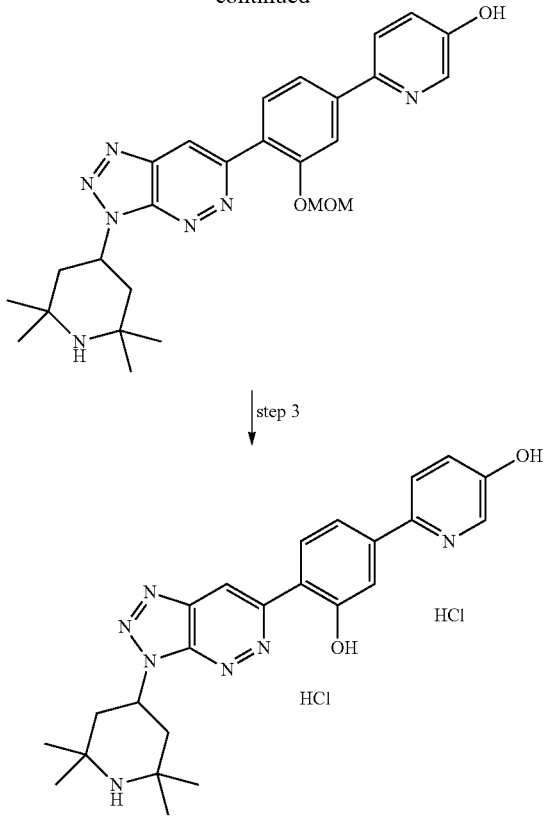

Step 1: An oven-dried flask was equipped with a magnetic stir bar and charged with [3-(methoxymethoxy)-4-[3-(2,2,6,6-tetramethyl-4-piperidyl)triazolo[4,5-c]pyridazin-6-yl]phenyl]trifluoromethanesulfonate (prepared in example 13, step 4, 60 mg, 0.11 mmol), 4,4,5,5-tetramethyl-2-(4,4,5,5-tetramethyl-1,3,2-dioxaborolan-2-yl)-1,3,2-dioxaborolane (35 mg, 0.14 mmol), 1,1'-bis(diphenylphosphino)ferrocene-palladium(II)dichloride dichloromethane complex (5 mg, 0.006 mmol) and potassium acetate (33 mg, 0.33 mmol). The flask was sealed with a rubber septum, and then evacuated and backfilled with argon (repeated a total of 3×). 1,4-Dioxane (1 mL) was added and the reaction was heated at 90° C. for 90 minutes, after which UPLC showed full conversion to the borylated product. The crude product was cooled to room temperature and used directly in the next step.

Step 2: To crude 6-(2-(methoxymethoxy)-4-(4,4,5,5-tetramethyl-1,3,2-dioxaborolan-2-yl)phenyl)-3-(2,2,6,6-tetramethylpiperidin-4-yl)-3H-[1,2,3]triazolo[4,5-c]pyridazine (~0.11 mmol) was added 6-bromopyridin-3-ol (25 mg, 0.14 mmol), 1,1'-bis(diphenylphosphino)ferrocene-palladium(II)dichloride dichloromethane complex (9 mg, 0.011 mmol), and aqueous 2 M $K_2CO_3$ (141 μL, 0.282 mmol). The mixture was purged with argon for 5 min, then heated to 85° C. for 16 h. The reaction was cooled to room temperature, diluted with water, and extracted with EtOAc (3×). The combined organic phases were dried over $Na_2SO_4$, concentrated under reduced pressure, and purified using silica-gel chromatography eluting with a $MeOH/CH_2Cl_2$ gradient (0% to 30% MeOH) to provide 6-[3-(methoxymethoxy)-4-[3-(2,2,6,6-tetramethyl-4-piperidyl)triazolo[4,5-c]pyridazin-6-yl]phenyl]pyridin-3-ol (37.5 mg, 68%) as a light brown solid. MS m/z 490.3 [M+H]$^+$.

Step 3: 6-[3-(methoxymethoxy)-4-[3-(2,2,6,6-tetramethyl-4-piperidyl)triazolo[4,5-c]pyridazin-6-yl]phenyl]pyridin-3-ol (37.5 mg, 0.077 mmol) was dissolved in 1 mL of methanol, then 4 N HCl in 1,4-dioxane (0.5 mL, 2 mmol) was added and the reaction stirred at room temperature for 2 h. The reaction was concentrated, triturated with 20% MeOH/ether, and the resultant precipitate was filtered to afford 6-[3-hydroxy-4-[3-(2,2,6,6-tetramethyl-4-piperidyl)triazolo[4,5-c]pyridazin-6-yl]phenyl]pyridin-3-ol dihydrochloride (31 mg, 78%) as a light brown solid.

MS m/z 446.4 [M+H]$^+$; $^1$H NMR (methanol-d4) δ: 9.23 (s, 1H), 8.36 (d, J=8.2 Hz, 1H), 8.34 (d, J=2.5 Hz, 1H), 8.30 (d, J=8.8 Hz, 1H), 8.12 (dd, J=9.1, 2.8 Hz, 1H), 7.54-7.59 (m, 2H), 5.95-6.04 (m, 1H), 2.62-2.77 (m, 4H), 1.75 (s, 6H), 1.65 (s, 6H); 3 Hs not observed (NH and 2 OHs).

Using the procedure described for Example 14, above, additional compounds described herein were prepared by substituting the appropriate starting materials, suitable reagents and reaction conditions, obtaining compounds such as those selected from:

| Cpd | Data |
|---|---|
| 60 | MS m/z 431.3 [M + H]$^+$; $^1$H NMR (methanol-d$_4$) δ: 9.23 (s, 1H), 9.17 (s, 1H), 8.79 (s, 1H), 8.64 (s, 1H), 8.24 (d, J = 8.2 Hz, 1H), 7.79-8.00 (m, 2H), 5.95-6.02 (m, 1H), 2.55-2.75 (m, 4H), 1.79 (s, 6H), 1.65 (s, 6H); 2 Hs not observed (NH and OH). |
| 61 | MS m/z 430.5 [M + H]$^+$; $^1$H NMR (methanol-d$_4$) δ: 9.25 (s, 1H), 8.91 (d, J = 5.4 Hz, 1H), 8.76 (t, J = 7.6 Hz, 1H), 8.51 (d, J = 7.9 Hz, 1H), 8.42 (d, J = 7.9 Hz, 1H), 8.13 (t, J = 6.5 Hz, 1H), 7.63-7.71 (m, 2H), 6.00 (m, 1H), 2.59-2.79 (m, 4H), 1.80 (s, 6H), 1.66 (s, 6H); 2 Hs not observed (NH and OH). |
| 68 | MS m/z 447.4 [M + H]$^+$; $^1$H NMR (methanol-d$_4$) δ: 9.15 (s, 1H), 8.47 (s, 2H), 8.13-8.19 (m, 1H), 7.98-8.02 (m, 2H), 5.92-6.04 (m, 1H), 2.65-2.74 (m, 4H), 1.79 (s, 6H), 1.64 (s, 6H); 3 Hs not observed (NH and 2 OHs). |
| 73 | MS m/z 444.6 [M + H]$^+$; $^1$H NMR (methanol-d$_4$) δ: 9.23 (s, 1H), 8.75 (d, J = 6.3 Hz, 1H), 8.32-8.37 (m, 2H), 8.26 (dd, J = 6.1, 1.7 Hz, 1H), 7.63-7.71 (m, 2H), 5.98-6.02 (m, 1H), 2.90 (s, 3H), 2.64-2.75 (m, 4H), 1.80 (s, 6H), 1.65 (s, 6H); 2 Hs not observed (NH and OH). |
| 74 | MS m/z 498.3 [M + H]$^+$; $^1$H NMR (methanol-d$_4$) δ: 9.18 (s, 1H), 8.82 (d, J = 5.4 Hz, 1H), 8.27 (d, J = 8.2 Hz, 1H), 8.15 (d, J = 1.9 Hz, 1H), 8.03 (dd, J = 5.0, 1.9 Hz, 1H), 7.55 (dd, J = 8.2, 1.9 Hz, 1H), 7.52 (d, J = 1.9 Hz, 1H), 5.89-6.05 (m, 1H), 2.57-2.79 (m, 4H), 1.79 (s, 6H), 1.64 (s, 6H); 2 Hs not observed (NH and OH). |
| 75 | MS m/z 431.5 [M + H]$^+$; $^1$H NMR (methanol-d$_4$) δ: 9.42 (d, J = 1.3 Hz, 1H), 9.21 (s, 1H), 8.97-9.03 (m, 1H), 8.35 (dd, J = 6.0, 1.3 Hz, 1H), 8.31 (d, J = 8.5 Hz, 1H), 8.04 (s, 1H), 7.99 (dd, J = 8.2, 1.9 Hz, 1H), 5.98-6.02 (m, 1H), 2.63-2.76 (m, 4H), 1.79 (s, 6H), 1.65 (s, 6H); 2 Hs not observed (NH and OH). |
| 76 | MS m/z 431.5 [M + H]$^+$; $^1$H NMR (methanol-d$_4$) δ: 9.96 (dd, J = 2.4, 1.1 Hz, 1H), 9.57 (dd, J = 6.0, 0.9 Hz, 1H), 9.24 (s, 1H), 8.71 (dd, J = 5.8, 2.4 Hz, 1H), 8.38 (d, J = 7.9 |

-continued

| Cpd | Data |
|---|---|
| | Hz, 1H), 7.71-7.78 (m, 2H), 5.98-6.02 (m, 1H), 2.57-2.78 (m, 4H), 1.79 (s, 6H), 1.65 (s, 6H); 2 Hs not observed (NH and OH). |
| 78 | MS m/z 431.4 [M + H]$^+$; $^1$H NMR (DMSO-d$_6$) δ: 9.24 (s, 1H), 9.20 (s, 3H), 8.23 (d, J = 8.2 Hz, 1H), 7.48 (d, J = 8.2 Hz, 1H), 7.46 (s, 1H), 5.68 (tt, J = 12.5, 3.4 Hz, 1H), 2.21 (dd, J = 12.5, 3.4 Hz, 2H), 2.11 (t, J = 12.5 Hz, 2H), 1.36 (s, 6H), 1.19 (s, 6H); 2 Hs not observed (NH and OH). |
| 79 | MS m/z 447.5 [M + H]$^+$; $^1$H NMR (methanol-d$_4$) δ: 9.12 (s, 1H); 8.64 (d, J = 1.3 Hz, 1H), 8.28 (d, J = 8.8 Hz, 1H), 7.94 (d, J = 1.3 Hz, 1H), 7.62 (d, J = 2.2 Hz, 1H), 7.57 (dd, J = 8.5, 2.2 Hz, 1H), 5.74-5.90 (m, 1H), 2.27-2.44 (m, 4H), 1.52 (s, 6H), 1.36 (s, 6H); 3 Hs not observed (2 OH and NH). |
| 84 | MS m/z 473.3 [M + H]$^+$; $^1$H NMR (DMSO-d$_6$) δ: 9.19 (s, 1H), 8.50 (d, J = 2.4 Hz, 1H), 8.14 (d, J = 8.8 Hz, 1H), 7.88 (dd, J = 8.9, 2.6 Hz, 1H), 7.18-7.36 (m, 2H), 6.75(d, J = 8.9 Hz, 1H), 5.67 (tt, J = 12.5, 3.9 Hz, 1H), 3.09 (s, 6H), 2.20 (dd, J = 12.5, 3.9 Hz, 2H), 2.11 (t, J = 12.5 Hz, 2H), 1.28-1.42 (m, 6H), 1.18 (s, 6H); 2 Hs not observed (NH and OH). |
| 85 | MS m/z 470.3 [M + H]$^+$; $^1$H NMR (DMSO-d$_6$) δ: 9.19 (d, J = 1.6 Hz, 1H), 9.17 (s, 1H), 8.72 (dd, J = 4.9, 1.6 Hz, 1H), 8.26 (d, J = 8.8 Hz, 1H), 8.16 (s, 1H), 8.01 (d, J = 4.9 Hz, 1H), 7.41-7.45 (m, 2H), 5.69 (tt, J = 12.2, 3.7 Hz, 1H), 2.22 (dd, J = 12.2, 3.7 Hz, 2H), 2.13 (t, J = 12.2 Hz, 2H), 1.37 (s, 6H), 1.20 (s, 6H); 2 Hs not observed (NH and OH). |
| 86 | MS m/z 486.4 [M + H]$^+$; $^1$H NMR (DMSO-d$_6$) δ: 9.13 (s, 1H), 8.14 (d, J = 7.8 Hz, 1H), 7.65 (d, J = 7.3 Hz, 1H), 7.24-7.42 (m, 2H), 6.67 (d, J = 2.0 Hz,1H), 6.54 (dd, J = 7.3, 2.0 Hz, 1H), 5.64-5.82 (m, 1H), 3.10-3.21 (m, 1H), 2.08-2.33 (m, 4H), 1.42 (s, 6H), 1.26 (s, 6H), 0.98-1.07 (m, 2H), 0.83-0.95 (m, 2H); 2 Hs not observed (NH and OH). |
| 88 | MS m/z 469.4 [M + H]$^+$; $^1$H NMR (DMSO-d$_6$) δ: 11.69 (br s, 2H), 9.18 (s, 1H), 8.45 (d, J = 7.3 Hz, 1H), 8.43 (s, 1H), 8.18 (d, J = 8.3 Hz, 1H), 7.97 (s, 1H), 7.48 (s, 1H), 7.44 (dd, J = 8.2, 1.8 Hz, 1H), 7.41 (d, J = 1.7 Hz, 1H), 7.09 (dd, J = 7.5, 1.8 Hz, 1H), 5.68 (tt, J = 13.0, 3.9 Hz, 1H), 2.21 (dd, J = 12.5, 3.7 Hz, 2H), 2.11 (t, J = 12.5 Hz, 2H), 1.36 (s, 6H), 1.19 (s, 6H). |
| 89 | MS m/z 435.5 [M + H]$^+$; $^1$H NMR (methanol-d$_4$) δ: 8.94-9.13 (m, 1H), 8.07 (d, J = 8.2 Hz, 1H), 7.75 (t, J = 2.2 Hz, 1H), 7.51 (d, J = 1.9 Hz, 2H), 7.38 (dd, J = 8.2, 1.6 Hz, 1H), 7.34 (d, J = 1.9 Hz, 1H), 5.76-5.96 (m, 1H), 2.42-2.58 (m, 4H), 1.63 (s, 6H), 1.48 (s, 6H); 2 Hs not observed (OH and NH). |
| 90 | MS m/z 469.4 [M + H]$^+$; $^1$H NMR (DMSO-d$_6$) δ: 11.64 (br s, 1H), 9.18 (s, 1H), 8.67 (d, J = 7.5 Hz, 1H), 8.12-8.24 (m, 2H), 8.01 (s, 1H), 7.93 (s, 1H), 7.66 (s, 1H), 7.51 (dd, J = 8.3, 1.9 Hz, 1H), 7.47 (d, J = 1.9 Hz, 1H), 7.33 (dd, J = 7.1, 1.9 Hz, 1H), 5.75 (tt, J = 12.5, 4.0 Hz, 1H), 2.17-2.36 (m, 4H), 1.44 (s, 6H), 1.28 (s, 6H). |
| 91 | MS m/z 419.3 [M + H]$^+$; $^1$H NMR (DMSO-d$_6$) δ: 12.64 (br s, 1H), 9.16 (s, 1H), 8.15 (d, J = 8.3 Hz, 1H), 7.67 (d, J = 1.9 Hz, 1H), 7.59 (dd, J = 8.3, 1.9 Hz, 1H), 7.30 (br s, 1H), 7.08 (br s, 1H), 5.67 (tt, J = 12.2, 3.7 Hz, 1H), 2.20 (dd, J = 12.2, 3.7 Hz, 2H), 2.10 (t, J = 12.2 Hz, 2H), 1.35 (s, 6H), 1.18 (s, 6H); 2 Hs not observed (NH and OH). |
| 95 | MS m/z 419.5 [M + H]$^+$; $^1$H NMR (methanol-d$_4$) δ: 9.10 (s, 1H), 8.08 (d, J = 8.2 Hz, 1H), 8.01-8.03 (m, 1H), 7.61-7.63 (m, 1H), 7.30 (dd, J = 7.9, 1.9 Hz, 1H), 7.26 (d, J = 1.9 Hz, 1H), 6.86-6.89 (m, 1H), 5.92-6.03 (m, 1H), 2.65-2.70 (m, 4H), 1.78 (s, 6H), 1.63 (s, 6H); 2 Hs not observed (OH and NH). |
| 96 | MS m/z 436.4 [M + H]$^+$; $^1$H NMR (methanol-d$_4$) δ: 9.16 (s, 1H), 8.16-8.29 (m, 1H), 7.96-8.07, (m, 1H), 7.80 (s, 1H), 7.68 (s, 2H), 5.84-6.06 (m, 1H), 2.67 (d, J = 4.4 Hz, 4H), 1.77 (s, 6H), 1.62 (s, 6H); 2 Hs not observed (OH and NH). |
| 99 | MS m/z 445.1 [M + H]$^+$; $^1$H NMR (DMSO-d$_6$) δ: 11.50 (br s, 2H), 9.12 (s, 1H), 8.15 (d, J = 8.5 Hz, 1H), 8.00 (d, J = 4.6 Hz, 1H), 7.19-7.40 (m, 2H), 6.81 (d,J = 4.6 Hz, 1H), 6.75 (s, 1H), 6.05 (s, 2H), 5.60-5.77 (m, 1H), 2.20 (d, J = 12.2 Hz, 2H), 2.11 (t, J = 12.5 Hz, 2H), 1.36 (s, 6H), 1.19 (s, 6H). |
| 100 | MS m/z 473.1 [M + H]$^+$; $^1$H NMR (DMSO-d$_6$) δ: 9.17 (s, 1H), 8.08-8.22 (m, 2H), 7.39 (s, 1H), 7.37 (d, J = 1.6 Hz, 1H), 6.87 (dd, J = 5.1, 1.6 Hz, 1H), 6.85 (s, 1H), 5.67 (tt, J = 12.2, 3.7 Hz, 1H), 3.10 (s, 6H), 2.20 (dd, J = 12.2, 3.7 Hz, 2H), 2.11 (t, J = 12.2 Hz, 2H), 1.35 (s, 6H), 1.18 (s, 6H); 2Hs not observed (NH and OH). |
| 101 | MS m/z 448.1 [M + H]$^+$; $^1$H NMR (DMSO-d$_6$) δ: 9.13 (s, 1H), 8.71 (d, J = 2.4 Hz, 1H), 8.55 (d, J = 5.1 Hz, 1H), 8.19 (d, J = 8.3 Hz, 1H), 7.71 (dd, J = 7.1, 5.1 Hz, 1H), 7.38 (s, 1H), 7.35 (d, J = 8.3 Hz, 1H), 5.69 (tt, J = 12.2, 4.2 Hz, 1H), 2.21 (dd, J = 12.2, 4.2 Hz, 2H), 2.12 (t, J = 12.2 Hz, 2H), 1.36 (s, 6H), 1.19 (s, 6H); 2Hs not observed (NH and OH). |
| 103 | MS m/z 496.7[M + H]$^+$; $^1$H NMR (DMSO-d$_6$) δ: 9.14 (s, 1H), 8.62 (d, J = 2.4 Hz, 1H), 8.35 (s, 1H), 8.17 (d, J = 8.0 Hz, 1H), 8.10 (d, J = 8.8 Hz, 1H), 7.79-7.84 (m, 2H), 7.71 (d, J = 6.4 Hz, 1H), 7.21-7.58 (m, 1H), 5.69-5.72 (m, 1H), 2.13-2.27 (m, 4H), 1.40 (s, 6H), 1.23 (s, 6H); 1 H is not observed (NH or OH). |
| 104 | MS m/z 459.8[M + H]$^+$; $^1$H NMR (DMSO-d$_6$) δ: 9.13 (s, 1H), 8.15 (d, J = 8.4 Hz, 1H), 8.08 (d, J = 5.2 Hz, 1H), 7.30-7.34 (m, 2H), 6.81 (dd, J = 5.2, 1.2 Hz, 1H), 6.72 (s, 1H), 6.58-6.62 (m, 1H), 5.63-5.72 (m, 1H), 2.83 (d, J = 4.8 Hz, 3H), 2.17-2.22 (m, 2H), 2.06-2.14 (m, 2H), 1.35 (s, 6H), 1.18 (s, 6H). |
| 106 | MS m/z 437.5 [M + H]$^+$; $^1$H NMR (methanol-d$_4$) δ: 9.10 (s, 1H), 8.09 (d, J = 9.2 Hz, 1H), 8.03 (d, J = 1.7 Hz, 1H), 7.32 (d, J = 7.2 Hz, 2H), 5.93-6.01 (m, 1H), 2.65-2.70 (m, 4H), 1.78 (s, 6H), 1.64 (s, 6H); 3Hs not observed (1 OH and 2 NHs). |
| 107 | MS m/z 436.5 [M + H]$^+$; $^1$H NMR (methanol-d$_4$) δ: 9.58 (s, 1H), 9.17 (s, 1H), 8.57 (s, 1H), 8.21 (d, J = 9.9 Hz, 1H), 7.44 (dd, J = 10.2, 3.2 Hz, 2H), 5.90-6.04 (m, 1H), 2.61-2.75 (m, 4H), 1.79 (s, 6H), 1.64 (s, 6H); 2Hs not observed (1 OH and 1 NH). |

| Cpd | Data |
|---|---|
| 108 | MS m/z 433.6 [M + H]$^+$; $^1$H NMR (DMSO-d$_6$) δ: 9.41-9.58 (m, 1H), 9.14 (s, 1H), 8.23-8.37 (m, 1H), 8.8 (d, J = 6.6 Hz, 1H), 7.86-7.91 (m, 1H), 7.14-7.19 (m, 2H), 5.83-5.95 (m, 1H), 2.56-2.65 (m, 2H), 2.46-2.56 (m, 2H), 2.44 (s, 3H), 1.66 (s, 6H),1.54 (s, 6H); 1H not observed (NH or OH). |
| 109 | MS m/z 444.5 [M + H]$^+$; $^1$H NMR (DMSO-d$_6$) δ: 9.17 (s, 1H), 8.55 (s, 1H), 8.18 (d, J = 10.5 Hz, 1H), 7.42 (d, J = 1.8 Hz, 1H), 7.34-7.38 (m, 1H), 5.65-5.83 (m, 1H), 2.11-2.34 (m, 4H), 1.41 (s, 6H), 1.24 (s, 6H); 3Hs not observed (2 NHs and OH). |
| 110 | MS m/z 461.5 [M + H]$^+$; $^1$H NMR (methanol-d$_4$) δ: 9.16 (s, 1H), 8.57 (s, 1H), 8.23 (d, J = 9.2 Hz, 1H), 7.68-7.74 (m, 2H), 5.95-6.02 (m, 1H), 2.65-2.71 (m, 4H), 1.79 (s, 6H), 1.64 (s, 6H); 2Hs not observed (OH and NH). |
| 111 | MS m/z 420.2 [M + H]$^+$; $^1$H NMR (DMSO-d$_6$) δ: 9.10 (s, 1H), 8.30-8.39 (m, 2H), 8.28 (s, 1H), 8.17 (d, J = 8.0 Hz, 1H), 7.71(d, J = 1.2 Hz, 1H), 7.63 (dd, J = 8.4, 1.6 Hz, 1H), 7.44 (d, J = 0.8 Hz, 1H), 5.68-5.71 (m, 1H), 2.11-2.25 (m, 4H), 1.38 (s, 6H), 1.21 (s, 6H). |
| 112 | MS m/z 420.1 [M + H]$^+$; $^1$H NMR (DMSO-d$_6$) δ: 9.13 (s, 1H), 8.42 (s, 1H), 8.15 (d, J = 8.4 Hz, 1H), 7.60 (d, J = 1.6 Hz, 1H), 7.53 (dd, J = 8.4, 1.6 Hz,1H), 5.66-5.69 (m, 1H), 2.06-2.23 (m, 4H), 1.36 (s, 6H), 1.19 (s, 6H); 3 Hs not observed (2NHs and OH). |
| 113 | MS m/z 461.2 [M + H]$^+$; $^1$H NMR (DMSO-d$_6$) δ: 9.14 (s, 1H), 8.89 (d, J = 1.2 Hz, 1H), 8.17 (d, J = 8.4 Hz, 1H), 7.91 (d, J = 1.6 Hz, 1H), 7.80 (dd, J = 8.0, 1.6 Hz, 1H), 7.51 (d, J = 0.8 Hz, 1H), 5.64-5.71 (m, 1H), 3.99 (s, 3H), 2.07-2.22 (m, 4H), 1.35 (s, 6H), 1.18 (s, 6H); 2 Hs not observed (NH and OH). |
| 114 | MS m/z 496.4 [M + H]$^+$; $^1$H NMR (methanol-d$_4$) δ: 9.15 (s, 1H), 8.32 (d, J = 5.5 Hz, 1H), 8.22 (d, J = 8.2 Hz, 1H), 7.63-7.78 (m, 1H), 7.57 (dd, J = 5.5, 1.5 Hz, 1H), 7.43-7.50 (m, 2H), 7.32 (d, J = 0.9 Hz, 1H), 5.99 (tt, J = 10.9, 5.4 Hz, 1H), 2.63- 2.75 (m, 4H), 1.79 (s, 6H), 1.64 (s, 6H); 2 Hs not observed (NH and OH). |
| 115 | MS m/z 419.1 [M + H]$^+$; $^1$H NMR (DMSO-d$_6$) δ: 12.27 (s, 1H), 11.59 (m, 1H), 9.13 (d, J = 8.0 Hz, 1H), 8.07 (d, J = 8.0 Hz, 1H), 7.10-7.76 (m, 2H), 7.40-7.53 (m, 2H), 5.61-5.70 (m, 1H), 2.06-2.22 (m, 4H), 1.35 (s, 6H), 1.18 (s, 6H); 1 H not observed (NH or OH). |
| 116 | MS m/z 437.4 [M + H]$^+$; $^1$H NMR (methanol-d$_4$) δ: 9.53 (s, 1H), 9.15 (s, 1H), 8.24 (d, J = 8.2 Hz, 1H), 7.74 (d, J = 1.8 Hz, 1H), 7.70 (dd, J = 7.9, 1.8 Hz, 1H), 5.87-6.00 (m, 1H), 2.57 (d, J = 7.6 Hz, 4H), 1.70 (s, 6H), 1.55(s, 6H); 2 Hs not observed (OH and NH). |
| 118 | MS m/z 469.5 [M + H]$^+$; $^1$H NMR (methanol-d$_4$) δ: 9.22 (s, 1H), 8.52 (d, J = 6.1 Hz, 1H), 8.33-8.38 (m, 1H), 7.83 (d, J = 3.4 Hz, 1H), 7.79 (d, J = 6.1 Hz, 1H), 7.58-7.64 (m, 2H), 7.13 (d, J = 3.4 Hz, 1H), 5.96-6.05 (m, 1H), 2.64-2.76 (m, 4H), 1.80 (s, 6H), 1.65 (s, 6H); 3 Hs not observed (2NHs and OH). |
| 119 | MS m/z 461.5 [M + H]$^+$; $^1$H NMR (methanol-d$_4$) δ: 9.24 (s, 1H), 8.70 (d, J = 6.4 Hz, 1H), 8.34 (d, J = 8.2 Hz, 1H), 8.10 (d, J = 1.5 Hz, 1H), 8.04 (dd, J = 8.2, 1.5 Hz, 1H), 7.20 (d, J = 6.7 Hz, 1H), 6.00 (tt, J = 11.0, 5.5 Hz, 1H), 4.33 (s, 3H), 2.61-2.77 (m, 4H), 1.79 (s, 6H), 1.65 (s, 6H),;2 Hs not observed (NH and OH). |
| 120 | MS m/z 420.5 [M + H]$^+$; $^1$H NMR (methanol-d$_4$) δ: 9.19-9.22 (m, 1H), 9.12-9.15 (m, 1H), 8.91-8.95 (m, 1H), 8.14 (d, J = 9.2 Hz, 1H), 7.35 (dd, J = 14.2, 8.4 Hz, 2H), 5.94-6.02 (m, 1H), 2.64-2.71 (m, 4H), 1.78 (s, 6H), 1.63 (s, 6H); 2Hs not observed (NH and OH). |
| 121 | MS m/z 451.5 [M + H]$^+$; $^1$H NMR (methanol-d$_4$) δ: 9.09 (s, 1H), 8.09 (d, J = 8.2 Hz, 1H), 7.77-7.89 (m, 1H), 7.27 (s, 2H), 5.91-6.02 (m, 1H), 3.84 (s, 3H), 2.59-2.70 (m, 4H), 1.78 (s, 6H), 1.63 (s, 6H); 2Hs not observed (NH and OH). |
| 122 | MS m/z 465.6 [M + H]$^+$; $^1$H NMR (methanol-d$_4$) δ: 9.04 (s, 1H), 8.10-8,08 (d, J = 9.6 Hz, 1H), 7.87 (d, J = 3.2 Hz, 1H), 7.24-7.31 (m, 2H), 5.74-5.88 (m, 1H), 4.20 (q, J = 7.2 Hz, 2H), 2.24-2.41 (m, 4H), 1.51 (s, 6H), 1.50 (t, J = 7.5 Hz, 3H), 1.40 (s, 6H); 2Hs not observed (NH and OH). |
| 123 | MS m/z 474.5 [M + H]$^+$; $^1$H NMR (methanol-d$_4$) δ: 9.21 (s, 1H), 8.38 (d, J = 6.1 Hz, 1H), 8.31 (d, J = 8.2 Hz, 1H), 7.77 (d, J = 6.4 Hz, 1H), 7.72 (s, 1H), 7.58-7.64 (m, 2H), 5.99 (tt, J = 10.7, 5.6 Hz, 1H), 4.65 (q, J = 6.9 Hz, 2H), 2.63-2.75 (m, 4H), 1.79 (s, 6H), 1.64 (s, 6H), 1.59 (t, J = 7.0 Hz, 3H); 2 Hs not observed (NH and OH). |
| 124 | MS m/z 475.5 [M + H]$^+$; $^1$H NMR (methanol-d$_4$) δ: 9.23 (s, 1H), 9.16 (s, 1H), 8.36 (d, J = 8.2 Hz, 1H), 7.63-7.74 (m, 3H), 5.98-6.02 (m, 1H), 4.71-4.79 (q, J = 7.2 Hz, 2H), 2.59-2.79 (m, 4H), 1.79 (s, 6H), 1.65 (s, 6H), 1.54 (t, J = 7.2 Hz, 3H); 2 Hs not observed (NH and OH). |
| 125 | MS m/z 470.5 [M + H]$^+$; $^1$H NMR (methanol-d$_4$) δ: 9.17 (s, 1H), 9.01 (d, J = 7.3 Hz, 1H), 8.27 (d, J = 4.9 Hz, 2H), 8.23 (d, J = 8.2 Hz, 1H), 7.61 (dd, J = 7.3, 1.8 Hz, 1H), 7.52 (dd, J = 8.2, 1.8 Hz, 1H), 7.50 (d, J = 1.8 Hz, 1H), 5.98 (ddd, J = 16.3, 10.2, 6.4 Hz, 1H), 2.60-2.76 (m, 4H), 1.80 (s, 6H), 1.65 (s, 6H); 2 Hs not observed (NH and OH). |
| 126 | MS m/z 470.5 [M + H]$^+$; $^1$H NMR (methanol-d$_4$) δ: 9.21 (s, 1H), 9.14 (d, J = 7.0 Hz, 1H), 9.04 (s, 1H), 8.27-8.35 (m, 2H), 7.97 (dd, J = 7.0, 1.5 Hz, 1H), 7.59-7.64 (m, 2H), 6.00 (tt, J = 10.9, 5.5 Hz, 1H), 2.64 -2.75 (m, 4H), 1.79 (s, 6H), 1.65 (s, 6H), 2 Hs not observed (NH and OH). |
| 127 | MS m/z 467.5 [M + H]$^+$; $^1$H NMR (methanol-d$_4$) δ: 9.12 (s, 1H), 8.08-8.10 (m, 1H), 8.07-8.11 (m, 1H), 8.01 (s, 1H), 7.28-7.44 (m, 2H), 5.89-6.05 (m, 1H), 3.90-3.96 (m, 3H), 2.63-2.71 (m, 4H), 1.76-1.80 (s,6H), 1.59-1.66 (s, 6H); 1H not observed (NH or OH). |
| 128 | MS m/z 447.5 [M + H]$^+$; $^1$H NMR (methanol-d$_4$) δ: 9.17 (s, 1H), 8.54 (s, 1H), 8.22 (d, J = 8.2 Hz, 1H), 7.71 (d, J = 1.8 Hz, 1H), 7.67 (dd, J = 8.2, 1.8 Hz, 1H), 7.01 (s, 1H), 5.99 (tt, J = 10.9, 5.5 Hz, 1H), 2.61-2.77 (m, 4H), 1.79 (s, 6H), 1.64 (s, 6H), 3 Hs not observed (2NHs and OH). |

-continued

| Cpd | Data |
|---|---|
| 129 | MS m/z 453.5 [M + H]⁺; ¹H NMR (methanol-d₄) δ: 9.08 (s, 1H), 8.01-8.11 (m, 2H), 7.30-7.41 (m, 2H), 5.86-5.99 (m, 1H), 2.56-2.63 (m, 4H), 1.71 (s, 6H), 1.56 (s, 6H); 3Hs not observed (2 NHs and OH). |
| 130 | MS m/z 451.5 [M + H]⁺; ¹H NMR (methanol-d₄) δ: 9.00-9.11 (m, 1H), 8.07-8.07 (m, 1H), 8.07-8.08 (m, 1H), 8.04-8.10 s, 1H), 7.97 (d, J = 2.0 Hz, 1H), 7.93-7.99 (s, 1H), 7.22-7.29 (m, 2H), 5.67-5.94 (m, 1H), 3.85 (s, 3H), 2.28-2.42 (m, 4H), 1.53 (s, 6H), 1.37 (s, 6H); 1 H not observed (NH or OH). |
| 131 | MS m/z 449.5 [M + H]⁺; ¹H NMR (methanol-d₄) δ: 9.06 (s, 1H), 8.02 (d, J = 8.5 Hz, 1H), 7.95 (s, 1H), 7.44-7.46 (m, 1H), 7.39 (d, J = 9.8 Hz, 1H), 5.90-6.01 (m, 1H), 4.05 (s, 3H), 2.62-2.74 (m, 4H), 1.78 (s, 6H), 1.63 (s, 6H); 3Hs not observed (2 NHs and OH). |
| 132 | MS m/z 458.5 [M + H]⁺; ¹H NMR (methanol-d₄) δ: 9.06-9.15 (m, 1H), 8.11-8.23 (m, 1H), 7.98-8.07 (m, 1H), 7.41-7.49 (m, 2H), 5.78-5.93 (m, 1H), 4.09-4.18 (m, 3H), 2.39-2.53 (m, 4H), 1.56 (s, 6H), 1.44 (s, 6H); 2Hs not observed (NH and OH). |
| 133 | MS m/z 450.5 [M + H]⁺; ¹H NMR (methanol-d₄) δ: 9.20 (s, 1H), 8.28 (d, J = 9.2 Hz, 1H), 7.68 (m, 2H), 7.55 (s, 1H), 5.94-6.05 (m, 1H), 2.61-2.73 (m, 4H), 2.61 (s, 3H), 1.79 (s, 6H), 1.63 (s, 6H); 2Hs not observed (NH and OH). |
| 134 | MS m/z 437.5 [M + H]⁺; ¹H NMR (methanol-d₄) δ: 9.16 (s, 1H), 8.83 (s, 1H), 8.25 (d, J = 7.9 Hz, 1H), 7.77 (s, 2H), 5.87-5.97 (m, 1H), 2.49-2.58 (m, 4H), 1.66 (s, 6H), 1.51 (s, 6H); 2Hs not observed (NH and OH). |
| 135 | MS m/z 488.5 [M + H]⁺; ¹H NMR (methanol-d₄) δ: 9.15 (s, 1H), 8.21 (d, J = 8.2 Hz, 1H), 7.95 (s, 1H), 7.57 (d, J = 12.2 Hz, 1H), 7.46 (d, J = 8.2 Hz, 1H), 7.43 (s,1H), 5.95-6.02 (m, 1H), 2.63-2.76 (m, 4H), 1.79 (s, 6H), 1.64 (s, 6H), 3 Hs not observed (2NHs and OH). |
| 137 | MS m/z 497.4, 499.4 [M + H]⁺; ¹H NMR (methanol-d₄) δ: 9.11 (s, 1H), 8.10 (d, J = 8.2 Hz, 1H), 8.00 (s, 1H), 7.40 (d, J = 1.4 Hz, 1H), 7.35 (dd, J = 8.3, 1.6 Hz, 1H), 5.92-6.01 (m, 1H), 2.64-2.70 (m, 4H), 1.78 (s, 6H), 1.63 (s, 6H); 3Hs not observed (2NHs and OH). |
| 138 | MS m/z 434.5 [M + H]⁺; ¹H NMR (methanol-d₄) δ: 9.17 (s, 1H), 8.48 (s, 1H), 8.15 (d, J = 7.8 Hz, 1H), 7.52-7.57 (m, 2H), 5.92-6.03 (m, 1H), 4.22-4.26 (m, 3H), 2.66-2.71 (m, 4H), 1.79 (s, 6H), 1.64 (s, 6H); 2Hs not observed (NH and OH). |
| 139 | MS m/z 487.4 [M + H]⁺; ¹H NMR (methanol-d₄) δ: 9.09 (s, 1H), 8.10 (d, J = 7.6 Hz, 1H), 8.05 (s, 1H), 7.19 (s, 2H), 5.93 (s, 1H), 2.40-2.53 (m, 4H), 1.57-1.66 (m, 6H), 1.42-1.50 (m, 6H); 3Hs not observed (NH and OH). |
| 142 | MS m/z 470.3 [M + H]⁺; ¹H NMR (methanol-d₄) δ: 9.12-9.15 (m, 3H), 8.21 (d, J = 8.1 Hz, 1H), 8.14 (s, 1H), 7.87 (d, J = 0.9 Hz, 1H), 7.79 (d, J = 1.7 Hz, 1H), 7.74 (dd, J = 8.2, 1.8 Hz, 1H), 5.83-5.95 (m, 1H), 2.23-2.69 (m, 4H), 1.63 (s, 6H), 1.49 (s, 6H); 2Hs not observed (NH and OH). |
| 145 | MS m/z 471.3 [M + H]⁺; ¹H NMR (DMSO-d₆) δ: 11.65 (br s, 1H), 9.23 (br s, 1H), 9.09 (br s, 1H), 8.71 (br s, 1H), 8.23 (d, J = 7.9 Hz, 1H), 7.45-7.64 (m, 2H), 7.37 (br s, 1H), 5.92 (br s, 1H), 2.56-2.72 (m, 4H), 1.67 (s, 6H), 1.55 (s, 6H); 1H not observed (NH or OH). |
| 146 | MS m/z 471.3 [M + H]⁺; ¹H NMR (methanol-d₄) δ: 9.89 (s, 1H), 9.23 (s, 1H), 8.59 (d, J = 0.9 Hz, 1H), 8.36 (d, J = 7.9 Hz, 1H), 7.72 (d, J = 1.8 Hz, 1H), 7.69 (dd, J = 8.2, 2.1 Hz, 1H), 6.00 (tt, J = 10.8, 5.6 Hz, 1H), 2.62-2.76 (m, 4H), 1.80 (s, 6H), 1.65 (s, 6H); 3 Hs not observed (2NHs and OH). |
| 147 | MS m/z 471.5 [M + H]⁺; ¹H NMR (methanol-d₄) δ: 9.18 (s, 1H), 8.48 (d, J = 8.9 Hz, 1H), 8.23 (d, J = 8.2 Hz, 1H), 8.14 (d, J = 8.5 Hz, 1H), 7.92 (d, J = 1.8 Hz, 1H), 7.88 (dd, J = 8.2, 1.8 Hz, 1H), 5.99 (tt, J = 10.8, 5.5 Hz, 1H), 2.61-2.76 (m, 4H), 1.80 (s, 6H), 1.65 (s, 6H); 3 Hs not observed (2NHs and OH). |
| 150 | MS m/z 450.4 [M + H]⁺; ¹H NMR (DMSO-d₆) δ: 11.51 (br s, 2H), 9.27 (d, J = 12.8 Hz, 1H), 9.15 (s, 1H), 8.23 (d, J = 13.4 Hz, 1H), 8.12 (s, 1H), 8.12 (d, J = 8.2 Hz, 1H), 7.35 (dd, J = 7.9, 1.8 Hz, 1H), 7.28 (d, J = 1.5 Hz, 1H), 5.92 (tt, J = 12.3, 3.9 Hz, 1H), 2.72 (s, 3H), 2.52-2.66 (m, 4H), 1.66 (s, 6H), 1.54 (s, 6H). |
| 151 | MS m/z 434.3 [M + H]⁺; ¹H NMR (methanol-d₄) δ: 9.09-9.13 (m, 1H), 8.14 (d, J = 8.7 Hz, 1H), 8.08 (s, 1H), 7.49-7.60 (m, 2H), 5.91-6.05 (m, 1H), 4.26 (s, 3H), 2.65-2.70 (m, 4H), 1.78 (s, 6H), 1.64 (s, 6H); 2Hs not observed (NH and OH). |
| 152 | MS m/z 471.3 [M + H]⁺; ¹H NMR (methanol-d₄) δ: 9.56 (s, 1H), 9.17 (s, 1H), 8.37 (d, J = 9.3 Hz, 1H), 8.29 (d, J = 8.5 Hz, 1H), 8.03 (d, J = 9.7 Hz, 1H), 7.77-7.86 (m, 2H), 5.83-5.91 (m, 1H), 2.42 (d, J = 2.9 Hz, 4H), 1.57 (s, 6H), 1.42 (s, 6H); 2Hs not observed (NH and OH). |
| 153 | MS m/z 451.3 [M + H]⁺; ¹H NMR (methanol-d₄) δ: 9.14 (s, 1H), 8.24 (d, J = 7.3 Hz, 1H), 7.71 (d, J = 1.5 Hz, 2H), 5.82-5.90 (m, 1H), 2.73 (s, 3H), 2.35-2.44 (m, 4H), 1.55 (s, 6H), 1.39 (s, 6H); 2Hs not observed (NH and OH). |
| 154 | MS m/z 468.4 [M + H]⁺; ¹H NMR (1:1 CDCl₃: methanol-d₄) δ: 8.88 (s, 1H), 7.95 (d, J = 7.9 Hz, 1H), 7.19 (d, J = 1.8 Hz, 1H), 7.16 (dd, J = 8.2, 1.8 Hz, 1H), 5.66-5.77 (m, 1H), 2.60 (s, 3H), 2.26-2.34 (m, 4H), 1.47 (s, 6H), 1.32 (s, 6H); 2 Hs not observed (NH and OH). |
| 158 | MS m/z 434.5 [M + H]⁺; ¹H NMR (methanol-d₄) δ: 8.89 (s, 1H), 7.99 (d, J = 8.2 Hz, 1H), 7.26-7.34 (m, 3H), 5.76 (tt, J = 12.5, 4.0 Hz, 1H), 2.56 (s, 3H), 2.47 (t, J = 12.5 Hz, 2H), 2.39 (dd, J = 13.1, 4.0 Hz, 2H), 1.60 (s, 6H), 1.47 (s, 6H); 2 Hs not observed (NH and OH). |
| 159 | MS m/z 462.6 [M + H]⁺; ¹H NMR (methanol-d₄) δ: 9.16 (s, 1H), 9.00 (s, 1H), 7.92-8.46 (m, 3H), 5.89-6.08 (m, 1H), 4.20 (s, 3H), 2.54-2.79 (m, 4H), 1.79 (s, 6H), 1.65 (s, 6H); 2 Hs not observed (NH and OH). |

-continued

| Cpd | Data |
|---|---|
| 160 | MS m/z 470.2 [M + H]+; 1H NMR (methanol-d4) δ: 9.18 (s, 1H), 8.23-8.28 (m, 2H), 8.14 (d, J = 9.5 Hz, 1H), 7.86 (d, J = 9.8 Hz, 1H), 7.79 (d, J = 8.2 Hz, 3H), 5.94-6.03 (m, 1H), 2.63-2.71 (m, 4H), 1.79 (s, 6H); 1.63 (s, 6H), 2Hs not observed (NH and OH). |
| 162 | MS m/z 470.4 [M + H]+; 1H NMR (methanol-d4) δ: 9.25-9.29 (m, 1H), 9.12 (s, 1H), 8.98 (s, 1H), 8.24 (d, J = 8.9 Hz, 1H), 7.94 (s, 1H), 7.80 (s, 1H), 7.42-7.47 (m, 2H), 5.80-5.85 (m, 1H), 2.34-2.42 (m, 4H), 1.55 (s, 6H), 1.39 (s, 6H); 2Hs not observed (NH and OH). |

Example 15

Preparation of Compound 70

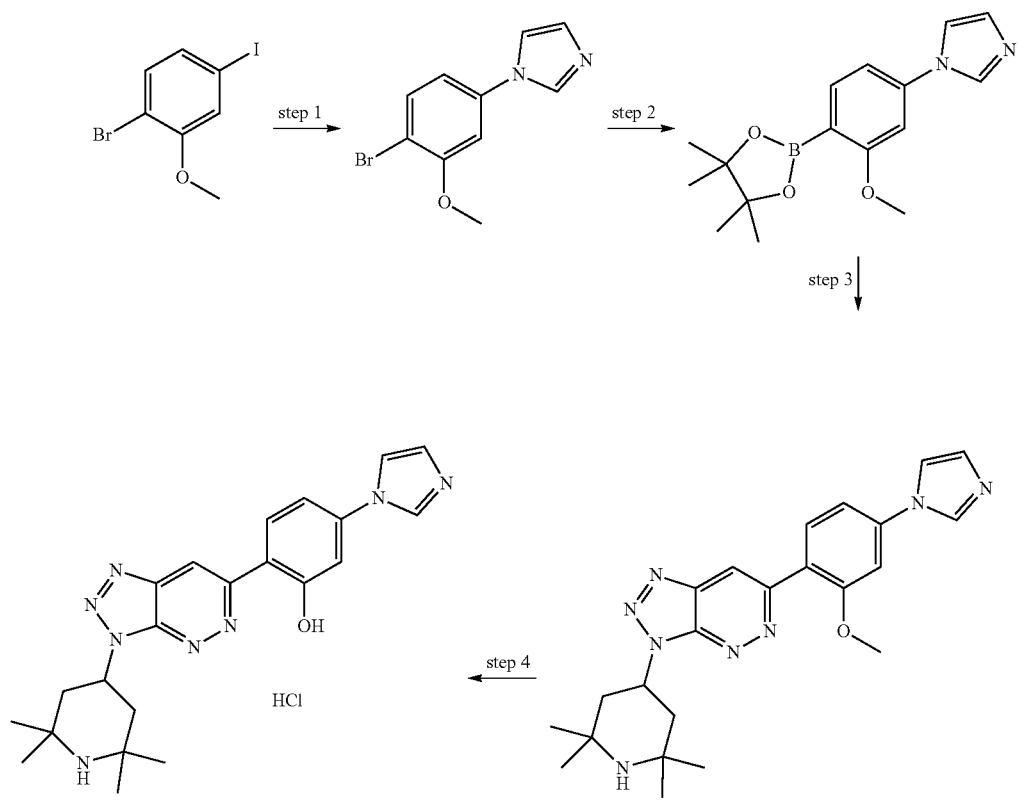

Step 1: A mixture imidazole (0.1 g, 1.47 mmol), 1-bromo-4-iodo-2-methoxybenzene (0.5 g, 1.6 mmol), 2-(2-pyridyl)benzimidazole (58.0 mg, 0.3 mmol), cesium carbonate (1.2 g, 3.66 mmol), copper (I) iodide (56 mg 0.29 mmol) in DMF (2 mL) was heated at 100° C. for 48 h. The reaction mixture was cooled to room temperature, filtered through Celite, washed with EtOAc, and concentrated. The crude material was purified by silica gel chromatography eluting with a EtOAc/hexane gradient (0-80% EtOAc) to provide 1-(4-bromo-3-methoxyphenyl)-1H-imidazole (0.25 g, 62%).

MS m/z 253.3, 255.3 [M+H]+; 1H NMR (methanol-d4) δ: 8.19 (s, 1H), 7.66 (d, J=8.5 Hz, 1H), 7.62 (t, J=1.4 Hz, 1H), 7.25 (d, J=2.2 Hz, 1H), 7.14-7.17 (m, 1H), 7.08 (dd, J=8.5, 2.2 Hz, 1H), 3.97 (s, 3H).

Step 2: An oven-dried flask was equipped with a magnetic stir bar and charged with 1-(4-bromo-3-methoxyphenyl)-1H-imidazole (127.0 mg, 0.5 mmol), 4,4,5,5-tetramethyl-2-(4,4,5,5-tetramethyl-1,3,2-dioxaborolan-2-yl)-1,3,2-dioxaborolane (254.0 mg, 1.0 mmol), 1,1'-bis(diphenylphosphino)ferrocene-palladium(II)dichloride dichloromethane complex (38.0 mg, 0.05 mmol) and potassium acetate (200.0 mg, 2.0 mmol). The flask was sealed with a rubber septum, and then evacuated and backfilled with argon (repeated a total of 3x). Dioxane (1 mL) was added and the reaction was heated at 90° C. for 90 min, after which UPLC showed full conversion to the borylated product. The crude mixture was cooled to room temperature and used directly in the next step.

Step 3: To the crude mixture from the above reaction was added 1,1'-bis(diphenylphosphino)ferrocene-palladium(II) dichloride dichloromethane complex (38.0 mg, 0.05 mmol) and 6-chloro-3-(2,2,6,6-tetramethyl-4-piperidyl)triazolo[4,5-c]pyridazine (prepared in example 13, step 2, 100.0 mg, 0.34 mmol). The tube was sealed with a rubber septum, and then evacuated and backfilled with argon (repeated a total of 3x). Aqueous 2.0 M K2CO3 (0.75 mL, 1.5 mmol) was added and the reaction was heated to 90° C. for 16 h. The reaction was cooled to room temperature, diluted with water, and extracted with EtOAc (3×). The combined organic phases were dried over Na$_2$SO$_4$, concentrated under reduced pressure, and purified by column chromatography, eluting with a MeOH/CH$_2$Cl$_2$ gradient (0% to 30% MeOH) to provide 6-(4-(1H-imidazol-1-yl)-2-methoxyphenyl)-3-(2,2,6,6-tetramethylpiperidin-4-yl)-3H-[1,2,3]triazolo[4,5-c]pyridazine (85 mg, 39%). MS m/z 433.3 [M+H]$^+$.

Step 4: To a solution of 6-(4-(1H-imidazol-1-yl)-2-methoxyphenyl)-3-(2,2,6,6-tetramethylpiperidin-4-yl)-3H-[1,2,3]triazolo[4,5-c]pyridazine (50 mg, 0.115 mmol) in dichloromethane (3 mL) was added 1 M BBr$_3$ in CH$_2$Cl$_2$ (0.6 mL, 0.6 mmol). The mixture was stirred at room temperature for 3 h. Methanol (3 mL) was added and the reaction was stirred for an additional 3 h. The mixture was concentrated at reduced pressure. The residue was purified by column chromatography, eluting with a MeOH/CH$_2$Cl$_2$ gradient (with 2.5% NH$_4$OH) (0% to 30% MeOH/NH$_4$OH) to provide 5-(1H-imidazol-1-yl)-2-(3-(2,2,6,6-tetramethylpiperidin-4-yl)-3H-[1,2,3]triazolo[4,5-c]pyridazin-6-yl)phenol (33 mg, 70%) as a yellow solid.

MS m/z 419.4 [M+H]$^+$; $^1$H NMR (methanol-d$_4$) δ: 9.08 (s, 1H), 8.25 (t, J=1.3 Hz, 1H), 8.20 (d, J=8.2 Hz, 1H), 7.67 (t, J=1.3 Hz, 1H), 7.27 (d, J=1.6 Hz, 2H), 7.19 (t, J=0.9 Hz, 1H), 5.72-5.87 (m, 1H), 2.24-2.40 (m, 4H), 1.51 (s, 6H), 1.35 (s, 6H); 2 Hs not observed (OH and NH).

Using the procedure described for Example 15, above, additional compounds described herein were prepared by substituting the appropriate starting materials, suitable reagents and reaction conditions, obtaining compounds such as those selected from:

Example 16

Preparation of Compound 52

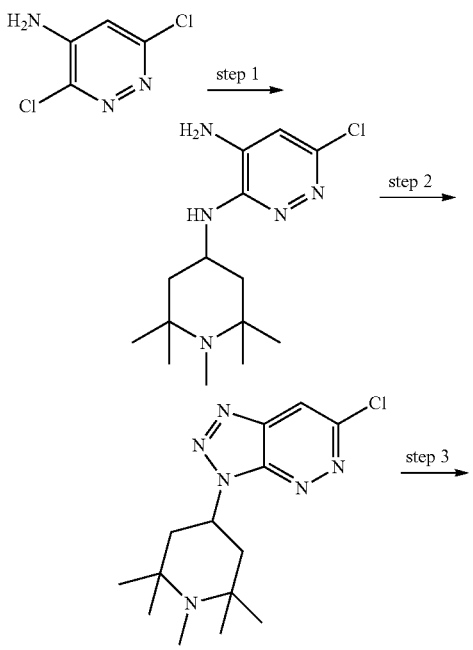

| Cpd | Data |
|---|---|
| 63 | MS m/z 420.4 [M + H]$^+$; $^1$H NMR (methanol-d$_4$) δ: 9.20 (s, 1H), 9.10 (s, 1H), 8.24 (d, J = 8.5 Hz, 1H), 8.21 (s, 1H), 7.57 (d, J = 2.2 Hz, 1H), 7.54 (dd, J = 8.5, 2.2 Hz, 1H), 5.75-5.91 (m, 1H), 2.30-2.47 (m, 4H), 1.55 (s, 6H), 1.40 (s, 6H); 2 Hs not observed (OH and NH). |
| 64 | MS m/z 420.5 [M + H]$^+$; $^1$H NMR (methanol-d$_4$) δ: 9.17 (s, 1H), 9.12 (s, 2H), 8.30 (d, J = 9.1 Hz, 1H), 7.35-7.41 (m, 2H), 5.93-6.03 (m, 1H), 2.67 (s, 4H), 1.78 (s, 6H),1.64 (s, 6H); 2 Hs not observed (OH and NH). |
| 72 | MS m/z 420.4 [M + H]$^+$; $^1$H NMR (methanol-d$_4$) δ: 9.11 (s, 1H), 8.63 (d, J = 1.3 Hz, 1H), 8.27 (d, J = 8.8 Hz, 1H), 7.94 (d, J = 1.3 Hz, 1H), 7.61 (d, J = 2.2 Hz, 1H), 7.57 (dd, J = 8.5, 2.2 Hz, 1H), 5.77-5.87 (m, 1H), 2.28-2.39 (m, 4H), 1.51 (s, 6H), 1.36 (s, 6H); 2 Hs not observed (OH and NH). |
| 143 | MS m/z 437.3 [M + H]$^+$; $^1$H NMR (DMSO-d$_6$) δ: 12.05 (s, 1H), 9.24 (s, 1H), 9.14 (d, J = 11.0 Hz, 1H), 8.22 (d, J = 8.5 Hz, 1H), 8.18 (d, J = 12.8 Hz, 1H), 8.13 (t, J = 1.5 Hz, 1H), 7.63 (dd, J = 8.1, 1.7 Hz, 1H), 7.36 (dd, J = 8.4, 2.3 Hz, 1H), 7.32 (d, J = 2.4 Hz, 1H), 5.92 (tt, J = 12.2, 4.0 Hz, 1H), 4.02-4.16 (m, 1H), 2.52-2.66 (m, 4H), 1.66 (s, 6H), 1.53 (s, 6H). |
| 144 | MS m/z 433.4 [M + H]$^+$; $^1$H NMR (methanol-d$_4$) δ: 9.50 (s, 1H), 9.21 (s, 1H), 8.33 (d, J = 9.5 Hz, 1H), 7.93 (s, 1H), 7.44 (br s, 2H), 5.93-6.05 (m, 1H), 2.62-2.78 (m, 4H), 2.45-2.54 (m, 3H), 1.80 (s, 6H), 1.67 (s, 6H); 2 Hs not observed (NH and OH). |
| 149 | MS m/z 447.5 [M + H]$^+$; $^1$H NMR (methanol-d$_4$) δ: 9.19 (s, 1H), 8.34 (d, J = 8.2 Hz, 1H), 7.48 (d, J = 1.2 Hz, 1H), 7.21-7.29 (m, 2H), 5.95-6.05 (m, 1H), 2.67-2.75 (m, 4H), 2.66 (s, 3H), 2.43 (d, J = 1.2 Hz, 3H), 1.79 (s, 6H), 1.64 (s, 6H); 2 Ns not observed (NH and OH). |
| 155 | MS m/z 433.5 [M + H]$^+$; $^1$H NMR (methanol-d$_4$) δ: 9.18 (s, 1H), 8.28 (d, J = 9.2 Hz, 1H), 7.92 (d, J = 2.1 Hz, 1H), 7.27 (sxt, J = 2.1 Hz, 2H), 6.52-6.55 (m, 1H), 5.99 (spt, J = 5.5 Hz, 1H), 2.64-2.75 (m, 4H), 2.50 (s, 3H), 1.79 (s, 6H), 1.65(s, 6H); 2 Hs not observed (NH and OH). |
| 156 | MS m/z 433.5 [M + H]$^+$; $^1$H NMR (DMSO-d$_6$) δ: 11.70 (s, 1H), 9.16 (s, 1H), 8.92-9.04 (m, 1H), 8.33 (s, 1H), 8.16 (d, J = 8.5 Hz, 1H), 7.61-7.64 (m, 1H), 7.54 (d, J = 2.1 Hz, 1H), 7.46 (dd, J = 8.5, 2.1 Hz, 1H), 5.89-5.97 (m, 1H), 2.53-2.67 (m, 4H), 2.40 (s, 3H), 1.65 (s, 6H), 1.52 (s, 6H). |
| 157 | MS m/z 433.6 [M + H]$^+$; $^1$H NMR (methanol-d$_4$) δ: 9.14 (s, 1H), 8.23 (d, J = 2.4 Hz, 1H), 8.18 (d, J = 8.8 Hz, 1H), 7.45 (s, 1H), 7.44 (dd, J = 10.7, 2.1 Hz, 1H), 6.42 (d, J = 2.4 Hz, 1H), 5.97 (tt, J = 10.4, 5.8 Hz, 1H), 2.64-2.75 (m, 4H), 2.41 (s, 3H),1.79 (s, 6H), 1.64 (s, 6H); 2 Hs not observed (NH and OH). |

-continued

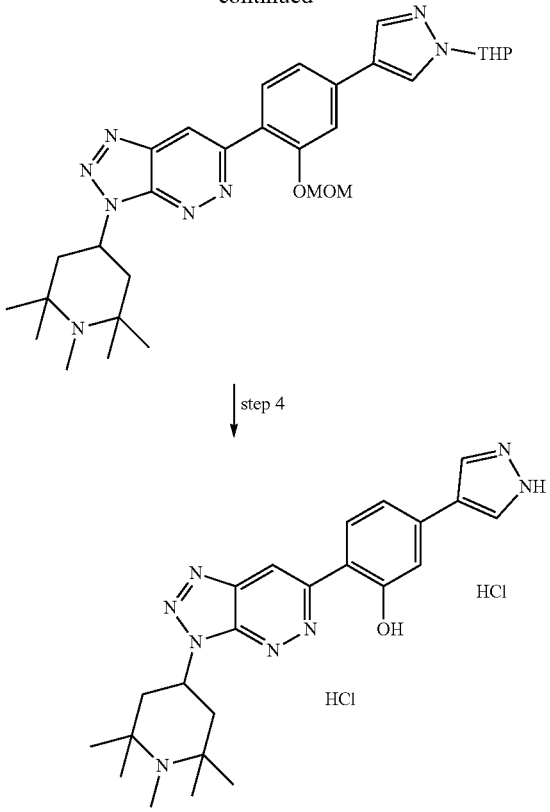

Step 1: A mixture of 3,6-dichloropyridazin-4-amine (1.0 g, 6.0 mmol), 1,2,2,6,6-pentamethylpiperidin-4-amine (1.0 g, 6.1 mmol) and DIPEA (1.6 mL, 9.1 mmol) in decanol (10 mL) was heated at 150° C. for 7 days. Solvent was removed by blowing air and the residue was purified using silica-gel chromatography eluting with a MeOH/CH$_2$Cl$_2$ gradient (2.5% NH$_4$OH) (0% to 30% MeOH/NH$_4$OH) to provide a mixture of 6-chloro-N3-(1,2,2,6,6-pentamethyl-4-piperidyl)pyridazine-3,5-diamine and 6-chloro-N3-(1,2,2,6,6-pentamethyl-4-piperidyl)pyridazine-3,4-diamine (0.85 g, 47%) as a brown solid which was used as is in the next step.

Step 2: To a solution of 6-chloro-N3-(1,2,2,6,6-pentamethyl-4-piperidyl)pyridazine-3,4-diamine, prepared above (0.85 g, 2.9 mmol, ~59% pure), in AcOH (4 mL) was added NaNO$_2$ (0.50 g, 1.21 mmol) and the mixture was stirred at room temperature for 1 h. The reaction was quenched by the addition of saturated aqueous sodium bicarbonate slowly until pH 7. The aqueous layer was extracted with ethyl acetate three times. The organic layer was dried over Na$_2$SO$_4$, filtered, and concentrated under reduced pressure. The crude product was purified by column chromatography on silica gel, eluting with a MeOH/CH$_2$Cl$_2$ gradient (0-20% MeOH) to yield 6-chloro-3-(1,2,2,6,6-pentamethyl-4-piperidyl)triazolo[4,5-c]pyridazine (375 g, 43%) as a tan solid. MS m/z 309.1 [M+H]$^+$.

Step 3: An oven-dried flask was equipped with a magnetic stir bar and charged with [6-chloro-3-(1,2,2,6,6-pentamethyl-4-piperidyl)triazolo[4,5-c]pyridazine (72 mg, 0.23 mmol), 4-[3-(methoxymethoxy)-4-(4,4,5,5-tetramethyl-1,3,2-dioxaborolan-2-yl)phenyl]-1-tetrahydropyran-2-yl-pyrazole (prepared in example 1, step 7, 116 mg, 0.28 mmol), [1,1'-bis(diphenylphosphino)ferrocene] dichloropalladium (I) (17 mg, 0.023 mmol), and K$_2$CO$_3$ (65 mg, 0.47 mmol). The flask was sealed with a rubber septum, and then evacuated and backfilled with argon (repeated a total of 3×). 1,4-Dioxane (2 mL) and water (0.5 mL) were added and the reaction was heated to 90° C. for 16 h. The reaction was cooled to room temperature, diluted with water, and extracted with EtOAc (3×). The combined organic layers were dried over Na$_2$SO$_4$, concentrated under reduced pressure, and purified using silica gel chromatography eluting with a MeOH/CH$_2$Cl$_2$ gradient (0% to 30% MeOH) to provide 6-(2-(methoxymethoxy)-4-(1-(tetrahydro-2H-pyran-2-yl)-1H-pyrazol-4-yl)phenyl)-3-(1,2,2,6,6-pentamethylpiperidin-4-yl)-3H-[1,2,3]triazolo[4,5-c]pyridazine (75 mg, 57%). MS m/z 561.4 [M+H]$^+$.

Step 4: To a solution of 6-[2-(methoxymethoxy)-4-(1-tetrahydropyran-2-ylpyrazol-4-yl)phenyl]-3-(1,2,2,6,6-pentamethyl-4-piperidyl)triazolo[4,5-c]pyridazine (61 mg, 0.11 mmol) in CH$_2$Cl$_2$ (1 mL) was added 4 N HCl in 1,4-dioxane (0.14 mL, 0.54 mmol) and the reaction mixture was stirred for 16 h. The precipitate formed during this time was collected by filtration, washed with CH$_2$Cl$_2$ (3×), and dried to provide 2-[3-(1,2,2,6,6-pentamethyl-4-piperidyl)triazolo[4,5-c]pyridazin-6-yl]-5-(1H-pyrazol-4-yl)phenol dihydrochloride (41 mg, 75%) as a yellow solid.

MS m/z 433.3 [M+H]$^+$; $^1$H NMR (methanol-d$_4$) δ: 9.13 (s, 1H), 8.52 (s, 2H), 8.12 (d, J=8.2 Hz, 1H), 7.40 (dd, J=8.2, 1.9 Hz, 1H), 7.37 (d, J=1.9 Hz, 1H), 5.95 (tt, J=12.9, 3.5 Hz, 1H), 3.03 (s, 3H), 2.95 (t, J=14.2 Hz, 2H), 2.77 (dd, J=14.2, 3.5 Hz, 2H), 1.76 (s, 6H), 1.70 (s, 6H); 2 Hs not observed (NH and OH).

Using the procedure described for Example 16, above, additional compounds described herein were prepared by substituting the appropriate starting materials, suitable reagents and reaction conditions, obtaining compounds such as those selected from:

| Cpd | Data |
|---|---|
| 56 | MS m/z 391.5 [M + H]$^+$; $^1$H NMR (methanol-d$_4$) δ: 9.09 (s, 1H), 8.37 (br s, 2H), 8.09 (d, J = 8.2 Hz, 1H), 7.36 (d, J = 8.5 Hz, 1H), 7.34 (s, 1H), 5.70-5.90 (m, 1H), 3.57-3.64 (m, 2H), 2.70 (br. s., 4H), 1.68 (s, 3H), 1.58 (s, 3H); 3 Hs not observed (OH and 2 NHs). |
| 57 | MS m/z 417.6 [M + H]$^+$; $^1$H NMR (methanol-d$_4$) δ: 9.09 (s, 1H), 8.26 (s, 2H), 8.08 (d, J = 8.5 Hz, 1H), 7.34 (dd, J = 8.2, 1.9 Hz, 1H), 7.32 (d, J = 1.6 Hz, 1H), 5.80-5.92 (m, 1H), 2.76 (dd, J = 13.6, 12.6 Hz, 2H), 2.61-2.66 (m, 2H), 2.50 (d, J = 9.5 Hz, 2H), 2.17 (d, J = 9.1 Hz, 2H), 1.64 (s, 6H); 3 Hs not observed (OH and 2 NHs). |

Example 17

Preparation of Compound 7

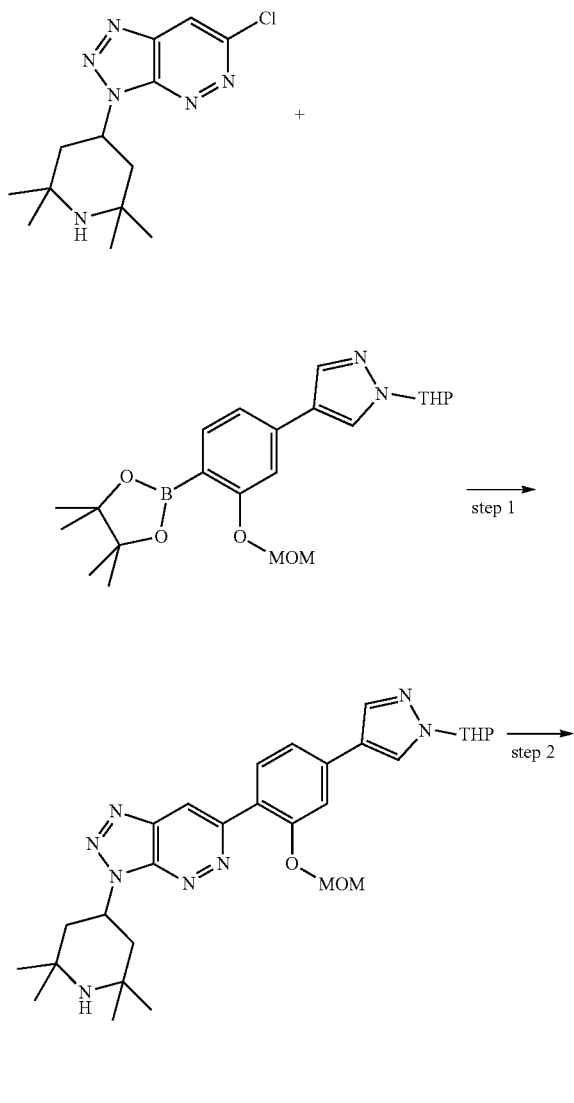

Step 1: An oven-dried flask was equipped with a magnetic stir bar and charged with 6-chloro-3-(2,2,6,6-tetramethylpiperidin-4-yl)-3H-[1,2,3]triazolo[4,5-c]pyridazine (prepared in example 13, step 2, 75 mg, 0.25 mmol), 4-(3-(methoxymethoxy)-4-(4,4,5,5-tetramethyl-1,3,2-dioxaborolan-2-yl)phenyl)-1-(tetrahydro-2H-pyran-2-yl)-H-pyrazole (prepared in example 1, step 7, 150 mg, 0.36 mmol), and [1,1'-bis(diphenylphosphino)ferrocene] dichloropalladium (I) complex with dichloromethane (25 mg, 0.029 mmol). The flask was sealed with a rubber septum, and then evacuated and backfilled with argon (repeated a total of 3×). 1,4-Dioxane (4 mL) and aqueous 2.0 M $K_2CO_3$ (0.3 mL, 0.60 mmol) were added and the reaction was heated to 90° C. for 16 h.

The reaction was cooled to room temperature, diluted with water (2 mL), and extracted with EtOAc (3×). The combined organic layers were dried over $Na_2SO_4$, concentrated under reduced pressure, and purified by column chromatography, eluting with a $MeOH/CH_2Cl_2$ gradient (0-20% MeOH) to provide 6-(2-(methoxymethoxy)-4-(1-(tetrahydro-2H-pyran-2-yl)-1H-pyrazol-4-yl)phenyl)-3-(2,2,6,6-tetramethylpiperidin-4-yl)-3H-[1,2,3]triazolo[4,5-c]pyridazine (125 mg, 90%) as a yellow solid. MS m/z 547.4 $[M+H]^+$.

Step 2: To a solution of 6-(2-(methoxymethoxy)-4-(1-(tetrahydro-2H-pyran-2-yl)-1H-pyrazol-4-yl)phenyl)-3-(2,2,6,6-tetramethylpiperidin-4-yl)-3H-[1,2,3]triazolo[4,5-c]pyridazine (125 mg, 0.23 mmol) in $CH_2Cl_2$ (1 mL) was added 4N HCl in dioxane (3 mL, 12 mmol) and the reaction was stirred at room temperature for 2 h. The yellow solid that precipitated was collected by vacuum filtration, washed with $CH_2Cl_2$ and $Et_2O$ and dried to afford 5-(1H-pyrazol-4-yl)-2-(3-(2,2,6,6-tetramethylpiperidin-4-yl)-3H-[1,2,3]triazolo[4,5-c]pyridazin-6-yl)phenol dihydrochloride (95 mg, 91%).

MS m/z 419.5 $[M+H]^+$; $^1H$ NMR (methanol-$d_4$) δ: 9.11 (s, 1H), 8.34 (s, 2H), 8.11 (d, J=8.2 Hz, 1H), 7.37 (dd, J=8.2, 1.9 Hz, 1H), 7.35 (d, J=1.9 Hz, 1H), 5.97 (tt, J=11.0, 5.4 Hz, 1H), 2.62-2.74 (m, 4H), 1.79 (s, 6H), 1.64 (s, 6H); 3 Hs not observed (2NHs and OH).

Example 18

Preparation of Compound 34

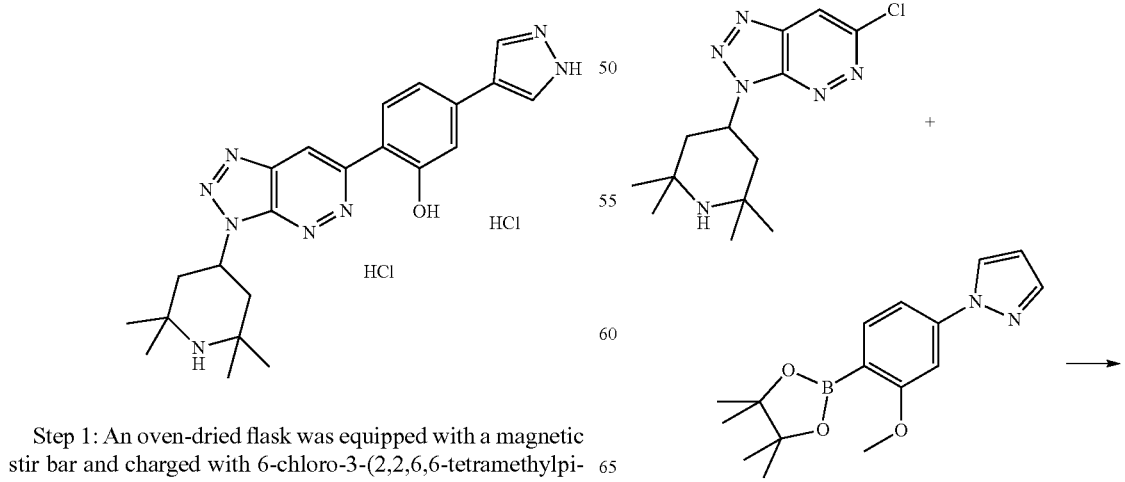

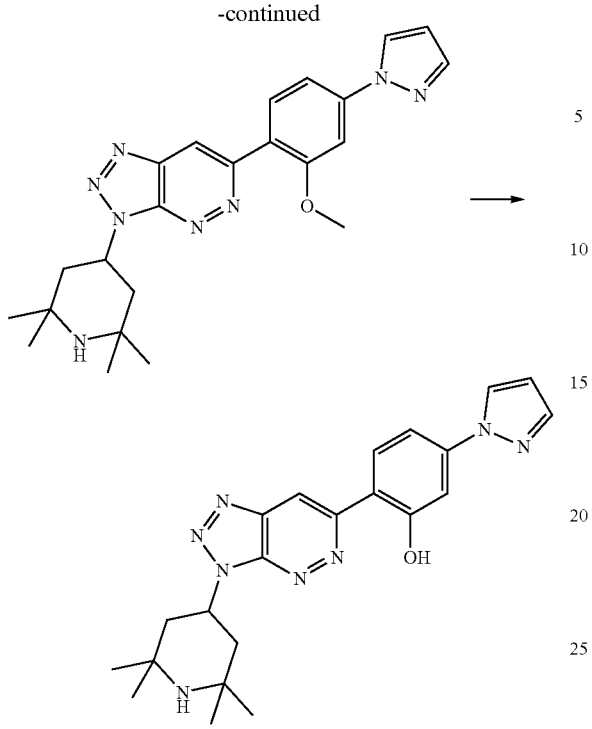

Example 19

Preparation of Compound 14

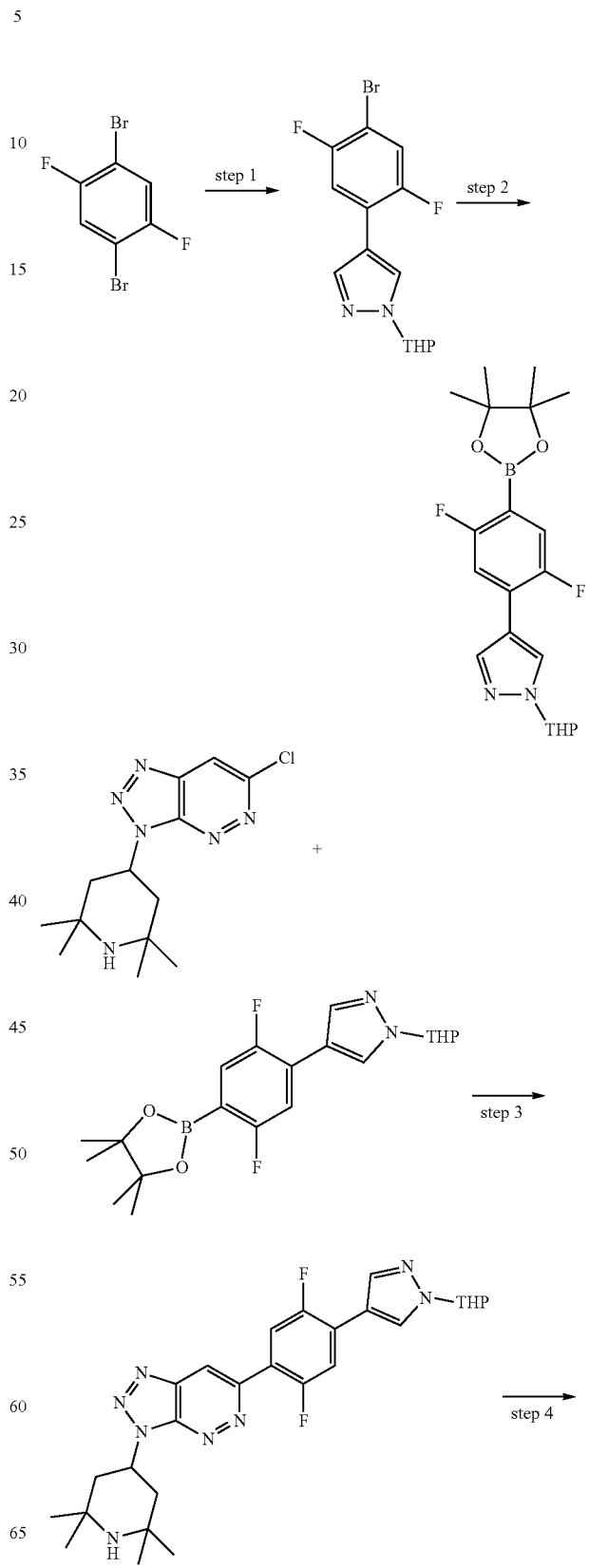

Step 1: An oven-dried flask was equipped with a magnetic stir bar and charged with 6-chloro-3-(2,2,6,6-tetramethylpiperidin-4-yl)-3H-[1,2,3]triazolo[4,5-c]pyridazine (prepared in example 13, step 2, 50 mg, 0.17 mmol), 1-[3-methoxy-4-(4,4,5,5-tetramethyl-1,3,2-dioxaborolan-2-yl)phenyl]pyrazole (61 mg, 0.20 mmol), [1,1'-bis(diphenylphosphino)ferrocene]dichloropalladium(I) (13 mg, 0.17 mmol), and $K_2CO_3$ (71 mg, 0.51 mmol). The flask was sealed with a rubber septum, and then evacuated and backfilled with argon (repeated a total of 3×). Dioxane (4 mL) and water (0.5 mL) were added and the reaction was heated to 90° C. for 16 h. The reaction was cooled to room temperature, diluted with water (2 mL), and extracted with EtOAc (3×). The combined organic phases were dried over $Na_2SO_4$, concentrated under reduced pressure, and purified by column chromatography, eluting with a $MeOH/CH_2Cl_2$ gradient (0-20% MeOH) to provide 6-(2-methoxy-4-pyrazol-1-yl-phenyl)-3-(2,2,6,6-tetramethyl-4-piperidyl)triazolo[4,5-c]pyridazine (55 mg, 75%) as a yellow solid. MS m/z 433.5 [M+H]$^+$.

Step 2: To a solution of 6-(2-methoxy-4-pyrazol-1-yl-phenyl)-3-(2,2,6,6-tetramethyl-4-piperidyl)triazolo[4,5-c]pyridazine (55 mg, 0.13 mmol) in $CH_2Cl_2$ (1 mL) was added 1 M $BBr_3$ in $CH_2Cl_2$ (0.64 mL, 0.64 mmol) and the reaction was stirred at room temperature for 16 h after which, UPLC showed complete consumption of the starting material. The reaction was quenched with MeOH (10 mL), concentrated under reduced pressure, and purified using silica gel chromatography, eluting with a $MeOH/CH_2Cl_2$ gradient (2.5% $NH_4OH$) (0% to 30% $MeOH/NH_4OH$) to provide 5-pyrazol-1-yl-2-[3-(2,2,6,6-tetramethyl-4-piperidyl)triazolo[4,5-c]pyridazin-6-yl]phenol (38 mg, 71%) as a yellow solid.

MS m/z 419.5 [M+H]$^+$; $^1$H NMR (DMSO-$d_6$) δ: 9.18 (s, 1H), 8.97-9.07 (m, 1H), 8.58 (d, J=2.2 Hz, 1H), 8.19 (d, J=8.8 Hz, 1H), 8.11-8.17 (m, 1H), 7.81 (d, J=1.3 Hz, 1H), 7.62 (d, J=2.5 Hz, 1H), 7.54 (dd, J=8.7, 2.4 Hz, 1H), 6.61 (dd, J=2.4, 1.7 Hz, 1H), 5.93 (tt, J=12.3, 4.1 Hz, 1H), 2.52-2.65 (m, 4H), 1.66 (s, 6H), 1.53 (s, 6H).

-continued

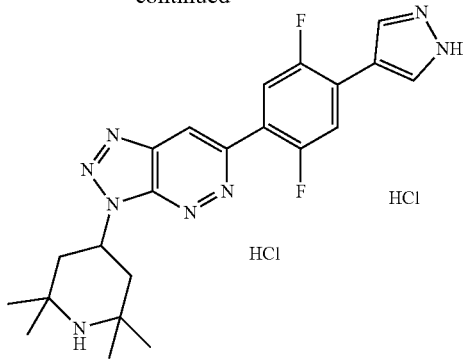

Step 1: An oven-dried flask was equipped with a magnetic stir bar and charged with 1,4-dibromo-2,5-difluoro-benzene (3.2 g, 12 mmol), 1-tetrahydropyran-2-yl-4-(4,4,5,5-tetramethyl-1,3,2-dioxaborolan-2-yl)pyrazole (2.95 g, 10.6 mmol) and Pd(dppf)Cl$_2$—CH$_2$Cl$_2$ (430 mg, 0.50 mmol). The flask was sealed with a rubber septum, and then evacuated and backfilled with argon (repeated a total of 3×). 1,4-Dioxane (50 mL) and aqueous 2.0 M K$_2$CO$_3$ (15 mL, 30 mmol) were added and the reaction was heated to 90° C. for 16 h. The reaction was cooled to room temperature, diluted with water, and extracted with EtOAc (3×). The combined organic phases were dried over Na$_2$SO$_4$, concentrated under reduced pressure, and purified by column chromatography, eluting with a EtOAc/hexanes gradient (0-50% EtOAc) to provide 4-(4-bromo-2,5-difluoro-phenyl)-1-tetrahydropyran-2-yl-pyrazole (1.51 g, 42%) as a brown oil. MS m/z 343.0, 345.0 [M+H]$^+$.

Step 2: An oven-dried flask was equipped with a magnetic stir bar and charged with Pd(dppf)Cl$_2$·CH$_2$Cl$_2$ (200 mg, 0.23 mmol), 4-(4-bromo-2,5-difluoro-phenyl)-1-tetrahydropyran-2-yl-pyrazole (1.51 g, 4.40 mmol), 4,4,5,5-tetramethyl-2-(4,4,5,5-tetramethyl-1,3,2-dioxaborolan-2-yl)-1,3,2-dioxaborolane (2.90 g, 11.4 mmol), and KOAc (1.73 g, 17.6 mmol). The flask was sealed with a rubber septum, and then evacuated and backfilled with argon (repeated a total of 3×). 1,4-Dioxane (22 mL) was added and the reaction was heated to 90° C. for 16 h. The reaction was cooled to room temperature, diluted with water, and extracted with EtOAc (3×). The combined organic phases were dried over Na$_2$SO$_4$, concentrated under reduced pressure, and purified by column chromatography, eluting with a EtOAc/hexanes gradient (5-50% EtOAc) to provide 4-[2,5-difluoro-4-(4,4,5,5-tetramethyl-1,3,2-dioxaborolan-2-yl)phenyl]-1-tetrahydropyran-2-yl-pyrazole (1.54 g, 89%) as a brownish solid.

$^1$H NMR (CDCl$_3$) δ: 8.09 (d, J=1.9 Hz, 1H), 7.95 (s, 1H), 7.47 (dd, J=10.7, 4.7 Hz, 1H), 7.23 (dd, J=9.5, 5.7 Hz, 1H), 5.38-5.51 (m, 1H), 4.01-4.16 (m, 1H), 3.73-3.78 (m, 1H), 2.05-2.20 (m, 3H), 1.66-1.79 (m, 3H), 1.39 (s, 12H).

Step 3: An oven-dried reaction tube was equipped with a magnetic stir bar and charged with 6-chloro-3-(2,2,6,6-tetramethyl-4-piperidyl)triazolo[4,5-c]pyridazine (prepared in example 13, step 2, 75 mg, 0.25 mmol), 4-[2,5-difluoro-4-(4,4,5,5-tetramethyl-1,3,2-dioxaborolan-2-yl)phenyl]-1-tetrahydropyran-2-yl-pyrazole (199 mg, 0.51 mmol), and Pd(dppf)Cl$_2$—CH$_2$Cl$_2$ (25 mg, 0.029 mmol). The tube was sealed with a rubber screw-cap, and then evacuated and backfilled with argon (repeated a total of 3×). 1,4-Dioxane (1 mL) and aqueous 2.0 M K$_2$CO$_3$ (0.3 mL, 0.6 mmol) were added and the reaction was heated to 90° C. for 16 h. The reaction was cooled to room temperature, diluted with water, and extracted with EtOAc (3×). The combined organic phases were dried over Na$_2$SO$_4$, concentrated under reduced pressure, and purified by column chromatography, eluting with a MeOH/CH$_2$Cl$_2$ gradient (0% to 30% MeOH) to provide 6-[2,5-difluoro-4-(1-tetrahydropyran-2-ylpyrazol-4-yl)phenyl]-3-(2,2,6,6-tetramethyl-4-piperidyl)triazolo[4,5-c]pyridazine (96 mg, 72%) as a brown solid. MS m/z 523.4 [M+H]$^+$;

Step 4: To a solution of 6-[2,5-difluoro-4-(1-tetrahydropyran-2-ylpyrazol-4-yl)phenyl]-3-(2,2,6,6-tetramethyl-4-piperidyl)triazolo[4,5-c]pyridazine (96 mg, 0.18 mmol) in CH$_2$Cl$_2$ (1 mL) was added 4N HCl in dioxane (2 mL, 8 mmol) and the reaction was stirred at room temperature for 1 h. The yellow solid that precipitated was collected by vacuum filtration, rinsed with CH$_2$Cl$_2$ and Et$_2$O and dried to afford 6-(2,5-difluoro-4-(1H-pyrazol-4-yl)phenyl)-3-(2,2,6,6-tetramethylpiperidin-4-yl)-3H-[1,2,3]triazolo[4,5-c]pyridazine dihydrochloride.

MS m/z 439.5 [M+H]$^+$; $^1$H NMR (DMSO-d$_6$) δ: 9.56 (d, J=15.8 Hz, 1H), 8.97 (d, J=1.6 Hz, 1H), 8.36 (d, J=12.9 Hz, 1H), 8.25 (s, 1H), 7.70-7.91 (m, 1H), 5.93 (tt, J=12.9, 4.1 Hz, 1H), 2.59-2.67 (m, 4H), 1.67 (s, 6H), 1.56 (s, 6H), 2 Hs not observed (2 NHs).

Using the procedure described for Example 19, above, additional compounds described herein were prepared by substituting the appropriate starting materials, suitable reagents and reaction conditions, obtaining compounds such as those selected from:

| Cpd | Data |
| --- | --- |
| 13 | MS m/z 439.5 [M + H]$^+$; $^1$H NMR (DMSO-d$_6$) δ: 9.64 (d, J = 12.8 Hz, 1H), 8.95 (d, J = 1.3 Hz, 1H), 8.39 (d, J = 12.8 Hz, 1H), 8.26 (d, J = 2.3 Hz, 1H), 7.92-7.99 (m, 1H), 5.93 (tt, J = 12.3, 3.8 Hz, 1H), 2.58-2.65 (m, 4H), 1.67 (s, 6H), 1.56 (s, 6H); 2 Hs not observed (2 NHs). |
| 58 | MS m/z 435.5 [M + H]$^+$; $^1$H NMR (methanol-d$_4$) δ: 9.02 (s, 1H), 8.79 (s, 2H), 7.61 (s, 1H), 7.37 (s, 1H), 5.97 (tt, J = 11.7, 4.7 Hz, 1H), 2.60-2.77 (m, 4H), 1.79 (s, 6H), 1.66 (s, 6H); 4 Hs not observed (2 NHs and 2 OHs). |

Example 20

Preparation of Compound 53

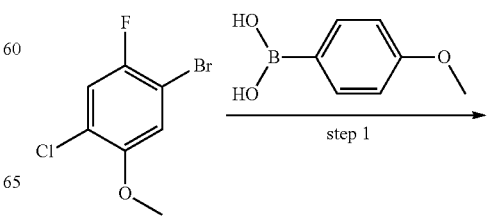

step 1

-continued

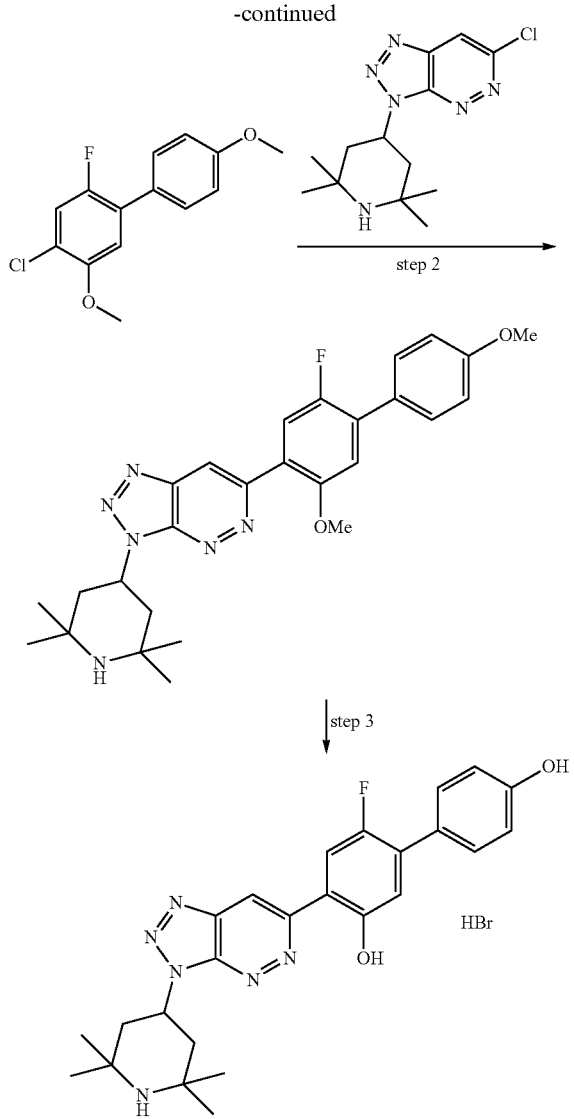

Step 1: An oven-dried flask equipped with a magnetic stir bar was charged with 1-bromo-4-chloro-2-fluoro-5-methoxy-benzene (100 mg, 0.42 mmol), (4-methoxyphenyl) boronic acid (69.8 mg, 0.46 mmol) and [1,1'-bis(diphenylphosphino)ferrocene] dichloropalladium(II) complex with dichloromethane (17.1 mg, 0.021 mmol). The flask was sealed with a rubber septum, and then evacuated and backfilled with argon (repeated a total of 3×). 1,4-Dioxane (1.0 mL) and aqueous 1 M $K_2CO_3$ (0.5 mL, 0.5 mmol) were added and the reaction was heated to 90° C. for 2 h. The reaction was cooled to room temperature, diluted with water (5 mL), and extracted with EtOAc (3×). The combined organic phases were dried over $Na_2SO_4$, and concentrated under reduced pressure. The residue was purified by column chromatography on silica gel, eluting with a EtOAc/hexanes gradient (0-10% EtOAc) to yield 1-chloro-5-fluoro-2-methoxy-4-(4-methoxyphenyl)benzene (89.2 mg, 80%) as an off white solid.

MS m/z 267.8 [M+H]$^+$; $^1$H NMR (CDCl$_3$) δ: 7.39 (dd, J=8.8, 1.6 Hz, 2H), 7.13 (d, J=9.5 Hz, 1H), 6.92 (d, J=8.8 Hz, 2H), 6.85 (d, J=6.9 Hz, 1H), 3.85 (s, 3H), 3.79 (s, 3H).

Step 2: An oven-dried flask was equipped with a magnetic stir bar and charged with 1-chloro-5-fluoro-2-methoxy-4-(4-methoxyphenyl)benzene (56 mg, 0.21 mmol), bis(pinacolato)diboron (66.6 mg, 0.26 mmol), potassium acetate (61.8 mg, 0.63 mmol), and chloro(2-dicyclohexylphosphino-2',4',6'-triisopropyl-1,1'-biphenyl)[2-(2'-amino-1,1'-biphenyl)]palladium(II) (8.3 mg, 0.011 mmol). The flask was sealed with a rubber septum, and then evacuated and backfilled with argon (repeated a total of 3×). 1,4-Dioxane (1.4 mL) was added and the reaction was heated to 120° C. for 64 h. The reaction was cooled to room temperature and aq. 1 M $K_2CO_3$ (0.7 mL, 0.7 mmol) was added followed by 6-chloro-3-(2,2,6,6-tetramethyl-4-piperidyl)triazolo[4,5-c]pyridazine (prepared in example 13, step 2, 40.9 mg, 0.14 mmol), and 1,1'-bis(diphenylphosphino)ferrocene-palladium(II)dichloride dichloromethane complex (8.6 mg, 0.011 mmol). The mixture was purged with argon and heated at 90° C. for 3 h.

The reaction was cooled to room temperature, diluted with water, and extracted with EtOAc (3×). The combined organic phases were dried over $Na_2SO_4$, and concentrated under reduced pressure. The residue was purified by column chromatography on silica gel, eluting with a MeOH/CH$_2$Cl$_2$ gradient (0-30% MeOH) to yield 6-[5-fluoro-2-methoxy-4-(4-methoxyphenyl)phenyl]-3-(2,2,6,6-tetramethyl-4-piperidyl)triazolo[4,5-c]pyridazine (28.5 mg, 29%). MS m/z 491.5 [M+H]$^+$.

Step 3: 6-[5-Fluoro-2-methoxy-4-(4-methoxyphenyl)phenyl]-3-(2,2,6,6-tetramethyl-4-piperidyl)triazolo[4,5-c]pyridazine (28.5 mg, 0.058 mmol) was combined with dichloromethane (2 mL) and 1N BBr$_3$ in dichloromethane (0.6 mL, 0.6 mmol). The mixture was stirred at room temperature for 3 h. Methanol (0.5 mL) was added and the reaction was stirred for 3 h. The mixture was concentrated at reduced pressure and the residue was triturated with MeOH (3×2 mL) and dried under vacuum to yield 6-fluoro-4-(3-(2,2,6,6-tetramethylpiperidin-4-yl)-3H-[1,2,3]triazolo[4,5-c]pyridazin-6-yl)-[1,1'-biphenyl]-3,4'-diol hydrobromide as an off white solid (11.3 mg, 36%).

MS m/z 463.5 [M+H]$^+$; $^1$H NMR (DMSO-d6) δ: 11.22 (s, 1H), 9.75 (s, 1H), 9.20 (s, 1H), 8.95 (d, J=12.0 Hz, 1H), 8.11 (d, J=12.0 Hz, 1H), 7.98 (d, J=11.7 Hz, 1H), 7.45 (dd, J=8.5, 1.6 Hz, 2H), 7.13 (d, J=6.9 Hz, 1H), 6.91 (d, J=8.5 Hz, 2H), 5.94 (tt, J=12.3, 4.1 Hz, 1H), 2.59 (d, J=12.0 Hz, 2H), 2.54 (d, J=10.1 Hz, 2H), 1.66 (s, 6H), 1.52 (s, 6H).

Using the procedure described for Example 20, above, additional compounds described herein were prepared by substituting the appropriate starting materials, suitable reagents and reaction conditions, obtaining compounds such as those selected from:

| Cpd | Data |
|---|---|
| 33 | MS m/z 437.5 [M + H]$^+$; $^1$H NMR (DMSO-d$_6$) δ: 10.13-10.31 (m, 1H), 9.55-9.70 (m, 1H), 8.82 (d, J = 1.3 Hz, 1H), 8.32-8.42 (m, 1H), 8.26 (s, 2H), 7.70 (d, J = 12.3 Hz, 1H), 7.64 (d, J = 6.9 Hz, 1H), 5.91 (tt, J = 12.3, 3.8 Hz, 1H), 2.56-2.70 (m, 4H), 1.67 (s, 6H), 1.56 (s, 6H). |

| Cpd | Data |
|---|---|
| 55 | MS m/z 478.2 [M + H]+; 1H NMR (methanol-d4) δ: 9.18 (s, 1H), 8.03 (d, J = 12.0 Hz, 1H), 7.79 (s, 1H), 7.22 (d, J = 6.6 Hz, 1H), 6.83 (s, 1H), 6.70 (dt, J = 6.9, 1.9 Hz, 1H), 5.99 (tt, J = 11.3, 5.4 Hz, 1H), 3.66 (s, 3 H), 2.63-2.71 (m, 4H), 1.78 (s, 6H), 1.63 (s, 6H); 2 Hs not observed (NH and OH). |
| 59 | MS m/z 437.5 [M + H]+; 1H NMR (methanol-d4) δ: 8.75 (s, 1H), 8.06 (s, 2H), 7.04 - 7.18 (m, 2H), 5.99 (tt, J = 12.0, 4.7 Hz, 1H), 2.62-2.74 (m, 4H), 1.78 (s, 6H), 1.63 (s, 6H); 3 Hs not observed (2 NHs and OH). |
| 62 | MS m/z 451.5 [M + H]+; 1H NMR (DMSO-d6) δ: 11.51 (br s, 2H), 9.48 (d, J = 12.3 Hz, 1H), 9.23 (s, 1H), 8.31 (d, J = 12.0 Hz, 1H), 8.21 (d, J = 1.9 Hz, 1H), 8.03 (d, J = 12.3 Hz, 1H), 7.92 (s, 1H), 7.35 (d, J = 6.9 Hz, 1H), 5.91 (tt, J = 12.6, 4.1 Hz, 1H), 3.94 (s, 3H), 2.59 (d, J = 12.9 Hz, 2H), 2.50-2.54 (m, 2H), 1.67 (s, 6H), 1.55 (s, 6H). |
| 87 | MS m/z 448.3 [M + H]+; 1H NMR (methanol-d4) δ: 9.26 (s, 1H), 8.96-9.03 (m, 2H), 8.44 (dd, J = 6.9, 1.3 Hz, 2H), 8.21 (d, J = 12.6 Hz, 1H), 7.50 (d, J = 6.6 Hz, 1H), 6.01 (tt, J = 10.7, 5.5 Hz, 1H), 2.63-2.73 (m, 4H), 1.80 (s, 6H), 1.65 (s, 6H); 2 Hs not observed (NH, and OH). |

Example 21

Preparation of Compound 35

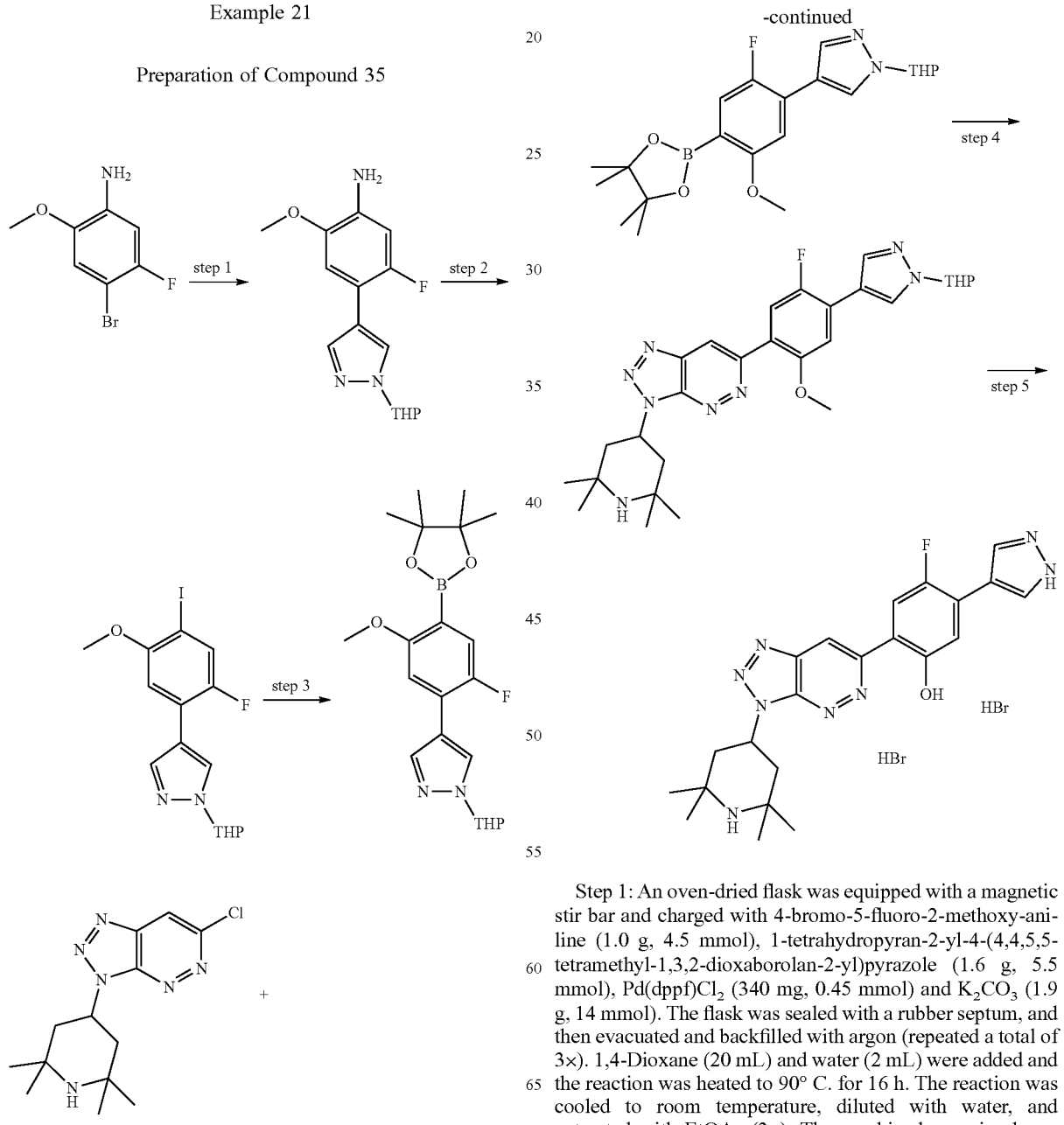

Step 1: An oven-dried flask was equipped with a magnetic stir bar and charged with 4-bromo-5-fluoro-2-methoxy-aniline (1.0 g, 4.5 mmol), 1-tetrahydropyran-2-yl-4-(4,4,5,5-tetramethyl-1,3,2-dioxaborolan-2-yl)pyrazole (1.6 g, 5.5 mmol), Pd(dppf)Cl$_2$ (340 mg, 0.45 mmol) and K$_2$CO$_3$ (1.9 g, 14 mmol). The flask was sealed with a rubber septum, and then evacuated and backfilled with argon (repeated a total of 3x). 1,4-Dioxane (20 mL) and water (2 mL) were added and the reaction was heated to 90° C. for 16 h. The reaction was cooled to room temperature, diluted with water, and extracted with EtOAc (3x). The combined organic phases were dried over Na$_2$SO$_4$, concentrated under reduced pressure, and purified by column chromatography, eluting with a EtOAc/hexanes gradient (0-60% EtOAc) to provide 5-fluoro-2-methoxy-4-(1-tetrahydropyran-2-ylpyrazol-4-yl) aniline (1.25 g, 94%) as a colorless oil. MS m/z 292.3 [M+H].

Step 2: To a well stirred suspension of 5-fluoro-2-methoxy-4-(1-tetrahydropyran-2-ylpyrazol-4-yl)aniline (1.25 g, 4.29 mmol) in THF (40 mL) under a nitrogen flow were sequentially added CsI (1.67 g, 6.44 mmol), 2 (1.09 g, 4.29 mmol), CuI (0.41 g, 2.15 mmol) and tBuONO (1.33 mL, 10.7 mmol). The reaction mixture was stirred vigorously at 65-70° C. for 6 h. After cooling in an ice-water bath, the solid was filtered off. The filtrate was diluted with dichloromethane (500 mL), washed with 30% aq. ammonium hydroxide (150 mL), sodium thiosulphate (300 mL), brine, and dried over anhydrous Na$_2$SO$_4$ and concentrated under reduced pressure. The residue was purified by column chromatography, eluting with a EtOAc/hexanes gradient (0-80% EtOAc) to provide 4-(2-fluoro-4-iodo-5-methoxyphenyl)-1-tetrahydropyran-2-yl-pyrazole (0.92 g, 53%) as a brownish solid. MS m/z 403.1 [M+H]$^+$.

Step 3: An oven-dried flask was equipped with a magnetic stir bar and charged with 4-(2-fluoro-4-iodo-5-methoxyphenyl)-1-tetrahydropyran-2-yl-pyrazole (0.92 g, 2.23 mmol), Pd(dppf)Cl$_2$ (171 mg, 0.23 mmol), 4,4,5,5-tetramethyl-2-(4,4,5,5-tetramethyl-1,3,2-dioxaborolan-2-yl)-1,3,2-dioxaborolane (1.17 g, 4.57 mmol), and KOAc (0.68 g, 6.85 mmol). The flask was sealed with a rubber septum, and then evacuated and backfilled with argon (repeated a total of 3×). 1,4-Dioxane (10 mL) was added and the reaction was heated to 90° C. for 16 h. The reaction was cooled to room temperature, diluted with water, and extracted with EtOAc (3×). The combined organic phases were dried over Na$_2$SO$_4$, concentrated under reduced pressure, and purified by column chromatography, eluting with a EtOAc/hexanes gradient (0-50% EtOAc) to provide 4-(2-fluoro-5-methoxy-4-(4,4,5,5-tetramethyl-1,3,2-dioxaborolan-2-yl)phenyl)-1-(tetrahydro-2H-pyran-2-yl)-1H-pyrazole (0.745 g, 81%) as a clear oil. MS m/z 403.3 [M+H]$^+$.

Step 4: An oven-dried reaction tube was equipped with a magnetic stir bar and charged with 6-chloro-3-(2,2,6,6-tetramethyl-4-piperidyl)triazolo[4,5-c]pyridazine (prepared in example 13, step 2, 98 mg, 0.33 mmol), 4-(2-fluoro-5-methoxy-4-(4,4,5,5-tetramethyl-1,3,2-dioxaborolan-2-yl)phenyl)-1-(tetrahydro-2H-pyran-2-yl)-1H-pyrazole (267 mg, 0.66 mmol), Pd(dppf)Cl$_2$—CH$_2$Cl$_2$ (50 mg, 0.066 mmol) and K$_2$CO$_3$ (276 mg, 2.0 mmol). The tube was sealed with a rubber screw-cap, and then evacuated and backfilled with argon (repeated a total of 3×). 1,4-Dioxane (2 mL) and water (0.5 mL) were added and the reaction was heated to 90° C. for 16 h. The reaction was cooled to room temperature, diluted with water, and extracted with EtOAc (3×). The combined organic layers were dried over Na$_2$SO$_4$, concentrated under reduced pressure, and purified by column chromatography, eluting with a MeOH/CH$_2$Cl$_2$ gradient (0% to 25% MeOH) To provide 6-(5-fluoro-2-methoxy-4-(1-(tetrahydro-2H-pyran-2-yl)-1H-pyrazol-4-yl)phenyl)-3-(2,2,6,6-tetramethylpiperidin-4-yl)-3H-[1,2,3]triazolo[4,5-c] pyridazine (150 mg, 42%) as a brownish solid. MS m/z 535.4 [M+H]$^+$.

Step 5: 6-(5-Fluoro-2-methoxy-4-(1-(tetrahydro-2H-pyran-2-yl)-1H-pyrazol-4-yl)phenyl)-3-(2,2,6,6-tetramethylpiperidin-4-yl)-3H-[1,2,3]triazolo[4,5-c]pyridazine (80 mg, 0.15 mmol) was dissolved in dichloromethane (2 mL) and treated with 1 N BBr$_3$ in dichloromethane (0.74 mL, 0.74 mmol). The mixture was stirred at room temperature for 3 h. Methanol (0.5 mL) was added and the reaction was stirred for 1 h. The reaction was concentrated at reduced pressure. The residue was triturated in MeOH, the resultant solid was filtered, washed with Et$_2$O and dried under vacuum to yield 4-fluoro-5-(1H-pyrazol-4-yl)-2-(3-(2,2,6,6-tetramethylpiperidin-4-yl)-3H-[1,2,3]triazolo[4,5-c] pyridazin-6-yl)phenol dihydrobromide (33 mg, 41%) as an orange solid.

MS m/z 437.5 [M+H]$^+$; $^1$H NMR (DMSO-d$_6$) δ:11.51 (br s, 1H), 9.25 (s, 1H), 8.92-9.03 (m, 1H), 8.07-8.16 (m, 2H), 8.03 (d, J=12.3 Hz, 1H), 7.38 (d, J=6.8 Hz, 1H), 5.93 (tt, J=12.3, 4.8 Hz, 1H), 2.53-2.63 (m, 4H), 1.66 (s, 6H), 1.52 (s, 6H); 1H not observed (NH or OH).

Using the procedure described for Example 21, above, additional compounds described herein were prepared by substituting the appropriate starting materials, suitable reagents and reaction conditions, obtaining compounds such as those selected from:

| Cpd | Data |
|---|---|
| 83 | MS m/z 453.9 [M + H]$^+$; $^1$H NMR (methanol-d$_4$) δ: 9.18 (s, 1H), 8.63 (s, 2H), 8.28 (s, 1H), 7.34 (s, 1H), 5.98 (tt, J = 12.0, 4.5 Hz, 1H), 2.61-2.79 (m, 4H), 1.80 (s, 6H), 1.66 (s, 6H); 3 Hs not observed (2 NHs and OH). |

Example 22

Preparation of Compound 54

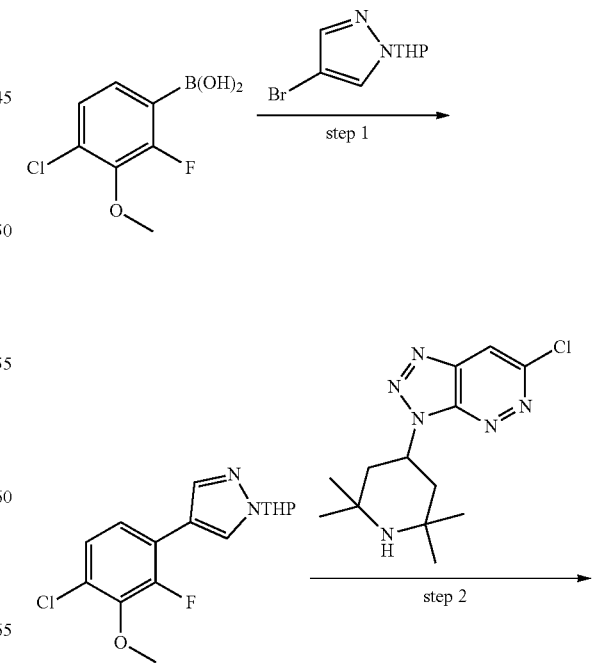

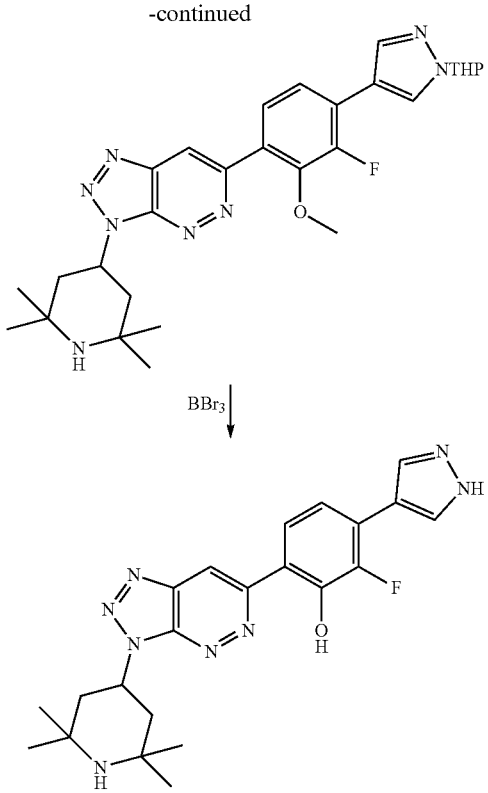

Step 1: (4-Chloro-2-fluoro-3-methoxy-phenyl)boronic acid (200 mg, 0.98 mmol) was combined with 4-bromo-1-tetrahydropyran-2-yl-pyrazole (271 mg, 1.17 mmol) and [1,1'-bis(diphenylphosphino)ferrocene] dichloropalladium (II) complex with dichloromethane (80.0 mg, 0.098 mmol), followed by addition of 1,4-dioxane (2.0 mL) and aqueous 1 M $K_2CO_3$ (1.0 mL, 1.0 mmol). The mixture was stirred at 110° C. for 2 h. The mixture was then partitioned between EtOAc and $H_2O$. The aqueous layer was extracted with EtOAc and the combined organic layers were dried over $Na_2SO_4$, filtered and concentrated. The residue was chromatographed on silica gel, eluting with 0-20% EtOAc in hexanes to yield 4-(4-chloro-2-fluoro-3-methoxy-phenyl)-1-tetrahydropyran-2-yl-pyrazole (165.7 mg, 54%) as an off white solid.

MS m/z 311.0 [M+H]$^+$; $^1$H NMR (CDCl$_3$) δ: 7.93 (d, J=1.9 Hz, 1H), 7.82 (s, 1H), 7.13 (dd, J=8.5, 7.3 Hz, 1H), 7.07 (dd, J=8.5, 1.3 Hz, 1H), 5.37 (dd, J=9.0, 3.0 Hz, 1H), 4.02 (d, J=9.8 Hz, 1H), 3.91 (s, 3H), 3.67 (td, J=11.2, 2.8 Hz, 1H), 2.08-2.18 (m, 2H), 1.88-2.01 (m, 1H), 1.60-1.72 (m, 2H), 1.57 (d, J=2.5 Hz, 1H).

Step 2: 4-(4-Chloro-2-fluoro-3-methoxy-phenyl)-1-tetrahydropyran-2-yl-pyrazole (48.0 mg, 0.15 mmol) was combined with bis(pinacolato)diboron (49.0 mg, 0.19 mmol), potassium acetate (45.5 mg, 0.46 mmol), chloro(2-dicyclohexylphosphino-2',6'-dimethoxy-1,1'-biphenyl)[2-(2'-amino-1,1'-biphenyl)]palladium(II) (5.6 mg, 0.008 mmol), and 1,4-dioxane (1.0 mL). The mixture was stirred at 120° C. for 24 h. The mixture was cooled to room temperature. To the mixture was added aqueous 1 M $K_2CO_3$ (0.5 mL, 0.5 mmol), 6-chloro-3-(2,2,6,6-tetramethyl-4-piperidyl)triazolo[4,5-c]pyridazine (prepared in example 13, step 2, 30.0 mg, 0.102 mmol), and [1,1'-bis(diphenylphosphino)ferrocene] dichloropalladium(II) complex with dichloromethane (4.2 mg, 0.008 mmol). The mixture was stirred at 90° C. for 6 h.

The mixture was then partitioned between EtOAc and $H_2O$. The aqueous layer was extracted with EtOAc. The combined organic layers were dried over $Na_2SO_4$, filtered and concentrated. The residue was chromatographed on silica gel, eluting with 0-30% MeOH in $CH_2Cl_2$ to yield 6-[3-fluoro-2-methoxy-4-(1-tetrahydropyran-2-ylpyrazol-4-yl)phenyl]-3-(2,2,6,6-tetramethyl-4-piperidyl)triazolo[4,5-c]pyridazine (10.6 mg, 20%). MS m/z 535.5 [M+H]$^+$.

Step 3: 6-[3-Fluoro-2-methoxy-4-(1-tetrahydropyran-2-ylpyrazol-4-yl)phenyl]-3-(2,2,6,6-tetramethyl-4-piperidyl) triazolo[4,5-c]pyridazine (11 mg, 0.02 mmol) was combined with dichloromethane (0.5 mL) and 1 N BBr$_3$ in dichloromethane (0.10 mL, 0.10 mmol). The mixture was stirred at room temperature for 5 h. Methanol (0.5 mL) was added and the reaction was stirred for 16 h. The reaction was concentrated at reduced pressure. The residue was partitioned between EtOAc and saturated aqueous NaHCO$_3$. The aqueous layer was extracted with EtOAc.

The combined organic layers were dried over Na$_2$SO$_4$, filtered and concentrated. The material was chromatographed on silica gel, eluting with 0-30% MeOH in CH$_2$Cl$_2$, and then further purified by reverse phase chromatography on C18 silica gel, eluting with 10-100% MeCN in H$_2$O, to provide 2-fluoro-3-(1H-pyrazol-4-yl)-6-[3-(2,2,6,6-tetramethyl-4-piperidyl)triazolo[4,5-c]pyridazin-6-yl]phenol dihydrochloride (1.1 mg, 11%).

MS m/z 437.3 [M+H]$^+$; $^1$H NMR (methanol-d$_4$) δ: 9.11 (s, 1H), 8.19 (br s, 1H), 8.10 (br s, 1H), 7.90 (dd, J=8.5, 1.3 Hz, 1H), 7.38 (dd, J=8.2, 6.9 Hz, 1H), 5.88-5.95 (m, 1H), 2.52-2.63 (m, 4H), 1.71 (s, 6H), 1.56 (s, 6H); 2 Hs not observed (NH and OH).

Example 23

Preparation of Compound 81

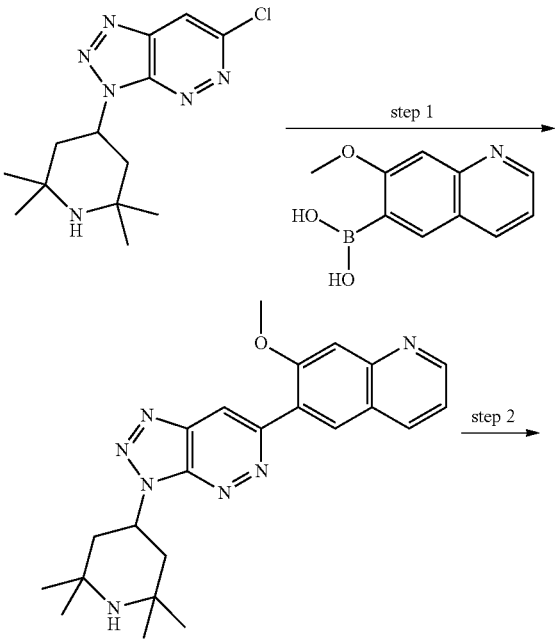

-continued

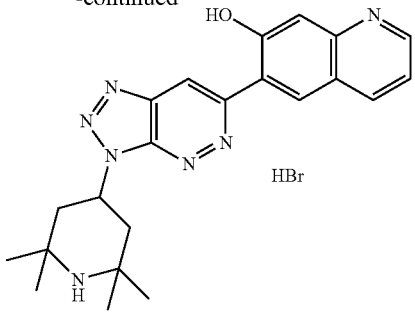

Step 1: An oven-dried flask was equipped with a magnetic stir bar and charged with 6-chloro-3-(2,2,6,6-tetramethyl-4-piperidyl)triazolo[4,5-c]pyridazine (prepared in example 13, step 2, 85 mg, 0.29 mmol), (7-methoxy-6-quinolyl)boronic acid (70 mg, 0.35 mmol), [1,1'-bis(diphenylphosphino)ferrocene] dichloropalladium(I) (22 mg, 0.029 mmol), and K$_2$CO$_3$ (811 mg, 0.58 mmol). The flask was sealed with a rubber septum, and then evacuated and backfilled with argon (repeated a total of 3×). Dioxane (2 mL) and water (0.5 mL) were added and the reaction was heated to 90° C. for 16 h. The reaction was cooled to room temperature, diluted with water, and extracted with EtOAc (3×). The combined organic phases were dried over Na$_2$SO$_4$, concentrated under reduced pressure, and the residue was purified by column chromatography on silica gel, eluting with a MeOH/CH$_2$Cl$_2$ gradient (0% to 30% MeOH) to provide 7-methoxy-6-(3-(2,2,6,6-tetramethylpiperidin-4-yl)-3H-[1,2,3]triazolo[4,5-c]pyridazin-6-yl)quinolone (110 mg, 91%) as a tan solid. MS m/z 418.4 [M+H]$^+$.

Step 2: 7-Methoxy-6-(3-(2,2,6,6-tetramethylpiperidin-4-yl)-3H-[1,2,3]triazolo[4,5-c]pyridazin-6-yl)quinolone (110 mg, 0.26 mmol) was dissolved in CH$_2$Cl$_2$ (2 mL) and 1 N BBr$_3$ in dichloromethane (1.3 mL, 1.3 mmol) was added dropwise. The mixture was stirred at room temperature for 16 h. Methanol (5 mL) was added and the reaction was stirred for 2 h. The reaction was concentrated at reduced pressure, the residue was triturated in Et$_2$O, and the resultant precipitate was collected by vacuum filtration, washed with CH$_2$Cl$_2$, Et$_2$O and dried to afford 6-(3-(2,2,6,6-tetramethylpiperidin-4-yl)-3H-[1,2,3]triazolo[4,5-c]pyridazin-6-yl)quinolin-7-ol hydrobromide (97 mg, 76%) as an orange solid.

MS m/z 404.5 [M+H]$^+$; $^1$H NMR (methanol-d$_4$) δ: 9.21-9.25 (m, 2H), 9.11 (dd, J=5.7, 1.3 Hz, 1H), 9.03 (s, 1H), 7.94 (dd, J=8.2, 5.7 Hz, 1H), 7.73 (s, 1H), 6.00-6.08 (m, 1H), 2.60-2.80 (m, 4H), 1.81 (s, 6H), 1.66 (s, 6H); 2 Hs not observed (NH and OH).

Example 24

Preparation of Compound 97

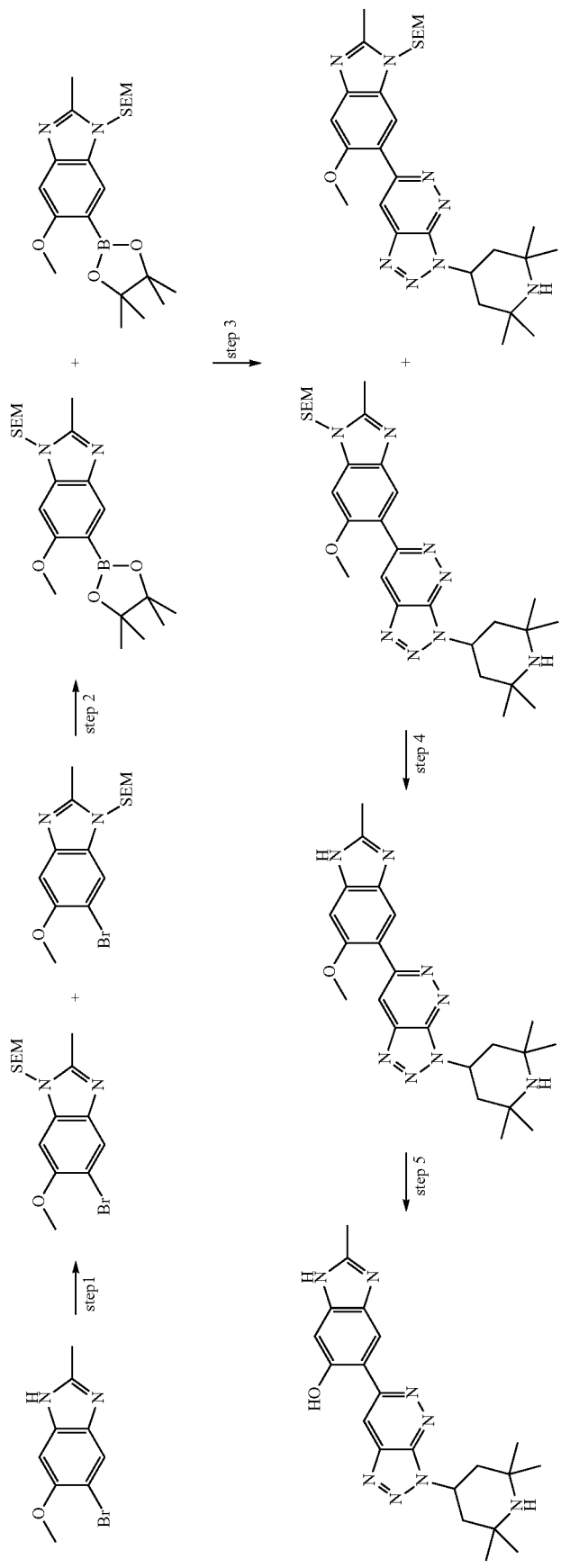

Step 1: To a solution of 5-bromo-6-methoxy-2-methyl-1H-benzo[d]imidazole (360 mg, 1.5 mmol) in DMF (5 mL) was added 60% NaH in mineral oil (90 mg, 2.25 mmol) at 0° C. under N2. The mixture was stirred at 0° C. for 15 min and then SEMCl (400 μL, 2.25 mmol) was added. The reaction was stirred at room temperature for 2 h and the mixture was quenched with ice-water (10 mL). The mixture was extracted with EtOAc (50 mL×2). The organic layer was washed with brine, dried over $Na_2SO_4$, filtered and concentrated to give the residue, which was purified by column chromatography on silica gel, eluting with a $MeOH/CH_2Cl_2$ gradient (2% to 5% MeOH) to obtain the mixture of 5-bromo-6-methoxy-2-methyl-1-((2-(trimethylsilyl)ethoxy)methyl)-1H-benzo[d]imidazole and (5-methoxy-2-methyl-1-((2-(trimethylsilyl)ethoxy)methyl)-1H-benzo[d]imidazol-6-yl)bromonium as brown oil (416 mg, 75%). MS m/z 371 [M+H]+.

Step 2: A mixture of 5-bromo-6-methoxy-2-methyl-1-((2-(trimethylsilyl)ethoxy)methyl)-1H-benzo[d]imidazole and (5-methoxy-2-methyl-1-((2-(trimethylsilyl)ethoxy)methyl)-1H-benzo[d]imidazol-6-yl)bromonium (370 mg, 1 mmol), $B_2(pin)_2$ (280 mg, 1.1 mmol), Pd $(dppf)Cl_2$ (73 mg, 0.1 mmol) and KOAc (196 mg, 2 mmol) in 1,4-dioxane (5 mL) was stirred at 90° C. under N2 for 3 h. The solution was concentrated to give a crude mixture of 6-methoxy-2-methyl-5-(4,4,5,5-tetramethyl-1,3,2-dioxaborolan-2-yl)-1-((2-(trimethylsilyl)ethoxy)methyl)-1H-benzo[d]imidazole and 2-(5-methoxy-2-methyl-1-((2-(trimethylsilyl)ethoxy)methyl)-1H-benzo[d]imidazol-6-yl)-4,4,5,5-tetramethyl-1,3,2-dioxaborolan-1-ium, which was used in the next step without purification.

Step 3: A mixture of above crude 6-methoxy-2-methyl-5-(4,4,5,5-tetramethyl-1,3,2-dioxaborolan-2-yl)-1-((2-(trimethylsilyl)ethoxy)methyl)-1H-benzo[d]imidazole and 2-(5-methoxy-2-methyl-1-((2-(trimethylsilyl)ethoxy)methyl)-1H-benzo[d]imidazol-6-yl)-4,4,5,5-tetramethyl-1,3,2-dioxaborolan-1-ium (150 mg, 0.51 mmol), 6-chloro-3-(2,2,6,6-tetramethylpiperidin-4-yl)-3H-[1,2,3]triazolo[4,5-c]pyridazine (prepared in Example 13, step 2, 147 mg, 0.5 mmol), Pd $(dppf)Cl_2$ (73 mg, 0.1 mmol), and $K_2CO_3$ (178 mg, 1.3 mmol) in 1,4-dioxane-$H_2O$ (4 mL, 3/1, v/v) was stirred at 90° C. under N2 for 3 h. The solution was concentrated and the residue was purified by column chromatography on silica gel, eluting with a $CH_2Cl_2$/MeOH gradient (0% to 5% MeOH) to give a mixture of 6-(6-methoxy-2-methyl-1-((2-(trimethylsilyl)ethoxy)methyl)-1H-benzo[d]imidazol-5-yl)-3-(2,2,6,6-tetramethylpiperidin-4-yl)-3H-[1,2,3]triazolo[4,5-c]pyridazine and 6-(5-methoxy-2-methyl-1-((2-(trimethylsilyl)ethoxy)methyl)-1H-benzo[d]imidazol-6-yl)-3-(2,2,6,6-tetramethylpiperidin-4-yl)-3H-[1,2,3]triazolo[4,5-c]pyridazine as brown oil (220 mg, 79%). MS m/z 551 [M+H]+.

Step 4: To a solution of a mixture of 6-(6-methoxy-2-methyl-1-((2-(trimethylsilyl)ethoxy)methyl)-1H-benzo[d]imidazol-5-yl)-3-(2,2,6,6-tetramethylpiperidin-4-yl)-3H-[1,2,3]triazolo[4,5-c]pyridazine and 6-(5-methoxy-2-methyl-1-((2-(trimethylsilyl)ethoxy)methyl)-1H-benzo[d]imidazol-6-yl)-3-(2,2,6,6-tetramethylpiperidin-4-yl)-3H-[1,2,3]triazolo[4,5-c]pyridazine (220 mg, 0.4 mmol) in $CH_2Cl_2$ (1 mL) was added TFA (912 mg, 8 mmol). The mixture was stirred at room temperature for 16 h. The mixture was concentrated to give crude 6-(6-methoxy-2-methyl-1H-benzo[d]imidazol-5-yl)-3-(2,2,6,6-tetramethylpiperidin-4-yl)-3H-[1,2,3]triazolo[4,5-c]pyridazine, which was used in the next step without further purification (151 mg, 90%). MS m/z 421 [M+H]+.

Step 5: To a solution of 6-(6-methoxy-2-methyl-1H-benzo[d]imidazol-5-yl)-3-(2,2,6,6-tetramethylpiperidin-4-yl)-3H-[1,2,3]triazolo[4,5-c]pyridazine (150 mg, 0.36 mmol) in $CH_2Cl_2$ (3 mL) was added 1.0M $BBr_3$ in $CH_2Cl_2$ (3 mL, 3 mmol). The reaction was stirred at room temperature for 16 h, then quenched with MeOH (5 mL) and concentrated. The residue was dissolved in MeOH (with 2.5% $NH_4OH$), filtered, concentrated and purified by prep-HPLC to obtain 2-methyl-5-(3-(2,2,6,6-tetramethylpiperidin-4-yl)-3H-[1,2,3]triazolo[4,5-c]pyridazin-6-yl)-1H-benzo[d]imidazol-6-ol as yellow solid (30 mg, 21%).

MS m/z 407.3 [M+H]+; $^1$H NMR (methanol-$d_4$) δ 9.00 (s, 1H), 8.11 (s, 1H), 7.09 (s, 1H), 5.83-5.79 (m, 1H), 2.58 (s, 3H), 2.39-2.24 (m, 4H), 2.18 (s, 1H), 1.50 (s, 6H), 1.35 (s, 6H); 2 Hs not observed (NH and OH).

Example 25

Preparation of Compound 92

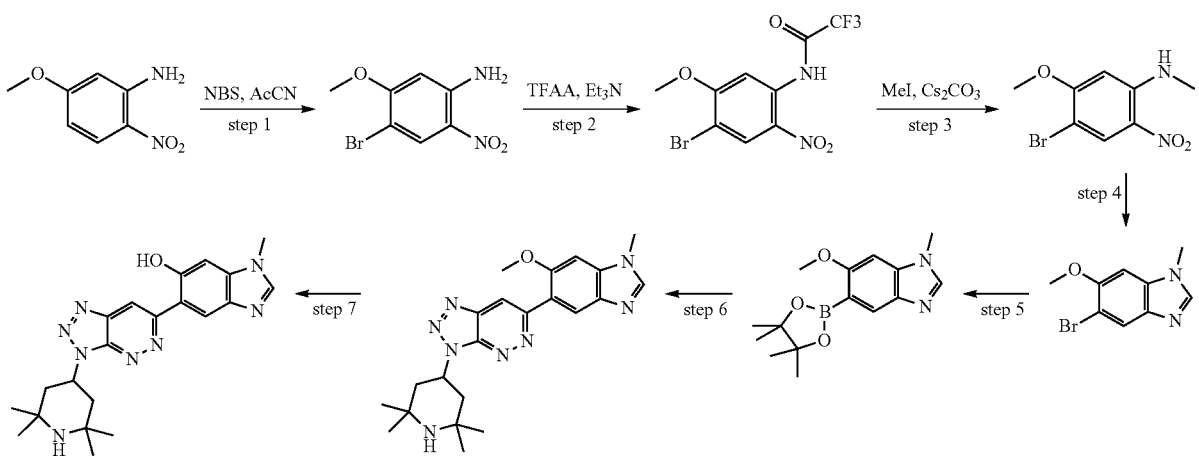

Step 1: 5-Methoxy-2-nitroaniline (7.2 g, 43 mmol) and NBS (7.5 g, 43 mmol) were dissolved in acetonitrile (70 mL) and cooled to 0° C. Then TFA (3.2 mL, 43 mmol) was added dropwise into the mixture. The ice-bath was removed and the reaction was stirred for 4 h at room temperature. Water (100 mL) was added and the pH was adjusted to 8 by adding 2.5 M NaOH. The formed precipitate was recrystallized from methanol to give 4-bromo-5-methoxy-2-nitroaniline as a yellow solid (9.65 g, 82%). MS m/z 247, 249 [M+H]$^+$ Step 2: To a solution of 4-bromo-5-methoxy-2-nitroaniline (4.92 g, 20 mmol) and TEA (5.6 mL, 40 mmol) in CH$_2$Cl$_2$ (50 mL) was added TFAA (5.6 mL, 40 mmol) at 0° C. The reaction mixture was stirred at room temperature for 2 h. The solution was concentrated to give a crude intermediate, which was purified by column chromatography on silica gel, eluting with a EtOAc/hexanes gradient (4% to 10% EtOAc) to obtain N-(4-bromo-5-methoxy-2-nitrophenyl)-2,2,2-trifluoroacetamide as yellow solid (4.5 g, 66%). MS m/z 343,345 [M+H]$^+$.

Step 3: To a solution of N-(4-bromo-5-methoxy-2-nitrophenyl)-2,2,2-trifluoroacetamide (3.42 g, 10 mmol) and Cs$_2$CO$_3$ (9.78 g, 3 mmol) in DMF (50 mL) was added MeI (3.8 mL, 25 mmol). The mixture was stirred at room temperature for 3 h. 1 M NaOH (10 mL) was added and the reaction was stirred for additional 1 h. The mixture was partitioned between EtOAc and H$_2$O. The organic layer was washed with brine and concentrated to give 4-bromo-5-methoxy-N-methyl-2-nitroaniline as yellow oil without further purification (2.34 g, 90%). MS m/z 261,263 [M+H]$^+$.

Step 4: A mixture of 4-bromo-5-methoxy-N-methyl-2-nitroaniline (2.0 g, 7.7 mmol) and Fe (4.3 g, 77 mmol) in formic acid (20 mL) was stirred at 100° C. overnight. The mixture was diluted with MeOH (100 mL). The filtrate was concentrated and then partitioned between EtOAc and H$_2$O. The organic layer was washed with brine, dried over anhydrous Na$_2$SO$_4$ and concentrated to give 5-bromo-6-methoxy-1-methyl-1H-benzo[d]imidazole, which was used to the next step without further purification (1.63 g, 88%).

$^1$H NMR (400 MHz, CDCl$_3$) δ 7.97 (s, 1H), 7.76 (s, 1H), 6.83 (s, 1H), 3.96 (s, 3H), 3.81 (s, 3H).

Step 5: A mixture of 5-bromo-6-methoxy-1-methyl-1H-benzo[d]imidazole (240 mg, 1 mmol), B$_2$(pin)$_2$ (280 mg, 1.1 mmol), Pd(dppf)Cl$_2$ (73 mg, 0.1 mmol) and KOAc (196 mg, 2 mmol) in 1,4-dioxane (4 mL) was stirred at 90° C. under N2 for 3 hours. The solution was filtered through Celite and concentrated to give the crude 6-methoxy-1-methyl-5-(4,4,5,5-tetramethyl-1,3,2-dioxaborolan-2-yl)-1H-benzo[d]imidazole without purification for next step. MS m/z 289 [M+H]$^+$.

Step 6: A mixture of above crude 6-methoxy-1-methyl-5-(4,4,5,5-tetramethyl-1,3,2-dioxaborolan-2-yl)-1H-benzo[d]imidazole, 6-chloro-3-(2,2,6,6-tetramethylpiperidin-4-yl)-3H-[1,2,3]triazolo[4,5-c]pyridazine (prepared in example 13, step 2, 200 mg, 0.68 mmol), Pd (dppf)Cl$_2$ (50 mg, 0.068 mmol) and K$_2$CO$_3$ (188 mg, 1.36 mmol) in 1,4-dioxane (4 mL) and water (1 mL) was stirred at 90° C. under N2 for 3 h. The solution was concentrated and the residue was purified by column chromatography on silica gel, eluting with a MeOH/CH$_2$Cl$_2$ gradient (0% to 5% MeOH) to give 6-(6-methoxy-1-methyl-1H-benzo[d]imidazol-5-yl)-3-(2,2,6,6-tetramethylpiperidin-4-yl)-3H-[1,2,3]triazolo[4,5-c]pyridazine as brown oil (228 mg, 80%). MS m/z 421 [M+H]$^+$.

Step 7: To a solution of 6-(6-methoxy-1-methyl-H-benzo[d]imidazol-5-yl)-3-(2,2,6,6-tetramethylpiperidin-4-yl)-3H-[1,2,3]triazolo[4,5-c]pyridazine (100 mg, 0.24 mmol) in CH$_2$Cl$_2$ (3 mL) was added 1 M BBr$_3$ in CH$_2$Cl$_2$ (3 mL, 3 mmol). The reaction was stirred at room temperature for 16 h. The reaction was quenched with MeOH (5 mL) and concentrated. The residue was dissolved in MeOH (with 2.5% NH$_4$OH), filtered and concentrated and purified by prep-TLC eluting with CH$_2$Cl/30% MeOH (with 2.5% NH$_4$OH) to obtain 1-methyl-5-(3-(2,2,6,6-tetramethylpiperidin-4-yl)-3H-[1,2,3]triazolo[4,5-c]pyridazin-6-yl)-1H-benzo[d]imidazol-6-ol, as yellow solid (48 mg, 50%).

MS m/z 407.1 [M+H]$^+$; $^1$H NMR (methanol-d$_4$) δ: 8.95 (s, 1H), 8.30 (s, 1H), 7.92 (s, 1H), 7.41 (s, 2H), 7.11 (s, 1H), 5.74 (tt, J=11.0, 5.5 Hz, 1H), 3.87 (s, 3H), 2.10-2.39 (m, 4H), 1.48 (s, 6H), 1.33 (s, 6H).

Example 26

Preparation of Compound 94

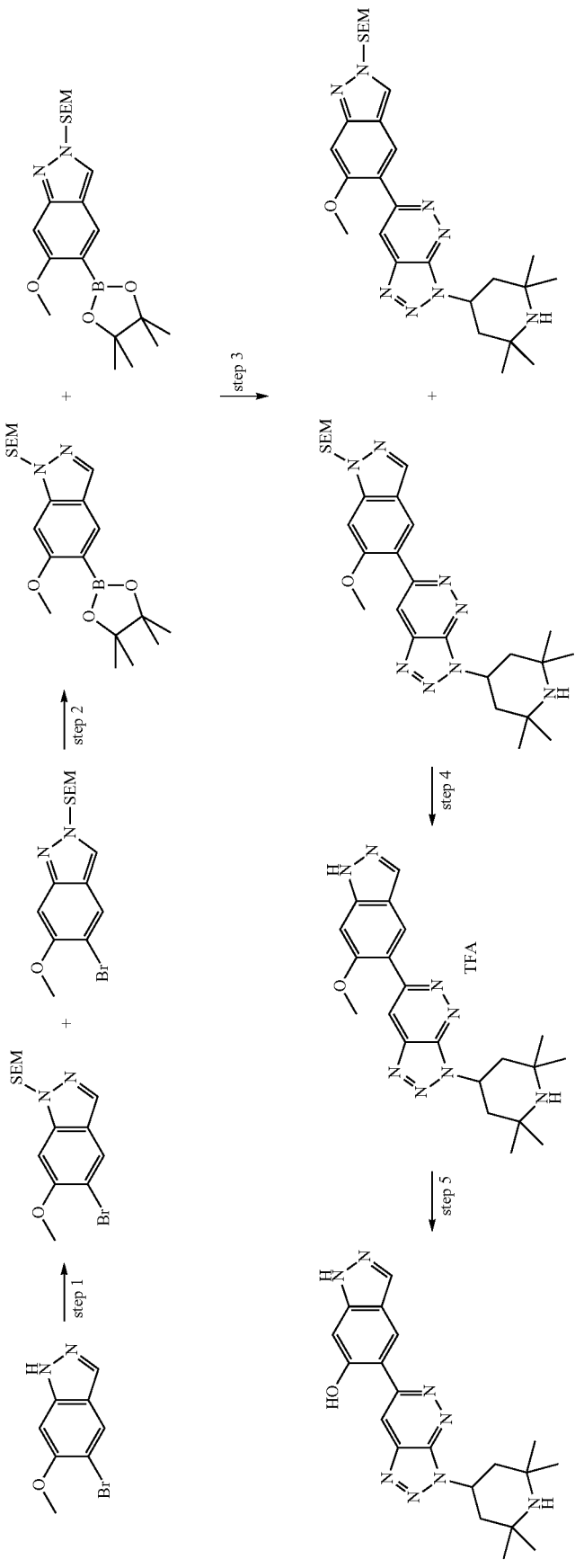

Step 1: To a solution of 5-bromo-6-methoxy-1H-indazole (250 mg, 1.1 mmol) in DMF (5 mL) was added 60% NaH in mineral oil (66 mg, 1.65 mmol) at 0° C. under N2. The mixture was stirred at 0° C. for 15 min and then SEMCl (300 µL, 1.65 mmol) was added. The reaction was stirred at room temperature for 2 h and then was quenched with ice-water (10 mL). The mixture was extracted with EtOAc (50 mL×2). The organic layer was washed with brine, dried over $Na_2SO_4$, filtered and concentrated to give the crude residue, which was purified by column chromatography on silica gel, eluting with a MeOH/$CH_2Cl_2$ gradient (0% to 3% MeOH) to give a mixture of 5-bromo-6-methoxy-1-((2-(trimethylsilyl)ethoxy)methyl)-1H-indazole and 5-bromo-6-methoxy-2-((2-(trimethylsilyl)ethoxy)methyl)-2H-indazole as brown oil (315 mg, 80%). MS m/z 357,359 [M+H]$^+$.

Step 2: A mixture of 5-bromo-6-methoxy-1-((2-(trimethylsilyl)ethoxy)methyl)-1H-indazole and 5-bromo-6-methoxy-2-((2-(trimethylsilyl)ethoxy)methyl)-2H-indazole (300 mg, 0.84 mmol), $B_2$(pin)$_2$ (235 mg, 0.924 mmol), Pd(dppf)Cl$_2$ (61 mg, 0.084 mmol) and KOAc (165 mg, 1.68 mmol) in 1,4-dioxane (5 mL) was stirred at 90° C. under N2 for 3 h. The solution was concentrated to give a crude mixture of 6-methoxy-5-(4,4,5,5-tetramethyl-1,3,2-dioxaborolan-2-yl)-1-((2-(trimethylsilyl)ethoxy)methyl)-1H-indazole and 6-methoxy-5-(4,4,5,5-tetramethyl-1,3,2-dioxaborolan-2-yl)-2-((2-(trimethylsilyl)ethoxy)methyl)-2H-indazole, which was used in the next step without further purification. MS m/z 405 [M+H]$^+$.

Step 3: A mixture of 6-methoxy-5-(4,4,5,5-tetramethyl-1,3,2-dioxaborolan-2-yl)-1-((2-(trimethylsilyl)ethoxy)methyl)-1H-indazole and 6-methoxy-5-(4,4,5,5-tetramethyl-1,3,2-dioxaborolan-2-yl)-2-((2-(trimethylsilyl)ethoxy)methyl)-2H-indazole, 6-chloro-3-(2,2,6,6-tetramethylpiperidin-4-yl)-3H-[1,2,3]triazolo[4,5-c]pyridazine (prepared in example 13, step 2, 170 mg, 0.58 mmol), Pd(dppf)Cl$_2$ (42 mg, 0.058 mmol) and K$_2$CO$_3$ (199 mg, 1.45 mmol) in 1,4-dioxane-H$_2$O (4 mL) was stirred at 90° C. under N2 for 3 h. The solution was concentrated and the residue was purified by column chromatography on silica gel, eluting with a MeOH/$CH_2Cl_2$ gradient (0% to 3% MeOH) to give a mixture of 6-(6-methoxy-1-((2-(trimethylsilyl)ethoxy)methyl)-1H-indazol-5-yl)-3-(2,2,6,6-tetramethylpiperidin-4-yl)-3H-[1,2,3]triazolo[4,5-c]pyridazine and 6-(6-methoxy-2-((2-(trimethylsilyl)ethoxy)methyl)-2H-indazol-5-yl)-3-(2,2,6,6-tetramethylpiperidin-4-yl)-3H-[1,2,3]triazolo[4,5-c]pyridazine as brown oil (217 mg, 70%). MS m/z 537 [M+H]$^+$.

Step 4: A solution of 6-(6-methoxy-1-((2-(trimethylsilyl)ethoxy)methyl)-1H-indazol-5-yl)-3-(2,2,6,6-tetramethylpiperidin-4-yl)-3H-[1,2,3]triazolo[4,5-c]pyridazine and 6-(6-methoxy-2-((2-(trimethylsilyl)ethoxy)methyl)-2H-indazol-5-yl)-3-(2,2,6,6-tetramethylpiperidin-4-yl)-3H-[1,2,3]triazolo[4,5-c]pyridazine (217 mg, 0.4 mmol) in $CH_2Cl_2$ (1 mL) was added TFA (912 mg, 8 mmol). The mixture was stirred at room temperature for 16 h. The mixture was concentrated to give the crude 6-(6-methoxy-1H-indazol-5-yl)-3-(2,2,6,6-tetramethylpiperidin-4-yl)-3H-[1,2,3]triazolo[4,5-c]pyridazine trifluoroacetic acid salt, which was used in the next step without further purification (150 mg, 90%). MS m/z 407 [M+H]$^+$.

Step 5: To a solution of 6-(6-methoxy-1H-indazol-5-yl)-3-(2,2,6,6-tetramethylpiperidin-4-yl)-3H-[1,2,3]triazolo[4,5-c]pyridazine (150 mg, 0.37 mmol) in $CH_2Cl_2$ (3 mL) was added 1 M BBr$_3$ in $CH_2Cl_2$ (3 mL, 3 mmol). The reaction was stirred at room temperature for 16 h. The reaction was quenched with MeOH (5 mL) and concentrated. The residue was dissolved in MeOH (with 2.5% NH$_4$OH), filtered and concentrated to give the crude product, which was purified by prep-TLC eluting with $CH_2Cl$/30% OMeOH (with 2.5% NH$_4$OH) to obtain 5-(3-(2,2,6,6-tetramethylpiperidin-4-yl)-3H-[1,2,3]triazolo[4,5-c]pyridazin-6-yl)-1H-indazol-6-ol as yellow solid (70 mg, 48%).

MS m/z 393.8 [M+H]$^+$; $^1$H NMR (DMSO-d$_6$) δ: 12.79 (br s, 1H), 11.00 (br s, 1H), 8.98 (s, 1H), 8.32 (s, 1H), 8.06 (s, 1H), 7.06 (s, 1H), 5.58-5.87 (m, 1H), 2.17-2.35 (m, 4H), 1.43 (s, 6H), 1.26 (s, 6H); 1H not observed (NH).

Example 27

Preparation of Compound 82

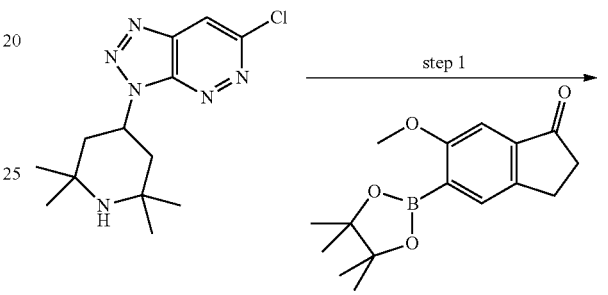

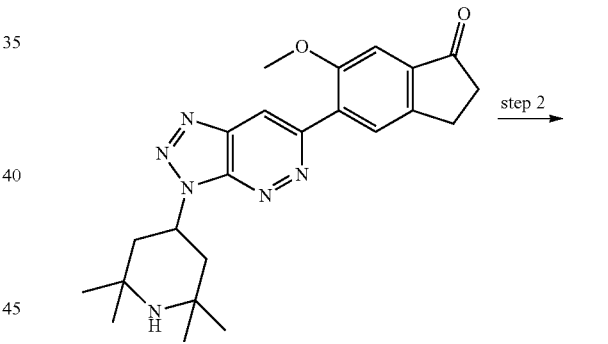

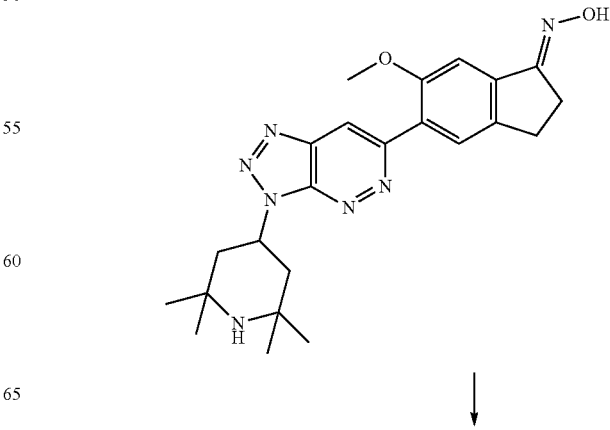

-continued

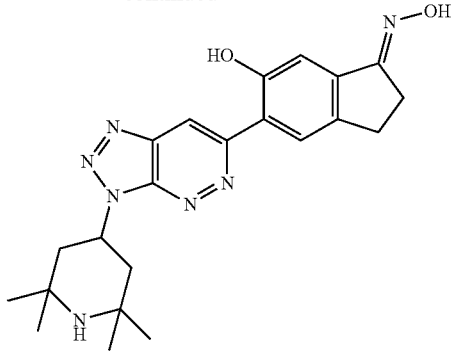

Step 1: A mixture of 6-methoxy-5-(4,4,5,5-tetramethyl-1,3,2-dioxaborolan-2-yl)-2,3-dihydro-1H-inden-1-one (1.04 g, 3.6 mmol), 6-chloro-3-(2,2,6,6-tetramethylpiperidin-4-yl)-3H-[1,2,3]triazolo[4,5-c]pyridazine (prepared in example 13, step 2, 882 mg, 3 mmol), Pd (dppf)Cl$_2$ (220 mg, 0.3 mmol) and K$_2$CO$_3$ (828 mg, 6 mmol) in 1,4-dioxane (12 mL) and water (3 mL) was stirred at 90° C. under N2 for 3 h. The solution was concentrated and the residue was purified by silica gel column chromatography eluting with a MeOH/CH$_2$Cl$_2$ gradient (0 to 5% MeOH) to afford 6-methoxy-5-(3-(2,2,6,6-tetramethylpiperidin-4-yl)-3H-[1,2,3]triazolo[4,5-c]pyridazin-6-yl)-2,3-dihydro-1H-inden-1-one as an orange-yellow solid (1 g, 79%).

MS m/z 421 [M+H]$^+$; $^1$H NMR (CDCl$_3$) δ 8.75 (s, 1H), 8.18 (s, 1H), 7.40 (d, J=5.0 Hz, 1H), 5.85-5.67 (m, 1H), 3.95 (s, 3H), 3.26-3.13 (m, 2H), 2.88-2.72 (m, 2H), 2.28 (d, J=7.3 Hz, 4H), 1.27 (d, J=21.2 Hz, 12H).

Step 2: A mixture of 6-methoxy-5-(3-(2,2,6,6-tetramethylpiperidin-4-yl)-3H-[1,2,3]triazolo[4,5-c]pyridazin-6-yl)-2,3-dihydro-1H-inden-1-one (210 mg, 0.5 mmol), NH$_2$OH·HCl (69 mg, 1 mmol) and Et$_3$N (0.17 mL, 1.25 mmol) in EtOH (4 mL) was stirred at 90° C. for 4 h. The reaction mixture was cooled to room temperature. The precipitate was collected by filtration, washed with Et$_2$O and dried to afford 6-methoxy-5-(3-(2,2,6,6-tetramethylpiperidin-4-yl)-3H-[1,2,3]triazolo[4,5-c]pyridazin-6-yl)-2,3-dihydro-1H-inden-1-one oxime as white solid (174 mg, 80%). MS m/z 436 [M+H]$^+$;

Step 3: To a solution of 6-methoxy-5-(3-(2,2,6,6-tetramethylpiperidin-4-yl)-3H-[1,2,3]triazolo[4,5-c]pyridazin-6-yl)-2,3-dihydro-1H-inden-1-one oxime (66 mg, 0.15 mmol) in CH$_2$Cl$_2$ (3 mL) was added 1 M BBr$_3$ in CH$_2$Cl$_2$ (2 mL, 2 mmol). The reaction was stirred at room temperature for 16 h, then quenched with MeOH (5 mL) and concentrated. The residue was dissolved in MeOH (with 2.5% NH$_4$OH), filtered, concentrated and then purified by prep-HPLC to afford 6-hydroxy-5-(3-(2,2,6,6-tetramethylpiperidin-4-yl)-3H-[1,2,3]triazolo[4,5-c]pyridazin-6-yl)-2,3-dihydro-1H-inden-1-one oxime as yellow solid (33 mg, 52%).

MS m/z 421.9 [M+H]$^+$; $^1$H NMR (DMSO-d$_6$) δ: 10.93-11.19 (m, 2H), 9.02 (s, 1H), 7.96 (s, 1H), 7.22 (s, 1H), 5.67 (tt, J=12.3, 3.4 Hz, 1H), 2.91-3.08 (m, 2H), 2.74-2.91 (m, 2H), 2.20 (dd, J=12.1, 3.3 Hz, 2H), 2.11 (t, J=12.3 Hz, 2H), 1.35 (s, 6H), 1.18 (s, 6H); 1H not observed (NH or OH).

Example 28

Preparation of Compound 42

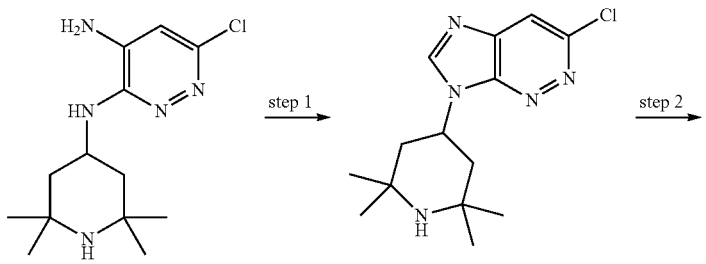

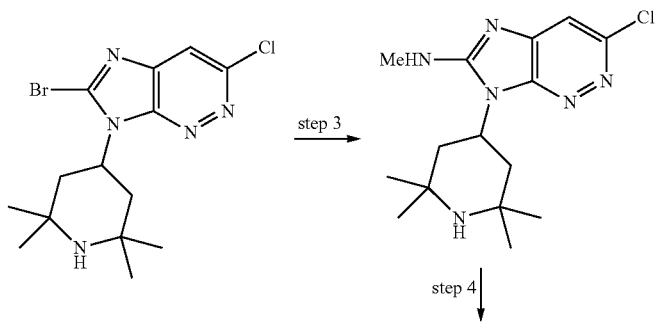

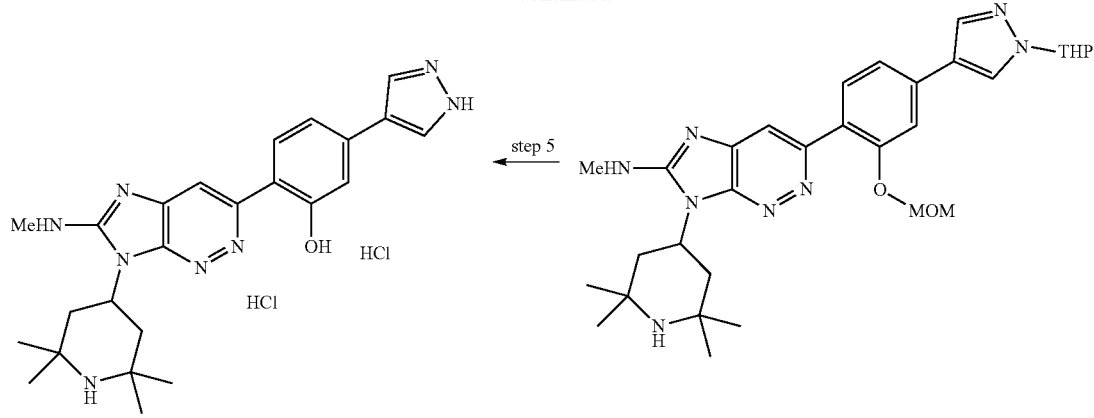

Step 1: A mixture of 6-chloro-N3-(2,2,6,6-tetramethyl-4-piperidyl)pyridazine-3,4-diamine (prepared in example 13, step 1, 200 mg, 0.35 mmol) in triethylorthoformate (8 mL) and aq. 4N HCl (1 drop) was stirred at 100° C. for 24 h. The crude reaction mixture was diluted with MeOH to afford a clear solution and concentrated. The residue was purified by silica gel column chromatography eluting with a MeOH (2.5% NH$_4$OH)/CH$_2$Cl$_2$ gradient (0 to 20% MeOH/NH$_4$OH) to afford 3-chloro-7-(2,2,6,6-tetramethyl-4-piperidyl)imidazo[4,5-c]pyridazine (144 mg, 70%) as a clear oil that solidified under high vacuum. MS m/z 294.5 [M+H]$^+$.

Step 2: To a suspension of 3-chloro-7-(2,2,6,6-tetramethyl-4-piperidyl)imidazo[4,5-c]pyridazine (95 mg, 0.32 mmol) in CHCl$_3$ (0.5 mL) and MeOH (0.5 mL) was added N-bromosuccinimide (178 mg, 0.98 mmol). The reaction was heated at 70° C. for 48 h. Solvents were removed under reduced pressure and the residue was purified by silica gel column chromatography eluting with a MeOH (with 2.5% NH$_4$OH)/CH$_2$Cl$_2$ gradient (0 to 10% MeOH/NH$_4$OH) to afford 6-bromo-3-chloro-7-(2,2,6,6-tetramethyl-4-piperidyl)imidazo[4,5-c]pyridazine (80 mg, 66%) as a white solid.

Step 3: To a solution of 6-bromo-3-chloro-7-(2,2,6,6-tetramethyl-4-piperidyl)imidazo[4,5-c]pyridazine (25 mg, 0.07 mmol) in MeOH (1 mL) was added 8 M methylamine in MeOH (63 µL, 0.5 mmol). The reaction was stirred at 50° C. until complete conversion of starting material was obtained. The reaction was concentrated and purified by silica gel column chromatography eluting with a MeOH (with 2.5% NH$_4$OH)/CH$_2$Cl$_2$ gradient (0 to 30% MeOH/NH$_4$OH) to afford 3-chloro-N-methyl-7-(2,2,6,6-tetramethyl-4-piperidyl)imidazo[4,5-c]pyridazin-6-amine (20 mg, 65%) as a clear solid. MS m/z 323.2 [M+H]$^+$.

Step 4: A mixture of 3-chloro-N-methyl-7-(2,2,6,6-tetramethyl-4-piperidyl)imidazo[4,5-c]pyridazin-6-amine (20 mg, 0.062 mmol), [1,1'-bis(diphenylphosphino)ferrocene]dichloropalladium(I) (3.3 mg, 0.004 mmol), and 4-[3-(methoxymethoxy)-4-(4,4,5,5-tetramethyl-1,3,2-dioxaborolan-2-yl)phenyl]-1-tetrahydropyran-2-yl-pyrazole (prepared in example 1, step 7, 32 mg, 0.077 mmol) in 1,4-dioxane (1 mL) was purged with argon for 10 min. Then a solution of potassium carbonate (15 mg, 0.11 mmol) in water (0.2 mL) was added and the reaction mixture was heated to 90° C. for 3 h. The reaction was diluted with EtOAc and filtered through a small pad of Celite (washing with 20% MeOH/CH$_2$Cl$_2$). The organic solution was concentrated and purified by silica gel column chromatography eluting with a MeOH/CH$_2$Cl$_2$ gradient (0-20% MeOH) to afford 3-[2-(methoxymethoxy)-4-(1-tetrahydropyran-2-ylpyrazol-4-yl)phenyl]-N-methyl-7-(2,2,6,6-tetramethyl-4-piperidyl)imidazo[4,5-c]pyridazin-6-amine (17 mg, 68%) as a light brown solid. MS m/z 575.4 [M+H]$^+$.

Step 5: To 3-[2-(methoxymethoxy)-4-(1-tetrahydropyran-2-ylpyrazol-4-yl)phenyl]-N-methyl-7-(2,2,6,6-tetramethyl-4-piperidyl)imidazo[4,5-c]pyridazin-6-amine (17 mg, 0.03 mmol) was added 4 N HCl in dioxane (1 mL, 4 mmol). The reaction was stirred for 4 h and then filtered to collect the solid precipitate. The solid was further washed with diethyl ether and dried to afford 2-[6-(methylamino)-7-(2,2,6,6-tetramethyl-4-piperidyl)imidazo[4,5-c]pyridazin-3-yl]-5-(1H-pyrazol-4-yl)phenol dihydrochloride as a yellow solid (12.6 mg, 60%).

MS m/z 447.9 [M+H]$^+$; $^1$H NMR (methanol-d$_4$) δ: 8.79 (s, 1H), 8.50-8.62 (m, 2H), 7.44-7.55 (m, 2H), 7.40 (s, 1H), 5.26-5.41 (m, 1H), 3.85 (s, 3H), 2.50-2.64 (m, 2H), 2.32-2.49 (m, 2H), 1.71 (s, 6H), 1.63 (s, 6H); 4 Hs not observed (3 NHs and OH).

Using the procedure described for Example 28, above, additional compounds described herein were prepared by substituting the appropriate starting materials, suitable reagents and reaction conditions, obtaining compounds such as those selected from:

| Cpd | Data |
|---|---|
| 9 | MS m/z 434.4 [M + H]$^+$; $^1$H NMR (methanol-d$_4$) δ: 8.15 (br s, 2H), 7.99 (s, 1H), 7.69 (d, J = 8.2 Hz, 1H), 7.40 (dd, J = 7.6, 1.3 Hz, 1H), 7.31 (d, J = 1.9 Hz, 1H), 4.96-5.07 (m, 1H), 2.71 (t, J = 13.6 Hz, 2H), 2.18 (dd, J = 13.6, 3.5 Hz, 2H), 1.66 (s, 6H), 1.58 (s, 6H); 4 Hs not observed (2 OH and 2 NH). |
| 40 | MS m/z 448.2 [M + H]$^+$; $^1$H NMR (methanol-d$_4$) δ : 9.13 (s, 1H), 8.26 (s, 2H), 7.55 (d, J = 8.2 Hz, 1H), 7.38 (d, J = 1.3 Hz, 1H), 7.31 (d, J = 1.3 Hz, 1H), 5.40-5.51 (m, 1H), 4.79 (s, 3H), 2.54-2.70 (m, 4H), 1.73 (s, 6H), 1.65 (s, 6H); 3 Hs not observed (2 NHs and OH). |

-continued

| Cpd | Data |
|---|---|
| 49 | MS m/z 461.9 [M + H]+; 1H NMR (methanol-d4) δ: 8.78 (s, 1H), 8.28-8.36 (m, 2H), 7.34-7.50 (m, 2H), 7.30 (s, 1H), 5.25-5.41 (m, 1H), 4.11-4.15 (q, J = 6.0 Hz, 2H), 2.51-2.65 (m, 2H), 2.33-2.49 (m, 2H), 1.71 (s, 6H), 1.63 (s, 6H), 1.38-1.41 (t, J = 6.0 Hz, 3H); 4 Hs not observed (3 NHs and OH). |

Example 29

Preparation of Compound 3

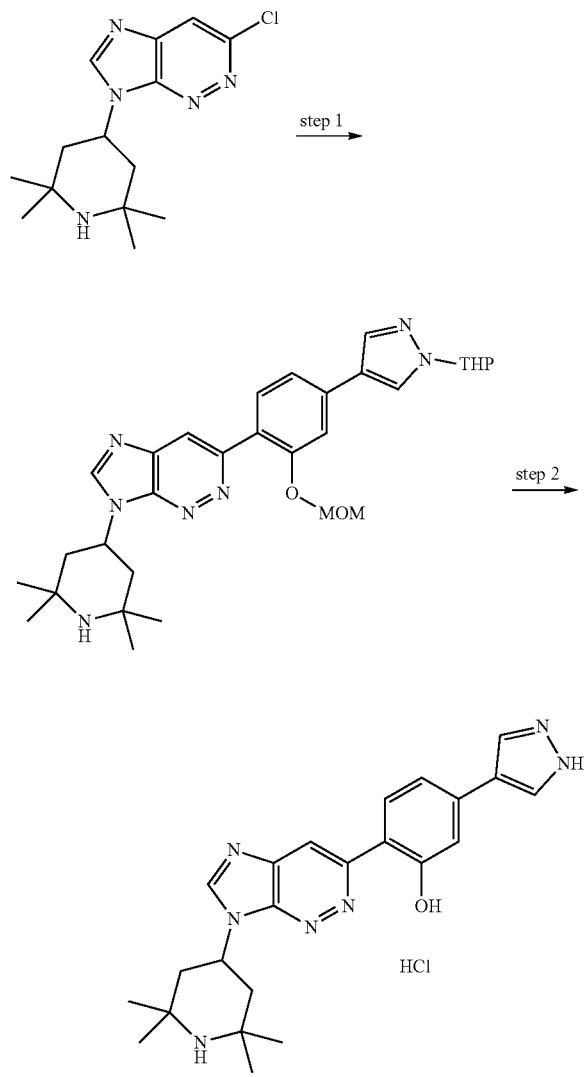

Step 1: An oven-dried flask was equipped with a magnetic stir bar and charged with 3-chloro-7-(2,2,6,6-tetramethylpiperidin-4-yl)-7H-imidazo[4,5-c]pyridazine (prepared in example 29, step 1, 60 mg, 0.15 mmol), tetrakis(triphenylphosphine)palladium(0) (25 mg, 0.015 mmol), and 4-[3-(methoxymethoxy)-4-(4,4,5,5-tetramethyl-1,3,2-dioxaborolan-2-yl)phenyl]-1-tetrahydropyran-2-yl-pyrazole (prepared in example 1, step 7, 75 mg, 0.15 mmol), and Na2CO3 (46 mg, 0.45 mmol).

The flask was sealed with a rubber septum, and then evacuated and backfilled with argon (repeated a total of 3×). 1,4-Dioxane (3 mL) and water (0.4 mL) were added and the reaction was heated to 90° C. for 16 h. The reaction was cooled to room temperature, diluted with water (2 mL), and extracted with EtOAc (3×). The combined organic phases were dried over Na2SO4, concentrated under reduced pressure, and purified by column chromatography, eluting with a MeOH/CH2Cl2 gradient (0-20% MeOH) to provide 3-(2-(methoxymethoxy)-4-(1-(tetrahydro-2H-pyran-2-yl)-1H-pyrazol-4-yl)phenyl)-7-(2,2,6,6-tetramethylpiperidin-4-yl)-7H-imidazo[4,5-c]pyridazine (60 mg, 75%) as a yellow solid. MS m/z 546.2 [M+H]+.

Step 2: 3-(2-(Methoxymethoxy)-4-(1-(tetrahydro-2H-pyran-2-yl)-1H-pyrazol-4-yl)phenyl)-7-(2,2,6,6-tetramethylpiperidin-4-yl)-7H-imidazo[4,5-c]pyridazine (35 mg, 0.05 mmol) was dissolved in 1 mL of methanol. 4 N HCl in 1,4-dioxane (500 µL, 2 mmol) was added and the reaction stirred at room temperature for 2 h. The reaction was concentrated, triturated with 20% MeOH/ether, and the precipitate was filtered, and dried to afford 5-(1H-pyrazol-4-yl)-2-(7-(2,2,6,6-tetramethylpiperidin-4-yl)-7H-imidazo[4,5-c]pyridazin-3-yl)phenol (25 mg, 86%).

MS m/z 418.1 [M+H]+, 1H NMR (methanol-d4) δ: 9.19 (s, 1H), 8.86 (s, 1H), 8.15 (s, 2H), 7.86 (d, J=8.2 Hz, 1H), 7.39 (dd, J=8.2, 1.9 Hz, 1H), 7.32 (d, J=1.6 Hz, 1H), 5.39-5.58 (m, 1H), 2.68 (t, J=13.9 Hz, 2H), 2.48 (dd, J=13.9, 3.5 Hz, 2H), 1.72 (s, 6H), 1.63 (s, 6H); 3 Hs not observed (OH and 2 NHs).

Using the procedure described for Example 29, above, additional compounds described herein were prepared by substituting the appropriate starting materials, suitable reagents and reaction conditions, obtaining compounds such as those selected from:

| Cpd | Data |
|---|---|
| 4 | MS m/z 438.3 [M + H]+; 1H NMR (methanol-d4) δ: 9.29 (s, 1H), 8.74 (d, J = 0.9 Hz, 1H), 8.41 (d, J = 1.3 Hz, 2H), 7.84-7.95 (m, 2H), 5.44-5.65 (m, 1H), 2.73 (t, J = 13.9 Hz, 2H), 2.51 (dd, J = 13.9, 3.2 Hz, 2H), 1.74 (s, 6H), 1.65 (s, 6H); 2 Hs not observed (2 NHs). |

Example 30

Preparation of Compound 5

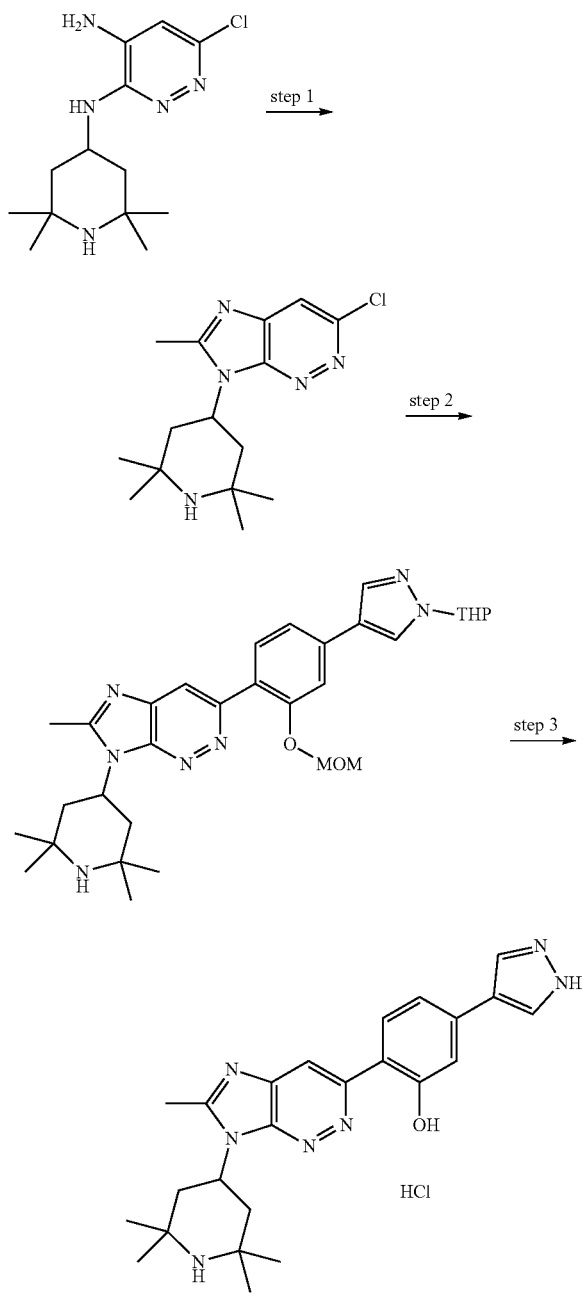

Step 1: A mixture of 6-chloro-N3-(2,2,6,6-tetramethyl-4-piperidyl)pyridazine-3,4-diamine (prepared in example 13, step 1, 180 mg, 0.63 mmol) in triethylorthoacetate (4 mL) and HCOOH (0.2 mL) was stirred at 100° C. for 24 h. The reaction was then cooled to room temperature and the precipitate was collected by filtration and dried under vacuum to afford 3-chloro-7-(2,2,6,6-tetramethyl-4-piperidyl)imidazo[4,5-c]pyridazine (112 mg, 56%). MS m/z 308.2 $[M+H]^+$.

Step 2: An oven-dried flask was equipped with a magnetic stir bar and charged with 3-chloro-6-methyl-7-(2,2,6,6-tetramethyl-4-piperidyl)imidazo[4,5-c]pyridazine (50 mg, 0.14 mmol), tetrakis(triphenylphosphine)palladium(0) (25 mg, 0.015 mmol), 4-[3-(methoxymethoxy)-4-(4,4,5,5-tetramethyl-1,3,2-dioxaborolan-2-yl)phenyl]-1-tetrahydropyran-2-yl-pyrazole (prepared in example 1, step 7, 75 mg, 0.15 mmol), and $Na_2CO_3$ (46 mg, 0.45 mmol). The flask was sealed with a rubber septum, and then evacuated and backfilled with argon (repeated a total of 3x). 1,4-Dioxane (1 mL) and water (0.25 mL) were added and the reaction was heated to 90° C. for 16 h. The reaction was cooled to room temperature, diluted with water, and extracted with EtOAc three times. The combined organic phases were dried over $Na_2SO_4$, concentrated under reduced pressure, and purified by column chromatography, eluting with a $MeOH/CH_2Cl_2$ gradient (0-20% MeOH) to provide 3-(2-(methoxymethoxy)-4-(1-(tetrahydro-2H-pyran-2-yl)-1H-pyrazol-4-yl)phenyl)-6-methyl-7-(2,2,6,6-tetramethylpiperidin-4-yl)-7H-imidazo[4,5-c]pyridazine (60 mg, 66%) as a yellow solid. MS m/z 560.5 $[M+H]^+$.

Step 3: To a solution of 3-(2-(methoxymethoxy)-4-(1-(tetrahydro-2H-pyran-2-yl)-1H-pyrazol-4-yl)phenyl)-6-methyl-7-(2,2,6,6-tetramethylpiperidin-4-yl)-7H-imidazo[4,5-c]pyridazine (45 mg, 0.05 mmol) in 1 mL of methanol was added 4 N HCl in 1,4-dioxane (500 μL, 2 mmol). The reaction was stirred at room temperature for 2 h. The reaction was concentrated, the residue was triturated in 20% MeOH/ether, and the precipitate was filtered and dried to afford 2-(6-methyl-7-(2,2,6,6-tetramethylpiperidin-4-yl)-7H-imidazo[4,5-c]pyridazin-3-yl)-5-(1H-pyrazol-4-yl)phenol hydrochloride (30 mg, 88%) as a yellow solid.

MS m/z 432.5 $[M+H]^+$; $^1H$ NMR (methanol-$d_4$) δ: 8.74 (s, 1H), 8.31-8.44 (m, 2H), 7.79 (d, J=8.2 Hz, 1H), 7.45 (dd, J=8.2, 1.6 Hz, 1H), 7.37 (s, 1H), 5.05-5.20 (m, 1H), 3.02 (s, 3H), 2.96 (t, J=13.6 Hz, 2H), 2.30-2.40 (m, 2H), 1.71 (s, 6H), 1.63 (s, 6H); 3 Hs not observed (OH and 2 NHs).

Using the procedure described for Example 30, above, additional compounds described herein were prepared by substituting the appropriate starting materials, suitable reagents and reaction conditions, obtaining compounds such as those selected from:

| Cpd | Data |
|---|---|
| 6 | MS m/z 452.4 $[M + H]^+$; $^1H$ NMR (methanol-$d_4$) δ: 8.65 (s, 1H), 8.38 (d, J = 1.6 Hz, 2H), 7.90 (dd, J = 11.3, 6.0 Hz, 1H), 7.85 (dd, J = 10.7, 6.0 Hz, 1H), 5.09-5.22 (m, 1H), 3.05 (s, 3H), 3.02 (t, J = 13.6 Hz, 2H), 2.37 (dd, J = 13.6, 3.8 Hz, 2H), 1.72 (s, 6H), 1.63 (s, 6H); 2 Hs not observed (2 NHs). |

Example 31

Preparation of Compound 1

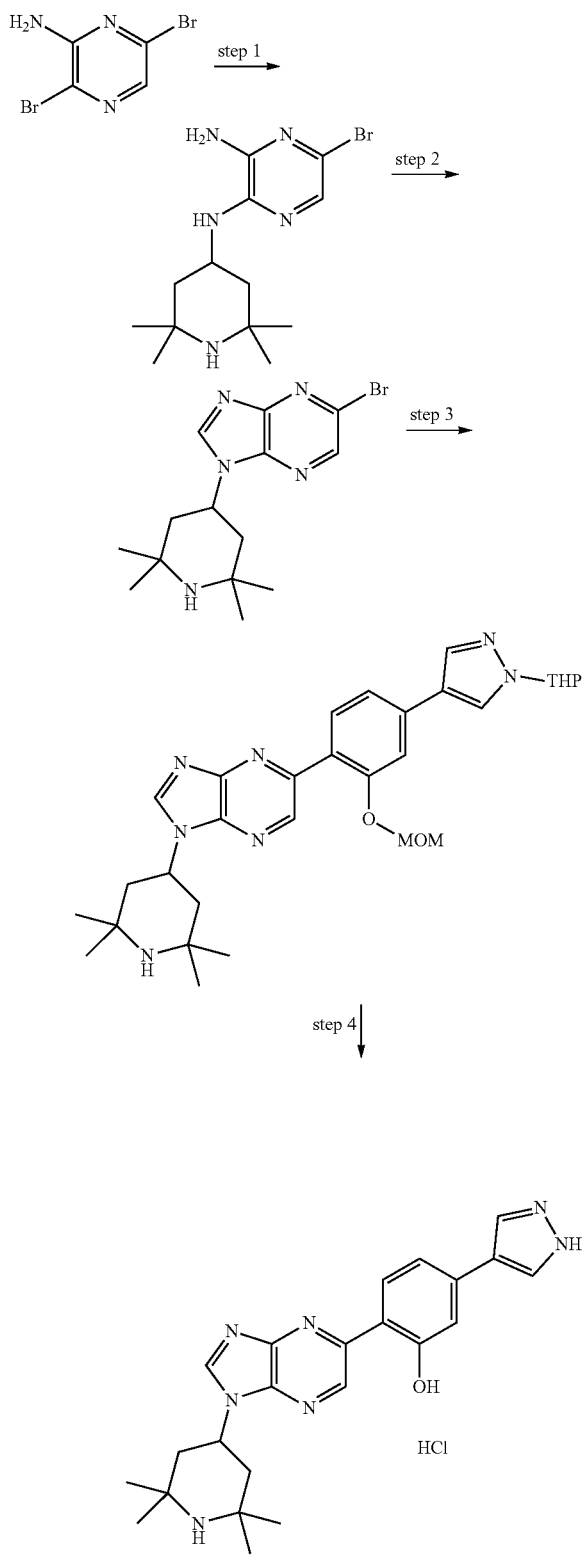

Step 1: To a solution of 3,6-dibromopyrazin-2-amine (504 mg, 2 mmol) and 2,2,6,6-tetramethylpiperidin-4-amine (0.35 mL, 2 mmol) in EtOH (2 mL) was added DIEA (0.38 mL, 2 mmol). The reaction mixture was subjected to microwave irradiation at 180° C. for 3.5 h. The reaction mixture was cooled and concentrated. The residue was purified by silica gel column chromatography eluting with a MeOH (2.5% NH$_4$OH)/CH$_2$Cl$_2$ gradient (0-30% MeOH/NH$_4$OH) to provide 5-bromo-N2-(2,2,6,6-tetramethylpiperidin-4-yl) pyrazine-2,3-diamine (0.35 g, 54%).

MS m/z 328.0, 330.0 [M+H]$^+$.

Step-2: 5-Bromo-N2-(2,2,6,6-tetramethylpiperidin-4-yl) pyrazine-2,3-diamine (0.18 mg, 0.54 mmol) was dissolved in formic acid (0.36 mL) and the resulting solution was heated to 100° C. for 3 h. The solution was concentrated to give crude 5-bromo-1-(2,2,6,6-tetramethylpiperidin-4-yl)-1H-imidazo[4,5-b]pyrazine (0.18 g, 97%). MS m/z 338.1, 340.1 [M+H]$^+$.

Step-3: An oven-dried flask was equipped with a magnetic stir bar and charged with 5-bromo-1-(2,2,6,6-tetramethylpiperidin-4-yl)-1H-imidazo[4,5-b]pyrazine (50 mg, 0.15 mmol), 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole (prepared in example 1, step 7, 62 mg, 0.15 mmol), tetrakis(triphenylphosphine)palladium(0) (25 mg, 0.015 mmol), and Na$_2$CO$_3$ (46 mg, 0.45 mmol). The flask was sealed with a rubber septum, and then evacuated and backfilled with argon (repeated a total of 3×). 1,4-Dioxane (3 mL), water (0.4 mL) were added and the reaction was heated to 90° C. for 16 h. The reaction was cooled to room temperature, diluted with water (2 mL), and extracted with EtOAc (3×). The combined organic phases were dried over Na$_2$SO$_4$, concentrated under reduced pressure, and purified by column chromatography, eluting with a MeOH/CH$_2$Cl$_2$ gradient (0-20% MeOH) to provide 5-(2-(methoxymethoxy)-4-(1-(tetrahydro-2H-pyran-2-yl)-1H-pyrazol-4-yl)phenyl)-1-(2,2,6,6-tetramethylpiperidin-4-yl)-1H-imidazo[4,5-b]pyrazine (60 mg, 75%) as a yellow solid. MS m/z 546.4 [M+H]$^+$.

Step-4: 5-(2-(Methoxymethoxy)-4-(1-(tetrahydro-2H-pyran-2-yl)-1H-pyrazol-4-yl)phenyl)-1-(2,2,6,6-tetramethylpiperidin-4-yl)-1H-imidazo[4,5-b]pyrazine (30 mg, 0.05 mmol) was dissolved in methanol (1 mL), then 4 N HCl in 1,4-dioxane (500 µL, 2 mmol) was added and the reaction stirred at room temperature for 2 h. The reaction was concentrated, triturated with 20% MeOH/ether, and the precipitate was filtered and dried to afford 5-(1H-pyrazol-4-yl)-2-(1-(2,2,6,6-tetramethylpiperidin-4-yl)-1H-imidazo[4,5-b]pyrazin-5-yl)phenol hydrochloride (22 mg, 86%) as a yellow solid.

MS m/z 418.5 [M+H]$^+$; $^1$H NMR (methanol-d$_4$) δ: 9.29 (s, 1H), 8.96-9.07 (m, 1H), 8.32 (s, 2H), 8.08-8.15 (m, 1H), 7.21-7.39 (m, 2H), 5.29-5.44 (m, 1H), 2.59-2.72 (m, 2H), 2.39-2.49 (m, 2H), 1.70 (s, 6H), 1.59 (s, 6H); 3 Hs not observed (OH and 2 NHs).

Using the procedure described for Example 31, above, additional compounds described herein were prepared by substituting the appropriate starting materials, suitable reagents and reaction conditions, obtaining compounds such as those selected from:

| Cpd | Data |
|---|---|
| 2 | MS m/z 438.4 [M + H]⁺; ¹H NMR (methanol-d₄) δ: 9.33 (s, 1H), 9.09 (d, J = 1.6 Hz, 1H), 8.36 (d, J = 1.3 Hz, 2H), 7.97 (dd, J = 11.7, 6.3 Hz, 1H), 7.77 (dd, J = 12.0, 6.3 Hz, 1H), 5.39-5.49 (m, 1H), 2.67 (t, J = 13.9 Hz, 2H), 2.46 (dd, J = 13.9, 3.5 Hz, 2H), 1.71 (s, 6H), 1.61 (s, 6H). 2 Hs not observed (2 NHs). |

Example 32

Preparation of Compound 140

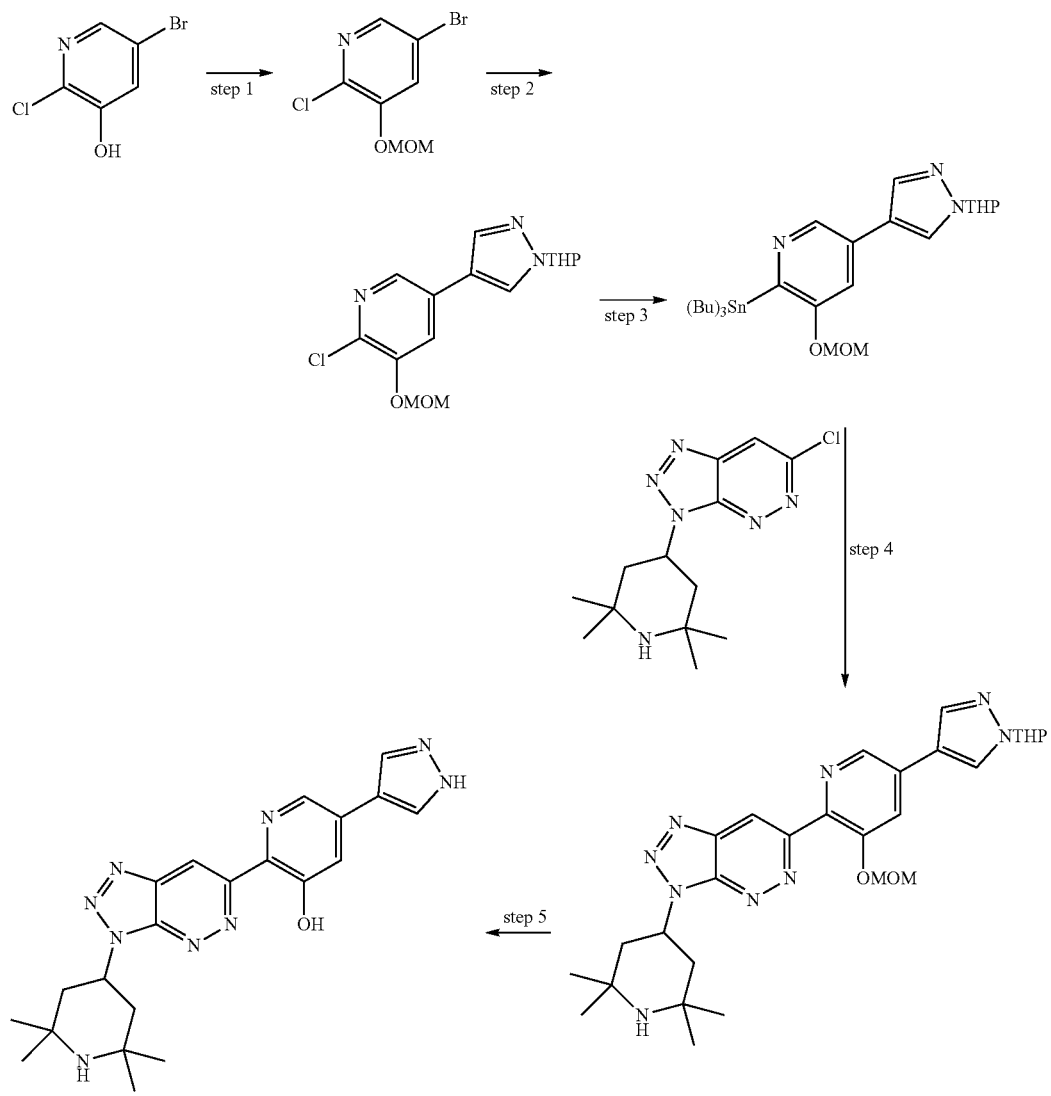

(0-25% EtOAc) to afford 5-bromo-2-chloro-3-(methoxymethoxy)pyridine (4.8 g) as white solid.

$^1$H NMR (CDCl$_3$) δ: 8.14 (d, J=2.1 Hz, 1H), 7.66 (d, J=2.0 Hz, 1H), 5.30 (s, 2H), 3.55 (s, 3H).

Step 1: To a solution of 5-bromo-2-chloro-pyridin-3-ol (5 g, 23.9 mmol) in DMF (50 mL) was added sodium hydride (1.2 g, 30 mmol, 60 mass % in mineral oil), and the reaction mixture was stirred for 30 min at room temperature. MOMCl (2.2 mL, 29.1 mmol) was added and the reaction was stirred for an additional hour. The reaction was quenched with water and partitioned between EtOAc and water. The combined organic layers were dried over MgSO$_4$ and concentrated. The crude product was purified by silica gel chromatography eluting with a EtOAc/hexanes gradient Step 2: A mixture of 5-bromo-2-chloro-3-(methoxymethoxy)pyridine (1 g, 3.96 mmol), 1-(tetrahydro-2H-pyran-2-yl)-4-(4,4,5,5-tetramethyl-1,3,2-dioxaborolan-2-yl)-1H-pyrazole (1.5 g, 5.40 mmol), 1,1'-bis(diphenylphosphino)ferrocene-palladium(II)dichlormethane complex (0.33 g, 0.40 mmol) and potassium acetate (1.3 g, 13 mmol) was purged with argon. 1,4-Dioxane (12 mL) and water (3 mL) were added and the reaction mixture was heated to 90° C. for 2 h. The reaction was cooled to room temperature, filtered through Celite, and washed with MeOH. The organic layers were concentrated and the residue chromatographed on silica gel, eluting with a EtOAc/hexanes gradient (0-50% EtOAc) to afford 2-chloro-3-(methoxymethoxy)-5-(1-tetrahydropyran-2-ylpyrazol-4-yl)pyridine (1.2 g, 93%).

MS m/z 324.2 [M+H]$^+$, $^1$H NMR (CDCl$_3$) δ: 8.20 (s, 1H), 7.92 (s, 1H), 7.82 (s, 1H), 7.56 (d, J=2.0 Hz, 1H), 5.42 (d, J=6.6 Hz, 1H), 5.32 (s, 2H), 4.08-4.16 (m, 1H), 3.74 (td, J=11.2, 2.8 Hz, 1H), 3.55 (s, 3H), 2.03-2.18 (m, 3H), 1.61-1.78 (m, 3H).

Step 3: To a microwave vial were added 2-chloro-3-(methoxymethoxy)-5-(1-tetrahydropyran-2-ylpyrazol-4-yl)pyridine (110 mg, 0.34 mmol), tributyl(tributylstannyl)stannane (410 mg, 0.71 mmol), tetrakis(triphenylphosphine)palladium(0) (40 mg, 0.03 mmol), and lithium chloride (90 mg, 2.0 mmol). The mixture was purged with argon. 1,4-Dioxane (2 mL) was added, and the reaction was heated in the microwave for 1.5 h at 150° C. The reaction was cooled to room temperature, filtered through Celite, and washed with MeOH. The organic layers were concentrated and the residue was purified using silica gel column chromatography eluting with a EtOAc/hexanes gradient (0-50% EtOAc) to afford 3-(methoxymethoxy)-5-(1-(tetrahydro-2H-pyran-2-yl)-1H-pyrazol-4-yl)-2-(tributylstannyl)pyridine (106 mg, 55%).

MS m/z 580.6 [M+H]$^+$, $^1$H NMR (CDCl$_3$) δ: 8.58 (s, 1H), 8.13 (s, 1H), 7.88 (s, 1H), 7.40 (s, 1H), 5.38-5.45 (m, 1H), 4.03 (br d, J=11.6 Hz, 1H), 3.93-4.07 (m, 1H), 3.66-3.77 (m, 1H), 3.63 (s, 1H), 2.16 (s, 3H), 1.26-1.40 (m, 18H), 1.11-1.18 (m, 6H), 0.90 (t, J=7.3 Hz, 9H).

Step 4: To a microwave vial were added 3-(methoxymethoxy)-5-(1-(tetrahydro-2H-pyran-2-yl)-1H-pyrazol-4-yl)-2-(tributylstannyl)pyridine (0.11 g, 0.19 mmol), 6-chloro-3-(2,2,6,6-tetramethylpiperidin-4-yl)-3H-[1,2,3]triazolo[4,5-c]pyridazine (300 mg, 0.10 mmol) tetrakis(triphenylphosphine)palladium(0) (12 mg, 0.01 mmol) and 1,4-dioxane (2 mL). The mixture was sparged with argon and heated in the microwave for 1.5 h at 150° C. The solvent was removed, and the crude mixture was purified by silica gel chromatography using a MeOH/CH$_2$Cl$_2$ gradient (0-15% MeOH) to afford 6-(2-(methoxymethoxy)-4-(4-methyl-1H-imidazol-1-yl)phenyl)-N-methyl-N-(2,2,6,6-tetramethylpiperidin-4-yl)-1,2,4-triazin-3-amine (0.04 g, 72%) with minor impurities. MS m/z 548.6 [M+H]$^+$. The compound was used in the next step without additional purification.

Step 5: To a solution of 6-(2-(methoxymethoxy)-4-(4-methyl-1H-imidazol-1-yl)phenyl)-N-methyl-N-(2,2,6,6-tetramethylpiperidin-4-yl)-1,2,4-triazin-3-amine (0.02 g, 0.04 mmol) in MeOH (0.5 mL) was added 4.0 M HCl in dioxane (1 mL). The mixture was stirred for 1 h at room temperature. The solvent was removed, and the crude mixture was purified by silica gel chromatography eluting with a MeOH/CH$_2$Cl$_2$ gradient (0-15% MeOH) to afford 5-(1H-pyrazol-4-yl)-2-(3-(2,2,6,6-tetramethylpiperidin-4-yl)-3H-[1,2,3]triazolo[4,5-c]pyridazin-6-yl)pyridin-3-ol (7 mg) as yellow solid.

MS m/z 420.5 [M+H]$^+$, $^1$H NMR (methanol-d$_4$) δ: 9.13-9.20 (m, 1H), 8.48 (s, 1H), 8.17 (d, J=8.9 Hz, 1H), 7.56 (m, 2H), 5.97 (dt, J=11.1, 5.5 Hz, 1H), 2.65-2.75 (m, 4H), 1.77-1.80 (m, 6H), 1.64 (s, 6H); 3Hs not observed (1 OH and 2 NH).

Example 33

Preparation of Compound 136

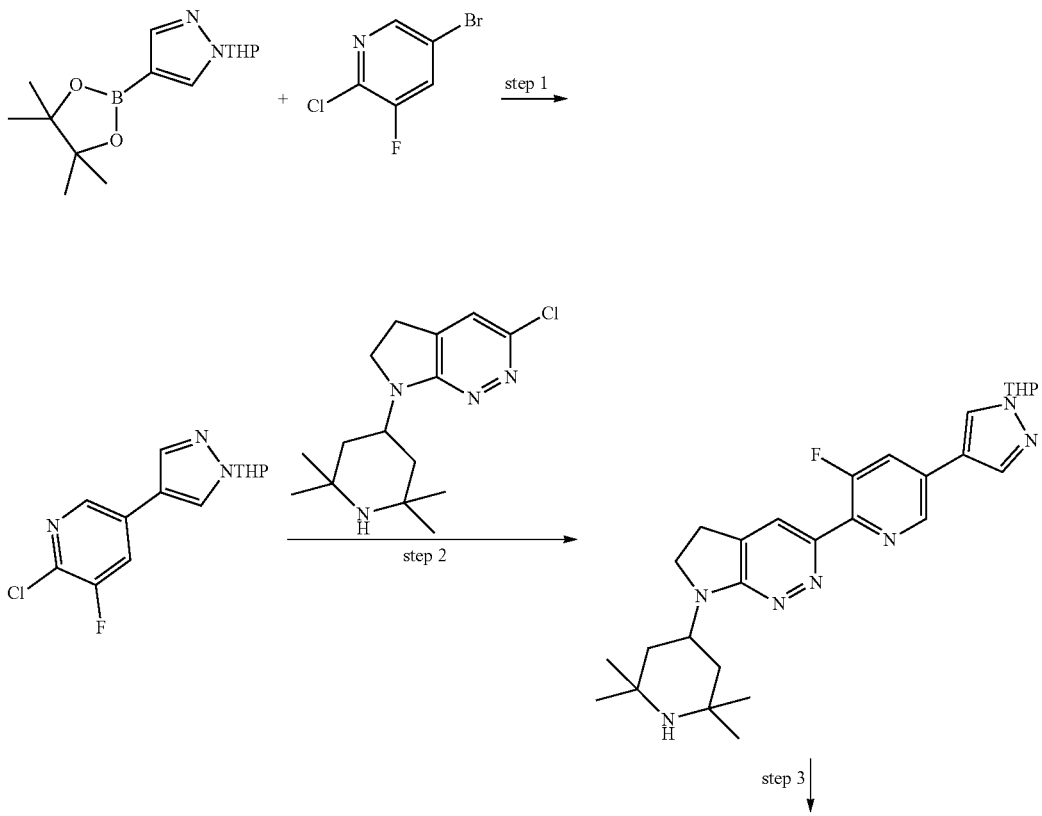

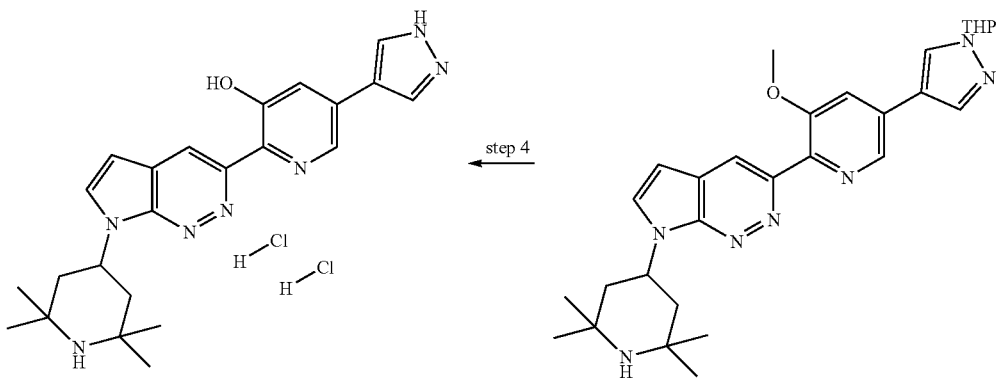

Step 1: 1-Tetrahydropyran-2-yl-4-(4,4,5,5-tetramethyl-1,3,2-dioxaborolan-2-yl)pyrazole (5.57 g, 20.0 mmol), 5-bromo-2-chloro-3-fluoro-pyridine (4.01 g, 19.05 mmol), [1,1'-bis(diphenylphosphino)ferrocene(dichloropalladium (II) (493.4 mg, 0.60 mmol), 1,4-dioxane (20.0 mL), and aqueous potassium carbonate (2.0 M, 12.0 mL) were combined, purged with argon and stirred at 80° C. for 3 h. The reaction was concentrated, and the residue was purified by silica gel chromatography eluting with a EtOAc/hexanes gradient (0-60% EtOAc) to yield 2-chloro-3-fluoro-5-(1-tetrahydropyran-2-ylpyrazol-4-yl)pyridine (3.89 g, 73%). MS m/z 282.3 [M+H]$^+$.

Step 2: Nickel(I) chloride (484.4 mg, 2.04 mmol), triphenylphosphine (2.14 g, 8.14 mmol), and N,N-dimethylformamide (11.0 mL) were combined, degassed with argon, then stirred at 50° C. for 45 min. 2-Chloro-3-fluoro-5-(1-tetrahydropyran-2-ylpyrazol-4-yl)pyridine (286.7 mg, 1.02 mmol) and 3-chloro-7-(2,2,6,6,-tetramethyl-4-piperidyl)-5,6-dihydropyrrolo[2,3-c]pyridazine (300.0 mg, 1.02 mmol) were added, the reaction degassed with argon, and then stirred at 50° C. for 16 h. The reaction was partitioned between CH$_2$Cl$_2$, MeOH, brine, and aqueous ammonium hydroxide (30%) (roughly 9:1:5:5). The aqueous layer was extracted twice with CH$_2$Cl$_2$/MeOH (9:1) and the combined organic phases were washed with brine, dried over Na$_2$SO$_4$, and then filtered and concentrated. The residue was purified by silica gel chromatography eluting with a MeOH/CH$_2$Cl$_2$ gradient (0-30% MeOH with 2.5% v/v 30% aqueous ammonium hydroxide additive) to yield 3-[3-fluoro-5-(1-tetrahydropyran-2-ylpyrazol-4-yl)-2-pyridyl]-7-(2,2,6,6-tetramethyl-4-piperidyl)-5,6-dihydropyrrolo[2,3-c]pyridazine (735.0 mg, 19%). MS m/z 506.4 [M+H]$^+$.

Step 3: 3-[3-Fluoro-5-(1-tetrahydropyran-2-ylpyrazol-4-yl)-2-pyridyl]-7-(2,2,6,6-tetramethyl-4-piperidyl)-5,6-dihydropyrrolo[2,3-c]pyridazine (413.7 mg, 0.82 mmol) was dissolved in methanolic sodium methoxide (25 wt %, 15.0 mL) and stirred at 50° C. for 3 h. The reaction was partitioned between CH$_2$Cl$_2$ and H$_2$O, the aqueous layer was extracted with CH$_2$Cl$_2$ and the combined organic layers were dried over Na$_2$SO$_4$, filtered and concentrated. The residue was combined with manganese dioxide (activated, 3.56 g, 41.11 mmol) in CH$_2$Cl$_2$ (6.0 mL) and stirred at 50° C. in a sealed tube for 16 h. The reaction was filtered through Celite and rinsed with minimal CH$_2$Cl$_2$. The filtrate was combined with manganese dioxide (activated, 3.7 g, 42.5 mmol) and stirred at 60° C. in a sealed tube for 24 h. The reaction was filtered through Celite, rinsed with CH$_2$Cl$_2$/MeOH, and the filtrate was concentrated. The residue was purified by silica gel chromatography eluting with a MeOH/CH$_2$Cl$_2$ gradient (0-100% MeOH with 2.5% v/v 30% aqueous ammonium hydroxide additive) to yield 3-[3-methoxy-5-(1-tetrahydropyran-2-ylpyrazol-4-yl)-2-pyridyl]-7-(2,2,6,6-tetramethyl-4-piperidyl)pyrrolo[2,3-c]pyridazine (47.3 mg, 11%). MS m/z 516.3 [M+H]$^+$.

Step 4: 3-[3-Methoxy-5-(1-tetrahydropyran-2-ylpyrazol-4-yl)-2-pyridyl]-7-(2,2,6,6-tetramethyl-4-piperidyl)pyrrolo[2,3-c]pyridazine (47.3 mg, 0.09 mmol) and boron tribromide (1.0 M in CH$_2$Cl$_2$, 2.0 mL, 2.0 mmol) were combined and stirred at room temperature under argon for 20 h.

The reaction was reverse quenched into MeOH and concentrated. The residue was chromatographed on a reversed phase C18 column, eluting with a 0-100% CH$_3$CN in H$_2$O (0.1% v/v TFA additive) gradient to yield 5-(1H-pyrazol-4-yl)-2-[7-(2,2,6,6-tetramethyl-4-piperidyl)pyrrolo[2,3-c]pyridazin-3-yl]pyridin-3-ol dihydrochloride (33.6 mg, 75%).

MS m/z 418.4 [M+H]$^+$, $^1$H NMR (methanol-d$_4$) δ: 9.53 (s, 1H), 8.79 (d, J=1.8 Hz, 1H), 8.71 (d, J=3.1 Hz, 1H), 8.67 (br s, 2H), 7.86 (s, 1H), 7.20 (d, J=3.4 Hz, 1H), 5.57 (tt, J=13.1, 2.8 Hz, 1H), 2.61 (t, J=13.1 Hz, 2H), 2.42 (dd, J=13.4, 2.7 Hz, 2H), 1.74 (s, 6H), 5.55 (s, 6H), 3 Hs not observed (2 NHs and OH).

Example 34

Preparation of Compound 141

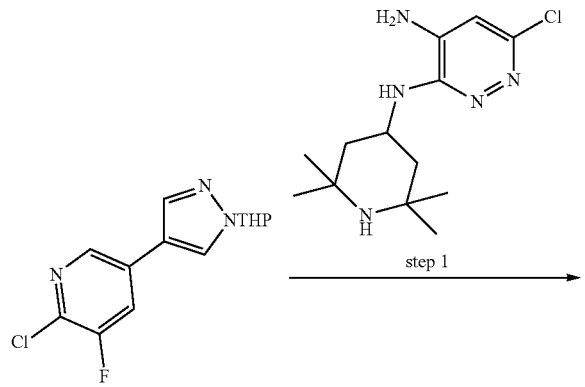

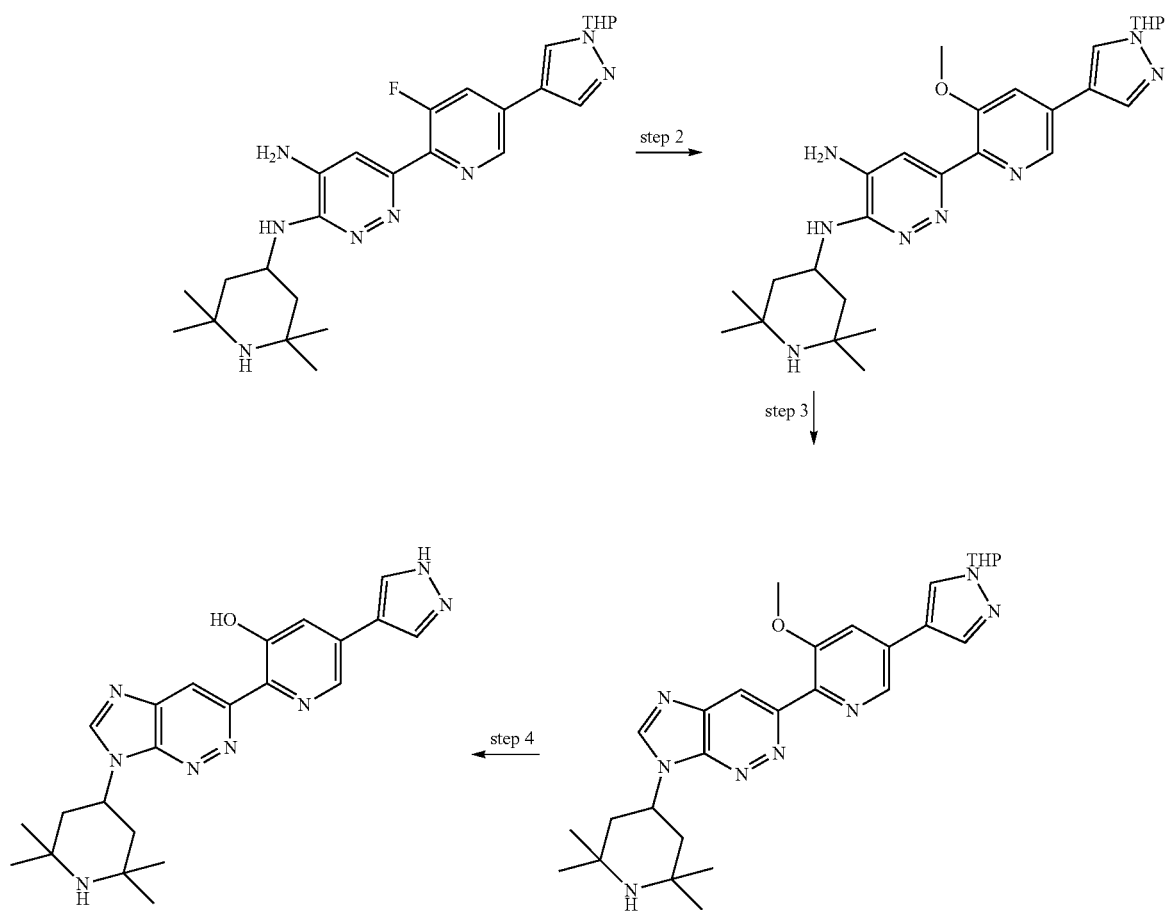

Step 1: Nickel(II) chloride hexahydrate (515.8 mg, 10.6 mmol), triphenylphosphine (11.1 g, 42.3 mmol), and N,N-dimethylformamide (52.5 mL) were combined, degassed with argon, and then stirred at 50° C. for 45 min. 2-Chloro-3-fluoro-5-(1-tetrahydropyran-2-ylpyrazol-4-yl)pyridine (1.49 g, 5.3 mmol) and 6-chloro-N3-(2,2,6,6-tetramethyl-4-piperidyl)pyridazine-3,4-diamine (1.5 g, 5.3 mmol) were added, the reaction was degassed with argon, and stirred at 50° C. for 16 h. The reaction was partitioned between $CH_2Cl_2$, MeOH, brine, and aqueous ammonium hydroxide (30%) (roughly 9:1:5:5). The aqueous layer was extracted twice with $CH_2Cl_2$/MeOH (9:1) and the combined organic phases were washed with brine, dried over $Na_2SO_4$, filtered and concentrated. The residue was chromatographed on a reversed phase C18 column, eluting with 0-100% $CH_3CN$ in $H_2O$ to yield 6-[3-fluoro-5-(1-tetrahydropyran-2-ylpyrazol- 4-yl)-2-pyridyl]-N3-(2,2,6,6-tetramethyl-4-piperidyl)pyridazine-3,4-diamine (540.0 mg, 21%). MS m/z 495.5 [M+H]+.

Step 2: 6-[3-Fluoro-5-(1-tetrahydropyran-2-ylpyrazol-4-yl)-2-pyridyl]-N3-(2,2,6,6-tetramethyl-4-piperidyl)pyridazine-3,4-diamine (102.0 mg, 0.21 mmol) was dissolved in methanolic sodium methoxide (25 wt %, 4.0 mL) and stirred at 50° C. for 2 h. The reaction was partitioned between $CH_2Cl_2$ and $H_2O$, the aqueous layer extracted with $CH_2Cl_2$ and the combined organic layers were dried over $Na_2SO_4$, filtered and concentrated. The residue was purified by silica gel chromatography eluting with a $MeOH/CH_2Cl_2$ gradient (0-100% MeOH with 2.5% v/v 30% aqueous ammonium hydroxide additive) to yield 6-[3-methoxy-5-(1-tetrahydropyran-2-ylpyrazol-4-yl)-2-pyridyl]-N3-(2,2,6,6-tetramethyl-4-piperidyl)pyridazine-3,4-diamine (48.1 mg, 46%). MS m/z 507.4 [M+H]+.

trated. The residue was purified on a reverse phase C18 column, eluting with 0-100% $CH_3CN$ in $H_2O$ (0.1% v/v TFA additive), and subsequently chromatographed on silica gel, eluting with 0-100% MeOH (2.5% v/v 30% aqueous ammonium hydroxide additive) in $CH_2Cl_2$ to yield 5-(1H-pyrazol-4-yl)-2-[7-(2,2,6,6-tetramethyl-4-piperidyl)imidazo[4,5-c]pyridazin-3-yl]pyridin-3-ol (12.3 mg, 25%).

MS m/z 419.4 [M+H]+; $^1$H NMR (methanol-$d_4$) δ: 9.28 (s, 1H), 9.22 (s, 1H), 8.71 (s, 1H), 8.52 (s, 2H), 8.01 (s, 1H), 5.50 (br t, J=12.7 Hz, 1H), 2.67 (br t, J=13.0 Hz, 2H), 2.41 (br d, J=11.6 Hz, 2H), 1.64 (s, 6H), 1.56 (s, 6H), 3 Hs not observed (2 NHs and OH).

Example 35

Preparation of Compound 117

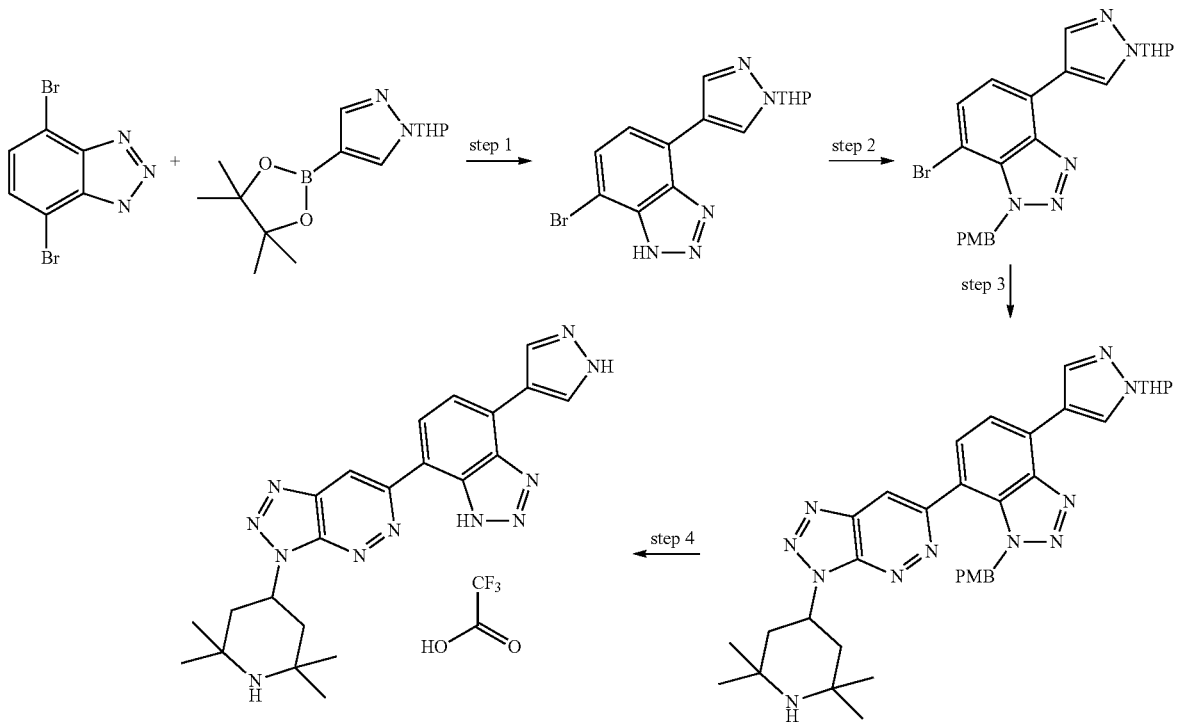

Step 3: 6-[3-Methoxy-5-(1-tetrahydropyran-2-ylpyrazol-4-yl)-2-pyridyl]-N3-(2,2,6,6-tetramethyl-4-piperidyl)pyridazine-3,4-diamine (48.1 mg, 0.095 mmol), N,N-dimethylformamide (3.0 mL), and Bredereck's reagent (0.2 mL, 0.99 mmol) were combined and stirred at 100° C. for 20 min. The reaction was concentrated to dryness. The residue was partitioned between brine and $CH_2Cl_2$, and the aqueous layer was extracted with $CH_2Cl_2$. The combined organic layers were dried over $Na_2SO_4$, filtered and concentrated to yield 3-[3-methoxy-5-(1-tetrahydropyran-2-ylpyrazol-4-yl)-2-pyridyl]-7-(2,2,6,6-tetramethyl-4-piperidyl)imidazo[4,5-c]pyridazine (50.9 mg, 104%). MS m/z 517.3 [M+H]+.

Step 4: 3-[3-Methoxy-5-(1-tetrahydropyran-2-ylpyrazol-4-yl)-2-pyridyl]-7-(2,2,6,6-tetramethyl-4-piperidyl)imidazo[4,5-c]pyridazine (50.9 mg, 0.099 mmol) and boron tribromide (1.0 M in $CH_2Cl_2$, 2.0 mL, 2.0 mmol) were combined and stirred at room temperature under argon for 16 h. The reaction was reverse quenched into MeOH and concen- Step 1: 1-Tetrahydropyran-2-yl-4-(4,4,5,5-tetramethyl-1,3,2-dioxaborolan-2-yl)pyrazole (105.0 mg, 0.38 mmol), 4,7-dibromo-1H-benzotriazole (195.7 mg, 0.71 mmol), [1,1'-bis(diphenylphosphino(ferrocene]dichloropalladium(I) (16.1 mg, 0.020 mmol), 1,4-dioxane (2.0 mL) and aqueous potassium carbonate (1.0 M, 1.0 mL) were combined and stirred at 80° C. for 16 h. The reaction was partitioned between EtOAc, $H_2O$, and AcOH, and the aqueous layer was extracted once with EtOAc. The combined organic layers were dried over $Na_2SO_4$, filtered and concentrated. The residue was purified using silica gel chromatography eluting with a EtOAc/hexanes gradient (0-100% EtOAc) to yield 7-bromo-4-(1-tetrahydropyran-2-ylpyrazol-4-yl)-1H-benzotriazole (67.6 mg, 51%). MS m/z 348.2 [M+H]+.

Step 2: 7-Bromo-4-(1-tetrahydropyran-2-ylpyrazol-4-yl)-1H-benzotriazole (67.6 mg, 0.19 mmol), cesium carbonate (238.5 mg, 0.73 mmol), acetonitrile (2.0 mL), and 1-(chloromethyl)-4-methoxy-benzene (70.0 μL, 0.516 mmol) were combined and stirred at room temperature for 18 h. The reaction was concentrated and the residue was partitioned between EtOAc and H$_2$O. The aqueous layer was extracted once with EtOAc, and the combined organic layers were dried over Na$_2$SO$_4$, filtered and concentrated. The residue was purified using silica gel chromatography eluting with a EtOAC/hexanes gradient (0-100% EtOAc) to yield 7-bromo-1-[(4-methoxyphenyl)methyl]-4-(1-tetrahydropyran-2-ylpyrazol-4-yl)benzotriazole (26.4 mg, 29%).

MS m/z 490.3 [M+Na]$^+$.

Step 3: 7-Bromo-1-[(4-methoxyphenyl)methyl]-4-(1-tetrahydropyran-2-ylpyrazol-4-yl)benzotriazole (26.4 mg, 0.056 mmol), chloro(2-dicyclohexylphosphino-2',6'-dimethoxy-1,1'-biphenyl)[2-(2'-amino-1,1'-biphenyl)]palladium(II) (4.8 mg, 0.0065 mmol), bis(pinacolato)diboron (18.5 mg, 0.072 mmol), and potassium acetate (dried at 250° C. under vacuum immediately prior to using, 21.7 mg, 0.22 mmol), and 1,4-dioxane (1.0 mL) were combined, degassed with argon, and stirred at 110° C. for 1 h. 6-chloro-3-(2,2,6,6-tetramethyl-4-piperidyl)triazolo[4,5-c]pyridazine (from Example 13, step 2, 16.6 mg, 0.0563 mmol), chloro(2-dicyclohexylphosphino-2',6'-dimethoxy-1,1'-biphenyl)[2-(2'-amino-1,1'-biphenyl)palladium(II) (4.1 mg, 0.006 mmol), and aqueous potassium carbonate (1.0 M, 0.5 mL) were added, the solution degassed with argon, and then stirred at 80° C. for 64 h. The reaction was partitioned between EtOAc and H$_2$O, and the aqueous layer was extracted once with EtOAc. The combined organic layers were dried over Na$_2$SO$_4$, filtered and concentrated. The residue was purified using silica gel chromatography eluting with a MeOH/CH$_2$Cl$_2$ gradient (0-30% MeOH) to yield 6-[3-[(4-methoxyphenyl)methyl]-7-(1-tetrahydropyran-2-ylpyrazol-4-yl)benzotriazol-4-yl]-3-(2,2,6,6-tetramethyl-4-piperidyl)triazolo[4,5-c]pyridazine (9.2 mg, 25%). MS m/z 648.7 [M+H]$^+$.

Step 4: 6-[3-[(4-Methoxyphenyl)methyl]-7-(1-tetrahydropyran-2-ylpyrazol-4-yl)benzotriazol-4-yl]-3-(2,2,6,6-tetramethyl-4-piperidyl)triazolo[4,5-c]pyridazine (9.2 mg, 0.014 mmol) was dissolved in trifluoroacetic acid (2.0 mL) and stirred at 60° C. for 2 h. The reaction was concentrated to dryness and the residue was chromatographed on a reverse phase C18 column, eluting with 0-100% CH$_3$CN in H$_2$O (0.1% v/v TFA additive) to yield 6-[7-(1H-pyrazol-4-yl)-3H-benzotriazol-4-yl]-3-(2,2,6,6-tetramethyl-4-piperidyl)triazolo[4,5-c]pyridazine; 2,2,2-trifluoroacetic acid (1.7 mg, 21%).

MS m/z 444.5 [M+H]$^+$; $^1$H NMR (methanol-d$_4$) δ: 9.24 (br s, 1H), 8.64 (s, 2H), 8.37-8.41 (m, 1H), 7.91 (d, J=7.6 Hz, 1H), 6.03 (ddd, J=16.1, 10.8, 5.5 Hz, 1H), 2.66-2.74 (m, 4H), 1.76-1.85 (m, 6H), 1.61-1.70 (m, 6H), 3 Hs not observed (NHs).

Example 36

Preparation of Compound 105

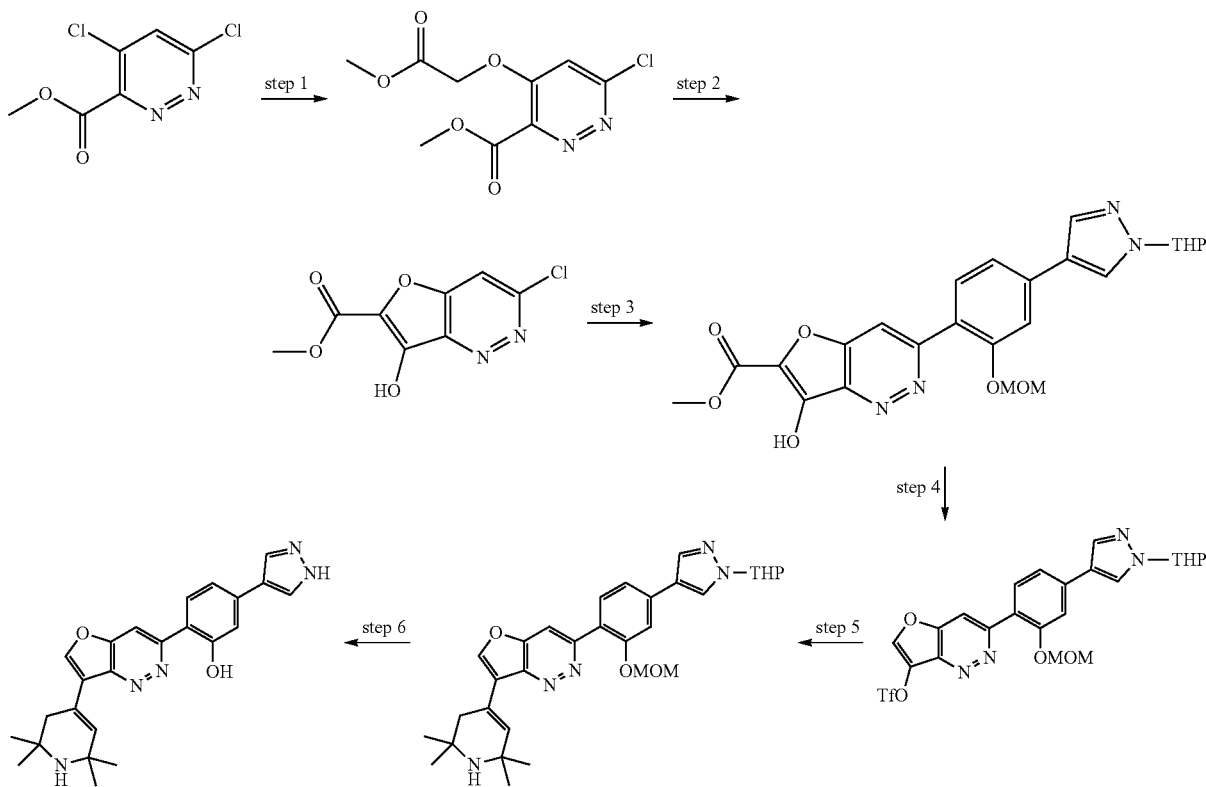

Step 1: To a solution of methyl 2-hydroxyacetate (218 mg, 2.37 mmol) in THF (3 mL) was added NaH (93 mg, 2.33 mmol, 60 mass %) at 0° C. The reaction was stirred for 30 min at 0° C., and the resultant slurry was added slowly to a solution of methyl 4,6-dichloropyridazine-3-carboxylate (500 mg, 2.37 mmol) in THF (3 mL) at 0° C. The mixture was stirred for 30 min at room temperature. The reaction was quenched with sat. aq. NH$_4$Cl and diluted with EtOAc and H$_2$O. The organic phase was dried over Na$_2$SO$_4$ and concentrated. The residue was purified using silica gel chromatography eluting with a EtOAc/hexanes gradient (20-50% EtOAc) to yield methyl 6-chloro-4-(2-methoxy-2-oxoethoxy)pyridazine-3-carboxylate (284 mg, 46%) as a white solid. MS m/z 261.4 [M+H]$^+$.

Step 2: To a solution of methyl 6-chloro-4-(2-methoxy-2-oxoethoxy)pyridazine-3-carboxylate (284 mg, 1.09 mmol) in THF (11.0 mL) was added sodium methoxide (0.22 mL, 1.2 mmol, 5.4 mol/L in MeOH) dropwise at room temperature. The reaction was stirred at room temperature for 15 min, then quenched with 1 M HCl. The mixture was partitioned between H$_2$O and EtOAc, and the organic phases were collected and washed with brine and concentrated to afford methyl 3-chloro-7-hydroxyfuro[3,2-c]pyridazine-6-carboxylate (230 mg, 92%) as an off-white solid. MS m/z 229.2 [M+H]$^+$.

Step 3: A mixture of 1,1'-bis(diphenylphosphino)ferrocene-palladium(II)dichloride dichloromethane complex (18 mg, 0.022 mmol), 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole (118 mg, 0.29 mmol), methyl 3-chloro-7-hydroxyfuro[3,2-c]pyridazine-6-carboxylate (50 mg, 0.22 mmol), and aqueous 2 M K$_2$CO$_3$ (0.22 mL, 0.44 mmol) in dioxane (1 mL) was sparged with argon for 10 minutes, then heated to 90° C. for 3 h. The reaction was cooled to room temperature and filtered through Celite, washing with MeOH. The organic layers were concentrated and the residue was purified using silica gel chromatography eluting with a MeOH/CH$_2$Cl$_2$ gradient (5-20% MeOH) to yield methyl 7-hydroxy-3-(2-(methoxymethoxy)-4-(1-(tetrahydro-2H-pyran-2-yl)-1H-pyrazol-4-yl)phenyl)furo[3,2-c]pyridazine-6-carboxylate (75 mg, 71%) as a light brown solid. MS m/z 481.4 [M+H]$^+$.

Step 4: To a solution of methyl 7-hydroxy-3-(2-(methoxymethoxy)-4-(1-(tetrahydro-2H-pyran-2-yl)-1H-pyrazol-4-yl)phenyl)furo[3,2-c]pyridazine-6-carboxylate (280 mg, 0.58 mmol) in DMSO (7 mL) was added aq. 1M NaOH (1.5 mL, 1.5 mmol). The reaction was heated to 50° C. for 1 h, then cooled to room temperature. DMF (7 mL), Cs$_2$CO$_3$ (360 mg, 1.1 mmol) and 1,1,1-trifluoro-N-phenyl-N-((trifluoromethyl)sulfonyl)methanesulfonamide (300 mg, 0.84 mmol) were added, and the mixture stirred at room temperature for 1 h. The reaction mixture was partitioned between CH$_2$Cl$_2$ and H$_2$O, and the aqueous layer was extracted once with CH$_2$Cl$_2$. The organic phase was dried over Na$_2$SO$_4$, concentrated, and the residue was purified using silica gel chromatography eluting with a EtOAc/hexanes gradient (20-60% EtOAc) to yield 3-(2-(methoxymethoxy)-4-(1-(tetrahydro-2H-pyran-2-yl)-1H-pyrazol-4-yl)phenyl)furo[3,2-c]pyridazin-7-yl trifluoromethanesulfonate (43 mg, 13%) as a white solid. MS m/z 555.2 [M+H]$^+$.

Step 5: A mixture of 2,2,6,6-tetramethyl-4-(4,4,5,5-tetramethyl-1,3,2-dioxaborolan-2-yl)-1,2,3,6-tetrahydropyridine (27 mg, 0.10 mmol), 1'-bis(diphenylphosphino)ferrocene-palladium(II)dichloride dichloromethane complex (7 mg, 0.0085 mmol), 3-(2-(methoxymethoxy)-4-(1-(tetrahydro-2H-pyran-2-yl)-1H-pyrazol-4-yl)phenyl)furo[3,2-c]pyridazin-7-yl trifluoromethanesulfonate (43 mg, 0.078 mmol), and aqueous 2 M K$_2$CO$_3$ (0.12 mL, 0.24 mmol) in dioxane (0.5 mL) was sparged with argon for 10 minutes, then heated to 90° C. for 2 h. The reaction was cooled to room temperature and filtered over celite, washing with MeOH. The organic layers were collected and the residue was purified using silica gel chromatography eluting with a MeOH/CH$_2$Cl$_2$ gradient (0-50% MeOH) to yield 3-(2-(methoxymethoxy)-4-(1-(tetrahydro-2H-pyran-2-yl)-1H-pyrazol-4-yl)phenyl)-7-(2,2,6,6-tetramethyl-1,2,3,6-tetrahydropyridin-4-yl)furo[3,2-c]pyridazine (7 mg, 16%) as a yellow film. MS m/z 544.5 [M+H]$^+$.

Step 6: 3-(2-(Methoxymethoxy)-4-(1-(tetrahydro-2H-pyran-2-yl)-1H-pyrazol-4-yl)phenyl)-7-(2,2,6,6-tetramethyl-1,2,3,6-tetrahydropyridin-4-yl)furo[3,2-c]pyridazine (7 mg, 0.013 mmol) was dissolved in MeOH (0.5 mL). HCl (0.3 mL, 1.2 mmol, 4M in dioxane) was added and the reaction was stirred at 40° C. for 30 min. The reaction was concentrated and the residue was purified by reverse-phase column chromatography, eluting with 0-100% MeCN/H$_2$O (0.1% TFA). The product was dissolved in HCl (2 mL, 1.25 M in MeOH) and concentrated to afford 5-(1H-pyrazol-4-yl)-2-(7-(2,2,6,6-tetramethyl-1,2,3,6-tetrahydropyridin-4-yl)furo[3,2-c]pyridazin-3-yl)phenol hydrochloride as a yellow film (2.0 mg, 34%).

MS m/z 416.5 [M+H]$^+$; $^1$H NMR (methanol-d$_4$) δ: 8.96 (s, 1H), 8.81 (s, 1H), 8.39 (br s, 2H), 7.92 (d, J=8.2 Hz, 1H), 7.47 (d, J=7.6 Hz, 1H), 7.40 (s, 1H), 7.19 (s, 1H), 2.85 (s, 2H), 1.72 (s, 6H), 1.60-1.66 (m, 6H), 3Hs not observed (2 NHs and OH).

Example 37

Preparation of Compound 163

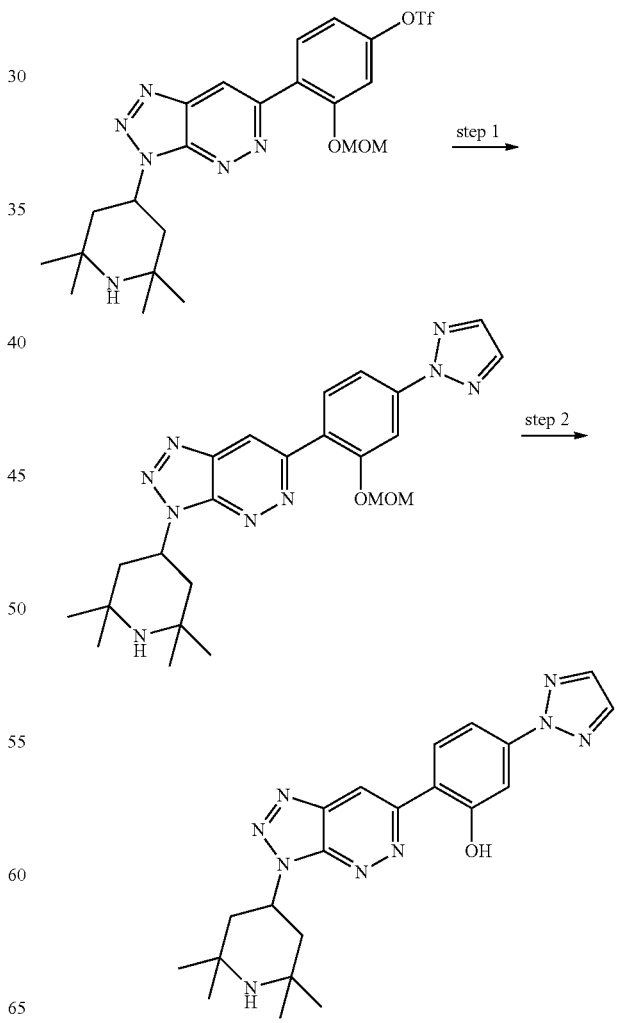

Step 1: A mixture of Pd$_2$(dba)$_3$ (4.3 mg, 0.0047 mmol), (Me)$_4$tButylXPhos (5.8 mg, 0.012 mmol), toluene (0.6 mL) and 1,4-dioxane (0.15 mL) was sparged with argon, then heated to 120° C. for 5 min and cooled to room temperature. Anhydrous K$_3$PO$_4$ (41.0 mg, 0.19 mmol), triazole (9.5 mg, 0.11 mmol), and 3-(methoxymethoxy)-4-(3-(2,2,6,6-tetramethylpiperidin-4-yl)-3H-[1,2,3]triazolo[4,5-c]pyridazin-6-yl)phenyl trifluoromethanesulfonate (Example 13, step 4, 50.0 mg, 0.091 mmol) were added and the reaction mixture was sparged with argon and stirred at 120° C. for 2 h. Upon completion, the mixture was cooled to room temperature, concentrated and the residue was purified by column chromatography on silica gel, eluting with a MeOH/CH$_2$Cl$_2$ gradient (0-30% MeOH) to give 6-(2-(methoxymethoxy)-4-(2H-1,2,3-triazol-2-yl)phenyl)-3-(2,2,6,6-tetramethylpiperidin-4-yl)-3H-[1,2,3]triazolo[4,5-c]pyridazine (30.0 mg, 71% yield) as a light yellow solid. MS m/z 464.4 [M+H]$^+$.

Step 2: 6-(2-(Methoxymethoxy)-4-(2H-1,2,3-triazol-2-yl)phenyl)-3-(2,2,6,6-tetramethylpiperidin-4-yl)-3H-[1,2,3]triazolo[4,5-c]pyridazine (30.0 mg, 0.065 mmol) was dissolved in methanol (0.5 mL) and HCl in dioxane (1.0 mL, 4.0 mmol, 4.0 mol/L) was added. The reaction mixture was stirred at 45° C. for 1 h and then concentrated. The residue was purified by column chromatography on silica gel, eluting with a MeOH/NH$_4$OH/CH$_2$Cl$_2$ gradient (0-30% MeOH/2.5% NH$_4$OH) to yield 2-(3-(2,2,6,6-tetramethylpiperidin-4-yl)-3H-[1,2,3]triazolo[4,5-c]pyridazin-6-yl)-5-(2H-1,2,3-triazol-2-yl)phenol (19.0 mg, 70% yield) as a yellow solid.

MS m/z 420.5 [M+H]$^+$; $^1$H NMR (methanol-d$_4$) δ: 9.09 (s, 1H), 8.19-8.25 (m, 1H), 7.98 (s, 2H), 7.71-7.83 (m, 2H), 5.74-5.94 (m, 1H), 2.31-2.41 (m, 4H), 1.53 (s, 6H), 1.37 (s, 6H); 2 Hs not observed (NH and OH).

Example 38

Preparation of Compound 171

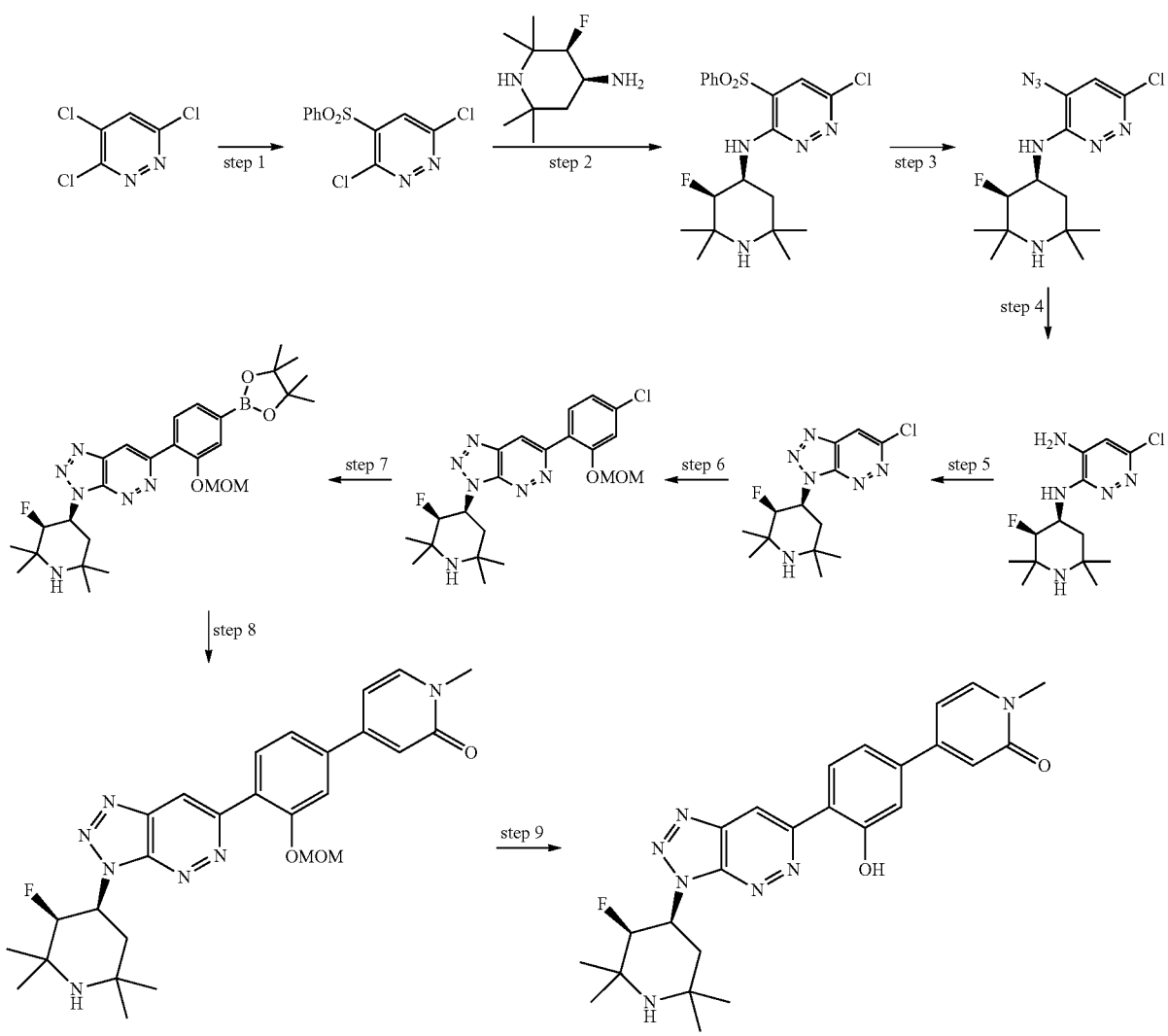

Step 1: To a solution of 3,4,6-trichloropyridazine (20.04 g, 106 mmol) in a mixture of THF and DMSO (5:1, 200 mL) was added sodium benzenesulfinate (18.6 g, 111.1 mmol) and the mixture was stirred vigorously at room temperature. Full conversion was observed in 40 minutes. After completion, the reaction mixture was diluted with EtOAc (100 mL) and washed with water and brine. The combined organic phases were dried over MgSO$_4$. The solvent volume was reduced by evaporation. Recrystallization from EtOAc/ hexanes yielded 3,6-dichloro-4-(phenylsulfonyl)pyridazine (28.5 g, 93% yield) as a white solid.

MS m/z 289.0 [M+H]+; 1H NMR (CDCl3) δ: 8.34 (s, 1H), 8.07-7.98 (m, 2H), 7.80-7.74 (m, 1H), 7.68-7.61 (m, 2H).

Step 2: To a round bottom flask were added 3,6-dichloro-4-(phenylsulfonyl)pyridazine (1.0 g, 3.46 mmol), (3S,4S)-3-fluoro-2,2,6,6-tetramethylpiperidin-4-amine (1.3 g, 5.2 mmol), $K_2CO_3$ (2.18 g, 15.6 mmol) and dioxane (14.0 mL). The mixture was stirred at 100° C. for 16 h, then cooled to room temperature. The reaction was partitioned between EtOAc and water. The organic phase was washed with brine, dried over $MgSO_4$, and the solvent was removed in vacuo to provide crude 6-chloro-N-((3S,4S)-3-fluoro-2,2,6,6-tetramethylpiperidin-4-yl)-4-(phenylsulfonyl)pyridazin-3-amine which was used in the next step without further purification.

MS m/z 427.2, 429.2 [M+H]+; 1H NMR (CDCl3) δ: 8.00-7.93 (m, 2H), 7.77 (s, 1H), 7.76-7.73 (m, 1H), 7.64-7.61 (m, 2H), 6.73 (d, J=7.9 Hz, 1H), 5.04-4.88 (m, 1H), 4.34 (d, J=50.0 Hz, 1H), 1.81-1.72 (m, 1H), 1.61-1.49 (m, 1H), 1.29 (s, 6H), 1.22 (s, 6H); 1H (NH) not observed.

Step 3: The crude mixture from Step 2 was dissolved in dioxane (8 mL) and DMSO (2 mL). $NaN_3$ (400.0 mg, 6.15 mmol) was added, and the mixture was stirred at 50° C. for 16 h, and then cooled to room temperature. The reaction mixture was diluted with EtOAc and washed with brine (4 times) to remove DMSO. The combined organic phases were dried over $MgSO_4$ and concentrated to provide crude 4-azido-6-chloro-N-((3S,4S)-3-fluoro-2,2,6,6-tetramethylpiperidin-4-yl)pyridazin-3-amine as a dark brown oil which was used in the next step without further purification.

MS m/z 328.2, 330.2 [M+H]+; 1H NMR (CDCl3) δ: 6.88 (s, 1H), 4.90-4.69 (m, 2H), 4.33 (d, J=50.0 Hz, 1H), 1.73-1.63 (m, 1H), 1.46-1.35 (m, 1H), 1.23 (s, 6H), 1.11 (s, 6H); 1H (NH) not observed.

Step 4: The crude product from Step 3 was dissolved in $CH_2Cl_2$ (10 mL) and AcOH (2 mL) and the mixture was cooled at 0° C. Zinc mesh (640.0 mg, 9.8 mmol) was added portionwise and the mixture was stirred for 3 h at 0° C. Upon completion, the reaction was quenched with aqueous saturated $NaHCO_3$. The organic phase was washed with brine, dried over $MgSO_4$, and the solvent was removed in vacuo. The crude product was purified by column chromatography on silica gel, eluting with a $MeOH/CH_2Cl_2$ gradient (0-30% MeOH) to yield 6-chloro-N3-((3S,4S)-3-fluoro-2,2,6,6-tetramethylpiperidin-4-yl)pyridazine-3,4-diamine (860 mg, 82% yield over 3 steps).

MS m/z 302.2, 304.2 [M+H]+; 1H NMR (DMSO-d6) δ: 6.46 (s, 2H), 6.41 (s, 1H), 6.02 (d, J=7.5 Hz, 1H), 4.76-4.62 (m, 1H), 4.45 (d, J=55.0 Hz, 1H), 1.61-1.54 (m, 2H), 1.23 (s, 3H), 1.22 (s, 3H), 1.13 (s, 3H), 1.09 (s, 3H); 1H (NH) not observed.

Step 5: A solution of 6-chloro-N3-((3S,4S)-3-fluoro-2,2,6,6-tetramethylpiperidin-4-yl)pyridazine-3,4-diamine (860 mg, 2.8 mmol) in AcOH (6 mL) was cooled to 0° C. $NaNO_2$ (280 mg, 4.0 mmol) was dissolved in water (1 mL) and the solution was slowly added dropwise to the reaction mixture. The mixture was then gradually warmed to room temperature and stirred for 1 h at room temperature. After completion, the solvent was removed in vacuo and the residue was purified by column chromatography on silica gel, eluting with a $MeOH/CH_2Cl_2$ gradient (0-10% MeOH) to provide 6-chloro-3-((3S,4S)-3-fluoro-2,2,6,6-tetramethylpiperidin-4-yl)-3H-[1,2,3]triazolo[4,5-c]pyridazine bishydrochloride (450 mg, 50% yield).

MS m/z 313.1, 315.1 [M+H]+; 1H NMR (DMSO-d6) δ: 9.87 (br s, 1H), 8.96 (s, 1H), 8.59 (br s, 1H), 6.31-6.16 (m, 1H), 5.30 (d, J=45.0 Hz, 1H), 3.08 (t, J=13.6 Hz, 1H), 2.61-2.54 (m, 1H), 1.73 (s, 3H), 1.66 (s, 3H), 1.61 (s, 3H), 1.52 (s, 3H); extra 2Hs are due to bis HCl salt.

Step 6: A dry screw cap vial was charged with 6-chloro-3-((3S,4S)-3-fluoro-2,2,6,6-tetramethylpiperidin-4-yl)-3H-[1,2,3]triazolo[4,5-c]pyridazine (200.0 mg, 0.64 mmol), Pd(PPh3)4 (70.0 mg, 10 mol %) and 2-(4-chloro-2-(methoxymethoxy)phenyl)-4,4,5,5-tetramethyl-1,3,2-dioxaborolane (270.0 mg, 0.90 mmol). The vial was evacuated under vacuum and purged with argon, followed by the addition of dioxane (2.2 mL) and aqueous $K_2CO_3$ solution (2.0 M, 0.8 mL, 1.92 mmol). The mixture was heated at 70° C. for 16 h. After completion, the solvent was removed in vacuo and the residue was purified by column chromatography on silica gel, eluting with a $MeOH/CH_2Cl_2$ gradient (0-15% MeOH) to yield 6-(4-chloro-2-(methoxymethoxy)phenyl)-3-((3S,4S)-3-fluoro-2,2,6,6-tetramethylpiperidin-4-yl)-3H-[1,2,3]triazolo[4,5-c]pyridazine (279.0 mg, 97%) as a brownish solid. MS m/z 449.4, 451.4 [M+H]+.

Step 7: A dry screw cap vial was charged with 6-(4-chloro-2-(methoxymethoxy)phenyl)-3-((3S,4S)-3-fluoro-2,2,6,6-tetramethylpiperidin-4-yl)-3H-[1,2,3]triazolo[4,5-c]pyridazine (40.0 mg, 0.9 mmol), bis(pinacolato)diboron (30.0 mg, 0.12 mmol), Pd X-Phos G3 (4.0 mg, 0.05 mmol) and KOAc (18.0 mg, 0.18 mmol). The vial was evacuated under vacuum and backfilled with argon. The argon/vacuum cycle was performed at least three times and then dioxane (0.5 mL) was added to the vial under Ar pressure. The reaction was then heated at 100° C. for 2 h. 3-((3S,4S)-3-Fluoro-2,2,6,6-tetramethylpiperidin-4-yl)-6-(2-(methoxymethoxy)-4-(4,4,5,5-tetramethyl-1,3,2-dioxaborolan-2-yl)phenyl)-3H-[1,2,3]triazolo[4,5-c]pyridazine was used for the next step without isolation. MS m/z 541.4 [M+H]+.

Step 8: To the mixture from Step 7, was added 2 M aqueous $K_2CO_3$ (0.1 mL), Pd X-Phos G3 (4.0 mg, 0.05 mmol) and 4-bromo-1-methylpyridin-2(1H)-one (20.0 mg, 0.11 mmol). The reaction was then heated at 100° C. for 12 h. The crude product was purified by column chromatography on silica gel, eluting with a $MeOH/CH_2Cl_2$ gradient (0-30% MeOH) to yield 4-(4-(3-((3S,4S)-3-fluoro-2,2,6,6-tetramethylpiperidin-4-yl)-3H-[1,2,3]triazolo[4,5-c]pyridazin-6-yl)-3-(methoxymethoxy)phenyl)-1-methylpyridin-2(1H)-one (35 mg, 75% yield). MS m/z 522.4 [M+H]+.

Step 9: To the solution of 4-(4-(3-((3S,4S)-3-fluoro-2,2,6,6-tetramethylpiperidin-4-yl)-3H-[1,2,3]triazolo[4,5-c]pyridazin-6-yl)-3-(methoxymethoxy)phenyl)-1-methylpyridin-2(1H)-one (35.0 mg, 0.067 mmol) in dichloromethane (1.0 mL) and MeOH (100 μL) was added 2.0 M HCl in $Et_2O$ (1.5 mL, 0.75 mmol) and the reaction mixture was stirred at room temperature for 5 h. The solvent volume was reduced by evaporation. The residue was purified by column chromatography on silica gel, eluting with a $MeOH/NH_4OH/CH_2Cl_2$ gradient (0-30% $MeOH/2.5\%$ $NH_4OH$) to yield 4-(4-(3-((3S,4S)-3-fluoro-2,2,6,6-tetramethylpiperidin-4-yl)-3H-[1,2,3]triazolo[4,5-c]pyridazin-6-yl)-3-hydroxyphenyl)-1-methylpyridin-2(1H)-one (16.0 mg, 50% yield) as a tan solid.

MS m/z 478.4 [M+H]+; 1H NMR (methanol-d4) δ: 9.19 (s, 1H), 8.23 (d, J=7.9 Hz, 1H), 8.00 (br d, J=6.9 Hz, 1H), 7.49-7.36 (m, 2H), 7.15-7.04 (m, 2H), 6.30-6.21 (m, 1H), 5.42 (d, J=50 Hz 1H), 3.79 (s, 3H), 3.55-3.45 (m, 1H), 2.80-2.69 (m, 1H), 1.88 (s, 3H), 1.81 (s, 3H), 1.74 (s, 3H), 1.67 (s, 3H); 2Hs not observed (NH and OH).

Using the procedure described for Example 38, above, additional compounds described herein were prepared by substituting the appropriate starting materials, suitable reagents and reaction conditions, obtaining compounds such as those selected from:

| Cpd | Data |
|---|---|
| 164 | MS m/z 437.3 [M + H]$^+$; $^1$H NMR (DMSO-d$_6$) δ: 10.74-10.49 (m, 1H), 9.22 (s, 1H), 8.47 (br d, J = 12.2 Hz, 1H), 8.15 (s, 2H), 8.13-8.05 (m, 1H), 7.32 (br s, 2H), 6.32-6.16 (m, 1H), 5.37 (d, J = 45 Hz, 1H), 3.09 (t, J = 13.6 Hz, 1H), 2.67-2.57 (m,1H), 1.79 (s, 3H), 1.71 (s, 3H), 1.68-1.61 (m, 3H), 1.61-1.49 (m, 3H); 1H not observed (OH). |
| 168 | MS m/z 437.3 [M + H]$^+$; $^1$H NMR (methanol-d$_4$) δ: 9.19 (s, 1H), 8.70 (s, 2H), 8.16 (d, J = 8.1 Hz, 1H), 7.47-7.39 (m, 2H), 6.22-6.10 (m, 1H), 5.52 (dd, J = 50.0, 10.0 Hz, 1H), 3.17-3.05 (m, 1H), 2.73-2.62 (m, 1H), 1.89-1.79 (m, 6H), 1.75 (s, 3H), 1.68 (s, 3H); 3Hs not observed (OH and 2 NHs). |
| 170 | MS m/z 405.5 [M + H]$^+$; $^1$H NMR (methanol-d$_4$) δ: 9.00 (s, 1H), 8.03 (br d, J = 8.2 Hz, 3H), 7.16-7.37 (m, 2H), 5.44-5.61 (m, 1H), 3.52-3.65 (m, 1H), 3.13-3.19 (m, 2H), 2.93 (br dd, J = 9.2, 2.5 Hz, 2H), 1.21 (s, 9H); 3 Hs not observed (2NHs and OH). |
| 172 | MS m/z 479.5 [M + H]$^+$; $^1$H NMR (methanol-d$_4$) δ: 9.22 (s, 1H), 9.08 (s, 1H), 8.25 (d, J = 8.1 Hz, 1H), 7.68-7.55 (m, 2H), 7.04 (s, 1H), 6.36-6.15 (m, 1H), 5.42 (d, J = 55.0 Hz, 1H), 3.72-3.65 (m, 1H), 3.68 (s, 4H), 2.75 (br d, J = 12.2 Hz, 1H), 1.88 (s, 3H), 1.81(s, 3H), 1.74 (s, 3H), 1.67 (s, 3H); 2Hs not observed (NH and OH). |
| 173 | MS m/z 455.4 [M + H]$^+$; $^1$H NMR (DMSO-d$_6$) δ: 12.69 (s, 1H), 11.55 (s, 1H), 9.15 (s, 1H), 8.26 (s, 1H), 8.11 (d, J = 10 Hz, 1H), 7.29-7.26 (m, 2H), 6.10-5.90 (m, 1H), 5.95 (d, J = 55 Hz, 1H), 2.67-2.57 (m, 1H), 2.19-2.25 (m, 1H), 1.41 (s, 3H), 1.34 (s, 3H), 1.26 (m, 3H), 1.14 (m, 3H); 1H not observed. |
| 175 | MS m/z 419.5 [M + H]$^+$; $^1$H NMR (methanol-d$_4$) δ: 9.00 (s, 1H), 8.02 (br d, J = 8.1 Hz, 3H), 7.24-7.30 (m, 2H), 5.92-6.00 (m, 1H), 4.30 (br t, J = 8.0 Hz, 1H), 2.98-3.06 (m, 1H), 2.75 (br dd, J = 8.6, 4.0 Hz, 1H), 2.55-2.67 (m, 3H), 1.99-2.11 (m, 1H), 1.45 (s, 9H); 3 Hs not observed (2 NHs and OH). |

Biological Examples

The following in vitro biological examples demonstrate the usefulness of the compounds of the present description for treating Huntington's disease.

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed.

Compounds of Formula (I) were tested using the Meso Scale Discovery (MSD) Assay provided in International Application No. PCT/US2016/066042, filed on Dec. 11, 2016 and claiming priority to United States Provisional Application U.S. 62/265,652 filed on Dec. 10, 2015, the entire contents of which are incorporated herein by reference.

The Endogenous Huntingtin Protein assay used in Example 1 was developed using the ELISA-based MSD electrochemiluminescence assay platform.

Example 1

Endogenous Huntingtin Protein Assay

Meso Scale Discovery (MSD) 96-well or 384-well plates were coated overnight at 4° C. with MW1 (expanded polyglutamine) or MAB2166 monoclonal antibody (for capture) at a concentration of 1 μg/mL in PBS (30 μL per well). Plates were then washed three times with 300 μL wash buffer (0.05% Tween-20 in PBS) and blocked (100 μL blocking buffer; 5% BSA in PBS) for 4-5 hours at room temperature with rotational shaking and then washed three times with wash buffer.

Samples (25 μL) were transferred to the antibody-coated MSD plate and incubated overnight at 4° C. After removal of the lysates, the plate was washed three times with wash buffer, and 25 μL of #5656S (Cell signaling; rabbit monoclonal) secondary antibody (diluted to 0.25 μg/mL in 0.05% Tween-20 in blocking buffer) was added to each well and incubated with shaking for 1 Hour at room temperature. Following incubation with the secondary antibody, the wells were rinsed with wash buffer after which 25 μL of goat anti-rabbit SULFO TAG secondary detection antibody (required aspect of the MSD system) (diluted to 0.25 μg/mL in 0.05% Tween-20 in blocking buffer) was added to each well and incubated with shaking for 1 hour at room temperature. After rinsing three times with wash buffer, 150 μL of read buffer T with surfactant (MSD) were added to each empty well, and the plate was imaged on a SI 6000 imager (MSD) according to manufacturers' instructions provided for 96- or 384-well plates. The resulting IC$_{50}$ values (μM) for compounds tested are shown in Table 1.

As shown in Table 1, test compounds described herein had the following IC$_{50}$ values, an IC$_{50}$ value between >3 μM and ≤9 μM is indicated by a single star (*), an IC$_{50}$ value between >1 μM and ≤3 μM is indicated by two stars (), an IC$_{50}$ value between >0.5 μM and ≤1 μM is indicated by three stars (*), an IC$_{50}$ value between >0.1 μM and ≤0.5 μM is indicated by four stars (**) and an IC$_{50}$ value of ≤0.1 μM is indicated by five stars (***).

TABLE 1

| Cpd | IC$_{50}$ |
|---|---|
| 1 | **** |
| 2 | **** |
| 3 | ***** |
| 4 | ***** |
| 5 | ***** |
| 6 | *** |
| 7 | ***** |
| 8 | ** |
| 9 | ** |
| 10 | ***** |
| 11 | ** |
| 12 | **** |
| 13 | **** |
| 14 | **** |

TABLE 1-continued

| Cpd | IC$_{50}$ |
|---|---|
| 15 | ** |
| 16 | **** |
| 17 | ***** |
| 18 | ***** |
| 19 | ** |
| 20 | ***** |
| 21 | ** |
| 22 | ***** |
| 23 | ***** |
| 24 | ***** |
| 25 | ***** |
| 26 | ***** |
| 27 | ***** |
| 28 | ** |
| 29 | ***** |
| 30 | *** |
| 31 | ***** |
| 32 | **** |
| 33 | *** |
| 34 | **** |
| 35 | ***** |
| 36 | **** |
| 37 | ***** |
| 38 | ***** |
| 39 | ***** |
| 40 | * |
| 42 | **** |
| 43 | *** |
| 46 | *** |
| 47 | ** |
| 48 | **** |
| 49 | ** |
| 50 | **** |
| 51 | **** |
| 52 | *** |
| 53 | ***** |
| 54 | ***** |
| 55 | **** |
| 56 | **** |
| 57 | ***** |
| 58 | **** |
| 59 | ***** |
| 60 | ** |
| 61 | ** |
| 62 | ***** |
| 63 | ***** |
| 64 | ** |
| 65 | *** |
| 66 | ***** |
| 67 | ***** |
| 68 | ***** |
| 69 | ***** |
| 70 | ***** |
| 71 | **** |
| 72 | **** |
| 73 | ***** |
| 74 | **** |
| 75 | **** |
| 76 | **** |
| 77 | ***** |
| 78 | ** |
| 79 | *** |
| 80 | **** |
| 81 | ** |
| 82 | **** |
| 83 | ***** |
| 84 | ** |
| 85 | ** |
| 86 | ** |
| 87 | **** |
| 88 | **** |
| 89 | **** |
| 90 | **** |
| 91 | ** |
| 92 | ** |
| 93 | ***** |
| 94 | *** |
| 95 | **** |

TABLE 1-continued

| Cpd | IC$_{50}$ |
|---|---|
| 96 | ***** |
| 97 | ***** |
| 98 | ***** |
| 99 | ***** |
| 100 | ** |
| 101 | *** |
| 102 | ***** |
| 103 | **** |
| 104 | ***** |
| 105 | ***** |
| 107 | ***** |
| 108 | ***** |
| 109 | ***** |
| 110 | **** |
| 111 | ***** |
| 112 | ***** |
| 113 | ***** |
| 114 | ** |
| 115 | **** |
| 116 | ***** |
| 117 | * |
| 118 | ** |
| 119 | **** |
| 120 | **** |
| 121 | ***** |
| 122 | ** |
| 123 | * |
| 124 | ***** |
| 125 | **** |
| 126 | **** |
| 127 | ***** |
| 128 | ***** |
| 129 | ***** |
| 130 | ***** |
| 131 | ***** |
| 132 | *** |
| 133 | **** |
| 134 | ***** |
| 135 | ***** |
| 136 | ***** |
| 137 | ***** |
| 138 | **** |
| 139 | **** |
| 140 | ***** |
| 141 | ***** |
| 142 | ***** |
| 143 | ***** |
| 144 | ***** |
| 145 | ** |
| 146 | ** |
| 147 | ** |
| 148 | ***** |
| 149 | ** |
| 150 | ***** |
| 151 | ***** |
| 152 | **** |
| 153 | ***** |
| 154 | ***** |
| 155 | * |
| 156 | **** |
| 157 | **** |
| 158 | ***** |
| 159 | ***** |
| 160 | **** |
| 161 | ***** |
| 162 | ***** |
| 163 | ***** |
| 164 | ***** |
| 165 | ***** |
| 166 | **** |
| 167 | ** |
| 168 | ***** |
| 169 | ***** |
| 170 | ** |
| 171 | **** |
| 172 | **** |
| 173 | ***** |
| 174 | ***** |

TABLE 1-continued

| Cpd | IC$_{50}$ |
|---|---|
| 175 | *** |
| 176 | ***** |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or particular aspects described herein. It is intended that the appended claims be interpreted to include all such equivalents.

What is claimed is:

1. A compound of Formula (Ibb1):

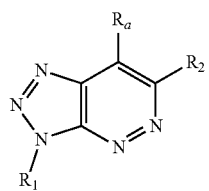

(Ibb1)

or a form thereof, wherein:
R$_a$ is selected from the group consisting of hydrogen, cyano, halogen, hydroxy, C$_{1-6}$ alkyl, deutero-C$_{1-4}$ alkyl, halo-C$_{1-6}$ alkyl, C$_{1-6}$ alkoxy, halo-C$_{1-6}$ alkoxy, C$_{1-6}$alkoxy-C$_{1-6}$ alkyl, amino, C$_{1-6}$ alkyl-amino, (C$_{1-6}$ alkyl)$_2$-amino, amino-C$_{1-6}$ alkyl, and hydroxy-C$_{1-6}$alkyl;
R$_1$ is selected from the group consisting of C$_{3-10}$ cycloalkyl and heterocyclyl,
wherein heterocyclyl in R$_1$ is a saturated or partially unsaturated 3-7 membered monocyclic, 6-10 membered bicyclic or 13-16 membered polycyclic ring system having 1, 2, or 3 heteroatom ring members independently selected from N, O, or S, and
wherein each instance of C$_{3-10}$ cycloalkyl and heterocyclyl in R$_1$ is optionally substituted with one, two or three R$_3$ substituents and optionally, with one additional R$_4$ substituent, or,
wherein, alternatively, each instance of C$_{3-10}$ cycloalkyl and heterocyclyl in R$_1$ is optionally substituted with one, two, three, or four R$_3$ substituents;
R$_2$ is selected from the group consisting of phenyl, heterocyclyl, and heteroaryl,
wherein heterocyclyl in R$_2$ is a saturated or partially unsaturated 3-7 membered monocyclic, 6-10 membered bicyclic or 13-16 membered polycyclic ring system having 1, 2, or 3 heteroatom ring members independently selected from N, O, or S,
wherein heteroaryl in R$_2$ is a 3-7 membered monocyclic or 6-10 membered bicyclic ring system having 1, 2, 3, or 4 heteroatom ring members independently selected from N, O, or S, and
wherein each instance of phenyl, heterocyclyl, and heteroaryl in R$_2$ is optionally substituted with one, two, or three R$_5$ substituents, and optionally, with one additional R$_6$ substituent;
R$_3$ is, in each instance, independently selected from the group consisting of cyano, halogen, hydroxy, C$_{1-6}$ alkyl, deutero-C$_{1-4}$alkyl, halo-C$_{1-6}$alkyl, C$_{1-6}$ alkoxy, halo-C$_{1-6}$ alkoxy, C$_{1-6}$alkoxy-C$_{1-6}$ alkyl, amino, C$_{1-6}$ alkyl-amino, (C$_{1-6}$ alkyl)$_2$-amino, amino-C$_{1-6}$alkyl, and hydroxy-C$_{1-6}$alkyl;
R$_4$ is selected from the group consisting of C$_{3-10}$cycloalkyl, phenyl, heteroaryl, and heterocyclyl,
wherein heterocyclyl in R$_4$ is a saturated or partially unsaturated 3-7 membered monocyclic, 6-10 membered bicyclic or 13-16 membered polycyclic ring system having 1, 2, or 3 heteroatom ring members independently selected from N, O, or S,
wherein heteroaryl in R$_4$ is a 3-7 membered monocyclic or 6-10 membered bicyclic ring system having 1, 2, 3, or 4 heteroatom ring members independently selected from N, O, or S, and
wherein, each instance of C$_{3-10}$cycloalkyl, phenyl, heterocyclyl, and heteroaryl in R$_4$ is optionally substituted with one, two, or three R$_7$ substituents;
R$_5$ is, in each instance, independently selected from the group consisting of halogen, hydroxy, cyano, nitro, C$_{1-6}$ alkyl, deutero-C$_{1-4}$ alkyl, halo-C$_{1-6}$ alkyl, C$_{1-6}$alkoxy, halo-C$_{1-6}$ alkoxy, oxime, amino, C$_{1-6}$alkyl-amino, (C$_{1-6}$ alkyl)$_2$-amino, and C$_{1-6}$alkyl-thio;
R$_6$ is selected from the group consisting of phenyl and heteroaryl,
wherein heteroaryl in R$_6$ is a 3-7 membered monocyclic or 6-10 membered bicyclic ring system having 1, 2, 3, or 4 heteroatom ring members independently selected from N, O, or S, and
wherein each instance of phenyl and heteroaryl in R$_6$ is optionally substituted with one, two, three or four R$_8$ substituents;
R$_7$ is, in each instance, independently selected from the group consisting of cyano, halogen, hydroxy, C$_{1-6}$ alkyl, deutero-C$_{1-4}$alkyl, halo-C$_{1-6}$alkyl, C$_{1-6}$ alkoxy, halo-C$_{1-6}$ alkoxy, C$_{1-6}$alkoxy-C$_{1-6}$ alkyl, amino, C$_{1-6}$ alkyl-amino, (C$_{1-6}$ alkyl)$_2$-amino, amino-C$_{1-6}$alkyl, and C$_{3-10}$ cycloalkyl; and
R$_8$ is, in each instance, independently selected from the group consisting of cyano, halogen, hydroxy, C$_{1-6}$ alkyl, deutero-C$_{1-4}$alkyl, halo-C$_{1-6}$alkyl, C$_{1-6}$ alkoxy, halo-C$_{1-6}$ alkoxy, C$_{1-6}$alkoxy-C$_{1-6}$ alkyl, amino, C$_{1-6}$ alkyl-amino, (C$_{1-6}$ alkyl)$_2$-amino, amino-C$_{1-6}$ alkyl, and C$_{3-10}$ cycloalkyl;
wherein a form of the compound is selected from the group consisting of a salt, hydrate, solvate, racemate, enantiomer, diastereomer, stereoisomer, and tautomer form thereof.

2. The compound or form thereof of claim 1, wherein R$_1$ is heterocyclyl selected from the group consisting of azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-en-yl, (1R,5S)-8-azabicyclo[3.2.1]oct-2-en-yl, 9-azabicyclo[3.3.1]nonyl, 0(1R,5S)-9-azabicyclo[3.3.1]nonyl, 3-oxa-9-azabicyclo[3.3.1]nonyl, and 3-oxa-9-azabicyclo[3.3.1]non-6-en-yl, wherein heterocyclyl is optionally substituted with one, two or three R$_3$ substituents and optionally, with one additional $R_4$ substituent, or, alternatively, wherein heterocyclyl is optionally substituted with one, two, three or four $R_3$ substituents.

3. The compound or form thereof of claim 1, wherein $R_2$ is phenyl, optionally substituted with one, two or three $R_5$ substituents and optionally, with one additional $R_6$ substituent.

4. The compound of claim 1, wherein the form of the compound is a compound salt selected from the group consisting of hydrochloride, hydrobromide, formate, dihydrochloride, and dihydrobromide salts.

5. A method for treating or ameliorating HD in a subject in need thereof, comprising administering to the subject an effective amount of the compound or form thereof of claim 1.

6. The method of claim 5, wherein the effective amount of the compound or form thereof is in a range of from about 0.001 mg/kg/day to about 500 mg/kg/day.

7. A pharmaceutical composition comprising the compound or form thereof of claim 1 and at least one pharmaceutically acceptable excipient.

8. (A method for treating or ameliorating HD in a subject in need thereof, comprising administering to the subject an effective amount of the compound or form thereof of claim 2.

9. The method of claim 8, wherein the effective amount of the compound or form thereof is in a range of from about 0.001 mg/kg/day to about 500 mg/kg/day.

10. A method for treating or ameliorating HD in a subject in need thereof, comprising administering to the subject an effective amount of the compound or form thereof of claim 3.

11. The method of claim 10, wherein the effective amount of the compound or form thereof is in a range of from about 0.001 mg/kg/day to about 500 mg/kg/day.

12. A method for treating or ameliorating HD in a subject in need thereof, comprising administering to the subject an effective amount of the compound salt of claim 4.

13. The method of claim 12, wherein the effective amount of the compound salt is in a range of from about 0.001 mg/kg/day to about 500 mg/kg/day.

14. A pharmaceutical composition comprising the compound or form thereof of claim 2 and at least one pharmaceutically acceptable excipient.

15. A pharmaceutical composition comprising the compound or form thereof of claim 3 and at least one pharmaceutically acceptable excipient.

16. A pharmaceutical composition comprising the compound salt of claim 4 and at least one pharmaceutically acceptable excipient.

\* \* \* \* \*